(12) United States Patent
Gegg et al.

(10) Patent No.: US 7,655,764 B2
(45) Date of Patent: Feb. 2, 2010

(54) MODIFIED FC MOLECULES

(75) Inventors: Colin Gegg, Newbury Park, CA (US); Fei Xiong, Thousand Oaks, CA (US); Karen C. Sitney, Weston, CT (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/221,412

(22) Filed: Aug. 1, 2008

(65) Prior Publication Data

US 2009/0022744 A1   Jan. 22, 2009

Related U.S. Application Data

(63) Continuation of application No. 11/234,731, filed on Sep. 23, 2005, now Pat. No. 7,442,778.

(60) Provisional application No. 60/612,680, filed on Sep. 24, 2004.

(51) Int. Cl.
C07K 16/00 (2006.01)
A61K 38/00 (2006.01)

(52) U.S. Cl. .............. 530/391.7; 530/350; 530/391.1

(58) Field of Classification Search .............. None
See application file for complete search history.

(56) References Cited

U.S. PATENT DOCUMENTS

| | | | |
|---|---|---|---|
| 3,691,016 A | 9/1972 | Patel | |
| 3,817,837 A | 6/1974 | Rubenstein et al. | |
| 3,850,752 A | 11/1974 | Hermanus | |
| 3,939,350 A | 2/1976 | Kronick et al. | |
| 3,941,763 A | 3/1976 | Sarantakis | |
| 3,969,287 A | 7/1976 | Jaworek et al. | |
| 3,996,345 A | 12/1976 | Ullman et al. | |
| 4,087,778 A | 5/1978 | Merz et al. | |
| 4,179,337 A | 12/1979 | Davis et al. | |
| 4,195,128 A | 3/1980 | Hildebrand et al. | |
| 4,229,537 A | 10/1980 | Hodgins et al. | |
| 4,247,642 A | 1/1981 | Hirohara | |
| 4,277,437 A | 7/1981 | Maggio | |
| 4,301,144 A | 11/1981 | Iwashita et al. | |
| 4,330,440 A | 5/1982 | Ayers et al. | |
| 4,496,689 A | 1/1985 | Mitra et al. | |
| 4,640,835 A | 2/1987 | Shimizu et al. | |
| 4,670,417 A | 6/1987 | Iwasaki et al. | |
| 4,719,192 A | 1/1988 | Schneider et al. | |
| 4,925,673 A | 5/1990 | Steiner et al. | |
| 5,013,556 A | 5/1991 | Woodle et al. | |
| 5,098,833 A | 3/1992 | Lasky et al. | |
| 5,116,964 A | 5/1992 | Capon et al. | |
| 5,216,131 A | 6/1993 | Lasky et al. | |
| 5,223,409 A | 6/1993 | Ladner et al. | |
| 5,225,538 A | 7/1993 | Capon et al. | |
| 5,284,656 A | 2/1994 | Platz et al. | |
| 5,336,603 A | 8/1994 | Capon et al. | |
| 5,338,665 A | 8/1994 | Schatz et al. | |
| 5,428,130 A | 6/1995 | Capon et al. | |
| 5,432,018 A | 7/1995 | Dower et al. | |
| 5,455,165 A | 10/1995 | Capon et al. | |
| 5,480,981 A | 1/1996 | Goodwin et al. | |
| 5,498,530 A | 3/1996 | Schatz et al. | |
| 5,514,582 A | 5/1996 | Capon et al. | |
| 5,608,035 A | 3/1997 | Yanofsky et al. | |
| 5,714,147 A | 2/1998 | Capon et al. | |
| 5,726,290 A | 3/1998 | Bodary et al. | |
| 5,733,731 A | 3/1998 | Schatz et al. | |
| 5,739,277 A | 4/1998 | Presta et al. | |
| 5,767,234 A | 6/1998 | Yanofsky et al. | |
| 5,773,569 A | 6/1998 | Wrighton et al. | |
| 5,786,331 A | 7/1998 | Barrett et al. | |
| 5,792,451 A | 8/1998 | Sarubbi et al. | |
| 5,800,096 A | 9/1998 | Barrow | |
| 5,808,029 A | 9/1998 | Brockhous et al. | |
| 5,840,844 A | 11/1998 | Lasky et al. | |
| 5,843,725 A | 12/1998 | Sledzlewski et al. | |
| 5,849,452 A | 12/1998 | Takenaka et al. | |
| 5,869,451 A | 2/1999 | Dower et al. | |
| 5,869,452 A | 2/1999 | Ng et al. | |
| 5,877,151 A | 3/1999 | Pereira | |
| 5,877,289 A | 3/1999 | Thorpe et al. | |
| 5,880,096 A | 3/1999 | Barret et al. | |
| 5,880,103 A | 3/1999 | Urban et al. | |
| 5,886,150 A | 3/1999 | Duchesne et al. | |
| 5,888,763 A | 3/1999 | Hanafusa et al. | |

(Continued)

FOREIGN PATENT DOCUMENTS

| | | |
|---|---|---|
| AU | 64763/98 | 7/1998 |
| EP | 0 315 062 A2 | 5/1989 |
| EP | 0 315 456 A2 | 5/1989 |
| EP | 0 714 912 A2 | 6/1996 |
| EP | 0 325 224 B1 | 7/1996 |
| EP | 0 911 393 A1 | 4/1999 |
| EP | 0 585 287 B1 | 10/1999 |
| EP | 0 958 829 A1 | 11/1999 |
| EP | 1 029 870 A2 | 8/2000 |
| EP | 0 526 452 B1 | 2/2001 |

(Continued)

OTHER PUBLICATIONS

U.S. Appl. No. 60/641,144, filed Jan. 5, 2005, Ruker, et al.
Abuchowski and Davis, "Soluble Polymer-Enzyme Adducts", *Enzymes as Drugs*, pp. 362-383 (1981).
Adey & Kay, Identification of Calmodulin-Binding Peptide Consensus Sequences from a Phage-Displayed Random Peptide Library, *Gene* 169: 133-134(1996).

(Continued)

*Primary Examiner*—Sheela J Huff
(74) *Attorney, Agent, or Firm*—Nisan A. Steinberg

(57) ABSTRACT

The present invention concerns compositions of matter, for example, but not limited to, modified antibodies, in which one or more biologically active peptides are incorporated into a loop region of a non-terminal domain of an immunoglobulin Fc domain.

18 Claims, 22 Drawing Sheets

U.S. PATENT DOCUMENTS

| | | |
|---|---|---|
| 5,922,545 A | 7/1999 | Mattheakis et al. |
| 5,932,546 A | 8/1999 | Barrett et al. |
| 5,945,507 A | 8/1999 | Montelaro et al. |
| 5,985,599 A | 11/1999 | McKenzie et al. |
| 6,004,555 A | 12/1999 | Thorpe et al. |
| 6,108,026 A | 8/2000 | Corbett |
| 6,117,655 A | 9/2000 | Capon et al. |
| 6,132,730 A | 10/2000 | Thorpe et al. |
| 6,133,426 A | 10/2000 | Gonzalez et al. |
| 6,156,321 A | 12/2000 | Thorpe et al. |
| 6,291,212 B1 | 9/2001 | Sledziewski et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,406,697 B1 | 6/2002 | Capon et al. |
| 6,660,843 B1 | 12/2003 | Feige et al. |
| 2003/0143220 A1 | 7/2003 | Capon et al. |
| 2003/0176352 A1 | 9/2003 | Min et al. |
| 2003/0195156 A1 | 10/2003 | Min et al. |
| 2003/0215914 A1 | 11/2003 | Houtzager et al. |
| 2003/0229023 A1 | 12/2003 | Oliner et al. |
| 2003/0236192 A1 | 12/2003 | Dasch et al. |
| 2003/0236193 A1 | 12/2003 | Oliner et al. |
| 2004/0087778 A1 | 5/2004 | Feige et al. |
| 2004/0181033 A1 | 9/2004 | Han et al. |

FOREIGN PATENT DOCUMENTS

| | | |
|---|---|---|
| EP | 0 770 624 B1 | 5/2003 |
| EP | 0 988 056 B1 | 7/2003 |
| EP | 1 752 471 A1 | 1/2006 |
| EP | 1 772 465 A1 | 1/2006 |
| WO | WO 91/08298 | 6/1981 |
| WO | WO 89/09622 | 10/1989 |
| WO | WO 94/04689 | 3/1994 |
| WO | WO 94/07921 | 4/1994 |
| WO | WO 95/09917 | 4/1995 |
| WO | WO 95/14714 | 6/1995 |
| WO | WO 95/18858 | 7/1995 |
| WO | WO 95/21919 | 8/1995 |
| WO | WO 95/21920 | 8/1995 |
| WO | WO 95/26746 | 10/1995 |
| WO | WO 96/05309 | 2/1996 |
| WO | WO 96/11214 | 4/1996 |
| WO | WO 96/11953 | 4/1996 |
| WO | WO 96/17942 | 6/1996 |
| WO | WO 96/18412 | 6/1996 |
| WO | WO 96/23899 | 8/1996 |
| WO | WO 96/30057 | 10/1996 |
| WO | WO 96/32478 | 10/1996 |
| WO | WO 96/40772 | 12/1996 |
| WO | WO 96/40987 | 12/1996 |
| WO | WO 97/00270 | 1/1997 |
| WO | WO 97/08203 | 3/1997 |
| WO | WO 97/08553 | 3/1997 |
| WO | WO 97/23614 | 7/1997 |
| WO | WO 97/28828 | 8/1997 |
| WO | WO 97/31019 | 8/1997 |
| WO | WO 97/34631 | 9/1997 |
| WO | WO 97/35969 | 10/1997 |
| WO | WO 97/40070 | 10/1997 |
| WO | WO 97/41220 | 11/1997 |
| WO | WO 97/44453 | 11/1997 |
| WO | WO 98/09985 | 3/1998 |
| WO | WO 98/10795 | 3/1998 |
| WO | WO 98/15833 | 4/1998 |
| WO | WO 98/24477 | 6/1998 |
| WO | WO 98/28427 | 7/1998 |
| WO | WO 98/31820 | 7/1998 |
| WO | WO 98/33812 | 8/1998 |
| WO | WO 98/46257 | 10/1998 |
| WO | WO 98/53842 | 12/1998 |
| WO | WO 98/55620 | 12/1998 |
| WO | WO 99/02711 | 1/1999 |
| WO | WO 99/05302 | 2/1999 |
| WO | WO 99/14244 | 3/1999 |
| WO | WO 99/17789 | 4/1999 |
| WO | WO 99/18243 | 4/1999 |
| WO | WO 99/18781 | 4/1999 |
| WO | WO 99/24462 | 5/1999 |
| WO | WO 99/24782 | 5/1999 |
| WO | WO 99/38008 | 7/1999 |
| WO | WO 99/38526 | 8/1999 |
| WO | WO 99/42592 | 8/1999 |
| WO | WO 99/45944 | 9/1999 |
| WO | WO 99/46283 | 9/1999 |
| WO | WO 99/47151 | 9/1999 |
| WO | WO 99/50282 | 10/1999 |
| WO | WO 99/51254 | 10/1999 |
| WO | WO 99/51720 | 10/1999 |
| WO | WO 99/51732 | 10/1999 |
| WO | WO 99/51748 | 10/1999 |
| WO | WO 99/60013 | 11/1999 |
| WO | WO 99/61476 | 12/1999 |
| WO | WO 99/62539 | 12/1999 |
| WO | WO 00/01402 | 1/2000 |
| WO | WO 00/04048 | 1/2000 |
| WO | WO 00/09560 | 2/2000 |
| WO | WO 00/11027 | 3/2000 |
| WO | WO 00/11028 | 3/2000 |
| WO | WO 00/12727 | 3/2000 |
| WO | WO 00/17226 | 3/2000 |
| WO | WO 00/17358 | 3/2000 |
| WO | WO 00/17370 | 3/2000 |
| WO | WO 00/17648 | 3/2000 |
| WO | WO 00/18895 | 4/2000 |
| WO | WO 00/23585 | 4/2000 |
| WO | WO 00/24770 | 5/2000 |
| WO | WO 00/24782 A2 | 5/2000 |
| WO | WO 01/02440 A1 | 1/2001 |
| WO | WO 01/04296 A1 | 1/2001 |
| WO | WO 01/83525 A2 | 11/2001 |
| WO | WO 02/32925 A2 | 4/2002 |
| WO | WO 02/32925 A3 | 4/2002 |
| WO | WO 02/32925 C2 | 4/2002 |
| WO | WO 02/44215 A2 | 6/2002 |
| WO | WO 02/092620 A2 | 11/2002 |
| WO | WO 02/092620 A3 | 11/2002 |
| WO | WO 03/031589 A2 | 4/2003 |
| WO | WO 03/057134 A2 | 7/2003 |
| WO | WO 2004/002417 A2 | 1/2004 |
| WO | WO 2004/002424 A2 | 1/2004 |
| WO | WO 2004/026329 A1 | 4/2004 |
| WO | WO 2004/058988 | 7/2004 |
| WO | WO 2004/092215 | 10/2004 |
| WO | WO 2005/047337 | 5/2005 |
| WO | WO 2006/072620 A1 | 1/2006 |

OTHER PUBLICATIONS

Adey & Kay, "Isolation of Peptides From Phage-Displayed Random Peptide Libraries That Interact With the Talin-Binding Domain of Vinculin", *Biochem. J.* 324: 523-528 (1997).

Adjei & Garren, Pulmonary Delivery of Peptide Drugs: Effect of Particle Size on Bioavailability of Leuprolide Acetate in Healthy Male Volunteers, *Pharma. Res.* 7: 556-569 (1990).

Adjei, et al., "Bioavailability of Leuprolide Following Intratracheal Administration to Beagle Dogs", *Internatl. J. Pharmaceutics*, 63: 135-144 (1990).

Ahern, et al., "Special Report: The Peptide-Oligonucleotide Partnership", *The Scientist* 4(19): 24-25 (1990).

Akerstrom, "Protein G: A Powerful Tool for Binding and Detection of Monoclonal and Ployclonal Antibodies", *J. Immunol.* 135(4): 2589-2592 (1985).

Akeson, et al., "AF12198, a Novel Low Molecular Weight Antagonist, Selectively Binds the Human Type I Interleukin (IL)-1 Receptor and Blocks in vivo Responses to IL-1", *J. Biol Chem.* 271: 30517-20523 (1996).

Asai, et al., *Methods in cell Biology*, vol. 37, Academic Press, Inc., New York (1993) (Table of Contents Provided Only).

Ball, et al., "Cell Cycle Arrest and Inhibition of Cdk4 Activity by Small Peptides Based on the Carboxy-Terminal Domain of p21$^{WAF1}$", *Current Biology* 7(1): 71-80 (1997).

Barna, et al., "Combination Therapy with a Synthetic Peptide of C-Reactive Protein and Interleukin 2: Augmented Survival and Eradication of Pulmonary Metastases", *Cancer Immunol. Immunotherapy* 38: 38-42 (1994).

Bhatnagar, et al., "Structure-Activity Relationships of Novel Hematoregulatory Pepticides", *J. Med. Chem.* 39: 3814-3819 (1996).

Böttger, et al., Molecular Characterization of the hdm2-p53 Interaction, *J. Mol. Biol.* 269: 744-756 (1997).

Böttger, et al., "Identification of novel mdm2 binding peptides by phage display", *Oncogene* 13: 2141-2147 (1996).

Brocks, et al., "A TNF Receptor Antagonistic scFv, which is not Secreted in Mammalian Cells, is Expressed as a Soluble Mono- and Bivalent scFv Derivative in Insect Cells", *Immunotechnology* 3(3): 173-184 (1997).

Burstein, et al., "Thymic Humoral Factor γ2: Purification and Amino Acid Sequence of an Immunoregulatory Peptide from Calf Thymus", *Biochemistry* 27: 4066-4071 (1988).

Capon et al., "Designing CD4 Immunoadhesins for AIDS Therapy", *Nature* 337: 525-531 (1989).

Carillo, et al., "The Multiple Sequence Alignment Problem in Biology", *SIAM J. Applied Math* 48: 1073-1082 (1988).

Chamow, S. M., et al., "Immunoadhesins: Principles and Applications", *Tibtech* 14: 52-60 (1996).

Chan and Kim, et al., "HIV Entry and Its Inhibition" *Cell* 93: 681-684 (1998).

Chaubert, et al., "Simultaneous Double Immunoenzymatic Labeling: A New Procedure for the Histopathlogic Routine", *Mod. Pathol.* 10: 585 (1997).

Chirinos-Rojas, et al., "A Peptidomimetic Antagonist of TNF-α-Mediated Cytotoxicity Identified from a Phage-Displayed Random Peptide Library", *Journal of Immunology* 161: 5621-5626 (1998).

Chou, et al., "Prediction of the β-Turns", *Biophys J.* 26: 367-384 (1979).

Chou, et al., "Prediction of the Secondary Structure of Proteins From Their Amino Acid Sequence", *Adv. Enzymol. Related. Areas Mol. Biol.* 47: 45-148 (1978).

Chou, et al., "Empirical Predictions of Protein Conformation", *Ann. Rev. Biochem.* 47: 251-276 (1979).

Clackson, et al., "A Hot Spot of Binding Energy in a Hormone-Receptor Interface", *Science* 267: 383-336 (1995).

Cooper, et al., "Purification and Characterization of a peptide from Anyloid-Rich Pancreases of Type 2 Diabetic Patients", *PNAS* 84: 8628-8632 (1987).

Cortese, et al., "Selection of Biologically Active Peptides by Phage Display of Random Peptide Libraries", *Current Opinion In Biotechnology* 7: 616-621 (1996).

Couet, et al., "Identification of Peptide and Protein Ligands for the Caveolin-Scaffolding Domain", *The Journal of Biological Chemistry* 272(10): 6525-6533 (1997).

Couet, et al., "Interaction of a Receptor Tyosine Kinase, EGF-R, with Caveolins", *The Journal of Biological Chemistry* 272(48): 30429-30438 (1997).

Creighton, "Proteins: Structures and Molecular Principles", (W. H. Freeman & Co., San Francisco) pp. 70-86 (1983).

Cuthbertson, et al., "Design of Low Molecular Weight Hematoregulatory Agents from the Structure-Activity Relationship of a Dimeric Pentapeptide", *J. Med. Chem.* 40: 2876-2882 (1997).

Cwirla, et al., "Peptide Agonist of the Thrombopoietin Receptor as Potent as the Natural Cytokine", *Science* 276: 1696-1699 (1997).

Davis, et al., "Preparation and Characterization of Antibodies with Specificity for the Amino-Terminal Tetrapeptide Sequence of the Platelet-Derived Connective Tissue", *Biochem Intl.* 10: 395-404 (1985).

Dayhoff, et al., *Atlas of Protein Sequence and Structure*, Nat'l Biomed. Research Foundation, 5(Supp. 3) (1978) (Table of Contents Provided Only).

Debs, et al., "Lung-Specific Delivery of Cytokines Induces Sustained Pulmonary and Systemic Immunomodulation in Rats", *J. Immunol.* 140: 3482-3488, (1988).

Dedman, et al., "Selection of Targeted Biological Modifiers from a Bacteriophage Library of Random Peptides", *J. Biol. Chem.* 268(31): 23025-23030 (1993).

Devereux, et al., "A Comprehensive Set of Sequence Analysis Programs for the VAX", *Nucleid Acids Research.*, 12: 387-395 (1984).

Devlin, et al., "Random Peptide Libraries: A Source of Specific Protein Binding Molecules", *Science* 249: 404-406 (1990).

Duncan, et al. "Localization of the Binding Site for the Human High-Affinity Fc Receptor on IgG", *Nature* 332: 563-564 (1988).

Dysan & Murray, "Selection of Peptide Inhibitors of Interactions Involved in Complex Protein Assemblies: Association of the Core and Surface Antigens of Hepatitis B Virus", *Proc. Natl. Acad. Sci. USA* 92: 2194-2198 (1995).

Ellison, et al., "The Nucleotide Sequence of a Human Immunoglobulin Cγ1 Gene", *Nucleic Acids Res.* 10: 4071-4079 (1982).

Engel, et al., "Insertion of Carrier Proteins Into Hydrophilic Loops of the *Escherichia coli* Lactose Permease", *Biochimica et Biophysica Acta* 1564: 38-46 (2002).

Erickson, et al., *The Proteins*, "Solid-Phase Peptide Synthesis", (3$^{rd}$ ed.), vol. II, pp. 257-527 (1976).

Fåhraeus, et al., "Inhibition of pRb Phosphorylation and Cell-Cycle Progression by a 20-Residue Peptide Derived from p16$^{CDKN2/}$INK4A", *Current Biology*. 6: 84-91 (1996).

Fairbrother, et al., "Novel Peptides Selected to Find Vascular Endothelial Growth Factor Target the Receptor-Binding Site", *Biochemistry* 37: 17754-17764 (1998).

Finn, et al., *The Proteins*, "The Synthesis of Peptides by Solution Methods with Emphasis on Peptide Hormones", (3$^{rd}$ ed.), vol. II, pp. 105-253 (1976).

Fisher, et al., "Treatment of Septic Shock with the Tumor Necrosis Factor Receptor : Fc Fusion Protein", *N Englad J.; Med.* 334(26): 1697-1702 (1996).

Francis, Gillian E., "Protein Modification and Fusion Proteins", *Royal Free Hospital School of Medicine* 3: 4-10 (1992).

Fukumoto, et al., "Peptide Mimics of the CTLAA4-Bindining Domain Stimulate T-Cell Proliferation", *Nature Biotechnology* 16: 267-270 (1998).

Gan, et al., "Echistatin", *J. Biol Chem.* 263: 19827-19832 (1988).

Ghetie, et al., "Increasing the Serum Persistence of an IgG Fragment by Random Mutagenesis", *Nature Biotechnology* 15: 637-640 (1997).

Gibbs, et al., "Farnesyltransferase Inhibitors: Ras Research Yields a Potential Cancer Therapeutic", *Cell* 77: 175-178 (1994).

Gibbs, et al., "Pharmaceutical Research in Molecular Oncology", *Cell* 79: 193-198 (1994).

Golub, E. S. and Green D. R. eds., *Immunology—A Synthesis, Sinauer Associates*, Sunderland, Mass.;2$^{nd}$ Edition, "The Structure of Immunoglobulins", Chapter 3, pp. 42-52; "The Constant Region", Chapter 6, pp. 92-107; "Amino Acid Abbreviations", Appendix 1, p. 716 (1991).

Gonzalez-Cadavid, et al., "Organization of the Human Myostatin Gene and Expression in Healthy Men and HIV-Infected Men with Muscle Wasting" *Proc. Natl. Acad. Sci.* 95:14938-14943 (1998).

Goodson, et al., "High -Affinity Urokinase Receptor Antagonists Identified with Bacteriophase Peptide Display", *Proc. Natl. Acad. Sci.* 91: 7129-7133 (1994).

Graf and Kastin, "Delta-Sleep-Inducing Peptide (DSIP): An Update", *Peptides* 7: 1165-1187(1986).

Gribskov, M. and Devereux, *Sequence Analysis Primer, Stockton Press, New York* (1991) (Table of Contents Provided Only).

Gribskov, et al., "Profile Analysis", *Meth. Enzym.* 183: 146-159 (1990).

Gribskov, et al., "Profile Analysis: Detection of Distantly Related Proteins", *Proc. Nat. Acad. Sci.* 84(13): 4355-4358 (1987).

Griffin, A.M., and Griffin, H.G., *Computer Analysis of Sequence Data, Part 1*, Humana Press, New Jersey (1994) (Table of Contents Provided Only).
Halaby, et al., "The Immunoglobulin Fold Family Sequence Analysis and 3D Structure Comparisons", *Protein Engineering*, 12(7): 563-571 (1999).
Hamrick, et al., "Bone Mineral Content and Density in the Humerus of Adult Myostatin-Feficient Mice" *Calcif Tissue Int.* 71(1): 63-68 (2002).
Harvill, et al., "An IgG3-IL2 Fusion Protein Activates Complement, Binds FcγRI, Generates LAK Activity and Shows Enhanced Binding to the High Affinity IL-2R", *Immunotech* 1: 95-105 (1995).
Harwig, et al., "Neutrophi Defenses: Purification, Characterization, and Antimicrobial Testing", *Methods Enzymology* 236: 160-172 (1994).
Henikoff, et al., *Proc. Nal Acad. Sci. USA* 89: 10915-10919 (1992).
Herz, et al., "Molecular Approaches to Receptors as Targets for Drug Discovery", *J. of Receptor & Signal Transduction Research* 17(5): 671-776 (1997).
Holm, et al., "Protein Folds and Families: Sequence and Structure Alignments", *Nucleic Acids Research.*, 27(1): 244-247 (1999).
Hong, et al., Protein Ligands of the Human Adenovirus Type 2 Outer Capsid Identified by Biopanning of a Phage-Displayed Peptide Library on Separate Domains of Wild-Type and Mutant Penton Capsomers, *The EMBO Journal* 14: 4714-4727 (1995).
Hubbard, et al., "Anti-Neutrophil-Elastase Defenses of the Lower Respiratory Tract in α1-Antitrypsin Deficiency Directly Augmented with an Aerosol of α1-Antitrypsin", *Annals Int. Med.* 3(3): 206-212 (1989).
Hughes, David, "Therapeutic Antibodies Make a Comeback", *Drug Discovery Today* 3(10): 439-442 (1998).
Inagaki-Ohara, et al., "Effects of a Nonapeptide Thymic Hormone on Intestinal Intraepithelial Lymphocytes in Mice Following Administration of 5-Fluorouracil", *Cellular Immunol.* 17: 30-40 (1996).
Inglot, Anna, D., "Classification of Cytokines According to the Receptor Code", *Archivum Immunologies et Therapine Experimentalis*, 45: 353-357 (1997).
Ishikawa, et al., "GD1α-Replica Peptides Functionally Mimic GD1α, an Adhesion Molecule of Metastatic Tumor Cell, and Suppress the Tumor Metastasis", *FEBS* 441: 20-24 (1998).
Jefferies, D., "Selection of Novel Ligands from Phage Display Libraries: An Alternative Approach to Drug and Vaccine Discovery?", *Parasitology Today* 14(5): 202-206 (1988).
Jefferis, et al., "Recognition Sites on Human IgG for Fey Receptors: the Role of Glycosylation", *Immunology Letters* 44: 111-117 (1995).
Jefferis, et al., Molecular Definition of Interaction Sites on Human IgG Fc Receptors (huFcy R), *Molecular Immunology* 27(12): 1237-1240 (1990).
Johnson, et al., Identification of a 13 Amino Acid Peptide Mimetic of Erythropoietin and Description of Amino Acids, Critical for the Mimetic Activity of EMP1, *Biochemistry* 37(11): 3699-3710 (1998).
Jones, et al., "Stromal Expression of Jagged 1 Promotes Colony Formation by Fetal Hematopoietic Progenitor Cells", *Blood* 92(5): 1505-1511 (1998).
Jones, D., "Progress in Protein Structure Prediction", *Curr. Opin. Struct. Biol.* 7(3): 377-387 (1997).
Junghans, R. P., "Finally! The Branbell Receptor (FcRB)", *Immunologic Research* 16(1): 29-57 (1997).
Kay, et al., "From Peptides to Drugs Via Phage Display", *Drug Disc. Today* 3: 370-378 (1998).
King, et al., "Modulation of Bone Marrow Stromal Cell Production of Colony Stimulating Activity by the Synthetic Peptide", *Exp. Hematol* 19: 481 (1991).
King, et al., "Hematoregulatory Peptide, SK&F Induced Stromal Cell Production of KC Enhances CFU-GM Growth and Effector Cell Function", *Blood* 86(1): 309a (1995).
Kitamura, et al., "Adrenomedullin: A Novel Hypotensive Peptide Isolated From Human Pheochromocytoma", *BBRC.* 192: 553-560 (1993).
Kluczyk, et al., "Immunomodulatory Activity of Oligopeptides Related to Interleukin 1 Receptor Antagonist Sequence", *Archivum Immunologiac et Therapiae Experimentalis* 45: 427-433 (1997).

Koivunen, et al., "Tumor Targeting with a Selective Gelatinase Inhibitor", *Nat. Biotech.* 17: 768-774 (1999).
Kraft, et al., "Definition of an Unexpected Ligand Recognition Motif for avβ6 Integrin", *Journal of Biological Chemistry* 274(4): 1979-1985 (1999).
Kyte, et al., "A Simple Method for Displaying the Hydropathic Character of a Protein", *J. Mol Biol.*, 157: 105-131 (1982).
Kreeger, Karen Young, "Immunological Applications Top List of Peptide-Synthesis Services", The Scientist 10(13): 19-20 (1998).
Kuai, et al., "Plasminogen Activator Inhibitor-1 Fused With Erythropoietin (EPO) Mimetic Peptide (EMP) Enhances the EPO Activity of EMP", *J. Peptide Research* 56: 59-61 (2000).
Laerum, et al., "The Dimer of Hemoregulatory Peptide (HP5B) Stimulates Mouse and Human Myelpoiesis in Vitro", *Exp. Hemat.* 16: 274-280 (1988).
Lalani, et al., "Myostatin and Insulin-Like Growth Factor-I and -II Expression in the Muscle of Rats Exposed to the Microgravity Environment of the NeuroLab Space Shuttle Flight", *J. Endocrin* 167(3): 417-428 (2000).
Lesk, A. M., *Computational Molecular Biology—Sources and Methods for Sequence Analysis*, Oxford University Press (1988) (Table of Contents Provided Only).
Lewin, B., *Genes V.*, Oxford University Press, p. 11 (1994).
Lin, et al., "Myostatin Knockout in Mice Increases Myogenesis and Decreases Adipogenesis" *Biochem Biophys. Res. Commun.* 291(3): 701-706 (2002).
Linse, et al., "A Region of Vitamin K-Dependent Protein S That binds to C4b Binding Protein (C4BP) Identified Using Bacteriophage Peptide Display Libraries", *The Journal Biological Chemistry* 272(23): 14658-14665 (1997).
Linsley, et al., "CTLA-4 is a Second Receptor for the B Cell Activation Antigen B7", *J. Exp. Med.* 174: 561-569 (1991).
Livnah, et al., "Functional Mimicry of a Protein Hormone by a Peptide Agonist: The EPO Receptor Complex at 2.8 Å", *Science* 273: 464-471 (1996).
Loetscher, et al., "Efficacy of a Chimeric TNFR-1gG Fusion Protein to Inhibit TNF Activity in Animal Models of Septic Shock", *Int'l. Congress Series 2*: Elsevier Science Publishers pp. 455-462 (1993).
Lowman, H. B., "Bacteriophage Display and Discovery of Peptide Leads for Drug Development", *Annu. Rev. Biophys. Biomol. Struct.* 26: 401-424 (1997).
Lundergan, et al., "Angiotensin-II Increases Cyctoplasmic Calcium, Cell Number and Total DNA or Human Periodontal Ligamental Cells In Vitro", *J. Periodontal Res.* 34(4): 223-228 (1999).
Mariuzza, Roy A. and Winter, Greg; "Secretion of a Homodimeric V.C.T-cell Receptor-Immunoglobulin Chimeric Protein" *The J. Biol. Chem.* 13: 7310-7316 (1989).
Marshall, K., "Solid Oral Dosage forms" *Modern Pharmaceutics*, edited by G.S. Banker and C.T. Thodes, Chap. *10* (1979).
Martens, et al., "Peptides Which Bind to E-Selectin and Block Neutrophil Adhesion", *The Journal of Biological Chemistry* 270(36): 21129-21136 (1995).
Maurer, et al. "Autodisplay: One-Component System for Efficient Surface Display and Release of Soluble Recombinant Proteins from Escherichia coli", *Journal of Bacteriology* 179(3): 794-780 (1997).
McGregor, Duncan, "Selection of Proteins and Peptides from Libraries Displayed on Filamentous Bacteriophage", *Molecular Biotechnology* 6: 155-162 (1996).
Merrifield, R.B., "Solid-Phase Peptide Synthesis", *Chem. Polypeptides* 335-361 (1973).
Merrifield, R.B., "Solid-Phase Peptide Synthesis. I. The Synthesis of a Tetrapeptide", *J. Am. Chem. Soc.* 85: 2149-2154 (1963).
Miura, Y, Kirito, K. and Komatsu, N., "Regulation of Both Erythroid and Megakaryocytic Differentiation of a Human Leukemia Cell Line, UT-7," *Acta Haematologica*, 99; 180-184 (1998).
Moodie, et al., "The 3Rs of life: Ras, Raf and Growth Regulation", *TIG* 10(2): 44-48 (1994).
Moonga,et al., Effects of Peptide Fragments of Protein Kinase C on Isolated Rat Osteoclasts, *Experimental Physiology* 83: 717-725 (1998).
Morikis, et al., "Solution Structure of Compstatin, a Potent Complement Inhibitor", *Protein Science* 7: 619-627 (1998).

Moult, J., "The Current State of the Art in Protein Structure Prediction", *Curr. Op. in Biotech.* 7(4): 422-427 (1996).

Nachman, et al., "Pseudodipeptide Analogs of the Pyrokinin/PBAN (FXPRLa) Insect Neuropeptide Family Containing Carbocyclic Pro-Mimetic Conformational Components", *Reglatory Peptides* 57: 359-370 (1995).

Naranda, et al., "Activation of Erythropoietin Receptor in the Absence of Hormone by a Peptide that Binds to a Domain Different from the Hormone Binding Site", *Proc. Natl. Acad, Sci. USA* 96: 7569-7574 (1999).

Needleman, et al., "A General Method Applicable to the Search for Similarities in the Amino Acid Sequence of Two Proteins", *J. Mol. Biol.* 48:443-453 (1970).

Newmark, et al., *J. Appl. Biochem* 4: 185-189 (1982).

Nishi, et al., "Tight-Binding Inhibitory Sequences Against $pp60^{c-arc}$ Identified Using a Random 15-Amino-Acid Peptide Library", *FEBS* 399: 237-240 (1996).

Park, et al., "Rationally Designed Anti-HER2/neu Peptide Mimetic Disables $P185^{HER2/neu}$ Tyrosine Kinases In Vitro and In Vivo", *Nat. Biotechnol.* 18: 194-198 (2000).

Pasquaimi, et al., "Órgan Targeting In Vivo Using Phage Display Peptide Libraries", *Nature* 380: 364-366 (1996).

Paukovitis, et al., Structural Investigations on a Peptide Regulating Hemopoiesis In Vitro and In Vivo *Hoppe-Seylers Z. Physio. Chem.* 365: 303-311 (1984).

Pawson, et al., "SH2 and SH3 Domains", *Current Biology*, 3: 434-442 (1993).

Picksley, et al., "Immunochemical Analysis of the Interaction of p53 with MDM2;—Fine Mapping of the MDM2 Binding Site on p53 Using Synthetic Peptides", *Oncogene* 9: 2523-2529 (1994).

Pierce, et al., "Identification of Cyclized Calmodulin Antagonists From a Phage Display Random Peptide Library", *Molec. Diversity* 1:259-265 (1995).

Piette, et al., "Mdm2, Keeping p53 Under Control", *Oncogene* 15: 1001-1010 (1997).

Powis, Garth, "Signaling Targets for Anticancer Drug Development", *TIPS* 12: 188-194 (1991).

RCSB, *Protein Data Book* File 1I1C PDB.

RCSB, *Protein Data Book* File 1IGY PDB.

RCSB, *Protein Data Book* File 1H3T PDB.

Rickles, et al., "Identification of Src, Fyn, Lyn, PI3K and AbI SH3 Domain Ligands Using Phage1 Display Libraries", *The EMBO Journal* 13(23): 5598-5604 (1994).

Roberts & Szostak, "RNA-Peptide Fusions for the In Vitro Selection of Peptides and Proteins", *Proc. Natl. Acad. Sci. USA*, 94: 12297-12303 (1997).

Rodriguez-Viciana, et al., "Phosphatidylinositol-3-OH Kinase as a Direct Target of Ras", *Nature* 370: 527-532 (1994).

Sahu, et al., "Inhibition of Human Complement by a C3-Binding Peptide Isolated from a Phage-Displayed Random Peptide Library", *The Journal of I. Immunology* 157: 884-891 (1996).

Sarmay, et al., "Mapping and Comparison of the Interaction Sites on the Fc Region of IgG Responsible for Triggering Antibody Dependent Cellular Cytotoxicity (ADCC) Through Different Types of Human Fcy Receptor", *Molecular Immunology* 29(5): 633-639 (1993).

Scott, et al., "Searching for Peptide Ligands with an Epitope Library", *Science* 249: 386-390 (1990).

Sharma, et al., "Myostatin, a Transforming Growth Factor-β Superfamily Member, Is Expressed in Heart Muscle and Is Upregulated in Carciomyocytes After Infarct", *J. Cell Physiol.* 180(1): 1-9 (1999).

Shinmei, et al., "Quantitation of Chondroitin 4-Sulfate and Chondroitin 6-Sulfate in Pathologic Joint Fluid", *Athritis Rheum.* 35: 1304-1308 (1992).

Siemion, et al., "The Evidence on the Possible Interleukin-1α Tuftsin Competition", *Archivium Immunologiae et Therapiae Experimentalis* 39: 605-611 (1991).

Silberberg, Anderson's Pathology, Kissane (ed.), II: 1828 (1985).

Sippl, et al., "Threading Thrills and Threats", *Structure* 4(1): 15-19 (1996).

Smith, et al., "Pulmonary Deposition and Clearance of Aerosolized Alpha-1-Proteinase Inhibitor Administered to Dogs and to Sheep" *L. Clin. Invest.* .84: 1145-1146 (α1-proteinase) (1989).

Smith, et al., "Isolation of Glucagon Antagonists by Random Molecular Mutagenesis and Screening", *Mol. Pharmacol*, 43: 741-748 (1993).

Sparks, et al., Distinct Ligand Preferences of Src Homology 3 Domains from Src, Yes, Abl, Cortactin, p53bp2, PLCγ, Crk, and Grb2, *Proc. Natl. Acad. Sci. USA* 93: 1540-1544 (1996).

Sparks, et al., "Identification and Characterization of Src SH3 Ligands from Phage-Displayed Random Peptide Libraries", *The Journal Biological Chemistry* 269(39): 23853-23856 (1994).

Staufer, et al., "Inhibition of Lyn Function in Mast Cell Activation by SH3 Domain Binding Peptides", *Biochemistry* 36: 9388-9394 (1997).

Stewart and Young, *Solid Phase Peptide Synthesis, W.H. Freeman and Co.* (1969) (Table of Contents Provided Only).

Suzuki, and Yoshino, "The Relationship Between Amino Acid Sequences of Sperm-Activiating Peptides and the Taxonomy of Echinoids" Comp. Biochem. Physiol. 102B: 679 (1992).

Tai, Mei-Sheng, et al., "A Bifunctional Fusion Protein Containing Fc-Binding Fragment B of Staphylococcal Protein A Amino Terminal to Antidigoxin Single-Chain $Fv^{t}$", *Biochemistry* 29: 8024-8030 (1990).

Takasaki, et al., "Structure-Based Design and Characterization of Exocyclic Peptidomimetics that Inhibit TNFα Binding to its Receptor", Nature Biotechnology 15: 1266-1270 (1997).

Thonar, et al., "Body Fluid Markers of Cartilage Changes in Osteoarthritis", *Rheumatoid Disease Clinics of North America*, 19: 635-657 (1993).

Van Zee, et al., "Protection Against Lethal *Escherichia coli* Bacteremia in Baboons (*Papio anubis*) by Pretreatment with a 55-kDa TNF Receptor (CD120a)-Ig. Fusion Protein, Ro 45-2081",*J. Immunol.* 156: 2221-2230 (1996).

Von Heinje, G., *Sequence Analysis in Molecular Biology, Academic Press* (1987) (Table of Contents Provided Only).

Wells, et al., "Rapid Evolution of Peptide and Protein Binding Properties In Vivo", *Current Opinion of Biotechnology* 3: 355-362 (1992).

Whitty, et al., "Small Molecule Cytokine Mimetics", *Chemistry & Biology* 6: R107-R118 (1996).

Wieczorek, et al., "The Immunomodulatory Activity of Tetra- and Tripeptides of Tuftsin_Kentsin Group", Peptides 15(2): 215-221 (1994).

Williams, G. T. and Neuberger, M. S.; "Production of Antibody-Tagged Enzymes by Myeloma Cells: Application to DNA Polymerase I Klenow Fragment", *Gene* 43: 319-324 (1986).

Wilson, et al., "Phage Display: Applications, Innovations, and Issues in Phage and Host Biology", *Can. J. Microbiol.* 44: 313-329 (1998).

Wright, et al., "The Importance of Loop Length in the Folding of an Immunoglobulin Domain", *Protein Engin. Design & Selection* 17: 443-453 (2004).

Wrighton, et al., "Small Peptides as Potent Mimetics of the Protein Hormone Erythropoietin", Science 273: 458-463 (1996).

Wrighton, et al., "Increased Potency of an Erythropoietin Peptide Mimetic through Covalent Dimerization", Nature Biotechnology 15: 1261-1265 (1997).

Van Zee, K. et al., "Protection Against Lethal *Escherichia coli* Bacteremia ni Baboons (*Papio anubis*) by Pretreatment with a 55-kDa TNF Receptor (CD120 a)-1g Fusion Protein, Ro 45-2081",*J. Immunol.* 156: 2221-2230 (1996).

Yanofsky, et al., "High Affinity Type I Interleukin 1 Receptor Antagonists Discovered by Screening Recombinant Peptide Libraries", *Proc. Natl. Acad. Sci.* 93: 7381-7386 (1996).

Yarasheski, et al., *J. Nutr. Aging* 6(5):343-8 (2002).

Yen, et al., "Obesity, Diabetes, and Neoplasia in Yellow $A^{vy}$/- Mice: Ectopic Expression of the *Agouti* Gene", *FASEB J.* 8: 479 (1994).

Yoshida, et al., "The Activity of Synthetic Analogs of Serum Thymic Factor (FTS) to Convert Mouse Pre-T Cells into Thy-1 Positive Cells", *Int. I. Immunopharmac* 6(2): 141-146 (1984).

Yu, et al., "Structural Basis for the Binding of Proline-Rich Peptides to SH3 Domains", *Cell.* 76; 933-945 (1994).

Zachwieja, et al., "Plasma Myostatin-Immunoreactive Protein is Increased After Prolonged Bed Rest with Low-Dow T, Administration", *J. Gravit Physiol.* 6(2): 11 (1999).

Zheng, et al., "Administration of Noncytolytic IL-10/Fc in Murine Models of Lipopolsaccharide-Induced Septic Shock and Allogeneic Islet Transplantation", *J. Immunol.* 154: 5590-5600 (1995).

Kuby, Immunology, *Eds.* Freeman and Co., p. 104 (1992).

Jones, T. et al., "The development of a modified human IFN-alpha2b linked to the Fc portion of human IgG1 as a novel potential therapeutic for the treatment of hepatitis C virus infection", Journal of Interferon and Cytokine, 24: 560-572, (2004).

Kumar, M. et al., "Gene therapy of diabetes using a novel GIP-1/IgG1-Fc fusion construct normalizes glucose levels in db/db mice", Gene Therapy, 14: 162-172, (2007).

Zaghouani, H. et al., "Presentation of a viral T cell epitope expressed in the CDR3 region of a self immunoglobulin molecule", Science, 259: 224-227, (1993).

FIG. 2A

1   MDKTHTCPPC PAPELLGGPS VFLFPPKPKD TLMISRTPEV TCVVVDVSHE
51  DPEVKFNWYV DGVEVHNAKT KPREEQYNST YRVVSVLTVL HQDWLNGKEY
101 KCKVSNKALP APIEKTISKA KGQPREPQVY TLPPSRDELT KNQVSLTCLV
151 KGFYPSDIAV EWESNGQPEN NYKTTPPVLD SDGSFFLYSK LTVDKSRWQQ
201 GNVFSCSVMH EALHNHYTQK SLSLSPGK*

FIG. 2B

```
              1                                                 50
huFc-IgA2  (1)  ------------------------------DGKSVTCHVKHYTNP
huFc-IgM   (1)  ---------------------------------------------EGK
huFc-IgG1  (1)  ---------------------------------------------EPK
huFc-nIgG1 (1)  ---------------------------------------------EPK
huFc-IgG3  (1)  ELKTPLGDTTHTCPRCPEPKSCDTPPPCPRCPEPKSCDTPPPCPRCPEPK
huFc-IgG2  (1)  --------------------------------------------------
huFc-IgG4  (1)  --------------------------------------------------
Consensus  (1)                                                 E K 51                                                100
huFc-IgA1  (16)  SQDVTVPCPVPSTPPTPSPSTPPTPSPSCCHPRLSLHRP-ALEDLLLGSE
huFc-IgA2  (16)  SQDVTVPCPVP--PPPP----------CCHPRLSLHRP-ALEDLLLGSE
huFc-IgM    (4)  QVGSGVTTDQVQAEAKESG-----------PTIYKMTSTLTIKEDHRGLT
huFc-IgG1   (4)  SCDKTHTCPPCPAPELLGG------------PSVFLFPPKPKDTLMISRT
huFc-nIgG1  (4)  SCDKTHTCPPCPAPELLGG------------PSVFLFPPKPKDTLMISRT
huFc-IgG3  (51)  SCDTPPPCPRCPAPELLGG------------PSVFLFPPKPKDTLMISRT
huFc-IgG2   (1)  ERKCCVECPPCPAPPVAG-------------PSVFLFPPKPKDTLMISRT
huFc-IgG4   (1)  ESKYGPPCPSCPAPEFLGG------------PSVFLFPPKPKDTLMISRT
Consensus   (4)  S D TVPCP CPAPELLGG            PSVFLFPPKPKDTLMISRT 101                                               150
huFc-IgA1  (65)  ANLTCTLTGLRDAS-GVTFTWTPS--SGKSAVQGPPERDLCGCYSVSSVL
huFc-IgA2  (52)  ANLTCTLTGLRDAS-GATFTWTPS--SGKSAVQGPPERDLCGCYSVSSVL
huFc-IgM   (43)  FQQNASSMCVPDQDTAIRVFAIPP---SFASIFLTKSTKLTCLVTDLTTY
huFc-IgG1  (42)  PEVTCVVVDVSHEDPEVKFNWYVDGVEVHNAKTKPREEQYNSTYRVVSVL
huFc-nIgG1 (42)  PEVTCVVVDVSHEDPEVKFNWYVDGVEVHNAKTKPREEQYNSTYRVVSVL
huFc-IgG3  (89)  PEVTCVVVDVSHEDPEVQFKWYVDGVEVHNAKTKPREEQFNSTFRVVSVL
huFc-IgG2  (38)  PEVTCVVVDVSHEDPEVQFNWYVDGVEVHNAKTKPREEQFNSTFRVVSVL
huFc-IgG4  (39)  PEVTCVVVDVSQEDPEVQFNWYVDGVEVHNAKTKPREEQFNSTYRVVSVL
Consensus  (54)  PEVTCVVVDVSHEDPEV FNWYVDGVEVHNAKTKPREEQFNSTYRVVSVL 151                                               200
huFc-IgA1 (112)  PGCAEPWNHGKTFTCTAAYPESKTPLTATLSKS--GNTFRPEVHLLPPPS
huFc-IgA2  (99)  PGCAQPWNHGETFTCTAAHPELKTPLTANITKS--GNTFRPEVHLLPPPS
huFc-IgM   (90)  DSVTISWNSGERFTCTVIHTDLPSPLKQTISRPAKGVALHRPDVYLLPPAR
huFc-IgG1  (92)  TVLHQDWLNGKEYKCKVSNKALPAPIEKTISKAK-GQPREPQVYTLPP-S
huFc-nIgG1 (92)  TVLHQDWLNGKEYKCKVSNKALPAPIEKTISKAK-GQPREPQVYTLPP-S
huFc-IgG3 (139)  TVLHQDWLNGKEYKCKVSNKALPAPIEKTISKTK-GQPREPQVYTLPP-S
huFc-IgG2  (88)  TVVHQDWLNGKEYKCKVSNKGLPAPIEKTISKTK-GQPREPQVYTLPP-S
huFc-IgG4  (89)  TVLHQDWLNGKEYKCKVSNKGLPSSIEKTISKAK-GQPREPQVYTLPP-S
Consensus (104)  TVLHQDWLNGKEYKCKVSNKALPAPIEKTISKAK GQPREPQVYTLPP S 201                                               250
huFc-IgA1 (160)  EELALNELVTLTCLARGFSPKDVLVRWLQGSQELP REKYLTWASRQEPS Q
huFc-IgA2 (147)  EELALNELVTLTCLARGFSPKDVLVRWLQGSQELP REKYLTWASRQEPS Q
huFc-IgM  (140)  EQLNLRESATITCLVTGFSPADVFVQWMQRGQPLS PEKYVTSAPMPEPQ A
huFc-IgG1 (140)  RDELTKNQVSLTCLVKGFYPSDIAVEWESNGQ--P ENNYKTTPPVLDSD G
huFc-nIgG1(140)  REEMTKNQVSLTCLVKGFYPSDIAVEWESNGQ--P ENNYKTTPPVLDSD G
huFc-IgG3 (187)  REEMTKNQVSLTCLVKGFYPSDIAVEWESSGQ--P ENNYNTTPPMLDSD G
huFc-IgG2 (136)  REEMTKNQVSLTCLVKGFYPSDIAVEWESNGQ--P ENNYKTTPPMLDSD G
huFc-IgG4 (137)  QEEMTKNQVSLTCLVKGFYPSDIAVEWESNGQ--P ENNYKTTPPVLDSD G
Consensus (154)  REEMTKNQVSLTCLVKGFYPSDIAVEWESNGQ  P ENNYKTTPPMLDSD G
```

FIG. 2C

```
              251                                                300
huFc-IgA1 (210) GTTFAMTSILRVAAEDWKKGDTFSCMVGHEALPLAFTQKTIDRLAGKPT
huFc-IgA2 (197) GTTFAMTSILRVAAEDWKKGDTFSCMVGHEALPLAFTQKTIDRLAGKPT
 huFc-IgM (190) PG-RMFAHSILTVSEEEWNTGETYTC-MAHDALPNRVTERTVDKSTGKPT
huFc-IgG1 (188) ---SFFLYSKLTVDKSRWQQGNVFSCSVMHEALHNHYTQKSLSLSPGK--
huFc-nIgG1(188) ---SFFLYSKLTVDKSRWQQGNVFSCSVMHEALHNHYTQKSLSLSPGK--
huFc-IgG3 (235) ---SFFLYSKLTVDKSRWQQGNIFSCSVMHEALHNRETQKSLSLSPGK--
huFc-IgG2 (184) ---SFFLYSKLTVDKSRWQQGNVFSCSVMHEALHNHYTQKSLSLSPGK--
huFc-IgG4 (185) ---SFFLYSRLTVDKSRWQEGNVFSCSVMHEALHNHYTQKSLSLSLGK--
Consensus (204)    SFFLYSKLTVDKSRWQQGNVFSCSVMHEALHNHYTQKSLSLSPGK 301          316
huFc-IgA1 (260) HVNVSVVMAEVDGTCY
huFc-IgA2 (247) HVNVSVVMAEVDGTCY
 huFc-IgM (238) LYNVSLVMSDTAGTCY
huFc-IgG1 (233) ----------------
huFc-nIgG1(233) ----------------
huFc-IgG3 (280) ----------------
huFc-IgG2 (229) ----------------
huFc-IgG4 (230) ----------------
Consensus
```

FIG. 2D

```
                     1                                                50
     Amgen Fc   (1) EGGGGGDKTHTCPPCPAPELLGGPSVFIFPPKPKDTLMISRTPEVTCVVV
1I1A.pdb Fc chain C:(1) -----------------------SVFIFPPKTKDVLTITITPKVTCVVV
     Consensus  (1)                         SVFIFPPK KD  L  IS TP VTCVVV
                     51                                               100
     Amgen Fc  (51) DVSHEDPEVKFNWYVDGVEVHNAKTKPREEQYNSTYRMVSMLTVLHQDWL
1I1A.pdb Fc chain C:(27) DISQNDPEVKFSWFIDVEVHTAQTHAPEKQSNSTLRSVSELPIVHRDWL
     Consensus (27) DIS  DPEVKF WFID VEVH A T   E Q NST R VS L ILH DWL
                     101                                              150
     Amgen Fc  (101) NGKEYKCKVSNKALPAPIEKTISKAKGQPREPQVYTLPPSRDELTKNQVS
1I1A.pdb Fc chain C:(77) NGKTFKCKVNSGAFPAPIEKSISKPEGTPRGPQVYTMAPKDELTQSQVS
     Consensus (77) NGK FKCKV  A PAPIEK ISK  G PR PQVYTL P KDELT  QVS
                     151                                              200
     Amgen Fc  (151) LTCLVKGFYPSDIAVEWESNGQPENNYKTTPPVLDSDGSFFLYSKLTVDK
1I1A.pdb Fc chain C:(127) ITCLVKGFYPPDIYTEWKMNGQPQENYKNTPPTMDTDGSYFLYSKINVKK
     Consensus (127) ITCLVKGFYP DI  EW  NGQP  NYK TPP  L DSDGSFFLYSKL V K
                     201         233
     Amgen Fc  (201) SRWQQGNVFSCSVMHEALHNHYTQKSLSLSPGK
1I1A.pdb Fc chain C:(177) ETWQQGNTFTCSVLHEGLHNHHTEKSLSE----
     Consensus (177)   WQQGN FSCSVLHEALHNHHT KSLS
```

FIG. 3A

1   MDKTHTCPPC PAPELLGGPS VFLFPPKPKD TLMISRTPEV TCVVVDVSHE
51  DPEVKFNWYV DGVEVHNAKT KPREEQYNST YRVVSVLTVL HQDWLNGKEY
101 KCKVSNKALP APIEKTISKA KGQPREPQVY TLPPSRDELG *GLADHGQCIR*
151 WPWMCPPEGW E*GG*TKNQVSL TCLVKGFYPS DIAVEWESNG QPENNYKTTP
201 PVLDSDGSFF LYSKLTVDKS RWQQGNVFSC SVMHEALHNH YTQKSLSLSP
251 GK*

FIG. 3B

1   MDKTHTCPPC PAPELLGGPS VFLFPPKPKD TLMISRTPEV TCVVVDVSHE
51  DPEVKFNWYV DGVEVHNAKT KPREEQYNST YRVVSVLTVL HQDWLNGKEY
101 KCKVSNKALP APIEKTISKA KGQPREPQVY TLPPSRDELT KNQVSLTCLV
151 KGFYPSDIAV EWESNGQPEN NYKTTPPVLD SDGSFFLYSK LTVDKSRWQQ
201 GNVFSCSVMH EALHNHYTQK SLSLSPGK*GG* *GGGA*QLADHG QCIRWPWMCP
251 PEGWE*

FIG. 3C

1   MDKTHTCPPC PAPELLGGPS VFLFPPKPKD TLMISRTPEV TCVVVDVSHE
51  DPEVKFNWYV DGVEVHNAKT KPREEQYNST YRVVSVLTVL HQDWLNGKEY
101 KCKVSNKALP APIEKTISKA KGQPREPQVY TLPPSRDEL *GGGG*TYSCHFGPL
151 TWVCKPQGG*GG* TKNQVSLTCLV KGFYPSDIAV EWESNGQPEN NYKTTPPVLD
201 SDGSFFLYSK LTVDKSRWQQ GNVFSCSVMH EALHNHYTQK SLSLSPGK*

FIG. 3D

```
  1  MDKTHTCPPC PAPELLGGPS VFLFPPKPKD TLMISRTPEV TCVVVDVSHE
 51  DPEVKFNWYV DGVEVHNAKT KPREEQYNST YRVVSVLTVL HQDWLNGKEY
101  KCKVSNKALP APIEKTISKA KGQPREPQVY TLPPSRDELG GIEGPTLRQW
151  LAARAGGTKN QVSLTCLVKG FYPSDIAVEW ESNGQPENNY KTTPPVLDSD
201  GSFFLYSKLT VDKSRWQQGN VFSCSVMHEA LHNHYTQKSL SLSPGK*
```

FIG. 3E

```
  1  MDKTHTCPPC PAPELLGGPS VFLFPPKPKD TLMISRTPEV TCVVVDVSHE
 51  DPEVKFNWYV DGVEVHNAKT KPREEQYNST YRVVSVLTVL HQDWLNGKEY
101  KCKVSNKALP APIEKTISKA KGQPREPQVY TLPPSRDELT KNQVSLTCLV
151  KGFYPSDIAV EWESNGQPEN NYKTTPPVLD SDGSFFLYSK LTVDKSRWQQ
201  GNVFSCSVMH EALHNHYTQK SLSLSPGKGG GGGIEGPTLR QWLAARAGGG
251  GGGGGIEGPT LRQWLAARA
```

M L I S

Fc-loop TN8-19-07
6951

M L I S

Fc-TN8-19-07
6826

1 2 M 3 4

Cell-based luciferase assay

|  | EC$_{50}$(nM) |
|---|---|
| ☐ #6826 | 1.214 |
| ▲ #6951 | 0.834 | concentration: nM (log)

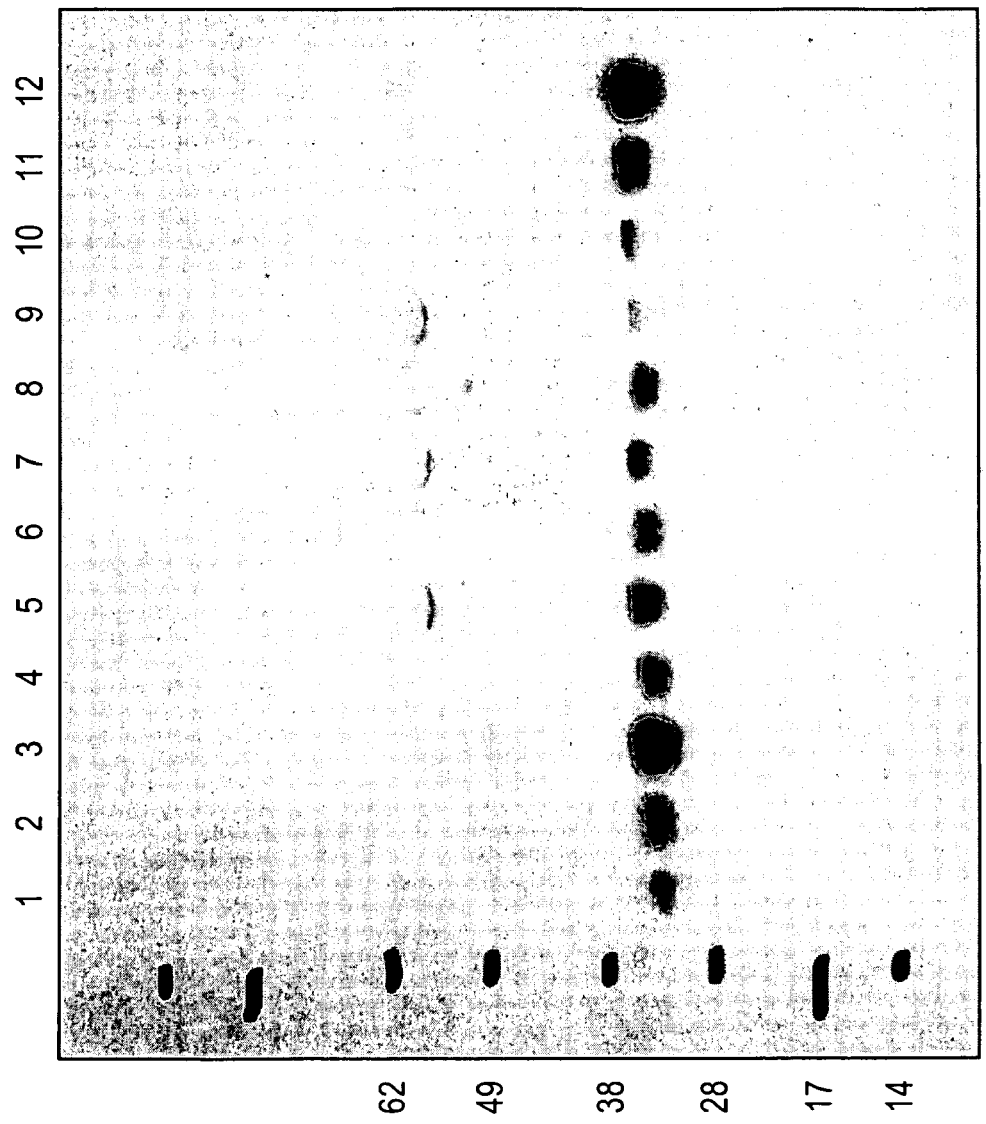

FIG. 10A

```
  1  MDKTHTCPPC PAPELLGGPS VFLFPPKPKD TLMISRTPEV TCVVVDVSHE
 51  DPEVKFNWYV DGVEVHNAKT KPREEQYNST YRVVSVLTVL HQDWLNGKEY
101  KCKVSNKALP APIEKTISKA KGQPREPQVY TLPPSRDELG GQEECEWDPW
151  TCEHMGGTKN QVSLTCLVKG FYPSDIAVEW ESNGQPENNY KTTPPVLDSD
201  GSFFLYSKLT VDKSRWQQGN VFSCSVMHEA LHNHYTQKSL SLSPGK*
```

FIG. 10B

```
  1  MDKTHTCPPC PAPELLGGPS VFLFPPKPKD TLMISRTPEV TCVVVDVSHE
 51  DPEVKFNWYV DGVEVHNAKT KPREEQYNST YRVVSVLTVL HQDWLNGKEY
101  KCKVSNKALP APIEKTISKA KGQPREPQVY TLPPSRDELT KNQVSLTCLV
151  KGFYPSDIAV EWESNGQPEN NYKTTPPVLD SDGSFFLYSK LTVDKSRWQQ
201  GNVFSCSVMH EALHNHYTQK SLSLSPGKGG GGGAQQEECE WDPWTCEHML
251  E*
```

6888  #5564

—□— TN8-Con4
—■— Fc-Loop Ang2

Lys  Insol.  Sol.

6875

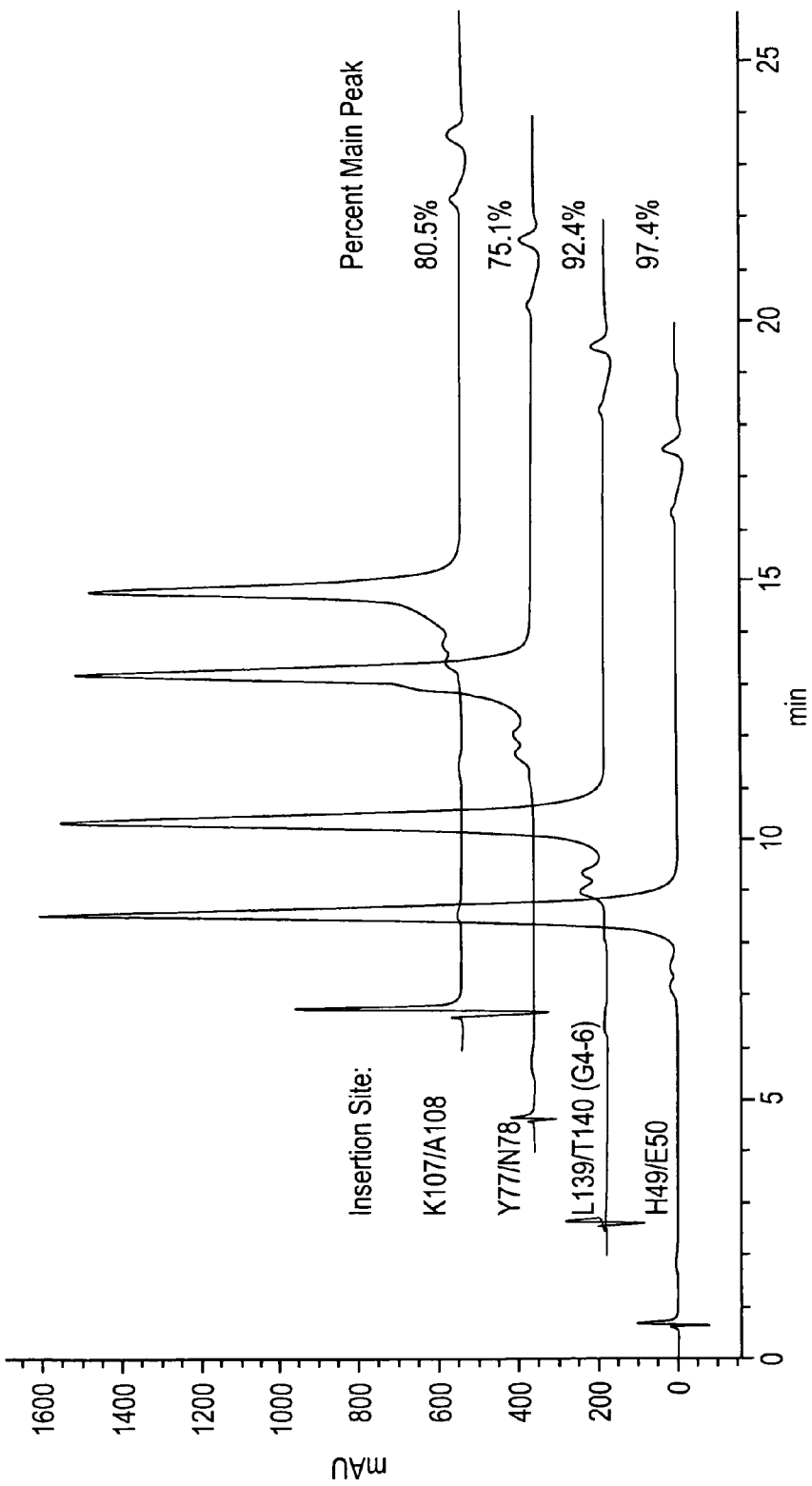

```
                              SEQUENCE LISTING

<160> NUMBER OF SEQ ID NOS: 659

<210> SEQ ID NO 1
<211> LENGTH: 14
<212> TYPE: PRT
<213> ORGANISM: Artificial Sequence
<220> FEATURE:
<223> OTHER INFORMATION: EPO-mimetic peptide
<220> FEATURE:
<221> NAME/KEY: misc_feature
<222> LOCATION: (2)..(2)
<223> OTHER INFORMATION: Xaa = any amino acid
<220> FEATURE:
<221> NAME/KEY: misc_feature
<222> LOCATION: (4)..(5)
<223> OTHER INFORMATION: Xaa = any amino acid
<220> FEATURE:
<221> NAME/KEY: misc_feature
<222> LOCATION: (8)..(8)
<223> OTHER INFORMATION: Xaa = any amino acid
<220> FEATURE:
<221> NAME/KEY: misc_feature
<222> LOCATION: (11)..(11)
<223> OTHER INFORMATION: Xaa = any amino acid
<220> FEATURE:
<221> NAME/KEY: misc_feature
<222> LOCATION: (13)..(13)
<223> OTHER INFORMATION: Xaa = any amino acid

<400> SEQUENCE: 1

Tyr Xaa Cys Xaa Xaa Gly Pro Xaa Thr Trp Xaa Cys Xaa Pro
1               5                   10

<210> SEQ ID NO 2
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 2

Gly Gly Thr Tyr Ser Cys His Phe Gly Pro Leu Thr Trp Val Cys Lys
1               5                   10                  15

Pro Gln Gly Gly
            20
```

```
<210> SEQ ID NO 3
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 3

Gly Gly Asp Tyr His Cys Arg Met Gly Pro Leu Thr Trp Val Cys Lys
1               5                   10                  15

Pro Leu Gly Gly
            20

<210> SEQ ID NO 4
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 4

Gly Gly Val Tyr Ala Cys Arg Met Gly Pro Ile Thr Trp Val Cys Ser
1               5                   10                  15

Pro Leu Gly Gly
            20

<210> SEQ ID NO 5
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 5

Val Gly Asn Tyr Met Cys His Phe Gly Pro Ile Thr Trp Val Cys Arg
1               5                   10                  15

Pro Gly Gly Gly
            20

<210> SEQ ID NO 6
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 6

Gly Gly Leu Tyr Leu Cys Arg Phe Gly Pro Val Thr Trp Asp Cys Gly
1               5                   10                  15

Tyr Lys Gly Gly
            20

<210> SEQ ID NO 7
<211> LENGTH: 23
<212> TYPE: PRT
<213> ORGANISM: Artificial Sequence
<220> FEATURE:
<223> OTHER INFORMATION: EPO-mimetic peptide

<400> SEQUENCE: 7

Gly Gly Thr Tyr Ser Cys His Phe Gly Pro Leu Thr Trp Val Cys Lys
1               5                   10                  15

Pro Gln Gly Gly Ser Ser Lys
            20
```

<210> SEQ ID NO 8
<211> LENGTH: 19
<212> TYPE: PRT
<213> ORGANISM: Artificial Sequence
<220> FEATURE:
<223> OTHER INFORMATION: EPO-mimetic peptide

<400> SEQUENCE: 8

Gly Gly Thr Tyr Ser Cys His Gly Pro Leu Thr Trp Val Cys Lys Pro
1               5                   10                  15

Gln Gly Gly

<210> SEQ ID NO 9
<211> LENGTH: 19
<212> TYPE: PRT
<213> ORGANISM: Artificial Sequence
<220> FEATURE:
<223> OTHER INFORMATION: EPO-mimetic peptide

<400> SEQUENCE: 9

Val Gly Asn Tyr Met Ala His Met Gly Pro Ile Thr Trp Val Cys Arg
1               5                   10                  15

Pro Gly Gly

<210> SEQ ID NO 10
<211> LENGTH: 18
<212> TYPE: PRT
<213> ORGANISM: Artificial Sequence
<220> FEATURE:
<223> OTHER INFORMATION: EPO-mimetic peptide

<400> SEQUENCE: 10

Gly Gly Pro His His Val Tyr Ala Cys Arg Met Gly Pro Leu Thr Trp
1               5                   10                  15

Ile Cys

<210> SEQ ID NO 11
<211> LENGTH: 18
<212> TYPE: PRT
<213> ORGANISM: Artificial Sequence
<220> FEATURE:
<223> OTHER INFORMATION: EPO-mimetic peptide

<400> SEQUENCE: 11

Gly Gly Thr Tyr Ser Cys His Phe Gly Pro Leu Thr Trp Val Cys Lys
1               5                   10                  15

Pro Gln

<210> SEQ ID NO 12
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 12

Gly Gly Leu Tyr Ala Cys His Met Gly Pro Met Thr Trp Val Cys Gln
1               5                   10                  15

Pro Leu Arg Gly
            20

<210> SEQ ID NO 13
<211> LENGTH: 22
<212> TYPE: PRT
<213> ORGANISM: Artificial Sequence
<220> FEATURE:
<223> OTHER INFORMATION: EPO-mimetic peptide

<400> SEQUENCE: 13

Thr Ile Ala Gln Tyr Ile Cys Tyr Met Gly Pro Glu Thr Trp Glu Cys
1               5                   10                  15

Arg Pro Ser Pro Lys Ala
            20

<210> SEQ ID NO 14
<211> LENGTH: 13
<212> TYPE: PRT
<213> ORGANISM: Artificial Sequence
<220> FEATURE:
<223> OTHER INFORMATION: EPO-mimetic peptide

<400> SEQUENCE: 14

Tyr Ser Cys His Phe Gly Pro Leu Thr Trp Val Cys Lys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: EPO-mimetic peptide

<400> SEQUENCE: 15

Tyr Cys His Phe Gly Pro Leu Thr Trp Val Cys
1               5                   10

<210> SEQ ID NO 16
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 16

Gly Gly Leu Tyr Leu Cys Arg Phe Gly Pro Val Thr Trp Asp Cys Gly
1               5                   10                  15

Tyr Lys Gly Gly
            20

<210> SEQ ID NO 17
<211> LENGTH: 20
<212> TYPE: PRT
<213> ORGANISM: Artificial Sequence
<220> FEATURE:
<223> OTHER INFORMATION: EPO-mimetic peptide

<400> SEQUENCE: 17

Gly Gly Thr Tyr Ser Cys His Phe Gly Pro Leu Thr Trp Val Cys Lys
1               5                   10                  15

Pro Gln Gly Gly
            20

<210> SEQ ID NO 18
<211> LENGTH: 20
<212> TYPE: PRT
<213> ORGANISM: Artificial Sequence

```
<220> FEATURE:
<223> OTHER INFORMATION: EPO-mimetic peptide

<400> SEQUENCE: 18

Gly Gly Asp Tyr His Cys Arg Met Gly Pro Leu Thr Trp Val Cys Lys
1               5                   10                  15

Pro Leu Gly Gly
            20

<210> SEQ ID NO 19
<211> LENGTH: 20
<212> TYPE: PRT
<213> ORGANISM: Artificial Sequence
<220> FEATURE:
<223> OTHER INFORMATION: MMP INHIBITOR

<400> SEQUENCE: 19

Val Gly Asn Tyr Met Cys His Phe Gly Pro Ile Thr Trp Val Cys Arg
1               5                   10                  15

Pro Gly Gly Gly
            20

<210> SEQ ID NO 20
<211> LENGTH: 20
<212> TYPE: PRT
<213> ORGANISM: Artificial Sequence
<220> FEATURE:
<223> OTHER INFORMATION: MMP INHIBITOR

<400> SEQUENCE: 20

Gly Gly Val Tyr Ala Cys Arg Met Gly Pro Ile Thr Trp Val Cys Ser
1               5                   10                  15

Pro Leu Gly Gly
            20

<210> SEQ ID NO 21
<211> LENGTH: 19
<212> TYPE: PRT
<213> ORGANISM: Artificial Sequence
<220> FEATURE:
<223> OTHER INFORMATION: EPO-MIMETIC PEPTIDE

<400> SEQUENCE: 21

Val Gly Asn Tyr Met Ala His Met Gly Pro Ile Thr Trp Val Cys Arg
1               5                   10                  15

Pro Gly Gly

<210> SEQ ID NO 22
<211> LENGTH: 18
<212> TYPE: PRT
<213> ORGANISM: Artificial Sequence
<220> FEATURE:
<223> OTHER INFORMATION: EPO-MIMETIC PEPTIDE

<400> SEQUENCE: 22

Gly Gly Thr Tyr Ser Cys His Phe Gly Pro Leu Thr Trp Val Cys Lys
1               5                   10                  15

Pro Gln

<210> SEQ ID NO 23
<211> LENGTH: 20
<212> TYPE: PRT
<213> ORGANISM: Artificial Sequence
```

<220> FEATURE:
<223> OTHER INFORMATION: EPO-MIMETIC PEPTIDE

<400> SEQUENCE: 23

Gly Gly Leu Tyr Ala Cys His Met Gly Pro Met Thr Trp Val Cys Gln
1               5                   10                  15
Pro Leu Arg Gly
            20

<210> SEQ ID NO 24
<211> LENGTH: 22
<212> TYPE: PRT
<213> ORGANISM: Artificial Sequence
<220> FEATURE:
<223> OTHER INFORMATION: EPO-MIMETIC PEPTIDE

<400> SEQUENCE: 24

Thr Ile Ala Gln Tyr Ile Cys Tyr Met Gly Pro Glu Thr Trp Glu Cys
1               5                   10                  15
Arg Pro Ser Pro Lys Ala
            20

<210> SEQ ID NO 25
<211> LENGTH: 13
<212> TYPE: PRT
<213> ORGANISM: Artificial Sequence
<220> FEATURE:
<223> OTHER INFORMATION: EPO-MIMETIC PEPTIDE

<400> SEQUENCE: 25

Tyr Ser Cys His Phe Gly Pro Leu Thr Trp Val Cys Lys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: EPO-MIMETIC PEPTIDE

<400> SEQUENCE: 26

Tyr Cys His Phe Gly Pro Leu Thr Trp Val Cys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: EPO-MIMETIC PEPTIDE

<400> SEQUENCE: 27

Ser Cys His Phe Gly Pro Leu Thr Trp Val Cys Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: TMP

```
<400> SEQUENCE: 28

Ile Glu Gly Pro Thr Leu Arg Gln Trp Leu Ala Ala Arg Ala
1               5                   10

<210> SEQ ID NO 29
<211> LENGTH: 14
<212> TYPE: PRT
<213> ORGANISM: Artificial Sequence
<220> FEATURE:
<223> OTHER INFORMATION: TPO mimetic peptide

<400> SEQUENCE: 29

Ile Glu Gly Pro Thr Leu Arg Gln Trp Leu Ala Ala Lys Ala
1               5                   10

<210> SEQ ID NO 30
<211> LENGTH: 14
<212> TYPE: PRT
<213> ORGANISM: Artificial Sequence
<220> FEATURE:
<223> OTHER INFORMATION: TPO mimetic peptide

<400> SEQUENCE: 30

Ile Glu Gly Pro Thr Leu Arg Glu Trp Leu Ala Ala Arg Ala
1               5                   10

<210> SEQ ID NO 31
<211> LENGTH: 6
<212> TYPE: PRT
<213> ORGANISM: Artificial Sequence
<220> FEATURE:
<223> OTHER INFORMATION: TPO-mimetic peptide

<400> SEQUENCE: 31

Thr Leu Arg Glu Trp Leu
1               5

<210> SEQ ID NO 32
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 32

Gly Arg Val Arg Asp Gln Val Ala Gly Trp
1               5                   10

<210> SEQ ID NO 33
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 33

Gly Arg Val Lys Asp Gln Ile Ala Gln Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: TPO-mimetic peptide
```

```
<400> SEQUENCE: 34

Gly Val Arg Asp Gln Val Ser Trp Ala Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 35

Glu Ser Val Arg Glu Gln Val Met Lys Tyr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 36

Ser Val Arg Ser Gln Ile Ser Ala Ser Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 37

Gly Val Arg Glu Thr Val Tyr Arg His Met
1               5                   10

<210> SEQ ID NO 38
<211> LENGTH: 11
<212> TYPE: PRT
<213> ORGANISM: Artificial Sequence
<220> FEATURE:
<223> OTHER INFORMATION: TPO-mimetic peptide

<400> SEQUENCE: 38

Gly Val Arg Glu Val Ile Val Met His Met Leu
1               5                   10

<210> SEQ ID NO 39
<211> LENGTH: 11
<212> TYPE: PRT
<213> ORGANISM: Artificial Sequence
<220> FEATURE:
<223> OTHER INFORMATION: TPO-mimetic peptide

<400> SEQUENCE: 39

Gly Arg Val Arg Asp Gln Ile Trp Ala Ala Leu
1               5                   10

<210> SEQ ID NO 40
<211> LENGTH: 11
<212> TYPE: PRT
<213> ORGANISM: Artificial Sequence
<220> FEATURE:
<223> OTHER INFORMATION: TPO-mimetic peptide
```

```
<400> SEQUENCE: 40

Ala Gly Val Arg Asp Gln Ile Leu Ile Trp Leu
1               5                   10

<210> SEQ ID NO 41
<211> LENGTH: 11
<212> TYPE: PRT
<213> ORGANISM: Artificial Sequence
<220> FEATURE:
<223> OTHER INFORMATION: TPO-mimetic peptide

<400> SEQUENCE: 41

Gly Arg Val Arg Asp Gln Ile Met Leu Ser Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 42

Cys Thr Leu Arg Gln Trp Leu Gln Gly Cys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 43

Cys Thr Leu Gln Glu Phe Leu Glu Gly Cys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 44

Cys Thr Arg Thr Glu Trp Leu His Gly Cys
1               5                   10

<210> SEQ ID NO 45
<211> LENGTH: 12
<212> TYPE: PRT
<213> ORGANISM: Artificial Sequence
<220> FEATURE:
<223> OTHER INFORMATION: TPO-mimetic peptide

<400> SEQUENCE: 45

Cys Thr Leu Arg Glu Trp Leu His Gly Gly Phe Cys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: TPO-mimetic peptide
```

```
<400> SEQUENCE: 46

Cys Thr Leu Arg Glu Trp Val Phe Ala Gly Leu Cys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: TPO-mimetic peptide

<400> SEQUENCE: 47

Cys Thr Leu Arg Gln Trp Leu Ile Leu Leu Gly Met Cys
1               5                   10

<210> SEQ ID NO 48
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 48

Cys Thr Leu Ala Glu Phe Leu Ala Ser Gly Val Glu Gln Cys
1               5                   10

<210> SEQ ID NO 49
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 49

Cys Ser Leu Gln Glu Phe Leu Ser His Gly Gly Tyr Val Cys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 50

Cys Thr Leu Arg Glu Phe Leu Asp Pro Thr Thr Ala Val Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 51

Cys Thr Leu Lys Glu Trp Leu Val Ser His Glu Val Trp Cys
1               5                   10

<210> SEQ ID NO 52
<211> LENGTH: 10
<212> TYPE: PRT
<213> ORGANISM: Artificial Sequence
<220> FEATURE:
<223> OTHER INFORMATION: TPO-mimetic peptide
```

```
<400> SEQUENCE: 52

Arg Glu Gly Pro Thr Leu Arg Gln Trp Met
1               5                   10

<210> SEQ ID NO 53
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 53

Glu Gly Pro Thr Leu Arg Gln Trp Leu Ala
1               5                   10

<210> SEQ ID NO 54
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 54

Glu Arg Gly Pro Phe Trp Ala Lys Ala Cys
1               5                   10

<210> SEQ ID NO 55
<211> LENGTH: 10
<212> TYPE: PRT
<213> ORGANISM: Artificial Sequence
<220> FEATURE:
<223> OTHER INFORMATION: TPO-mimetic peptide

<400> SEQUENCE: 55

Arg Glu Gly Pro Arg Cys Val Met Trp Met
1               5                   10

<210> SEQ ID NO 56
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 56

Cys Gly Thr Glu Gly Pro Thr Leu Ser Thr Trp Leu Asp Cys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 57

Cys Glu Gln Asp Gly Pro Thr Leu Leu Glu Trp Leu Lys Cys
1               5                   10

<210> SEQ ID NO 58
<211> LENGTH: 14
<212> TYPE: PRT
<213> ORGANISM: Artificial Sequence
<220> FEATURE:
<223> OTHER INFORMATION: TPO-mimetic peptide
```

```
<400> SEQUENCE: 58

Cys Glu Leu Val Gly Pro Ser Leu Met Ser Trp Leu Thr Cys
1               5                   10

<210> SEQ ID NO 59
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 59

Cys Leu Thr Gly Pro Phe Val Thr Gln Trp Leu Tyr Glu Cys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 60

Cys Arg Ala Gly Pro Thr Leu Leu Glu Trp Leu Thr Leu Cys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: TPO-mimetic peptide

<400> SEQUENCE: 61

Cys Ala Asp Gly Pro Thr Leu Arg Glu Trp Ile Ser Phe Cys
1               5                   10

<210> SEQ ID NO 62
<211> LENGTH: 16
<212> TYPE: PRT
<213> ORGANISM: Artificial Sequence
<220> FEATURE:
<223> OTHER INFORMATION: TPO-mimetic peptide

<400> SEQUENCE: 62

Gly Gly Cys Thr Leu Arg Glu Trp Leu His Gly Gly Phe Cys Gly Gly
1               5                   10                  15

<210> SEQ ID NO 63
<211> LENGTH: 18
<212> TYPE: PRT
<213> ORGANISM: Artificial Sequence
<220> FEATURE:
<223> OTHER INFORMATION: TPO-mimetic peptide

<400> SEQUENCE: 63

Gly Gly Cys Ala Asp Gly Pro Thr Leu Arg Glu Trp Ile Ser Phe Cys
1               5                   10                  15

Gly Gly

<210> SEQ ID NO 64
<211> LENGTH: 19
<212> TYPE: PRT
<213> ORGANISM: Artificial Sequence
<220> FEATURE:
<223> OTHER INFORMATION: TPO-mimetic peptide
```

-continued

```
<400> SEQUENCE: 64

Gly Asn Ala Asp Gly Pro Thr Leu Arg Gln Trp Leu Glu Gly Arg Arg
1               5                   10                  15

Pro Lys Asn

<210> SEQ ID NO 65
<211> LENGTH: 19
<212> TYPE: PRT
<213> ORGANISM: Artificial Sequence
<220> FEATURE:
<223> OTHER INFORMATION: TPO-mimetic peptide

<400> SEQUENCE: 65

Leu Ala Ile Glu Gly Pro Thr Leu Arg Gln Trp Leu His Gly Asn Gly
1               5                   10                  15

Arg Asp Thr

<210> SEQ ID NO 66
<211> LENGTH: 19
<212> TYPE: PRT
<213> ORGANISM: Artificial Sequence
<220> FEATURE:
<223> OTHER INFORMATION: TPO-mimetic peptide

<400> SEQUENCE: 66

His Gly Arg Val Gly Pro Thr Leu Arg Glu Trp Lys Thr Gln Val Ala
1               5                   10                  15

Thr Lys Lys

<210> SEQ ID NO 67
<211> LENGTH: 18
<212> TYPE: PRT
<213> ORGANISM: Artificial Sequence
<220> FEATURE:
<223> OTHER INFORMATION: TPO-mimetic peptide

<400> SEQUENCE: 67

Thr Ile Lys Gly Pro Thr Leu Arg Gln Trp Leu Lys Ser Arg Glu His
1               5                   10                  15

Thr Ser

<210> SEQ ID NO 68
<211> LENGTH: 18
<212> TYPE: PRT
<213> ORGANISM: Artificial Sequence
<220> FEATURE:
<223> OTHER INFORMATION: TPO-mimetic peptide

<400> SEQUENCE: 68

Ile Ser Asp Gly Pro Thr Leu Lys Glu Trp Leu Ser Val Thr Arg Gly
1               5                   10                  15

Ala Ser

<210> SEQ ID NO 69
<211> LENGTH: 18
<212> TYPE: PRT
<213> ORGANISM: Artificial Sequencd
<220> FEATURE:
<223> OTHER INFORMATION: TPO-mimetic peptide
```

<400> SEQUENCE: 69

Ser Ile Glu Gly Pro Thr Leu Arg Glu Trp Leu Thr Ser Arg Thr Pro
1               5                   10                  15

His Ser

<210> SEQ ID NO 70
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 70

Gly Ala Arg Glu Gly Pro Thr Leu Arg Gln Trp Leu Glu Trp Val Arg
1               5                   10                  15

Val Gly

<210> SEQ ID NO 71
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 71

Arg Asp Leu Asp Gly Pro Thr Leu Arg Gln Trp Leu Pro Leu Pro Ser
1               5                   10                  15

Val Gln

<210> SEQ ID NO 72
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 72

Ala Leu Arg Asp Gly Pro Thr Leu Lys Gln Trp Leu Glu Tyr Arg Arg
1               5                   10                  15

Gln Ala

<210> SEQ ID NO 73
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 73

Ala Arg Gln Glu Gly Pro Thr Leu Lys Glu Trp Leu Phe Trp Val Arg
1               5                   10                  15

Met Gly

<210> SEQ ID NO 74
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 74

Glu Ala Leu Leu Gly Pro Thr Leu Arg Glu Trp Leu Ala Trp Arg Arg
1               5                   10                  15

Ala Gln

<210> SEQ ID NO 75
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 75

Met Ala Arg Asp Gly Pro Thr Leu Arg Glu Trp Leu Arg Thr Tyr Arg
1               5                   10                  15

Met Met

<210> SEQ ID NO 76
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 76

Trp Met Pro Glu Gly Pro Thr Leu Lys Gln Trp Leu Phe His Gly Arg
1               5                   10                  15

Gly Gln

<210> SEQ ID NO 77
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 77

His Ile Arg Glu Gly Pro Thr Leu Arg Gln Trp Leu Val Ala Leu Arg
1               5                   10                  15

Met Val

<210> SEQ ID NO 78
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 78

Gln Leu Gly His Gly Pro Thr Leu Arg Gln Trp Leu Ser Trp Tyr Arg
1               5                   10                  15

Gly Met

<210> SEQ ID NO 79
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 79

Glu Leu Arg Gln Gly Pro Thr Leu His Glu Trp Leu Gln His Leu Ala
1               5                   10                  15

Ser Lys

<210> SEQ ID NO 80
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 80

Val Gly Ile Glu Gly Pro Thr Leu Arg Gln Trp Leu Ala Gln Arg Leu
1               5                   10                  15

Asn Pro

<210> SEQ ID NO 81
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 81

Trp Ser Arg Asp Gly Pro Thr Leu Arg Glu Trp Leu Ala Trp Arg Ala
1               5                   10                  15

Val Gly

<210> SEQ ID NO 82
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 82

Ala Val Pro Gln Gly Pro Thr Leu Lys Gln Trp Leu Leu Trp Arg Arg
1               5                   10                  15

Cys Ala

<210> SEQ ID NO 83
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 83

Arg Ile Arg Glu Gly Pro Thr Leu Lys Glu Trp Leu Ala Gln Arg Arg
1               5                   10                  15

Gly Phe

<210> SEQ ID NO 84
<211> LENGTH: 18
<212> TYPE: PRT
<213> ORGANISM: Artificial Sequence
<220> FEATURE:
<223> OTHER INFORMATION: Synthesized Peptide Sequence -continued

```
<400> SEQUENCE: 84

Arg Phe Ala Glu Gly Pro Thr Leu Arg Glu Trp Leu Glu Gln Arg Lys
1               5                   10                  15

Leu Val

<210> SEQ ID NO 85
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 85

Asp Arg Phe Gln Gly Pro Thr Leu Arg Glu Trp Leu Ala Ala Ile Arg
1               5                   10                  15

Ser Val

<210> SEQ ID NO 86
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 86

Ala Gly Arg Glu Gly Pro Thr Leu Arg Glu Trp Leu Asn Met Arg Val
1               5                   10                  15

Trp Gln

<210> SEQ ID NO 87
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 87

Ala Leu Gln Glu Gly Pro Thr Leu Arg Gln Trp Leu Gly Trp Gly Gln
1               5                   10                  15

Trp Gly

<210> SEQ ID NO 88
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 88

Tyr Cys Asp Glu Gly Pro Thr Leu Lys Gln Trp Leu Val Cys Leu Gly
1               5                   10                  15

Leu Gln

<210> SEQ ID NO 89
<211> LENGTH: 18
<212> TYPE: PRT
<213> ORGANISM: Artificial Sequence
<220> FEATURE:
<223> OTHER INFORMATION: Synthesized Peptide Sequence
```

-continued

```
<400> SEQUENCE: 89

Trp Cys Lys Glu Gly Pro Thr Leu Arg Glu Trp Leu Arg Trp Gly Phe
1               5                   10                  15

Leu Cys

<210> SEQ ID NO 90
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 90

Cys Ser Ser Gly Gly Pro Thr Leu Arg Glu Trp Leu Gln Cys Arg Arg
1               5                   10                  15

Met Gln

<210> SEQ ID NO 91
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 91

Cys Ser Trp Gly Gly Pro Thr Leu Lys Gln Trp Leu Gln Cys Val Arg
1               5                   10                  15

Ala Lys

<210> SEQ ID NO 92
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 92

Cys Gln Leu Gly Gly Pro Thr Leu Arg Glu Trp Leu Ala Cys Arg Leu
1               5                   10                  15

Gly Ala

<210> SEQ ID NO 93
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 93

Cys Trp Glu Gly Gly Pro Thr Leu Lys Glu Trp Leu Gln Cys Leu Val
1               5                   10                  15

Glu Arg

<210> SEQ ID NO 94
<211> LENGTH: 18
<212> TYPE: PRT
<213> ORGANISM: Artificial Sequence
<220> FEATURE:
<223> OTHER INFORMATION: Synthesized Peptide Sequence
```

<400> SEQUENCE: 94

Cys Arg Gly Gly Gly Pro Thr Leu His Gln Trp Leu Ser Cys Phe Arg
1               5                   10                  15

Trp Gln

<210> SEQ ID NO 95
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 95

Cys Arg Asp Gly Gly Pro Thr Leu Arg Gln Trp Leu Ala Cys Leu Gln
1               5                   10                  15

Gln Lys

<210> SEQ ID NO 96
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 96

Glu Leu Arg Ser Gly Pro Thr Leu Lys Glu Trp Leu Val Trp Arg Leu
1               5                   10                  15

Ala Gln

<210> SEQ ID NO 97
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 97

Gly Cys Arg Ser Gly Pro Thr Leu Arg Glu Trp Leu Ala Cys Arg Glu
1               5                   10                  15

Val Gln

<210> SEQ ID NO 98
<211> LENGTH: 18
<212> TYPE: PRT
<213> ORGANISM: Artificial Sequence
<220> FEATURE:
<223> OTHER INFORMATION: Synthesized Peptide Sequence

<400> SEQUENCE: 98

Thr Cys Glu Gln Gly Pro Thr Leu Arg Gln Trp Leu Leu Cys Arg Gln
1               5                   10                  15

Gly Arg

<210> SEQ ID NO 99
<211> LENGTH: 5
<212> TYPE: PRT
<213> ORGANISM: Artificial Sequence
<220> FEATURE:
<223> OTHER INFORMATION: Polypeptide capable of binding to Ang-2

```
<400> SEQUENCE: 99

Trp Asp Pro Trp Thr
1               5

<210> SEQ ID NO 100
<211> LENGTH: 6
<212> TYPE: PRT
<213> ORGANISM: Artificial Sequence
<220> FEATURE:
<223> OTHER INFORMATION: Polypeptide capable of binding to Ang-2

<400> SEQUENCE: 100

Trp Asp Pro Trp Thr Cys
1               5

<210> SEQ ID NO 101
<211> LENGTH: 6
<212> TYPE: PRT
<213> ORGANISM: Artificial Sequence
<220> FEATURE:
<223> OTHER INFORMATION: Polypeptide capable of binding to Ang-2

<400> SEQUENCE: 101

Trp Asp Pro Trp Thr Cys
1               5

<210> SEQ ID NO 102
<211> LENGTH: 7
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (2)..(2)
<223> OTHER INFORMATION: Xaa is an acidic or neutral polar amino acid
      residue

<400> SEQUENCE: 102

Cys Xaa Trp Asp Pro Trp Thr
1               5

<210> SEQ ID NO 103
<211> LENGTH: 8
<212> TYPE: PRT
<213> ORGANISM: Artificial Sequence
<220> FEATURE:
<223> OTHER INFORMATION: Polypeptide capable of binding to Ang-2
<220> FEATURE:
<221> NAME/KEY: misc_feature
<222> LOCATION: (2)..(2)
<223> OTHER INFORMATION: Xaa can be any naturally occurring amino acid

<400> SEQUENCE: 103

Cys Xaa Trp Asp Pro Trp Thr Cys
1               5

<210> SEQ ID NO 104
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 104

Pro Ile Arg Gln Glu Glu Cys Asp Trp Asp Pro Trp Thr Cys Glu His
1               5                   10                  15

Met Trp Glu Val
            20

<210> SEQ ID NO 105
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 105

Thr Asn Ile Gln Glu Glu Cys Glu Trp Asp Pro Trp Thr Cys Asp His
1               5                   10                  15

Met Pro Gly Lys
            20

<210> SEQ ID NO 106
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 106

Trp Tyr Glu Gln Asp Ala Cys Glu Trp Asp Pro Trp Thr Cys Glu His
1               5                   10                  15

Met Ala Glu Val
            20

<210> SEQ ID NO 107
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 107

Asn Arg Leu Gln Glu Val Cys Glu Trp Asp Pro Trp Thr Cys Glu His
1               5                   10                  15

Met Glu Asn Val
            20

<210> SEQ ID NO 108
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 108

Ala Ala Thr Gln Glu Glu Cys Glu Trp Asp Pro Trp Thr Cys Glu His
1               5                   10                  15

Met Pro Arg Ser
            20

<210> SEQ ID NO 109
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 109

Leu Arg His Gln Glu Gly Cys Glu Trp Asp Pro Trp Thr Cys Glu His
1               5                   10                  15

Met Phe Asp Trp
            20

<210> SEQ ID NO 110
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 110

Val Pro Arg Gln Lys Asp Cys Glu Trp Asp Pro Trp Thr Cys Glu His
1               5                   10                  15

Met Tyr Val Gly
            20

<210> SEQ ID NO 111
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 111

Ser Ile Ser His Glu Glu Cys Glu Trp Asp Pro Trp Thr Cys Glu His
1               5                   10                  15

Met Gln Val Gly
            20

<210> SEQ ID NO 112
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 112

Trp Ala Ala Gln Glu Glu Cys Glu Trp Asp Pro Trp Thr Cys Glu His
1               5                   10                  15

Met Gly Arg Met
            20

<210> SEQ ID NO 113
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 113

Thr Trp Pro Gln Asp Lys Cys Glu Trp Asp Pro Trp Thr Cys Glu His
1               5                   10                  15

Met Gly Ser Thr
            20

<210> SEQ ID NO 114
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 114

Gly His Ser Gln Glu Glu Cys Gly Trp Asp Pro Trp Thr Cys Glu His
1               5                   10                  15

Met Gly Thr Ser
            20

<210> SEQ ID NO 115
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 115

Gln His Trp Gln Glu Glu Cys Glu Trp Asp Pro Trp Thr Cys Asp His
1               5                   10                  15

Met Pro Ser Lys
            20

<210> SEQ ID NO 116
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 116

Asn Val Arg Gln Glu Lys Cys Glu Trp Asp Pro Trp Thr Cys Glu His
1               5                   10                  15

Met Pro Val Arg
            20

<210> SEQ ID NO 117
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 117

Lys Ser Gly Gln Val Glu Cys Asn Trp Asp Pro Trp Thr Cys Glu His
1               5                   10                  15

Met Pro Arg Asn
            20

<210> SEQ ID NO 118
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 118

Val Lys Thr Gln Glu His Cys Asp Trp Asp Pro Trp Thr Cys Glu His
1               5                   10                  15

Met Arg Glu Trp
            20

<210> SEQ ID NO 119
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 119

Ala Trp Gly Gln Glu Gly Cys Asp Trp Asp Pro Trp Thr Cys Glu His
1               5                   10                  15

Met Leu Pro Met
            20

<210> SEQ ID NO 120
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 120

Pro Val Asn Gln Glu Asp Cys Glu Trp Asp Pro Trp Thr Cys Glu His
1               5                   10                  15

Met Pro Pro Met
            20

<210> SEQ ID NO 121
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 121

Arg Ala Pro Gln Glu Asp Cys Glu Trp Asp Pro Trp Thr Cys Ala His
1               5                   10                  15

Met Asp Ile Lys
            20

<210> SEQ ID NO 122
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 122

His Gly Gln Asn Met Glu Cys Glu Trp Asp Pro Trp Thr Cys Glu His
1               5                   10                  15

Met Phe Arg Tyr
            20

<210> SEQ ID NO 123
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 123

Pro Arg Leu Gln Glu Glu Cys Val Trp Asp Pro Trp Thr Cys Glu His
1               5                   10                  15

Met Pro Leu Arg
            20

<210> SEQ ID NO 124
<211> LENGTH: 20
<212> TYPE: PRT
<213> ORGANISM: Artificial Sequence
<220> FEATURE:
<223> OTHER INFORMATION: Polypeptide capable of binding to Ang-2
```

-continued

```
<400> SEQUENCE: 124

Arg Thr Thr Gln Glu Lys Cys Glu Trp Asp Pro Trp Thr Cys Glu His
1               5                   10                  15

Met Glu Ser Gln
            20

<210> SEQ ID NO 125
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 125

Gln Thr Ser Gln Glu Asp Cys Val Trp Asp Pro Trp Thr Cys Asp His
1               5                   10                  15

Met Val Ser Ser
            20

<210> SEQ ID NO 126
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 126

Gln Val Ile Gly Arg Pro Cys Glu Trp Asp Pro Trp Thr Cys Glu His
1               5                   10                  15

Leu Glu Gly Leu
            20

<210> SEQ ID NO 127
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 127

Trp Ala Gln Gln Glu Glu Cys Ala Trp Asp Pro Trp Thr Cys Asp His
1               5                   10                  15

Met Val Gly Leu
            20

<210> SEQ ID NO 128
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 128

Leu Pro Gly Gln Glu Asp Cys Glu Trp Asp Pro Trp Thr Cys Glu His
1               5                   10                  15

Met Val Arg Ser
            20

<210> SEQ ID NO 129
<211> LENGTH: 20
<212> TYPE: PRT
<213> ORGANISM: Artificial Sequence
<220> FEATURE:
<223> OTHER INFORMATION: Polypeptide capable of binding to Ang-2
```

-continued

```
<400> SEQUENCE: 129

Pro Met Asn Gln Val Glu Cys Asp Trp Asp Pro Trp Thr Cys Glu His
1               5                   10                  15

Met Pro Arg Ser
            20

<210> SEQ ID NO 130
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 130

Phe Gly Trp Ser His Gly Cys Glu Trp Asp Pro Trp Thr Cys Glu His
1               5                   10                  15

Met Gly Ser Thr
            20

<210> SEQ ID NO 131
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 131

Lys Ser Thr Gln Asp Asp Cys Asp Trp Asp Pro Trp Thr Cys Glu His
1               5                   10                  15

Met Val Gly Pro
            20

<210> SEQ ID NO 132
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 132

Gly Pro Arg Ile Ser Thr Cys Gln Trp Asp Pro Trp Thr Cys Glu His
1               5                   10                  15

Met Asp Gln Leu
            20

<210> SEQ ID NO 133
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 133

Ser Thr Ile Gly Asp Met Cys Glu Trp Asp Pro Trp Thr Cys Ala His
1               5                   10                  15

Met Gln Val Asp
            20

<210> SEQ ID NO 134
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 134

Val Leu Gly Gly Gln Gly Cys Glu Trp Asp Pro Trp Thr Cys Arg Leu
1               5                   10                  15

Leu Gln Gly Trp
            20

<210> SEQ ID NO 135
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 135

Val Leu Gly Gly Gln Gly Cys Gln Trp Asp Pro Trp Thr Cys Ser His
1               5                   10                  15

Leu Glu Asp Gly
            20

<210> SEQ ID NO 136
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 136

Thr Thr Ile Gly Ser Met Cys Glu Trp Asp Pro Trp Thr Cys Ala His
1               5                   10                  15

Met Gln Gly Gly
            20

<210> SEQ ID NO 137
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 137

Thr Lys Gly Lys Ser Val Cys Gln Trp Asp Pro Trp Thr Cys Ser His
1               5                   10                  15

Met Gln Ser Gly
            20

<210> SEQ ID NO 138
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 138

Thr Thr Ile Gly Ser Met Cys Gln Trp Asp Pro Trp Thr Cys Ala His
1               5                   10                  15

Met Gln Gly Gly
            20

<210> SEQ ID NO 139
<211> LENGTH: 20
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 139

Trp Val Asn Glu Val Val Cys Glu Trp Asp Pro Trp Thr Cys Asn His
1               5                   10                  15

Trp Asp Thr Pro
            20

<210> SEQ ID NO 140
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 140

Val Val Gln Val Gly Met Cys Gln Trp Asp Pro Trp Thr Cys Lys His
1               5                   10                  15

Met Arg Leu Gln
            20

<210> SEQ ID NO 141
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 141

Ala Val Gly Ser Gln Thr Cys Glu Trp Asp Pro Trp Thr Cys Ala His
1               5                   10                  15

Leu Val Glu Val
            20

<210> SEQ ID NO 142
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 142

Gln Gly Met Lys Met Phe Cys Glu Trp Asp Pro Trp Thr Cys Ala His
1               5                   10                  15

Ile Val Tyr Arg
            20

<210> SEQ ID NO 143
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 143

Thr Thr Ile Gly Ser Met Cys Gln Trp Asp Pro Trp Thr Cys Glu His
1               5                   10                  15

Met Gln Gly Gly
            20

<210> SEQ ID NO 144
<211> LENGTH: 20
<212> TYPE: PRT
<213> ORGANISM: Artificial Sequence
<220> FEATURE:
<223> OTHER INFORMATION: Polypeptide capable of binding to Ang-2
```

-continued

```
<400> SEQUENCE: 144

Thr Ser Gln Arg Val Gly Cys Glu Trp Asp Pro Trp Thr Cys Gln His
1               5                   10                  15

Leu Thr Tyr Thr
            20

<210> SEQ ID NO 145
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 145

Gln Trp Ser Trp Pro Pro Cys Glu Trp Asp Pro Trp Thr Cys Gln Thr
1               5                   10                  15

Val Trp Pro Ser
            20

<210> SEQ ID NO 146
<211> LENGTH: 20
<212> TYPE: PRT
<213> ORGANISM: Artificial Sequence
<220> FEATURE:
<223> OTHER INFORMATION: Ang-2 binding Polypeptide

<400> SEQUENCE: 146

Gly Thr Ser Pro Ser Phe Cys Gln Trp Asp Pro Trp Thr Cys Ser His
1               5                   10                  15

Met Val Gln Gly
            20

<210> SEQ ID NO 147
<211> LENGTH: 14
<212> TYPE: PRT
<213> ORGANISM: Artificial Sequence
<220> FEATURE:
<223> OTHER INFORMATION: Polypeptide capable of binding to Ang-2

<400> SEQUENCE: 147

Gln Glu Glu Cys Glu Trp Asp Pro Trp Thr Cys Glu His Met
1               5                   10

<210> SEQ ID NO 148
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 148

Gln Asn Tyr Lys Pro Leu Asp Glu Leu Asp Ala Thr Leu Tyr Glu His
1               5                   10                  15

Phe Ile Phe His Tyr Thr
            20

<210> SEQ ID NO 149
<211> LENGTH: 22
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 149

Leu Asn Phe Thr Pro Leu Asp Glu Leu Glu Gln Thr Leu Tyr Glu Gln
1               5                   10                  15

Trp Thr Leu Gln Gln Ser
            20

<210> SEQ ID NO 150
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 150

Thr Lys Phe Asn Pro Leu Asp Glu Leu Glu Gln Thr Leu Tyr Glu Gln
1               5                   10                  15

Trp Thr Leu Gln His Gln
            20

<210> SEQ ID NO 151
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 151

Val Lys Phe Lys Pro Leu Asp Ala Leu Glu Gln Thr Leu Tyr Glu His
1               5                   10                  15

Trp Met Phe Gln Gln Ala
            20

<210> SEQ ID NO 152
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 152

Val Lys Tyr Lys Pro Leu Asp Glu Leu Asp Glu Ile Leu Tyr Glu Gln
1               5                   10                  15

Gln Thr Phe Gln Glu Arg
            20

<210> SEQ ID NO 153
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 153

Thr Asn Phe Met Pro Met Asp Asp Leu Glu Gln Arg Leu Tyr Glu Gln
1               5                   10                  15

Phe Ile Leu Gln Gln Gly
            20

<210> SEQ ID NO 154
<211> LENGTH: 22
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 154

Ser Lys Phe Lys Pro Leu Asp Glu Leu Glu Gln Thr Leu Tyr Glu Gln
1               5                   10                  15

Trp Thr Leu Gln His Ala
            20

<210> SEQ ID NO 155
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 155

Gln Lys Phe Gln Pro Leu Asp Glu Leu Glu Gln Thr Leu Tyr Glu Gln
1               5                   10                  15

Phe Met Leu Gln Gln Ala
            20

<210> SEQ ID NO 156
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 156

Gln Asn Phe Lys Pro Met Asp Glu Leu Glu Asp Thr Leu Tyr Lys Gln
1               5                   10                  15

Phe Leu Phe Gln His Ser
            20

<210> SEQ ID NO 157
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 157

Tyr Lys Phe Thr Pro Leu Asp Asp Leu Glu Gln Thr Leu Tyr Glu Gln
1               5                   10                  15

Trp Thr Leu Gln His Val
            20

<210> SEQ ID NO 158
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 158

Gln Glu Tyr Glu Pro Leu Asp Glu Leu Asp Glu Thr Leu Tyr Asn Gln
1               5                   10                  15

Trp Met Phe His Gln Arg
            20

<210> SEQ ID NO 159
<211> LENGTH: 22
<212> TYPE: PRT
<213> ORGANISM: Artificial Sequence
<220> FEATURE:
<223> OTHER INFORMATION: Polypeptide capable of binding to Ang-2
```

-continued

```
<400> SEQUENCE: 159

Ser Asn Phe Met Pro Leu Asp Glu Leu Glu Gln Thr Leu Tyr Glu Gln
1               5                   10                  15

Phe Met Leu Gln His Gln
            20

<210> SEQ ID NO 160
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 160

Gln Lys Tyr Gln Pro Leu Asp Glu Leu Asp Lys Thr Leu Tyr Asp Gln
1               5                   10                  15

Phe Met Leu Gln Gln Gly
            20

<210> SEQ ID NO 161
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 161

Gln Lys Phe Gln Pro Leu Asp Glu Leu Glu Glu Thr Leu Tyr Lys Gln
1               5                   10                  15

Trp Thr Leu Gln Gln Arg
            20

<210> SEQ ID NO 162
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 162

Val Lys Tyr Lys Pro Leu Asp Glu Leu Asp Glu Trp Leu Tyr His Gln
1               5                   10                  15

Phe Thr Leu His His Gln
            20

<210> SEQ ID NO 163
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 163

Gln Lys Phe Met Pro Leu Asp Glu Leu Asp Glu Ile Leu Tyr Glu Gln
1               5                   10                  15

Phe Met Phe Gln Gln Ser
            20

<210> SEQ ID NO 164
<211> LENGTH: 22
<212> TYPE: PRT
<213> ORGANISM: Artificial Sequence
<220> FEATURE:
<223> OTHER INFORMATION: Polypeptide capable of binding to Ang-2
```

-continued

```
<400> SEQUENCE: 164

Gln Thr Phe Gln Pro Leu Asp Asp Leu Glu Glu Tyr Leu Tyr Glu Gln
1               5                   10                  15

Trp Ile Arg Arg Tyr His
            20

<210> SEQ ID NO 165
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 165

Glu Asp Tyr Met Pro Leu Asp Ala Leu Asp Ala Gln Leu Tyr Glu Gln
1               5                   10                  15

Phe Ile Leu Leu His Gly
            20

<210> SEQ ID NO 166
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 166

His Thr Phe Gln Pro Leu Asp Glu Leu Glu Glu Thr Leu Tyr Tyr Gln
1               5                   10                  15

Trp Leu Tyr Asp Gln Leu
            20

<210> SEQ ID NO 167
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 167

Tyr Lys Phe Asn Pro Met Asp Glu Leu Glu Gln Thr Leu Tyr Glu Glu
1               5                   10                  15

Phe Leu Phe Gln His Ala
            20

<210> SEQ ID NO 168
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 168

Thr Asn Tyr Lys Pro Leu Asp Glu Leu Asp Ala Thr Leu Tyr Glu His
1               5                   10                  15

Trp Ile Leu Gln His Ser
            20

<210> SEQ ID NO 169
<211> LENGTH: 22
<212> TYPE: PRT
<213> ORGANISM: Artificial Sequence
<220> FEATURE:
<223> OTHER INFORMATION: Polypeptide capable of binding to Ang-2
```

-continued

```
<400> SEQUENCE: 169

Gln Lys Phe Lys Pro Leu Asp Glu Leu Glu Gln Thr Leu Tyr Glu Gln
1               5                   10                  15

Trp Thr Leu Gln Gln Arg
            20

<210> SEQ ID NO 170
<211> LENGTH: 22
<212> TYPE: PRT
<213> ORGANISM: Artificial Sequence
<220> FEATURE:
<223> OTHER INFORMATION: Polypeptide capable of binding to Ang-2

<400> SEQUENCE: 170

Thr Lys Phe Gln Pro Leu Asp Glu Leu Asp Gln Thr Leu Tyr Glu Gln
1               5                   10                  15

Trp Thr Leu Gln Gln Arg
            20

<210> SEQ ID NO 171
<211> LENGTH: 22
<212> TYPE: PRT
<213> ORGANISM: Artificial Sequence
<220> FEATURE:
<223> OTHER INFORMATION: Ang-2 binding Polypeptide

<400> SEQUENCE: 171

Thr Asn Phe Gln Pro Leu Asp Glu Leu Asp Gln Thr Leu Tyr Glu Gln
1               5                   10                  15

Trp Thr Leu Gln Gln Arg
            20

<210> SEQ ID NO 172
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 172

Lys Phe Asn Pro Leu Asp Glu Leu Glu Glu Thr Leu Tyr Glu Gln Phe
1               5                   10                  15

Thr Phe Gln Gln
            20

<210> SEQ ID NO 173
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 173

Ala Gly Gly Met Arg Pro Tyr Asp Gly Met Leu Gly Trp Pro Asn Tyr
1               5                   10                  15

Asp Val Gln Ala
            20

<210> SEQ ID NO 174
<211> LENGTH: 20
<212> TYPE: PRT
<213> ORGANISM: Artificial Sequence
<220> FEATURE:
<223> OTHER INFORMATION: Polypeptide capable of binding to Ang-2
```

-continued

```
<400> SEQUENCE: 174

Gln Thr Trp Asp Asp Pro Cys Met His Ile Leu Gly Pro Val Thr Trp
1               5                   10                  15

Arg Arg Cys Ile
            20

<210> SEQ ID NO 175
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 175

Ala Pro Gly Gln Arg Pro Tyr Asp Gly Met Leu Gly Trp Pro Thr Tyr
1               5                   10                  15

Gln Arg Ile Val
            20

<210> SEQ ID NO 176
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 176

Ser Gly Gln Leu Arg Pro Cys Glu Glu Ile Phe Gly Cys Gly Thr Gln
1               5                   10                  15

Asn Leu Ala Leu
            20

<210> SEQ ID NO 177
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 177

Phe Gly Asp Lys Arg Pro Leu Glu Cys Met Phe Gly Gly Pro Ile Gln
1               5                   10                  15

Leu Cys Pro Arg
            20

<210> SEQ ID NO 178
<211> LENGTH: 20
<212> TYPE: PRT
<213> ORGANISM: Artificial Sequence
<220> FEATURE:
<223> OTHER INFORMATION: Ang-2 binding Polypeptide

<400> SEQUENCE: 178

Gly Gln Asp Leu Arg Pro Cys Glu Asp Met Phe Gly Cys Gly Thr Lys
1               5                   10                  15

Asp Trp Tyr Gly
            20

<210> SEQ ID NO 179
<211> LENGTH: 14
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 179

Lys Arg Pro Cys Glu Glu Ile Phe Gly Gly Cys Thr Tyr Gln
1               5                   10

<210> SEQ ID NO 180
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 180

Gly Phe Glu Tyr Cys Asp Gly Met Glu Asp Pro Phe Thr Phe Gly Cys
1               5                   10                  15

Asp Lys Gln Thr
            20

<210> SEQ ID NO 181
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 181

Lys Leu Glu Tyr Cys Asp Gly Met Glu Asp Pro Phe Thr Gln Gly Cys
1               5                   10                  15

Asp Asn Gln Ser
            20

<210> SEQ ID NO 182
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 182

Leu Gln Glu Trp Cys Glu Gly Val Glu Asp Pro Phe Thr Phe Gly Cys
1               5                   10                  15

Glu Lys Gln Arg
            20

<210> SEQ ID NO 183
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 183

Ala Gln Asp Tyr Cys Glu Gly Met Glu Asp Pro Phe Thr Phe Gly Cys
1               5                   10                  15

Glu Met Gln Lys
            20

<210> SEQ ID NO 184
<211> LENGTH: 20
<212> TYPE: PRT
<213> ORGANISM: Artificial Sequence
<220> FEATURE:
<223> OTHER INFORMATION: Polypeptide capable of binding to Ang-2
```

<400> SEQUENCE: 184

Leu Leu Asp Tyr Cys Glu Gly Val Gln Asp Pro Phe Thr Phe Gly Cys
1               5                   10                  15

Glu Asn Leu Asp
            20

<210> SEQ ID NO 185
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 185

His Gln Glu Tyr Cys Glu Gly Met Glu Asp Pro Phe Thr Phe Gly Cys
1               5                   10                  15

Glu Tyr Gln Gly
            20

<210> SEQ ID NO 186
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 186

Met Leu Asp Tyr Cys Glu Gly Met Asp Asp Pro Phe Thr Phe Gly Cys
1               5                   10                  15

Asp Lys Gln Met
            20

<210> SEQ ID NO 187
<211> LENGTH: 20
<212> TYPE: PRT
<213> ORGANISM: Artificial Sequence
<220> FEATURE:
<223> OTHER INFORMATION: Polypeptide capable of binding to Ang-2

<400> SEQUENCE: 187

Leu Gln Asp Tyr Cys Glu Gly Val Glu Asp Pro Phe Thr Phe Gly Cys
1               5                   10                  15

Glu Asn Gln Arg
            20

<210> SEQ ID NO 188
<211> LENGTH: 20
<212> TYPE: PRT
<213> ORGANISM: Artificial Sequence
<220> FEATURE:
<223> OTHER INFORMATION: Ang-2 binding Polypeptide

<400> SEQUENCE: 188

Leu Gln Asp Tyr Cys Glu Gly Val Glu Asp Pro Phe Thr Phe Gly Cys
1               5                   10                  15

Glu Lys Gln Arg
            20

<210> SEQ ID NO 189
<211> LENGTH: 18
<212> TYPE: PRT
<213> ORGANISM: Artificial Sequence

```
<220> FEATURE:
<223> OTHER INFORMATION: Therapeutically active peptide of randomly
      generated, non-naturally occurring sequence.

<400> SEQUENCE: 189

Phe Asp Tyr Cys Glu Gly Val Glu Asp Pro Phe Thr Phe Gly Cys Asp
1               5                   10                  15

Asn His

<210> SEQ ID NO 190
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 190

Thr Gly Tyr Thr Glu Tyr Thr Glu Glu Trp Pro Met Gly Phe Gly Tyr
1               5                   10                  15

Gln Trp Ser Phe
            20

<210> SEQ ID NO 191
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 191

Thr Asp Trp Leu Ser Asp Phe Pro Phe Tyr Glu Gln Tyr Phe Gly Leu
1               5                   10                  15

Met Pro Pro Gly
            20

<210> SEQ ID NO 192
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 192

Phe Met Arg Phe Pro Asn Pro Trp Lys Leu Val Glu Pro Pro Gln Gly
1               5                   10                  15

Trp Tyr Tyr Gly
            20

<210> SEQ ID NO 193
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 193

Val Val Lys Ala Pro His Phe Glu Phe Leu Ala Pro Pro His Phe His
1               5                   10                  15

Glu Phe Pro Phe
            20
```

<210> SEQ ID NO 194
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 194

Phe Ser Tyr Ile Trp Ile Asp Glu Thr Pro Ser Asn Ile Asp Arg Tyr
1               5                   10                  15

Met Leu Trp Leu
            20

<210> SEQ ID NO 195
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 195

Val Asn Phe Pro Lys Val Pro Glu Asp Val Glu Pro Trp Pro Trp Ser
1               5                   10                  15

Leu Lys Leu Tyr
            20

<210> SEQ ID NO 196
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 196

Thr Trp His Pro Lys Thr Tyr Glu Glu Phe Ala Leu Pro Phe Phe Val
1               5                   10                  15

Pro Glu Ala Pro
            20

<210> SEQ ID NO 197
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 197

Trp His Phe Gly Thr Pro Tyr Ile Gln Gln Gln Pro Gly Val Tyr Trp
1               5                   10                  15

Leu Gln Ala Pro
            20

<210> SEQ ID NO 198
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

```
<400> SEQUENCE: 198

Val Trp Asn Tyr Gly Pro Phe Phe Met Asn Phe Pro Asp Ser Thr Tyr
1               5                   10                  15

Phe Leu His Glu
            20

<210> SEQ ID NO 199
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 199

Trp Arg Ile His Ser Lys Pro Leu Asp Tyr Ser His Val Trp Phe Phe
1               5                   10                  15

Pro Ala Asp Phe
            20

<210> SEQ ID NO 200
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 200

Phe Trp Asp Gly Asn Gln Pro Pro Asp Ile Leu Val Asp Trp Pro Trp
1               5                   10                  15

Asn Pro Pro Val
            20

<210> SEQ ID NO 201
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 201

Phe Tyr Ser Leu Glu Trp Leu Lys Asp His Ser Glu Phe Phe Gln Thr
1               5                   10                  15

Val Thr Glu Trp
            20

<210> SEQ ID NO 202
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 202

Gln Phe Met Glu Leu Leu Lys Phe Phe Asn Ser Pro Gly Asp Ser Ser
1               5                   10                  15

His His Phe Leu
            20
```

```
<210> SEQ ID NO 203
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 203

Thr Asn Val Asp Trp Ile Ser Asn Asn Trp Glu His Met Lys Ser Phe
1               5                   10                  15

Phe Thr Glu Asp
            20

<210> SEQ ID NO 204
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 204

Pro Asn Glu Lys Pro Tyr Gln Met Gln Ser Trp Phe Pro Pro Asp Trp
1               5                   10                  15

Pro Val Pro Tyr
            20

<210> SEQ ID NO 205
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 205

Trp Ser His Thr Glu Trp Val Pro Gln Val Trp Trp Lys Pro Pro Asn
1               5                   10                  15

His Phe Tyr Val
            20

<210> SEQ ID NO 206
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 206

Trp Gly Glu Trp Ile Asn Asp Ala Gln Val His Met His Glu Gly Phe
1               5                   10                  15

Ile Ser Glu Ser
            20

<210> SEQ ID NO 207
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.
```

```
<400> SEQUENCE: 207

Val Pro Trp Glu His Asp His Asp Leu Trp Glu Ile Ile Ser Gln Asp
1               5                   10                  15

Trp His Ile Ala
            20

<210> SEQ ID NO 208
<211> LENGTH: 20
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 208

Val Leu His Leu Gln Asp Pro Arg Gly Trp Ser Asn Phe Pro Pro Gly
1               5                   10                  15

Val Leu Glu Leu
            20

<210> SEQ ID NO 209
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 209

Ile His Gly Cys Trp Phe Thr Glu Glu Gly Cys Val Trp Gln
1               5                   10

<210> SEQ ID NO 210
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 210

Tyr Met Gln Cys Gln Phe Ala Arg Asp Gly Cys Pro Gln Trp
1               5                   10

<210> SEQ ID NO 211
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 211

Lys Leu Gln Cys Gln Tyr Ser Glu Ser Gly Cys Pro Thr Ile
1               5                   10

<210> SEQ ID NO 212
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.
```

```
<400> SEQUENCE: 212

Phe Leu Gln Cys Glu Ile Ser Gly Gly Ala Cys Pro Ala Pro
1               5                   10

<210> SEQ ID NO 213
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 213

Lys Leu Gln Cys Glu Phe Ser Thr Ser Gly Cys Pro Asp Leu
1               5                   10

<210> SEQ ID NO 214
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 214

Lys Leu Gln Cys Glu Phe Ser Thr Gln Gly Cys Pro Asp Leu
1               5                   10

<210> SEQ ID NO 215
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 215

Lys Leu Gln Cys Glu Phe Ser Thr Ser Gly Cys Pro Trp Leu
1               5                   10

<210> SEQ ID NO 216
<211> LENGTH: 14
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 216

Ile Gln Gly Cys Trp Phe Thr Glu Glu Gly Cys Pro Trp Gln
1               5                   10

<210> SEQ ID NO 217
<211> LENGTH: 18
<212> TYPE: PRT
<213> ORGANISM: Artificial Sequence
<220> FEATURE:
<223> OTHER INFORMATION: Therapeutically active peptide of randomly
      generated, non-naturally occurring sequence.

<400> SEQUENCE: 217

Ser Phe Asp Cys Asp Asn Pro Trp Gly His Val Leu Gln Ser Cys Phe
1               5                   10                  15

Gly Phe
```

-continued

```
<210> SEQ ID NO 218
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 218

Ser Phe Asp Cys Asp Asn Pro Trp Gly His Lys Leu Gln Ser Cys Phe
1               5                   10                  15

Gly Phe

<210> SEQ ID NO 219
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 219

Lys Asp Leu Cys Ala Met Trp His Trp Met Cys Lys Pro Pro
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 220

Lys Asp Leu Cys Lys Met Trp Lys Trp Met Cys Lys Pro Pro
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 221

Lys Asp Leu Cys Lys Met Trp His Trp Met Cys Lys Pro Lys
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 222

Trp Tyr Pro Cys Tyr Glu Phe His Phe Trp Cys Tyr Asp Leu
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Myostatin Binding Peptide
```

-continued

```
<400> SEQUENCE: 223

Trp Tyr Pro Cys Tyr Glu Gly His Phe Trp Cys Tyr Asp Leu
1               5

-continued

```
<400> SEQUENCE: 229

Ile Asp Lys Cys Ala Ile Trp Gly Trp Met Cys Pro Pro Leu
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 230

Trp Tyr Pro Cys Gly Glu Phe Gly Met Trp Cys Leu Asn Val
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Myostatin Binding Peptide

<400> SEQUENCE: 231

Trp Phe Thr Cys Leu Trp Asn Cys Asp Asn Glu
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 232

His Thr Pro Cys Pro Trp Phe Ala Pro Leu Cys Val Glu Trp
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 233

Lys Glu Trp Cys Trp Arg Trp Lys Trp Met Cys Lys Pro Glu
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 234

Phe Glu Thr Cys Pro Ser Trp Ala Tyr Phe Cys Leu Asp Ile
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Myostatin Binding Peptide
```

<400> SEQUENCE: 235

Ala Tyr Lys Cys Glu Ala Asn Asp Trp Gly Cys Trp Trp Leu
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 236

Asn Ser Trp Cys Glu Asp Gln Trp His Arg Cys Trp Trp Leu
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 237

Trp Ser Ala Cys Tyr Ala Gly His Phe Trp Cys Tyr Asp Leu
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 238

Ala Asn Trp Cys Val Ser Pro Asn Trp Phe Cys Met Val Met
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 239

Trp Thr Glu Cys Tyr Gln Gln Glu Phe Trp Cys Trp Asn Leu
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 240

Glu Asn Thr Cys Glu Arg Trp Lys Trp Met Cys Pro Pro Lys
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Myostatin Binding Peptide -continued

```
<400> SEQUENCE: 241

Trp Leu Pro Cys His Gln Glu Gly Phe Trp Cys Met Asn Phe
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 242

Ser Thr Met Cys Ser Gln Trp His Trp Met Cys Asn Pro Phe
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 243

Ile Phe Gly Cys His Trp Trp Asp Val Asp Cys Tyr Gln Phe
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 244

Ile Tyr Gly Cys Lys Trp Trp Asp Ile Gln Cys Tyr Asp Ile
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 245

Pro Asp Trp Cys Ile Asp Pro Asp Trp Trp Cys Lys Phe Trp
1               5                   10

<210> SEQ ID NO 246
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 246

Gln Gly His Cys Thr Arg Trp Pro Trp Met Cys Pro Pro Tyr
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Myostatin Binding Peptide
```

```
<400> SEQUENCE: 247

Trp Gln Glu Cys Tyr Arg Glu Gly Phe Trp Cys Leu Gln Thr
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 248

Trp Phe Asp Cys Tyr Gly Pro Gly Phe Lys Cys Trp Ser Pro
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 249

Gly Val Arg Cys Pro Lys Gly His Leu Trp Cys Leu Tyr Pro
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 250

His Trp Ala Cys Gly Tyr Trp Pro Trp Ser Cys Lys Trp Val
1               5                   10

<210> SEQ ID NO 251
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 251

Gly Pro Ala Cys His Ser Pro Trp Trp Cys Val Phe Gly
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 252

Thr Thr Trp Cys Ile Ser Pro Met Trp Phe Cys Ser Gln Gln
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Myostatin Binding Peptide
```

```
<400> SEQUENCE: 253

His Lys Phe Cys Pro Pro Trp Ala Ile Phe Cys Trp Asp Phe
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 254

Pro Asp Trp Cys Val Ser Pro Arg Trp Tyr Cys Asn Met Trp
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 255

Val Trp Lys Cys His Trp Phe Gly Met Asp Cys Glu Pro Thr
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 256

Lys Lys His Cys Gln Ile Trp Thr Trp Met Cys Ala Pro Lys
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 257

Trp Phe Gln Cys Gly Ser Thr Leu Phe Trp Cys Tyr Asn Leu
1               5                   10

<210> SEQ ID NO 258
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 258

Trp Ser Pro Cys Tyr Asp His Tyr Phe Tyr Cys Tyr Thr Ile
1               5                   10

<210> SEQ ID NO 259
<211> LENGTH: 14
<212> TYPE: PRT
<213> ORGANISM: Artificial Sequence
<220> FEATURE:
<223> OTHER INFORMATION: Myostatin Binding Peptide
```

```
<400> SEQUENCE: 259

Ser Trp Met Cys Gly Phe Phe Lys Glu Val Cys Met Trp Val
1               5                   10

<210> SEQ ID NO 260
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 260

Glu Met Leu Cys Met Ile His Pro Val Phe Cys Asn Pro His
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 261

Leu Lys Thr Cys Asn Leu Trp Pro Trp Met Cys Pro Pro Leu
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 262

Val Val Gly Cys Lys Trp Tyr Glu Ala Trp Cys Tyr Asn Lys
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 263

Pro Ile His Cys Thr Gln Trp Ala Trp Met Cys Pro Pro Thr
1               5                   10

<210> SEQ ID NO 264
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 264

Asp Ser Asn Cys Pro Trp Tyr Phe Leu Ser Cys Val Ile Phe
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Myostatin Binding Peptide
```

```
<400> SEQUENCE: 265

His Ile Trp Cys Asn Leu Ala Met Met Lys Cys Val Glu Met
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 266

Asn Leu Gln Cys Ile Tyr Phe Leu Gly Lys Cys Ile Tyr Phe
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 267

Ala Trp Arg Cys Met Trp Phe Ser Asp Val Cys Thr Pro Gly
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 268

Trp Phe Arg Cys Phe Leu Asp Ala Asp Trp Cys Thr Ser Val
1               5                   10

<210> SEQ ID NO 269
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 269

Glu Lys Ile Cys Gln Met Trp Ser Trp Met Cys Ala Pro Pro
1               5                   10

<210> SEQ ID NO 270
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 270

Trp Phe Tyr Cys His Leu Asn Lys Ser Glu Cys Thr Glu Pro
1               5                   10

<210> SEQ ID NO 271
<211> LENGTH: 14
<212> TYPE: PRT
<213> ORGANISM: Artificial Sequence
<220> FEATURE:
<223> OTHER INFORMATION: Myostatin Binding Peptide
```

```
<400> SEQUENCE: 271

Phe Trp Arg Cys Ala Ile Gly Ile Asp Lys Cys Lys Arg Val
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 272

Asn Leu Gly Cys Lys Trp Tyr Glu Val Trp Cys Phe Thr Tyr
1               5                   10

<210> SEQ ID NO 273
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 273

Ile Asp Leu Cys Asn Met Trp Asp Gly Met Cys Tyr Pro Pro
1               5                   10

<210> SEQ ID NO 274
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 274

Glu Met Pro Cys Asn Ile Trp Gly Trp Met Cys Pro Pro Val
1               5                   10

<210> SEQ ID NO 275
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 275

Trp Phe Arg Cys Val Leu Thr Gly Ile Val Asp Trp Ser Glu Cys Phe
1               5                   10                  15

Gly Leu

<210> SEQ ID NO 276
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 276

Gly Phe Ser Cys Thr Phe Gly Leu Asp Glu Phe Tyr Val Asp Cys Ser
1               5                   10                  15

Pro Phe

<210> SEQ ID NO 277
<211> LENGTH: 18
<212> TYPE: PRT
<213> ORGANISM: Artificial Sequence
```

<220> FEATURE:
<223> OTHER INFORMATION: Myostatin Binding Peptide

<400> SEQUENCE: 277

Leu Pro Trp Cys His Asp Gln Val Asn Ala Asp Trp Gly Phe Cys Met
1 5 10 15

Leu Trp

<210> SEQ ID NO 278
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 278

Tyr Pro Thr Cys Ser Glu Lys Phe Trp Ile Tyr Gly Gln Thr Cys Val
1 5 10 15

Leu Trp

<210> SEQ ID NO 279
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 279

Leu Gly Pro Cys Pro Ile His His Gly Pro Trp Pro Gln Tyr Cys Val
1 5 10 15

Tyr Trp

<210> SEQ ID NO 280
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 280

Pro Phe Pro Cys Glu Thr His Gln Ile Ser Trp Leu Gly His Cys Leu
1 5 10 15

Ser Phe

<210> SEQ ID NO 281
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 281

His Trp Gly Cys Glu Asp Leu Met Trp Ser Trp His Pro Leu Cys Arg
1 5 10 15

Arg Pro

<210> SEQ ID NO 282
<211> LENGTH: 18
<212> TYPE: PRT
<213> ORGANISM: Artificial Sequence
<220> FEATURE:
<223> OTHER INFORMATION: Myostatin Binding Peptide -continued

```
<400> SEQUENCE: 282

Leu Pro Leu Cys Asp Ala Asp Met Met Pro Thr Ile Gly Phe Cys Val
1               5                   10                  15

Ala Tyr

<210> SEQ ID NO 283
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 283

Ser His Trp Cys Glu Thr Thr Phe Trp Met Asn Tyr Ala Lys Cys Val
1               5                   10                  15

His Ala

<210> SEQ ID NO 284
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 284

Leu Pro Lys Cys Thr His Val Pro Phe Asp Gln Gly Gly Phe Cys Leu
1               5                   10                  15

Trp Tyr

<210> SEQ ID NO 285
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 285

Phe Ser Ser Cys Trp Ser Pro Val Ser Arg Gln Asp Met Phe Cys Val
1               5                   10                  15

Phe Tyr

<210> SEQ ID NO 286
<211> LENGTH: 17
<212> TYPE: PRT
<213> ORGANISM: Artificial Sequence
<220> FEATURE:
<223> OTHER INFORMATION: Myostatin Binding Peptide

<400> SEQUENCE: 286

Ser His Lys Cys Glu Tyr Ser Gly Trp Leu Gln Pro Leu Cys Tyr Arg
1               5                   10                  15

Pro

<210> SEQ ID NO 287
<211> LENGTH: 18
<212> TYPE: PRT
<213> ORGANISM: Artificial Sequence
<220> FEATURE:
<223> OTHER INFORMATION: Myostatin Binding Peptide
```

-continued

<400> SEQUENCE: 287

Pro Trp Trp Cys Gln Asp Asn Tyr Val Gln His Met Leu His Cys Asp
1               5                   10                  15

Ser Pro

<210> SEQ ID NO 288
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 288

Trp Phe Arg Cys Met Leu Met Asn Ser Phe Asp Ala Phe Gln Cys Val
1               5                   10                  15

Ser Tyr

<210> SEQ ID NO 289
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 289

Pro Asp Ala Cys Arg Asp Gln Pro Trp Tyr Met Phe Met Gly Cys Met
1               5                   10                  15

Leu Gly

<210> SEQ ID NO 290
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 290

Phe Leu Ala Cys Phe Val Glu Phe Glu Leu Cys Phe Asp Ser
1               5                   10

<210> SEQ ID NO 291
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 291

Ser Ala Tyr Cys Ile Ile Thr Glu Ser Asp Pro Tyr Val Leu Cys Val
1               5                   10                  15

Pro Leu

<210> SEQ ID NO 292
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 292

Pro Ser Ile Cys Glu Ser Tyr Ser Thr Met Trp Leu Pro Met Cys Gln
1               5                   10                  15

His Asn

<210> SEQ ID NO 293
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 293

Trp Leu Asp Cys His Asp Asp Ser Trp Ala Trp Thr Lys Met Cys Arg
1               5                   10                  15

Ser His

<210> SEQ ID NO 294
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 294

Tyr Leu Asn Cys Val Met Met Asn Thr Ser Pro Phe Val Glu Cys Val
1               5                   10                  15

Phe Asn

<210> SEQ ID NO 295
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 295

Tyr Pro Trp Cys Asp Gly Phe Met Ile Gln Gln Gly Ile Thr Cys Met
1               5                   10                  15

Phe Tyr

<210> SEQ ID NO 296
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 296

Phe Asp Tyr Cys Thr Trp Leu Asn Gly Phe Lys Asp Trp Lys Cys Trp
1               5                   10                  15

Ser Arg

<210> SEQ ID NO 297
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 297

Leu Pro Leu Cys Asn Leu Lys Glu Ile Ser His Val Gln Ala Cys Val
1               5                   10                  15

Leu Phe

<210> SEQ ID NO 298
<211> LENGTH: 18
<212> TYPE: PRT
<213> ORGANISM: Artificial Sequence -continued
<220> FEATURE:
<223> OTHER INFORMATION: Myostatin Binding Peptide

<400> SEQUENCE: 298

Ser Pro Glu Cys Ala Phe Ala Arg Trp Leu Gly Ile Glu Gln Cys Gln
1 5 10 15

Arg Asp

<210> SEQ ID NO 299
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 299

Tyr Pro Gln Cys Phe Asn Leu His Leu Leu Glu Trp Thr Glu Cys Asp
1 5 10 15

Trp Phe

<210> SEQ ID NO 300
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 300

Arg Trp Arg Cys Glu Ile Tyr Asp Ser Glu Phe Leu Pro Lys Cys Trp
1 5 10 15

Phe Phe

<210> SEQ ID NO 301
<211> LENGTH: 14
<212> TYPE: PRT
<213> ORGANISM: Artificial Sequence
<220> FEATURE:
<223> OTHER INFORMATION: Myostatin Binding Peptide

<400> SEQUENCE: 301

Leu Val Gly Cys Asp Asn Val Trp His Arg Cys Lys Leu Phe
1 5 10

<210> SEQ ID NO 302
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 302

Ala Gly Trp Cys His Val Trp Gly Glu Met Phe Gly Met Gly Cys Ser
1 5 10 15

Ala Leu

<210> SEQ ID NO 303
<211> LENGTH: 18
<212> TYPE: PRT
<213> ORGANISM: Artificial Sequence
<220> FEATURE:
<223> OTHER INFORMATION: Myostatin Binding Peptide

```
<400> SEQUENCE: 303

His His Glu Cys Glu Trp Met Ala Arg Trp Met Ser Leu Asp Cys Val
1               5                   10                  15

Gly Leu

<210> SEQ ID NO 304
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 304

Phe Pro Met Cys Gly Ile Ala Gly Met Lys Asp Phe Asp Phe Cys Val
1               5                   10                  15

Trp Tyr

<210> SEQ ID NO 305
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 305

Arg Asp Asp Cys Thr Phe Trp Pro Glu Trp Leu Trp Lys Leu Cys Glu
1               5                   10                  15

Arg Pro

<210> SEQ ID NO 306
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 306

Tyr Asn Phe Cys Ser Tyr Leu Phe Gly Val Ser Lys Glu Ala Cys Gln
1               5                   10                  15

Leu Pro

<210> SEQ ID NO 307
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 307

Ala His Trp Cys Glu Gln Gly Pro Trp Arg Tyr Gly Asn Ile Cys Met
1               5                   10                  15

Ala Tyr

<210> SEQ ID NO 308
<211> LENGTH: 18
<212> TYPE: PRT
<213> ORGANISM: Artificial Sequence
<220> FEATURE:
<223> OTHER INFORMATION: Myostatin Binding Peptide
```

```
<400> SEQUENCE: 308

Asn Leu Val Cys Gly Lys Ile Ser Ala Trp Gly Asp Glu Ala Cys Ala
1               5                   10                  15

Arg Ala

<210> SEQ ID NO 309
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 309

His Asn Val Cys Thr Ile Met Gly Pro Ser Met Lys Trp Phe Cys Trp
1               5                   10                  15

Asn Asp

<210> SEQ ID NO 310
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 310

Asn Asp Leu Cys Ala Met Trp Gly Trp Arg Asn Thr Ile Trp Cys Gln
1               5                   10                  15

Asn Ser

<210> SEQ ID NO 311
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 311

Pro Pro Phe Cys Gln Asn Asp Asn Asp Met Leu Gln Ser Leu Cys Lys
1               5                   10                  15

Leu Leu

<210> SEQ ID NO 312
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 312

Trp Tyr Asp Cys Asn Val Pro Asn Glu Leu Leu Ser Gly Leu Cys Arg
1               5                   10                  15

Leu Phe

<210> SEQ ID NO 313
<211> LENGTH: 18
<212> TYPE: PRT
<213> ORGANISM: Artificial Sequence
<220> FEATURE:
<223> OTHER INFORMATION: Myostatin Binding Peptide
```

```
<400> SEQUENCE: 313

Tyr Gly Asp Cys Asp Gln Asn His Trp Met Trp Pro Phe Thr Cys Leu
1               5                   10                  15

Ser Leu

<210> SEQ ID NO 314
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 314

Gly Trp Met Cys His Phe Asp Leu His Asp Trp Gly Ala Thr Cys Gln
1               5                   10                  15

Pro Asp

<210> SEQ ID NO 315
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 315

Tyr Phe His Cys Met Phe Gly Gly His Glu Phe Glu Val His Cys Glu
1               5                   10                  15

Ser Phe

<210> SEQ ID NO 316
<211> LENGTH: 12
<212> TYPE: PRT
<213> ORGANISM: Artificial Sequence
<220> FEATURE:
<223> OTHER INFORMATION: Myostatin Binding Peptide

<400> SEQUENCE: 316

Ala Tyr Trp Cys Trp His Gly Gln Cys Val Arg Phe
1               5                   10

<210> SEQ ID NO 317
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 317

Ser Glu His Trp Thr Phe Thr Asp Trp Asp Gly Asn Glu Trp Trp Val
1               5                   10                  15

Arg Pro Phe

<210> SEQ ID NO 318
<211> LENGTH: 20
<212> TYPE: PRT
<213> ORGANISM: Artificial Sequence
<220> FEATURE:
<223> OTHER INFORMATION: Myostatin Binding Peptide
```

<400> SEQUENCE: 318

Met Glu Met Leu Asp Ser Leu Phe Glu Leu Leu Lys Asp Met Val Pro
1               5                   10                  15

Ile Ser Lys Ala
            20

<210> SEQ ID NO 319
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 319

Ser Pro Pro Glu Glu Ala Leu Met Glu Trp Leu Gly Trp Gln Tyr Gly
1               5                   10                  15

Lys Phe Thr

<210> SEQ ID NO 320
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 320

Ser Pro Glu Asn Leu Leu Asn Asp Leu Tyr Ile Leu Met Thr Lys Gln
1               5                   10                  15

Glu Trp Tyr Gly
            20

<210> SEQ ID NO 321
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 321

Phe His Trp Glu Glu Gly Ile Pro Phe His Val Val Thr Pro Tyr Ser
1               5                   10                  15

Tyr Asp Arg Met
            20

<210> SEQ ID NO 322
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 322

Lys Arg Leu Leu Glu Gln Phe Met Asn Asp Leu Ala Glu Leu Val Ser
1               5                   10                  15

Gly His Ser

<210> SEQ ID NO 323
<211> LENGTH: 20
<212> TYPE: PRT
<213> ORGANISM: Artificial Sequence
<220> FEATURE:
<223> OTHER INFORMATION: Myostatin Binding Peptide

```
<400> SEQUENCE: 323

Asp Thr Arg Asp Ala Leu Phe Gln Glu Phe Tyr Glu Phe Val Arg Ser
1               5                   10                  15

Arg Leu Val Ile
            20

<210> SEQ ID NO 324
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 324

Arg Met Ser Ala Ala Pro Arg Pro Leu Thr Tyr Arg Asp Ile Met Asp
1               5                   10                  15

Gln Tyr Trp His
            20

<210> SEQ ID NO 325
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 325

Asn Asp Lys Ala His Phe Phe Glu Met Phe Met Phe Asp Val His Asn
1               5                   10                  15

Phe Val Glu Ser
            20

<210> SEQ ID NO 326
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 326

Gln Thr Gln Ala Gln Lys Ile Asp Gly Leu Trp Glu Leu Leu Gln Ser
1               5                   10                  15

Ile Arg Asn Gln
            20

<210> SEQ ID NO 327
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 327

Met Leu Ser Glu Phe Glu Glu Phe Leu Gly Asn Leu Val His Arg Gln
1               5                   10                  15

Glu Ala

<210> SEQ ID NO 328
<211> LENGTH: 20
<212> TYPE: PRT
<213> ORGANISM: Artificial Sequence
<220> FEATURE:
<223> OTHER INFORMATION: Myostatin Binding Peptide
```

```
<400> SEQUENCE: 328

Tyr Thr Pro Lys Met Gly Ser Glu Trp Thr Ser Phe Trp His Asn Arg
1               5                   10                  15

Ile His Tyr Leu
            20

<210> SEQ ID NO 329
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 329

Leu Asn Asp Thr Leu Leu Arg Glu Leu Lys Met Val Leu Asn Ser Leu
1               5                   10                  15

Ser Asp Met Lys
            20

<210> SEQ ID NO 330
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 330

Phe Asp Val Glu Arg Asp Leu Met Arg Trp Leu Glu Gly Phe Met Gln
1               5                   10                  15

Ser Ala Ala Thr
            20

<210> SEQ ID NO 331
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 331

His His Gly Trp Asn Tyr Leu Arg Lys Gly Ser Ala Pro Gln Trp Phe
1               5                   10                  15

Glu Ala Trp Val
            20

<210> SEQ ID NO 332
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 332

Val Glu Ser Leu His Gln Leu Gln Met Trp Leu Asp Gln Lys Leu Ala
1               5                   10                  15

Ser Gly Pro His
            20

<210> SEQ ID NO 333
<211> LENGTH: 18
<212> TYPE: PRT
<213> ORGANISM: Artificial Sequence
<220> FEATURE:
<223> OTHER INFORMATION: Myostatin Binding Peptide
```

<400> SEQUENCE: 333

Arg Ala Thr Leu Leu Lys Asp Phe Trp Gln Leu Val Glu Gly Tyr Gly
1               5                   10                  15

Asp Asn

<210> SEQ ID NO 334
<211> LENGTH: 16
<212> TYPE: PRT
<213> ORGANISM: Artificial Sequence
<220> FEATURE:
<223> OTHER INFORMATION: Myostatin Binding Peptide

<400> SEQUENCE: 334

Glu Glu Leu Leu Arg Glu Phe Tyr Arg Phe Val Ser Ala Phe Asp Tyr
1               5                   10                  15

<210> SEQ ID NO 335
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 335

Gly Leu Leu Asp Glu Phe Ser His Phe Ile Ala Glu Gln Phe Tyr Gln
1               5                   10                  15

Met Pro Gly Gly
            20

<210> SEQ ID NO 336
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 336

Tyr Arg Glu Met Ser Met Leu Glu Gly Leu Leu Asp Val Leu Glu Arg
1               5                   10                  15

Leu Gln His Tyr
            20

<210> SEQ ID NO 337
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 337

His Asn Ser Ser Gln Met Leu Leu Ser Glu Leu Ile Met Leu Val Gly
1               5                   10                  15

Ser Met Met Gln
            20

<210> SEQ ID NO 338
<211> LENGTH: 20
<212> TYPE: PRT
<213> ORGANISM: Artificial Sequence
<220> FEATURE:
<223> OTHER INFORMATION: Myostatin Binding Peptide

```
<400> SEQUENCE: 338

Trp Arg Glu His Phe Leu Asn Ser Asp Tyr Ile Arg Asp Lys Leu Ile
1               5                   10                  15

Ala Ile Asp Gly
            20

<210> SEQ ID NO 339
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 339

Gln Phe Pro Phe Tyr Val Phe Asp Asp Leu Pro Ala Gln Leu Glu Tyr
1               5                   10                  15

Trp Ile Ala

<210> SEQ ID NO 340
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 340

Glu Phe Phe His Trp Leu His Asn His Arg Ser Glu Val Asn His Trp
1               5                   10                  15

Leu Asp Met Asn
            20

<210> SEQ ID NO 341
<211> LENGTH: 19
<212> TYPE: PRT
<213> ORGANISM: Artificial Sequence
<220> FEATURE:
<223> OTHER INFORMATION: Myostatin Binding Peptide

<400> SEQUENCE: 341

Glu Ala Leu Phe Gln Asn Phe Phe Arg Asp Val Leu Thr Leu Ser Glu
1               5                   10                  15

Arg Glu Tyr

<210> SEQ ID NO 342
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 342

Gln Tyr Trp Glu Gln Gln Trp Met Thr Tyr Phe Arg Glu Asn Gly Leu
1               5                   10                  15

His Val Gln Tyr
            20

<210> SEQ ID NO 343
<211> LENGTH: 20
<212> TYPE: PRT
<213> ORGANISM: Artificial Sequence
<220> FEATURE:
<223> OTHER INFORMATION: Myostatin Binding Peptide
```

-continued

<400> SEQUENCE: 343

Asn Gln Arg Met Met Leu Glu Asp Leu Trp Arg Ile Met Thr Pro Met
1               5                   10                  15

Phe Gly Arg Ser
            20

<210> SEQ ID NO 344
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 344

Phe Leu Asp Glu Leu Lys Ala Glu Leu Ser Arg His Tyr Ala Leu Asp
1               5                   10                  15

Asp Leu Asp Glu
            20

<210> SEQ ID NO 345
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 345

Gly Lys Leu Ile Glu Gly Leu Leu Asn Glu Leu Met Gln Leu Glu Thr
1               5                   10                  15

Phe Met Pro Asp
            20

<210> SEQ ID NO 346
<211> LENGTH: 15
<212> TYPE: PRT
<213> ORGANISM: Artificial Sequence
<220> FEATURE:
<223> OTHER INFORMATION: Myostatin Binding Peptide

<400> SEQUENCE: 346

Ile Leu Leu Leu Asp Glu Tyr Lys Lys Asp Trp Lys Ser Trp Phe
1               5                   10                  15

<210> SEQ ID NO 347
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 347

Gln Gly His Cys Thr Arg Trp Pro Trp Met Cys Pro Pro Tyr Gly Ser
1               5                   10                  15

Gly Ser Ala Thr Gly Gly Ser Gly Ser Thr Ala Ser Ser Gly Ser Gly
            20                  25                  30

Ser Ala Thr Gly Gln Gly His Cys Thr Arg Trp Pro Trp Met Cys Pro
        35                  40                  45

Pro Tyr
    50

```
<210> SEQ ID NO 348
<211> LENGTH: 43
<212> TYPE: PRT
<213> ORGANISM: Artificial Sequence
<220> FEATURE:
<223> OTHER INFORMATION: Myostatin Binding Peptide

<400> SEQUENCE: 348

Trp Tyr Pro Cys Tyr Glu Gly His Phe Trp Cys Tyr Asp Leu Gly Ser
1               5                   10                  15

Gly Ser Thr Ala Ser Ser Gly Ser Gly Ser Ala Thr Gly Trp Tyr Pro
            20                  25                  30

Cys Tyr Glu Gly His Phe Trp Cys Tyr Asp Leu
        35                  40

<210> SEQ ID NO 349
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 349

His Thr Pro Cys Pro Trp Phe Ala Pro Leu Cys Val Glu Trp Gly Ser
1               5                   10                  15

Gly Ser Ala Thr Gly Gly Ser Gly Ser Thr Ala Ser Ser Gly Ser Gly
            20                  25                  30

Ser Ala Thr Gly His Thr Pro Cys Pro Trp Phe Ala Pro Leu Cys Val
        35                  40                  45

Glu Trp
    50

<210> SEQ ID NO 350
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 350

Pro Asp Trp Cys Ile Asp Pro Asp Trp Trp Cys Lys Phe Trp Gly Ser
1               5                   10                  15

Gly Ser Ala Thr Gly Gly Ser Gly Ser Thr Ala Ser Ser Gly Ser Gly
            20                  25                  30

Ser Ala Thr Gly Pro Asp Trp Cys Ile Asp Pro Asp Trp Trp Cys Lys
        35                  40                  45

Phe Trp
    50

<210> SEQ ID NO 351
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 351

Ala Asn Trp Cys Val Ser Pro Asn Trp Phe Cys Met Val Met Gly Ser
1               5                   10                  15

Gly Ser Ala Thr Gly Gly Ser Gly Ser Thr Ala Ser Ser Gly Ser Gly
            20                  25                  30
```

-continued

Ser Ala Thr Gly Ala Asn Trp Cys Val Ser Pro Asn Trp Phe Cys Met
        35                  40                  45

Val Met
    50

<210> SEQ ID NO 352
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 352

Pro Asp Trp Cys Ile Asp Pro Asp Trp Trp Cys Lys Phe Trp Gly Ser
1               5                   10                  15

Gly Ser Ala Thr Gly Gly Ser Gly Ser Thr Ala Ser Ser Gly Ser Gly
            20                  25                  30

Ser Ala Thr Gly Pro Asp Trp Cys Ile Asp Pro Asp Trp Trp Cys Lys
        35                  40                  45

Phe Trp
    50

<210> SEQ ID NO 353
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 353

His Trp Ala Cys Gly Tyr Trp Pro Trp Ser Cys Lys Trp Val Gly Ser
1               5                   10                  15

Gly Ser Ala Thr Gly Gly Ser Gly Ser Thr Ala Ser Ser Gly Ser Gly
            20                  25                  30

Ser Ala Thr Gly His Trp Ala Cys Gly Tyr Trp Pro Trp Ser Cys Lys
        35                  40                  45

Trp Val
    50

<210> SEQ ID NO 354
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 354

Lys Lys His Cys Gln Ile Trp Thr Trp Met Cys Ala Pro Lys Gly Ser
1               5                   10                  15

Gly Ser Ala Thr Gly Gly Ser Gly Ser Thr Ala Ser Ser Gly Ser Gly
            20                  25                  30

Ser Ala Thr Gly Gln Gly His Cys Thr Arg Trp Pro Trp Met Cys Pro
        35                  40                  45

Pro Tyr
    50

<210> SEQ ID NO 355
<211> LENGTH: 50
<212> TYPE: PRT
<213> ORGANISM: Artificial Sequence
<220> FEATURE:
<223> OTHER INFORMATION: Myostatin Binding Peptide -continued

<400> SEQUENCE: 355

Gln Gly His Cys Thr Arg Trp Pro Trp Met Cys Pro Pro Tyr Gly Ser
1               5                   10                  15

Gly Ser Ala Thr Gly Gly Ser Gly Ser Thr Ala Ser Ser Gly Ser Gly
            20                  25                  30

Ser Ala Thr Gly Lys Lys His Cys Gln Ile Trp Thr Trp Met Cys Ala
        35                  40                  45

Pro Lys
    50

<210> SEQ ID NO 356
<211> LENGTH: 50
<212> TYPE: PRT
<213> ORGANISM: Artificial Sequence
<220> FEATURE:
<223> OTHER INFORMATION: Myostatin Binding Peptide

<400> SEQUENCE: 356

Lys Lys His Cys Gln Ile Trp Thr Trp Met Cys Ala Pro Lys Gly Ser
1               5                   10                  15

Gly Ser Ala Thr Gly Gly Ser Gly Ser Thr Ala Ser Ser Gly Ser Gly
            20                  25                  30

Ser Ala Thr Gly Gln Gly His Cys Thr Arg Trp Pro Trp Met Cys Pro
        35                  40                  45

Pro Tyr
    50

<210> SEQ ID NO 357
<211> LENGTH: 36
<212> TYPE: PRT
<213> ORGANISM: Artificial Sequence
<220> FEATURE:
<223> OTHER INFORMATION: Myostatin Binding Peptide

<400> SEQUENCE: 357

Lys Lys His Cys Gln Ile Trp Thr Trp Met Cys Ala Pro Lys Gly Gly
1               5                   10                  15

Gly Gly Gly Gly Gly Gly Gln Gly His Cys Thr Arg Trp Pro Trp Met
            20                  25                  30

Cys Pro Pro Tyr
        35

<210> SEQ ID NO 358
<211> LENGTH: 34
<212> TYPE: PRT
<213> ORGANISM: Artificial Sequence
<220> FEATURE:
<223> OTHER INFORMATION: Myostatin Binding Peptide

<400> SEQUENCE: 358

Gln Gly His Cys Thr Arg Trp Pro Trp Met Cys Pro Pro Tyr Gly Gly
1               5                   10                  15

Gly Gly Gly Gly Lys Lys His Cys Gln Ile Trp Thr Trp Met Cys Ala
            20                  25                  30

Pro Lys

<210> SEQ ID NO 359
<211> LENGTH: 20
<212> TYPE: PRT
<213> ORGANISM: Artificial Sequence

```
<220> FEATURE:
<223> OTHER INFORMATION: Myostatin Binding Peptide

<400> SEQUENCE: 359

Val Ala Leu His Gly Gln Cys Thr Arg Trp Pro Trp Met Cys Pro Pro
1               5                   10                  15

Gln Arg Glu Gly
            20

<210> SEQ ID NO 360
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 360

Tyr Pro Glu Gln Gly Leu Cys Thr Arg Trp Pro Trp Met Cys Pro Pro
1               5                   10                  15

Gln Thr Leu Ala
            20

<210> SEQ ID NO 361
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 361

Gly Leu Asn Gln Gly His Cys Thr Arg Trp Pro Trp Met Cys Pro Pro
1               5                   10                  15

Gln Asp Ser Asn
            20

<210> SEQ ID NO 362
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 362

Met Ile Thr Gln Gly Gln Cys Thr Arg Trp Pro Trp Met Cys Pro Pro
1               5                   10                  15

Gln Pro Ser Gly
            20

<210> SEQ ID NO 363
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 363

Ala Gly Ala Gln Glu His Cys Thr Arg Trp Pro Trp Met Cys Ala Pro
1               5                   10                  15

Asn Asp Trp Ile
            20
```

```
<210> SEQ ID NO 364
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 364

Gly Val Asn Gln Gly Gln Cys Thr Arg Trp Arg Trp Met Cys Pro Pro
1               5                   10                  15

Asn Gly Trp Glu
            20

<210> SEQ ID NO 365
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 365

Leu Ala Asp His Gly Gln Cys Ile Arg Trp Pro Trp Met Cys Pro Pro
1               5                   10                  15

Glu Gly Trp Glu
            20

<210> SEQ ID NO 366
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 366

Ile Leu Glu Gln Ala Gln Cys Thr Arg Trp Pro Trp Met Cys Pro Pro
1               5                   10                  15

Gln Arg Gly Gly
            20

<210> SEQ ID NO 367
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 367

Thr Gln Thr His Ala Gln Cys Thr Arg Trp Pro Trp Met Cys Pro Pro
1               5                   10                  15

Gln Trp Glu Gly
            20

<210> SEQ ID NO 368
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 368

Val Val Thr Gln Gly His Cys Thr Leu Trp Pro Trp Met Cys Pro Pro
1               5                   10                  15

Gln Arg Trp Arg
            20
```

```
<210> SEQ ID NO 369
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 369

Ile Tyr Pro His Asp Gln Cys Thr Arg Trp Pro Trp Met Cys Pro Pro
1               5                   10                  15

Gln Pro Tyr Pro
            20

<210> SEQ ID NO 370
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 370

Ser Tyr Trp Gln Gly Gln Cys Thr Arg Trp Pro Trp Met Cys Pro Pro
1               5                   10                  15

Gln Trp Arg Gly
            20

<210> SEQ ID NO 371
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 371

Met Trp Gln Gln Gly His Cys Thr Arg Trp Pro Trp Met Cys Pro Pro
1               5                   10                  15

Gln Gly Trp Gly
            20

<210> SEQ ID NO 372
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 372

Glu Phe Thr Gln Trp His Cys Thr Arg Trp Pro Trp Met Cys Pro Pro
1               5                   10                  15

Gln Arg Ser Gln
            20

<210> SEQ ID NO 373
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 373

Leu Asp Asp Gln Trp Gln Cys Thr Arg Trp Pro Trp Met Cys Pro Pro
1               5                   10                  15

Gln Gly Phe Ser
            20
```

<210> SEQ ID NO 374
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 374

Tyr Gln Thr Gln Gly Leu Cys Thr Arg Trp Pro Trp Met Cys Pro Pro
1               5                   10                  15

Gln Ser Gln Arg
            20

<210> SEQ ID NO 375
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 375

Glu Ser Asn Gln Gly Gln Cys Thr Arg Trp Pro Trp Met Cys Pro Pro
1               5                   10                  15

Gln Gly Gly Trp
            20

<210> SEQ ID NO 376
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 376

Trp Thr Asp Arg Gly Pro Cys Thr Arg Trp Pro Trp Met Cys Pro Pro
1               5                   10                  15

Gln Ala Asn Gly
            20

<210> SEQ ID NO 377
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 377

Val Gly Thr Gln Gly Gln Cys Thr Arg Trp Pro Trp Met Cys Pro Pro
1               5                   10                  15

Tyr Glu Thr Gly
            20

<210> SEQ ID NO 378
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 378

Pro Tyr Glu Gln Gly Lys Cys Thr Arg Trp Pro Trp Met Cys Pro Pro
1               5                   10                  15

Tyr Glu Val Glu
            20

```
<210> SEQ ID NO 379
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 379

Ser Glu Tyr Gln Gly Leu Cys Thr Arg Trp Pro Trp Met Cys Pro Pro
1               5                   10                  15

Gln Gly Trp Lys
            20

<210> SEQ ID NO 380
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 380

Thr Phe Ser Gln Gly His Cys Thr Arg Trp Pro Trp Met Cys Pro Pro
1               5                   10                  15

Gln Gly Trp Gly
            20

<210> SEQ ID NO 381
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 381

Pro Gly Ala His Asp His Cys Thr Arg Trp Pro Trp Met Cys Pro Pro
1               5                   10                  15

Gln Ser Arg Tyr
            20

<210> SEQ ID NO 382
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 382

Val Ala Glu Glu Trp His Cys Arg Arg Trp Pro Trp Met Cys Pro Pro
1               5                   10                  15

Gln Asp Trp Arg
            20

<210> SEQ ID NO 383
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 383

Val Gly Thr Gln Gly His Cys Thr Arg Trp Pro Trp Met Cys Pro Pro
1               5                   10                  15

Gln Pro Ala Gly
            20
```

<210> SEQ ID NO 384
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 384

Glu Glu Asp Gln Ala His Cys Arg Ser Trp Pro Trp Met Cys Pro Pro
1               5                   10                  15

Gln Gly Trp Val
            20

<210> SEQ ID NO 385
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 385

Ala Asp Thr Gln Gly His Cys Thr Arg Trp Pro Trp Met Cys Pro Pro
1               5                   10                  15

Gln His Trp Phe
            20

<210> SEQ ID NO 386
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 386

Ser Gly Pro Gln Gly His Cys Thr Arg Trp Pro Trp Met Cys Ala Pro
1               5                   10                  15

Gln Gly Trp Phe
            20

<210> SEQ ID NO 387
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 387

Thr Leu Val Gln Gly His Cys Thr Arg Trp Pro Trp Met Cys Pro Pro
1               5                   10                  15

Gln Arg Trp Val
            20

<210> SEQ ID NO 388
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 388

Gly Met Ala His Gly Lys Cys Thr Arg Trp Ala Trp Met Cys Pro Pro
1               5                   10                  15

Gln Ser Trp Lys
            20

<210> SEQ ID NO 389
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 389

Glu Leu Tyr His Gly Gln Cys Thr Arg Trp Pro Trp Met Cys Pro Pro
1               5                   10                  15

Gln Ser Trp Ala
            20

<210> SEQ ID NO 390
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 390

Val Ala Asp His Gly His Cys Thr Arg Trp Pro Trp Met Cys Pro Pro
1               5                   10                  15

Gln Gly Trp Gly
            20

<210> SEQ ID NO 391
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 391

Pro Glu Ser Gln Gly His Cys Thr Arg Trp Pro Trp Met Cys Pro Pro
1               5                   10                  15

Gln Gly Trp Gly
            20

<210> SEQ ID NO 392
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 392

Ile Pro Ala His Gly His Cys Thr Arg Trp Pro Trp Met Cys Pro Pro
1               5                   10                  15

Gln Arg Trp Arg
            20

<210> SEQ ID NO 393
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 393

Phe Thr Val His Gly His Cys Thr Arg Trp Pro Trp Met Cys Pro Pro
1               5                   10                  15

Tyr Gly Trp Val
            20

```
<210> SEQ ID NO 394
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 394

Pro Asp Phe Pro Gly His Cys Thr Arg Trp Arg Trp Met Cys Pro Pro
1               5                   10                  15

Gln Gly Trp Glu
            20

<210> SEQ ID NO 395
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 395

Gln Leu Trp Gln Gly Pro Cys Thr Gln Trp Pro Trp Met Cys Pro Pro
1               5                   10                  15

Lys Gly Arg Tyr
            20

<210> SEQ ID NO 396
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 396

His Ala Asn Asp Gly His Cys Thr Arg Trp Gln Trp Met Cys Pro Pro
1               5                   10                  15

Gln Trp Gly Gly
            20

<210> SEQ ID NO 397
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 397

Glu Thr Asp His Gly Leu Cys Thr Arg Trp Pro Trp Met Cys Pro Pro
1               5                   10                  15

Tyr Gly Ala Arg
            20

<210> SEQ ID NO 398
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 398

Gly Thr Trp Gln Gly Leu Cys Thr Arg Trp Pro Trp Met Cys Pro Pro
1               5                   10                  15

Gln Gly Trp Gln
            20
```

```
<210> SEQ ID NO 399
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 399

Val Ala Thr Gln Gly Gln Cys Thr Arg Trp Pro Trp Met Cys Pro Pro
1               5                   10                  15

Gln Gly Trp Gly
            20

<210> SEQ ID NO 400
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 400

Val Ala Thr Gln Gly Gln Cys Thr Arg Trp Pro Trp Met Cys Pro Pro
1               5                   10                  15

Gln Arg Trp Gly
            20

<210> SEQ ID NO 401
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 401

Gln Arg Glu Trp Tyr Pro Cys Tyr Gly Gly His Leu Trp Cys Tyr Asp
1               5                   10                  15

Leu His Lys Ala
            20

<210> SEQ ID NO 402
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 402

Ile Ser Ala Trp Tyr Ser Cys Tyr Ala Gly His Phe Trp Cys Trp Asp
1               5                   10                  15

Leu Lys Gln Lys
            20

<210> SEQ ID NO 403
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 403

Trp Thr Gly Trp Tyr Gln Cys Tyr Gly Gly His Leu Trp Cys Tyr Asp
1               5                   10                  15

Leu Arg Arg Lys
            20
```

-continued

```
<210> SEQ ID NO 404
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 404

Lys Thr Phe Trp Tyr Pro Cys Tyr Asp Gly His Phe Trp Cys Tyr Asn
1               5                   10                  15

Leu Lys Ser Ser
            20

<210> SEQ ID NO 405
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 405

Glu Ser Arg Trp Tyr Pro Cys Tyr Glu Gly His Leu Trp Cys Phe Asp
1               5                   10                  15

Leu Thr Glu Thr
            20

<210> SEQ ID NO 406
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 406

Met Glu Met Leu Asp Ser Leu Phe Glu Leu Leu Lys Asp Met Val Pro
1               5                   10                  15

Ile Ser Lys Ala
            20

<210> SEQ ID NO 407
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 407

Arg Met Glu Met Leu Glu Ser Leu Leu Glu Leu Leu Lys Glu Ile Val
1               5                   10                  15

Pro Met Ser Lys Ala Gly
            20

<210> SEQ ID NO 408
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 408

Arg Met Glu Met Leu Glu Ser Leu Leu Glu Leu Leu Lys Glu Ile Val
1               5                   10                  15

Pro Met Ser Lys Ala Arg
            20
```

```
<210> SEQ ID NO 409
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 409

Arg Met Glu Met Leu Glu Ser Leu Leu Glu Leu Leu Lys Asp Ile Val
1               5                   10                  15

Pro Met Ser Lys Pro Ser
            20

<210> SEQ ID NO 410
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 410

Gly Met Glu Met Leu Glu Ser Leu Phe Glu Leu Leu Gln Glu Ile Val
1               5                   10                  15

Pro Met Ser Lys Ala Pro
            20

<210> SEQ ID NO 411
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 411

Arg Met Glu Met Leu Glu Ser Leu Leu Glu Leu Leu Lys Asp Ile Val
1               5                   10                  15

Pro Ile Ser Asn Pro Pro
            20

<210> SEQ ID NO 412
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 412

Arg Ile Glu Met Leu Glu Ser Leu Leu Glu Leu Leu Gln Glu Ile Val
1               5                   10                  15

Pro Ile Ser Lys Ala Glu
            20

<210> SEQ ID NO 413
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 413

Arg Met Glu Met Leu Gln Ser Leu Leu Glu Leu Leu Lys Asp Ile Val
1               5                   10                  15

Pro Met Ser Asn Ala Arg
            20
```

<210> SEQ ID NO 414
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 414

Arg Met Glu Met Leu Glu Ser Leu Leu Glu Leu Leu Lys Glu Ile Val
1               5                   10                  15

Pro Thr Ser Asn Gly Thr
            20

<210> SEQ ID NO 415
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 415

Arg Met Glu Met Leu Glu Ser Leu Phe Glu Leu Leu Lys Glu Ile Val
1               5                   10                  15

Pro Met Ser Lys Ala Gly
            20

<210> SEQ ID NO 416
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 416

Arg Met Glu Met Leu Gly Ser Leu Leu Glu Leu Leu Lys Glu Ile Val
1               5                   10                  15

Pro Met Ser Lys Ala Arg
            20

<210> SEQ ID NO 417
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 417

Gln Met Glu Leu Leu Asp Ser Leu Phe Glu Leu Leu Lys Glu Ile Val
1               5                   10                  15

Pro Lys Ser Gln Pro Ala
            20

<210> SEQ ID NO 418
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 418

Arg Met Glu Met Leu Asp Ser Leu Leu Glu Leu Leu Lys Glu Ile Val
1               5                   10                  15

Pro Met Ser Asn Ala Arg
            20

```
<210> SEQ ID NO 419
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 419

Arg Met Glu Met Leu Glu Ser Leu Leu Glu Leu Leu His Glu Ile Val
1               5                   10                  15

Pro Met Ser Gln Ala Gly
            20

<210> SEQ ID NO 420
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 420

Gln Met Glu Met Leu Glu Ser Leu Leu Gln Leu Leu Lys Glu Ile Val
1               5                   10                  15

Pro Met Ser Lys Ala Ser
            20

<210> SEQ ID NO 421
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 421

Arg Met Glu Met Leu Asp Ser Leu Leu Glu Leu Leu Lys Asp Met Val
1               5                   10                  15

Pro Met Thr Thr Gly Ala
            20

<210> SEQ ID NO 422
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 422

Arg Ile Glu Met Leu Glu Ser Leu Leu Glu Leu Leu Lys Asp Met Val
1               5                   10                  15

Pro Met Ala Asn Ala Ser
            20

<210> SEQ ID NO 423
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 423

Arg Met Glu Met Leu Glu Ser Leu Leu Gln Leu Leu Asn Glu Ile Val
1               5                   10                  15

Pro Met Ser Arg Ala Arg
            20
```

<210> SEQ ID NO 424
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 424

Arg Met Glu Met Leu Glu Ser Leu Phe Asp Leu Leu Lys Glu Leu Val
1               5                   10                  15

Pro Met Ser Lys Gly Val
            20

<210> SEQ ID NO 425
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 425

Arg Ile Glu Met Leu Glu Ser Leu Leu Glu Leu Leu Lys Asp Ile Val
1               5                   10                  15

Pro Ile Gln Lys Ala Arg
            20

<210> SEQ ID NO 426
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 426

Arg Met Glu Leu Leu Glu Ser Leu Phe Glu Leu Leu Lys Asp Met Val
1               5                   10                  15

Pro Met Ser Asp Ser Ser
            20

<210> SEQ ID NO 427
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 427

Arg Met Glu Met Leu Glu Ser Leu Leu Glu Val Leu Gln Glu Ile Val
1               5                   10                  15

Pro Arg Ala Lys Gly Ala
            20

<210> SEQ ID NO 428
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 428

Arg Met Glu Met Leu Asp Ser Leu Leu Gln Leu Leu Asn Glu Ile Val
1               5                   10                  15

Pro Met Ser His Ala Arg
            20

```
<210> SEQ ID NO 429
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 429

Arg Met Glu Met Leu Glu Ser Leu Leu Glu Leu Leu Lys Asp Ile Val
1               5                   10                  15

Pro Met Ser Asn Ala Gly
            20

<210> SEQ ID NO 430
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 430

Arg Met Glu Met Leu Gln Ser Leu Phe Glu Leu Leu Lys Gly Met Val
1               5                   10                  15

Pro Ile Ser Lys Ala Gly
            20

<210> SEQ ID NO 431
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 431

Arg Met Glu Met Leu Glu Ser Leu Leu Glu Leu Leu Lys Glu Ile Val
1               5                   10                  15

Pro Asn Ser Thr Ala Ala
            20

<210> SEQ ID NO 432
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 432

Arg Met Glu Met Leu Gln Ser Leu Leu Glu Leu Leu Lys Glu Ile Val
1               5                   10                  15

Pro Ile Ser Lys Ala Gly
            20

<210> SEQ ID NO 433
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 433

Arg Ile Glu Met Leu Asp Ser Leu Leu Glu Leu Leu Asn Glu Leu Val
1               5                   10                  15

Pro Met Ser Lys Ala Arg
            20
```

```
<210> SEQ ID NO 434
<211> LENGTH: 20
<212> TYPE: PRT
<213> ORGANISM: Artificial Sequence
<220> FEATURE:
<223> OTHER INFORMATION: Myostatin Binding Peptid

<400> SEQUENCE: 434

His His Gly Trp Asn Tyr Leu Arg Lys Gly Ser Ala Pro Gln Trp Phe
1               5                   10                  15

Glu Ala Trp Val
        20

<210> SEQ ID NO 435
<211> LENGTH: 22
<212> TYPE: PRT
<213> ORGANISM: Artificial Sequence
<220> FEATURE:
<223> OTHER INFORMATION: Myostatin Binding Peptid

<400> SEQUENCE: 435

Gln Val Glu Ser Leu Gln Gln Leu Leu Met Trp Leu Asp Gln Lys Leu
1               5                   10                  15

Ala Ser Gly Pro Gln Gly
        20

<210> SEQ ID NO 436
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 436

Arg Met Glu Leu Leu Glu Ser Leu Phe Glu Leu Leu Lys Glu Met Val
1               5                   10                  15

Pro Arg Ser Lys Ala Val
        20

<210> SEQ ID NO 437
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 437

Gln Ala Val Ser Leu Gln His Leu Leu Met Trp Leu Asp Gln Lys Leu
1               5                   10                  15

Ala Ser Gly Pro Gln His
        20

<210> SEQ ID NO 438
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 438

Asp Glu Asp Ser Leu Gln Gln Leu Leu Met Trp Leu Asp Gln Lys Leu
1               5                   10                  15

Ala Ser Gly Pro Gln Leu
        20
```

```
<210> SEQ ID NO 439
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 439

Pro Val Ala Ser Leu Gln Gln Leu Leu Ile Trp Leu Asp Gln Lys Leu
1               5                   10                  15

Ala Gln Gly Pro His Ala
            20

<210> SEQ ID NO 440
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 440

Glu Val Asp Glu Leu Gln Gln Leu Leu Asn Trp Leu Asp His Lys Leu
1               5                   10                  15

Ala Ser Gly Pro Leu Gln
            20

<210> SEQ ID NO 441
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 441

Asp Val Glu Ser Leu Glu Gln Leu Leu Met Trp Leu Asp His Gln Leu
1               5                   10                  15

Ala Ser Gly Pro His Gly
            20

<210> SEQ ID NO 442
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 442

Gln Val Asp Ser Leu Gln Gln Val Leu Leu Trp Leu Glu His Lys Leu
1               5                   10                  15

Ala Leu Gly Pro Gln Val
            20

<210> SEQ ID NO 443
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 443

Gly Asp Glu Ser Leu Gln His Leu Leu Met Trp Leu Glu Gln Lys Leu
1               5                   10                  15

Ala Leu Gly Pro His Gly
            20
```

```
<210> SEQ ID NO 444
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 444

Gln Ile Glu Met Leu Glu Ser Leu Leu Asp Leu Leu Arg Asp Met Val
1               5                   10                  15

Pro Met Ser Asn Ala Phe
            20

<210> SEQ ID NO 445
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 445

Glu Val Asp Ser Leu Gln Gln Leu Leu Met Trp Leu Asp Gln Lys Leu
1               5                   10                  15

Ala Ser Gly Pro Gln Ala
            20

<210> SEQ ID NO 446
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 446

Glu Asp Glu Ser Leu Gln Gln Leu Leu Ile Tyr Leu Asp Lys Met Leu
1               5                   10                  15

Ser Ser Gly Pro Gln Val
            20

<210> SEQ ID NO 447
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 447

Ala Met Asp Gln Leu His Gln Leu Leu Ile Trp Leu Asp His Lys Leu
1               5                   10                  15

Ala Ser Gly Pro Gln Ala
            20

<210> SEQ ID NO 448
<211> LENGTH: 22
<212> TYPE: PRT
<213> ORGANISM: Artificial Sequencee
<220> FEATURE:
<223> OTHER INFORMATION: Myostatin Binding Peptide

<400> SEQUENCE: 448

Arg Ile Glu Met Leu Glu Ser Leu Leu Glu Leu Leu Asp Glu Ile Ala
1               5                   10                  15

Leu Ile Pro Lys Ala Trp
            20
```

-continued

<210> SEQ ID NO 449
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 449

Glu Val Val Ser Leu Gln His Leu Leu Met Trp Leu Glu His Lys Leu
1               5                   10                  15

Ala Ser Gly Pro Asp Gly
            20

<210> SEQ ID NO 450
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 450

Gly Gly Glu Ser Leu Gln Gln Leu Leu Met Trp Leu Asp Gln Gln Leu
1               5                   10                  15

Ala Ser Gly Pro Gln Arg
            20

<210> SEQ ID NO 451
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 451

Gly Val Glu Ser Leu Gln Gln Leu Leu Ile Phe Leu Asp His Met Leu
1               5                   10                  15

Val Ser Gly Pro His Asp
            20

<210> SEQ ID NO 452
<211> LENGTH: 22
<212> TYPE: PRT
<213> ORGANISM: Artificial Sequenc
<220> FEATURE:
<223> OTHER INFORMATION: Myostatin Binding Peptide

<400> SEQUENCE: 452

Asn Val Glu Ser Leu Glu His Leu Met Met Trp Leu Glu Arg Leu Leu
1               5                   10                  15

Ala Ser Gly Pro Tyr Ala
            20

<210> SEQ ID NO 453
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 453

Gln Val Asp Ser Leu Gln Gln Leu Leu Ile Trp Leu Asp His Gln Leu
1               5                   10                  15

Ala Ser Gly Pro Lys Arg
            20

<210> SEQ ID NO 454
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 454

Glu Val Glu Ser Leu Gln Gln Leu Leu Met Trp Leu Glu His Lys Leu
1               5                   10                  15

Ala Gln Gly Pro Gln Gly
            20

<210> SEQ ID NO 455
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 455

Glu Val Asp Ser Leu Gln Gln Leu Leu Met Trp Leu Asp Gln Lys Leu
1               5                   10                  15

Ala Ser Gly Pro His Ala
            20

<210> SEQ ID NO 456
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 456

Glu Val Asp Ser Leu Gln Gln Leu Leu Met Trp Leu Asp Gln Gln Leu
1               5                   10                  15

Ala Ser Gly Pro Gln Lys
            20

<210> SEQ ID NO 457
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 457

Gly Val Glu Gln Leu Pro Gln Leu Leu Met Trp Leu Glu Gln Lys Leu
1               5                   10                  15

Ala Ser Gly Pro Gln Arg
            20

<210> SEQ ID NO 458
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 458

Gly Glu Asp Ser Leu Gln Gln Leu Leu Met Trp Leu Asp Gln Gln Leu
1               5                   10                  15

Ala Ala Gly Pro Gln Val
            20

```
<210> SEQ ID NO 459
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 459

Ala Asp Asp Ser Leu Gln Gln Leu Leu Met Trp Leu Asp Arg Lys Leu
1               5                   10                  15

Ala Ser Gly Pro His Val
            20

<210> SEQ ID NO 460
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 460

Pro Val Asp Ser Leu Gln Gln Leu Leu Ile Trp Leu Asp Gln Lys Leu
1               5                   10                  15

Ala Ser Gly Pro Gln Gly
            20

<210> SEQ ID NO 461
<211> LENGTH: 18
<212> TYPE: PRT
<213> ORGANISM: Artificial Sequence
<220> FEATURE:
<223> OTHER INFORMATION: Myostatin Binding Peptide

<400> SEQUENCE: 461

Arg Ala Thr Leu Leu Lys Asp Phe Trp Gln Leu Val Glu Gly Tyr Gly
1               5                   10                  15

Asp Asn

<210> SEQ ID NO 462
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 462

Asp Trp Arg Ala Thr Leu Leu Lys Glu Phe Trp Gln Leu Val Glu Gly
1               5                   10                  15

Leu Gly Asp Asn Leu Val
            20

<210> SEQ ID NO 463
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 463

Gln Ser Arg Ala Thr Leu Leu Lys Glu Phe Trp Gln Leu Val Glu Gly
1               5                   10                  15

Leu Gly Asp Lys Gln Ala
            20
```

```
<210> SEQ ID NO 464
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 464

Asp Gly Arg Ala Thr Leu Leu Thr Glu Phe Trp Gln Leu Val Gln Gly
1               5                   10                  15

Leu Gly Gln Lys Glu Ala
            20

<210> SEQ ID NO 465
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 465

Leu Ala Arg Ala Thr Leu Leu Lys Glu Phe Trp Gln Leu Val Glu Gly
1               5                   10                  15

Leu Gly Glu Lys Val Val
            20

<210> SEQ ID NO 466
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 466

Gly Ser Arg Asp Thr Leu Leu Lys Glu Phe Trp Gln Leu Val Val Gly
1               5                   10                  15

Leu Gly Asp Met Gln Thr
            20

<210> SEQ ID NO 467
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 467

Asp Ala Arg Ala Thr Leu Leu Lys Glu Phe Trp Gln Leu Val Asp Ala
1               5                   10                  15

Tyr Gly Asp Arg Met Val
            20

<210> SEQ ID NO 468
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 468

Asn Asp Arg Ala Gln Leu Leu Arg Asp Phe Trp Gln Leu Val Asp Gly
1               5                   10                  15

Leu Gly Val Lys Ser Trp
            20
```

```
<210> SEQ ID NO 469
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 469

Gly Val Arg Glu Thr Leu Leu Tyr Glu Leu Trp Tyr Leu Leu Lys Gly
1               5                   10                  15

Leu Gly Ala Asn Gln Gly
            20

<210> SEQ ID NO 470
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 470

Gln Ala Arg Ala Thr Leu Leu Lys Glu Phe Cys Gln Leu Val Gly Cys
1               5                   10                  15

Gln Gly Asp Lys Leu Ser
            20

<210> SEQ ID NO 471
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 471

Gln Glu Arg Ala Thr Leu Leu Lys Glu Phe Trp Gln Leu Val Ala Gly
1               5                   10                  15

Leu Gly Gln Asn Met Arg
            20

<210> SEQ ID NO 472
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 472

Ser Gly Arg Ala Thr Leu Leu Lys Glu Phe Trp Gln Leu Val Gln Gly
1               5                   10                  15

Leu Gly Glu Tyr Arg Trp
            20

<210> SEQ ID NO 473
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 473

Thr Met Arg Ala Thr Leu Leu Lys Glu Phe Trp Leu Phe Val Asp Gly
1               5                   10                  15

Gln Arg Glu Met Gln Trp
            20
```

```
<210> SEQ ID NO 474
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 474

Gly Glu Arg Ala Thr Leu Leu Asn Asp Phe Trp Gln Leu Val Asp Gly
1               5                   10                  15

Gln Gly Asp Asn Thr Gly
            20

<210> SEQ ID NO 475
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 475

Asp Glu Arg Glu Thr Leu Leu Lys Glu Phe Trp Gln Leu Val His Gly
1               5                   10                  15

Trp Gly Asp Asn Val Ala
            20

<210> SEQ ID NO 476
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 476

Gly Gly Arg Ala Thr Leu Leu Lys Glu Leu Trp Gln Leu Leu Glu Gly
1               5                   10                  15

Gln Gly Ala Asn Leu Val
            20

<210> SEQ ID NO 477
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 477

Thr Ala Arg Ala Thr Leu Leu Asn Glu Leu Val Gln Leu Val Lys Gly
1               5                   10                  15

Tyr Gly Asp Lys Leu Val
            20

<210> SEQ ID NO 478
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 478

Gly Met Arg Ala Thr Leu Leu Gln Glu Phe Trp Gln Leu Val Gly Gly
1               5                   10                  15

Gln Gly Asp Asn Trp Met
            20
```

```
<210> SEQ ID NO 479
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 479

Ser Thr Arg Ala Thr Leu Leu Asn Asp Leu Trp Gln Leu Met Lys Gly
1               5                   10                  15

Trp Ala Glu Asp Arg Gly
            20

<210> SEQ ID NO 480
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 480

Ser Glu Arg Ala Thr Leu Leu Lys Glu Leu Trp Gln Leu Val Gly Gly
1               5                   10                  15

Trp Gly Asp Asn Phe Gly
            20

<210> SEQ ID NO 481
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 481

Val Gly Arg Ala Thr Leu Leu Lys Glu Phe Trp Gln Leu Val Glu Gly
1               5                   10                  15

Leu Val Gly Gln Ser Arg
            20

<210> SEQ ID NO 482
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 482

Glu Ile Arg Ala Thr Leu Leu Lys Glu Phe Trp Gln Leu Val Asp Glu
1               5                   10                  15

Trp Arg Glu Gln Pro Asn
            20

<210> SEQ ID NO 483
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 483

Gln Leu Arg Ala Thr Leu Leu Lys Glu Phe Leu Gln Leu Val His Gly
1               5                   10                  15

Leu Gly Glu Thr Asp Ser
            20
```

```
<210> SEQ ID NO 484
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 484

Thr Gln Arg Ala Thr Leu Leu Lys Glu Phe Trp Gln Leu Ile Glu Gly
1               5                   10                  15

Leu Gly Gly Lys His Val
            20

<210> SEQ ID NO 485
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 485

His Tyr Arg Ala Thr Leu Leu Lys Glu Phe Trp Gln Leu Val Asp Gly
1               5                   10                  15

Leu Arg Glu Gln Gly Val
            20

<210> SEQ ID NO 486
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 486

Gln Ser Arg Val Thr Leu Leu Arg Glu Phe Trp Gln Leu Val Glu Ser
1               5                   10                  15

Tyr Arg Pro Ile Val Asn
            20

<210> SEQ ID NO 487
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 487

Leu Ser Arg Ala Thr Leu Leu Asn Glu Phe Trp Gln Phe Val Asp Gly
1               5                   10                  15

Gln Arg Asp Lys Arg Met
            20

<210> SEQ ID NO 488
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 488

Trp Asp Arg Ala Thr Leu Leu Asn Asp Phe Trp His Leu Met Glu Glu
1               5                   10                  15

Leu Ser Gln Lys Pro Gly
            20
```

```
<210> SEQ ID NO 489
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 489

Gln Glu Arg Ala Thr Leu Leu Lys Glu Phe Trp Arg Met Val Glu Gly
1               5                   10                  15

Leu Gly Lys Asn Arg Gly
            20

<210> SEQ ID NO 490
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 490

Asn Glu Arg Ala Thr Leu Leu Arg Glu Phe Trp Gln Leu Val Gly Gly
1               5                   10                  15

Tyr Gly Val Asn Gln Arg
            20

<210> SEQ ID NO 491
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 491

Tyr Arg Glu Met Ser Met Leu Glu Gly Leu Leu Asp Val Leu Glu Arg
1               5                   10                  15

Leu Gln His Tyr
            20

<210> SEQ ID NO 492
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 492

His Gln Arg Asp Met Ser Met Leu Trp Glu Leu Leu Asp Val Leu Asp
1               5                   10                  15

Gly Leu Arg Gln Tyr Ser
            20

<210> SEQ ID NO 493
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 493

Thr Gln Arg Asp Met Ser Met Leu Asp Gly Leu Leu Glu Val Leu Asp
1               5                   10                  15

Gln Leu Arg Gln Gln Arg
            20
```

```
<210> SEQ ID NO 494
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 494

Thr Ser Arg Asp Met Ser Leu Leu Trp Glu Leu Leu Glu Glu Leu Asp
1               5                   10                  15

Arg Leu Gly His Gln Arg
            20

<210> SEQ ID NO 495
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 495

Met Gln His Asp Met Ser Met Leu Tyr Gly Leu Val Glu Leu Leu Glu
1               5                   10                  15

Ser Leu Gly His Gln Ile
            20

<210> SEQ ID NO 496
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 496

Trp Asn Arg Asp Met Arg Met Leu Glu Ser Leu Phe Glu Val Leu Asp
1               5                   10                  15

Gly Leu Arg Gln Gln Val
            20

<210> SEQ ID NO 497
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 497

Gly Tyr Arg Asp Met Ser Met Leu Glu Gly Leu Leu Ala Val Leu Asp
1               5                   10                  15

Arg Leu Gly Pro Gln Leu
            20

<210> SEQ ID NO 498
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 498

Thr Gln Arg Asp Met Ser Met Leu Glu Gly Leu Leu Glu Val Leu Asp
1               5                   10                  15

Arg Leu Gly Gln Gln Arg
            20
```

```
<210> SEQ ID NO 499
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 499

Trp Tyr Arg Asp Met Ser Met Leu Glu Gly Leu Leu Glu Val Leu Asp
1               5                   10                  15

Arg Leu Gly Gln Gln Arg
            20

<210> SEQ ID NO 500
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 500

His Asn Ser Ser Gln Met Leu Leu Ser Glu Leu Ile Met Leu Val Gly
1               5                   10                  15

Ser Met Met Gln
            20

<210> SEQ ID NO 501
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 501

Thr Gln Asn Ser Arg Gln Met Leu Leu Ser Asp Phe Met Met Leu Val
1               5                   10                  15

Gly Ser Met Ile Gln Gly
            20

<210> SEQ ID NO 502
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 502

Met Gln Thr Ser Arg His Ile Leu Leu Ser Glu Phe Met Met Leu Val
1               5                   10                  15

Gly Ser Ile Met His Gly
            20

<210> SEQ ID NO 503
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 503

His Asp Asn Ser Arg Gln Met Leu Leu Ser Asp Leu Leu His Leu Val
1               5                   10                  15

Gly Thr Met Ile Gln Gly
            20
```

```
<210> SEQ ID NO 504
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 504

Met Glu Asn Ser Arg Gln Asn Leu Leu Arg Glu Leu Ile Met Leu Val
1               5                   10                  15

Gly Asn Met Ser His Gln
            20

<210> SEQ ID NO 505
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 505

Gln Asp Thr Ser Arg His Met Leu Leu Arg Glu Phe Met Met Leu Val
1               5                   10                  15

Gly Glu Met Ile Gln Gly
            20

<210> SEQ ID NO 506
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 506

Asp Gln Asn Ser Arg Gln Met Leu Leu Ser Asp Leu Met Ile Leu Val
1               5                   10                  15

Gly Ser Met Ile Gln Gly
            20

<210> SEQ ID NO 507
<211> LENGTH: 20
<212> TYPE: PRT
<213> ORGANISM: Artificial Sequence
<220> FEATURE:
<223> OTHER INFORMATION: Myostatin Binding Peptide

<400> SEQUENCE: 507

Glu Phe Phe His Trp Leu His Asn His Arg Ser Glu Val Asn His Trp
1               5                   10                  15

Leu Asp Met Asn
            20

<210> SEQ ID NO 508
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 508

Asn Val Phe Phe Gln Trp Val Gln Lys His Gly Arg Val Val Tyr Gln
1               5                   10                  15

Trp Leu Asp Ile Asn Val
            20
```

```
<210> SEQ ID NO 509
<211> LENGTH: 22
<212> TYPE: PRT
<213> ORGANISM: Artificial Sequence
<220> FEATURE:
<223> OTHER INFORMATION: Myostatin Binding Peptide

<400> SEQUENCE: 509

Phe Asp Phe Leu Gln Trp Leu Gln Asn His Arg Ser Glu Val Glu His
1               5                   10                  15

Trp Leu Val Met Asp Val
            20

<210> SEQ ID NO 510
<211> LENGTH: 14
<212> TYPE: PRT
<213> ORGANISM: Artificial Sequence
<220> FEATURE:
<223> OTHER INFORMATION: Preferred TALL-1 Modulating Domains

<400> SEQUENCE: 510

Pro Gly Thr Cys Phe Pro Phe Pro Trp Glu Cys Thr His Ala
1               5                   10

<210> SEQ ID NO 511
<211> LENGTH: 14
<212> TYPE: PRT
<213> ORGANISM: Artificial Sequence
<220> FEATURE:
<223> OTHER INFORMATION: Preferred TALL-1 Modulating Domains

<400> SEQUENCE: 511

Trp Gly Ala Cys Trp Pro Phe Pro Trp Glu Cys Phe Lys Glu
1               5                   10

<210> SEQ ID NO 512
<211> LENGTH: 14
<212> TYPE: PRT
<213> ORGANISM: Artificial Sequence
<220> FEATURE:
<223> OTHER INFORMATION: Preferred TALL-1 Modulating Domains

<400> SEQUENCE: 512

Val Pro Phe Cys Asp Leu Leu Thr Lys His Cys Phe Glu Ala
1               5                   10

<210> SEQ ID NO 513
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 513

Gly Ser Arg Cys Lys Tyr Lys Trp Asp Val Leu Thr Lys Gln Cys Phe
1               5                   10                  15

His His

<210> SEQ ID NO 514
<211> LENGTH: 18
<212> TYPE: PRT
<213> ORGANISM: Artificial Sequence
<220> FEATURE:
<223> OTHER INFORMATION: Preferred TALL-1 Modulating Domains
```

```
<400> SEQUENCE: 514

Leu Pro Gly Cys Lys Trp Asp Leu Leu Ile Lys Gln Trp Val Cys Asp
1               5                   10                  15

Pro Leu

<210> SEQ ID NO 515
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 515

Ser Ala Asp Cys Tyr Phe Asp Ile Leu Thr Lys Ser Asp Val Cys Thr
1               5                   10                  15

Ser Ser

<210> SEQ ID NO 516
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 516

Ser Asp Asp Cys Met Tyr Asp Gln Leu Thr Arg Met Phe Ile Cys Ser
1               5                   10                  15

Asn Leu

<210> SEQ ID NO 517
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 517

Asp Leu Asn Cys Lys Tyr Asp Glu Leu Thr Tyr Lys Glu Trp Cys Gln
1               5                   10                  15

Phe Asn

<210> SEQ ID NO 518
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 518

Phe His Asp Cys Lys Tyr Asp Leu Leu Thr Arg Gln Met Val Cys His
1               5                   10                  15

Gly Leu

<210> SEQ ID NO 519
<211> LENGTH: 18
<212> TYPE: PRT
<213> ORGANISM: Artificial Sequence
<220> FEATURE:
<223> OTHER INFORMATION: Preferred TALL-1 Modulating Domains
```

```
<400> SEQUENCE: 519

Arg Asn His Cys Phe Trp Asp His Leu Leu Lys Gln Asp Ile Cys Pro
1               5                   10                  15

Ser Pro

<210> SEQ ID NO 520
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 520

Ala Asn Gln Cys Trp Trp Asp Ser Leu Thr Lys Lys Asn Val Cys Glu
1               5                   10                  15

Phe Phe

<210> SEQ ID NO 521
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 521

Tyr Lys Gly Arg Gln Gln Met Trp Asp Ile Leu Thr Arg Ser Trp Val
1               5                   10                  15

Val Ser Leu

<210> SEQ ID NO 522
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 522

Gln Gln Asp Val Gly Leu Trp Trp Asp Ile Leu Thr Arg Ala Trp Met
1               5                   10                  15

Pro Asn Ile

<210> SEQ ID NO 523
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 523

Gln Gln Asn Ala Gln Arg Val Trp Asp Leu Leu Ile Arg Thr Trp Val
1               5                   10                  15

Tyr Pro Gln

<210> SEQ ID NO 524
<211> LENGTH: 19
<212> TYPE: PRT
<213> ORGANISM: Artificial Sequence
<220> FEATURE:
<223> OTHER INFORMATION: Preferred TALL-1 Modulating Domains
```

-continued

<400> SEQUENCE: 524

Gly Trp Asn Glu Ala Trp Trp Asp Glu Leu Thr Lys Ile Trp Val Leu
1 5 10 15

Glu Gln Gln

<210> SEQ ID NO 525
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 525

Arg Ile Thr Cys Asp Thr Trp Asp Ser Leu Ile Lys Lys Cys Val Pro
1 5 10 15

Gln Gln Ser

<210> SEQ ID NO 526
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 526

Gly Ala Ile Met Gln Gln Phe Trp Asp Ser Leu Thr Lys Thr Trp Leu
1 5 10 15

Arg Gln Ser

<210> SEQ ID NO 527
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 527

Trp Leu His Ser Gly Trp Trp Asp Pro Leu Thr Lys His Trp Leu Gln
1 5 10 15

Gln Lys Val

<210> SEQ ID NO 528
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 528

Ser Glu Trp Phe Phe Trp Phe Asp Pro Leu Thr Arg Ala Gln Gln Leu
1 5 10 15

Lys Phe Arg

<210> SEQ ID NO 529
<211> LENGTH: 19
<212> TYPE: PRT
<213> ORGANISM: Artificial Sequence
<220> FEATURE:
<223> OTHER INFORMATION: Preferred TALL-1 Modulating Domains

```
<400> SEQUENCE: 529

Gly Val Trp Phe Trp Trp Phe Asp Pro Leu Thr Lys Gln Trp Thr Gln
1               5                   10                  15

Gln Ala Gly

<210> SEQ ID NO 530
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 530

Met Gln Gln Cys Lys Gly Tyr Tyr Asp Ile Leu Thr Lys Trp Cys Val
1               5                   10                  15

Thr Asn Gly

<210> SEQ ID NO 531
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 531

Leu Trp Ser Lys Glu Val Trp Asp Ile Leu Thr Lys Ser Trp Val Ser
1               5                   10                  15

Gln Gln Ala

<210> SEQ ID NO 532
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 532

Lys Ala Ala Gly Trp Trp Phe Asp Trp Leu Thr Lys Val Trp Val Pro
1               5                   10                  15

Ala Pro

<210> SEQ ID NO 533
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 533

Ala Tyr Gln Gln Thr Trp Phe Trp Asp Ser Leu Thr Arg Leu Trp Leu
1               5                   10                  15

Ser Thr Thr

<210> SEQ ID NO 534
<211> LENGTH: 19
<212> TYPE: PRT
<213> ORGANISM: Artificial Sequence
<220> FEATURE:
<223> OTHER INFORMATION: Preferred TALL-1 Modulating Domains
```

-continued

<400> SEQUENCE: 534

Ser Gly Gln Gln His Phe Trp Trp Asp Leu Leu Thr Arg Ser Trp Thr
1 5 10 15

Pro Ser Thr

<210> SEQ ID NO 535
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 535

Leu Gly Val Gly Gln Gln Lys Trp Asp Pro Leu Thr Lys Gln Trp Val
1 5 10 15

Ser Arg Gly

<210> SEQ ID NO 536
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 536

Val Gly Lys Met Cys Gln Gln Trp Asp Pro Leu Ile Lys Arg Thr Val
1 5 10 15

Cys Val Gly

<210> SEQ ID NO 537
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 537

Cys Arg Gln Gly Ala Lys Phe Asp Leu Leu Thr Lys Gln Cys Leu Leu
1 5 10 15

Gly Arg

<210> SEQ ID NO 538
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 538

Gly Gln Ala Ile Arg His Trp Asp Val Leu Thr Lys Gln Trp Val Asp
1 5 10 15

Ser Gln Gln

<210> SEQ ID NO 539
<211> LENGTH: 19
<212> TYPE: PRT
<213> ORGANISM: Artificial Sequence
<220> FEATURE:
<223> OTHER INFORMATION: Preferred TALL-1 Modulating Domains -continued

```
<400> SEQUENCE: 539

Arg Gly Pro Cys Gly Ser Trp Asp Leu Leu Thr Lys His Cys Leu Asp
1               5                   10                  15

Ser Gln Gln

<210> SEQ ID NO 540
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 540

Trp Gln Trp Lys Gln Gln Gln Trp Asp Leu Leu Thr Lys Gln Met Val
1               5                   10                  15

Trp Val Gly

<210> SEQ ID NO 541
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 541

Pro Ile Thr Ile Cys Arg Lys Asp Leu Leu Thr Lys Gln Val Val Cys
1               5                   10                  15

Leu Asp

<210> SEQ ID NO 542
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 542

Lys Thr Cys Asn Gly Lys Trp Asp Leu Leu Thr Lys Gln Cys Leu Gln
1               5                   10                  15

Gln Gln Ala

<210> SEQ ID NO 543
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 543

Lys Cys Leu Lys Gly Lys Trp Asp Leu Leu Thr Lys Gln Cys Val Thr
1               5                   10                  15

Glu Val

<210> SEQ ID NO 544
<211> LENGTH: 18
<212> TYPE: PRT
<213> ORGANISM: Artificial Sequence
<220> FEATURE:
<223> OTHER INFORMATION: Preferred TALL-1 Modulating Domains
```

-continued

```
<400> SEQUENCE: 544

Arg Cys Trp Asn Gly Lys Trp Asp Leu Leu Thr Lys Gln Cys Ile His
1               5                   10                  15

Pro Trp

<210> SEQ ID NO 545
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 545

Asn Arg Asp Met Arg Lys Trp Asp Pro Leu Ile Lys Gln Trp Ile Val
1               5                   10                  15

Arg Pro

<210> SEQ ID NO 546
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 546

Gln Gln Ala Ala Ala Ala Thr Trp Asp Leu Leu Thr Lys Gln Trp Leu
1               5                   10                  15

Val Pro Pro

<210> SEQ ID NO 547
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 547

Pro Glu Gly Gly Pro Lys Trp Asp Pro Leu Thr Lys Gln Gln Phe Leu
1               5                   10                  15

Pro Pro Val

<210> SEQ ID NO 548
<211> LENGTH: 20
<212> TYPE: PRT
<213> ORGANISM: Artificial Sequence
<220> FEATURE:
<223> OTHER INFORMATION: Preferred TALL-1 Modulating Domains

<400> SEQUENCE: 548

Gln Gln Thr Pro Gln Gln Lys Lys Trp Asp Leu Leu Thr Lys Gln Trp
1               5                   10                  15

Phe Thr Arg Asn
            20

<210> SEQ ID NO 549
<211> LENGTH: 19
<212> TYPE: PRT
<213> ORGANISM: Artificial Sequence
<220> FEATURE:
<223> OTHER INFORM -continued

<400> SEQUENCE: 549

Ile Gly Ser Pro Cys Lys Trp Asp Leu Leu Thr Lys Gln Met Ile Cys
1 5 10 15

Gln Gln Thr

<210> SEQ ID NO 550
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 550

Cys Thr Ala Ala Gly Lys Trp Asp Leu Leu Thr Lys Gln Cys Ile Gln
1 5 10 15

Gln Glu Lys

<210> SEQ ID NO 551
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 551

Val Ser Gln Cys Met Lys Trp Asp Leu Leu Thr Lys Gln Cys Leu Gln
1 5 10 15

Gln Gly Trp

<210> SEQ ID NO 552
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 552

Val Trp Gly Thr Trp Lys Trp Asp Leu Leu Thr Lys Gln Tyr Leu Pro
1 5 10 15

Pro Gln Gln

<210> SEQ ID NO 553
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 553

Gly Trp Trp Glu Met Lys Trp Asp Leu Leu Thr Lys Gln Trp Tyr Arg
1 5 10 15

Pro Gln Gln

<210> SEQ ID NO 554
<211> LENGTH: 19
<212> TYPE: PRT
<213> ORGANISM: Artificial Sequence
<220> FEATURE:
<223> OTHER INFORMATION: Preferred TALL-1 Modulating Domains

```
<400> SEQUENCE: 554

Thr Ala Gln Gln Val Ser Lys Trp Asp Leu Leu Thr Lys Gln Trp Leu
1               5                   10                  15

Pro Leu Ala

<210> SEQ ID NO 555
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 555

Gln Leu Trp Gly Thr Lys Trp Asp Leu Leu Thr Lys Gln Tyr Ile Gln
1               5                   10                  15

Gln Ile Met

<210> SEQ ID NO 556
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 556

Trp Ala Thr Ser Gln Lys Trp Asp Leu Leu Thr Lys Gln Trp Val Gln
1               5                   10                  15

Gln Asn Met

<210> SEQ ID NO 557
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 557

Gln Gln Arg Gln Cys Ala Lys Trp Asp Leu Leu Thr Lys Gln Cys Val
1               5                   10                  15

Leu Phe Tyr

<210> SEQ ID NO 558
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 558

Lys Thr Thr Asp Cys Lys Trp Asp Leu Leu Thr Lys Gln Arg Ile Cys
1               5                   10                  15

Gln Gln Val

<210> SEQ ID NO 559
<211> LENGTH: 19
<212> TYPE: PRT
<213> ORGANISM: Artificial Sequence
<220> FEATURE:
<223> OTHER INFORMATION: Preferred T -continued

```
<400> SEQUENCE: 559

Leu Leu Cys Gln Gln Gly Lys Trp Asp Leu Leu Thr Lys Gln Cys Leu
1               5                   10                  15

Lys Leu Arg

<210> SEQ ID NO 560
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 560

Leu Met Trp Phe Trp Lys Trp Asp Leu Leu Thr Lys Gln Leu Val Pro
1               5                   10                  15

Thr Phe

<210> SEQ ID NO 561
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 561

Gln Gln Thr Trp Ala Trp Lys Trp Asp Leu Leu Thr Lys Gln Trp Ile
1               5                   10                  15

Gly Pro Met

<210> SEQ ID NO 562
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 562

Asn Lys Glu Leu Leu Lys Trp Asp Leu Leu Thr Lys Gln Cys Arg Gly
1               5                   10                  15

Arg Ser

<210> SEQ ID NO 563
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 563

Gly Gln Gln Lys Asp Leu Lys Trp Asp Leu Leu Thr Lys Gln Tyr Val
1               5                   10                  15

Arg Gln Ser

<210> SEQ ID NO 564
<211> LENGTH: 19
<212> TYPE: PRT
<213> ORGANISM: Artificial Sequence
<220> FEATURE:
<223> OTHER INFORMATION: Preferred TALL-1 Modulating Domains
```

-continued

```
<400> SEQUENCE: 564

Pro Lys Pro Cys Gln Gln Lys Trp Asp Leu Leu Thr Lys Gln Cys Leu
1               5                   10                  15

Gly Ser Val

<210> SEQ ID NO 565
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 565

Gly Gln Ile Gly Trp Lys Trp Asp Leu Leu Thr Lys Gln Trp Ile Gln
1               5                   10                  15

Gln Thr Arg

<210> SEQ ID NO 566
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 566

Val Trp Leu Asp Trp Lys Trp Asp Leu Leu Thr Lys Gln Trp Ile His
1               5                   10                  15

Pro Gln Gln

<210> SEQ ID NO 567
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 567

Gln Gln Glu Trp Glu Tyr Lys Trp Asp Leu Leu Thr Lys Gln Trp Gly
1               5                   10                  15

Trp Leu Arg

<210> SEQ ID NO 568
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 568

His Trp Asp Ser Trp Lys Trp Asp Leu Leu Thr Lys Gln Trp Val Val
1               5                   10                  15

Gln Gln Ala

<210> SEQ ID NO 569
<211> LENGTH: 19
<212> TYPE: PRT
<213> ORGANISM: Artificial Sequence
<220> FEATURE:
<223> OTHER INFORMATION: Preferred TALL-1 Modulating Domains
```

-continued

<400> SEQUENCE: 569

Thr Arg Pro Leu Gln Gln Lys Trp Asp Leu Leu Thr Lys Gln Trp Leu
1 5 10 15

Arg Val Gly

<210> SEQ ID NO 570
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 570

Ser Asp Gln Trp Gln Gln Lys Trp Asp Leu Leu Thr Lys Gln Trp Phe
1 5 10 15

Trp Asp Val

<210> SEQ ID NO 571
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 571

Gln Gln Gln Thr Phe Met Lys Trp Asp Leu Leu Thr Lys Gln Trp Ile
1 5 10 15

Arg Arg His

<210> SEQ ID NO 572
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 572

Gln Gln Gly Glu Cys Arg Lys Trp Asp Leu Leu Thr Lys Gln Cys Phe
1 5 10 15

Pro Gly Gln

<210> SEQ ID NO 573
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 573

Gly Gln Gln Met Gly Trp Arg Trp Asp Pro Leu Ile Lys Met Cys Leu
1 5 10 15

Gly Pro Ser

<210> SEQ ID NO 574
<211> LENGTH: 19
<212> TYPE: PRT
<213> ORGANISM: Artificial Sequence
<220> FEATURE:
<223> OTHER INFORMATION: Preferred TALL-1 Modulating Domains -continued

<400> SEQUENCE: 574

Gln Gln Leu Asp Gly Cys Lys Trp Asp Leu Leu Thr Lys Gln Lys Val
1 5 10 15

Cys Ile Pro

<210> SEQ ID NO 575
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 575

His Gly Tyr Trp Gln Gln Lys Trp Asp Leu Leu Thr Lys Gln Trp Val
1 5 10 15

Ser Ser Glu

<210> SEQ ID NO 576
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 576

His Gln Gln Gly Gln Cys Gly Trp Asp Leu Leu Thr Arg Ile Tyr Leu
1 5 10 15

Pro Cys His

<210> SEQ ID NO 577
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 577

Leu His Lys Ala Cys Lys Trp Asp Leu Leu Thr Lys Gln Cys Trp Pro
1 5 10 15

Met Gln Gln

<210> SEQ ID NO 578
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 578

Gly Pro Pro Gly Ser Val Trp Asp Leu Leu Thr Lys Ile Trp Ile Gln
1 5 10 15

Gln Thr Gly

<210> SEQ ID NO 579
<211> LENGTH: 19
<212> TYPE: PRT
<213> ORGANISM: Artificial Sequence
<220> FEATURE:
<223> OTHER INFORMATION: Preferred TALL-1 Modulating Domains -continued

```
<400> SEQUENCE: 579

Ile Thr Gln Gln Asp Trp Arg Phe Asp Thr Leu Thr Arg Leu Trp Leu
1               5                   10                  15

Pro Leu Arg

<210> SEQ ID NO 580
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 580

Gln Gln Gly Gly Phe Ala Ala Trp Asp Val Leu Thr Lys Met Trp Ile
1               5                   10                  15

Thr Val Pro

<210> SEQ ID NO 581
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 581

Gly His Gly Thr Pro Trp Trp Asp Ala Leu Thr Arg Ile Trp Ile Leu
1               5                   10                  15

Gly Val

<210> SEQ ID NO 582
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 582

Val Trp Pro Trp Gln Gln Lys Trp Asp Leu Leu Thr Lys Gln Phe Val
1               5                   10                  15

Phe Gln Asp

<210> SEQ ID NO 583
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 583

Trp Gln Gln Trp Ser Trp Lys Trp Asp Leu Leu Thr Arg Gln Tyr Ile
1               5                   10                  15

Ser Ser Ser

<210> SEQ ID NO 584
<211> LENGTH: 19
<212> TYPE: PRT
<213> ORGANISM: Artificial Sequence
<220> FEATURE:
<223> OTHER INFORMATION: Preferred TALL-1 Modulating Domains
```

-continued

```
<400> SEQUENCE: 584

Asn Gln Gln Thr Leu Trp Lys Trp Asp Leu Leu Thr Lys Gln Phe Ile
1 5 10 15

Thr Tyr Met

<210> SEQ ID NO 585
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 585

Pro Val Tyr Gln Gln Gly Trp Trp Asp Thr Leu Thr Lys Leu Tyr Ile
1 5 10 15

Trp Asp Gly

<210> SEQ ID NO 586
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 586

Trp Leu Asp Gly Gly Trp Arg Asp Pro Leu Ile Lys Arg Ser Val Gln
1 5 10 15

Gln Leu Gly

<210> SEQ ID NO 587
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 587

Gly His Gln Gln Gln Phe Lys Trp Asp Leu Leu Thr Lys Gln Trp Val
1 5 10 15

Gln Ser Asn

<210> SEQ ID NO 588
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 588

Gln Gln Arg Val Gly Gln Phe Trp Asp Val Leu Thr Lys Met Phe Ile
1 5 10 15

Thr Gly Ser

<210> SEQ ID NO 589
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 589

Gln Gln Ala Gln Gly Trp Ser Tyr Asp Ala Leu Ile Lys Thr Trp Ile
1               5                   10                  15

Arg Trp Pro

<210> SEQ ID NO 590
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 590

Gly Trp Met His Trp Lys Trp Asp Pro Leu Thr Lys Gln Gln Ala Leu
1               5                   10                  15

Pro Trp Met

<210> SEQ ID NO 591
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 591

Gly His Pro Thr Tyr Lys Trp Asp Leu Leu Thr Lys Gln Trp Ile Leu
1               5                   10                  15

Gln Gln Met

<210> SEQ ID NO 592
<211> LENGTH: 19
<212> TYPE: PRT
<213> ORGANISM: Artificial Sequence
<220> FEATURE:
<223> OTHER INFORMATION: Preferred TALL-1 Modulating Domains

<400> SEQUENCE: 592

Trp Asn Asn Trp Ser Leu Trp Asp Pro Leu Thr Lys Leu Trp Leu Gln
1 5 10 15

Gln Gln Asn

<210> SEQ ID NO 593
<211> LENGTH: 18
<212> TYPE: PRT
<213> ORGANISM: Artificial Sequence
<220> FEATURE:
<223> OTHER INFORMATION: Preferred TALL-1 Modulating Domains

<400> SEQUENCE: 593

Trp Gln Trp Gly Trp Lys Trp Asp Leu Leu Thr Lys Gln Trp Val Gln
1 5 10 15

Gln Gln

<210> SEQ ID NO 594
<211> LENGTH: 18
<212> TYPE: PRT
<213> ORGANISM: Artificial Sequence
<220> FEATURE:
<223> OTHER INFORMATION: Preferred TALL-1 Modulating Domains -continued

```
<400> SEQUENCE: 594

Gly Gln Met Gly Trp Arg Trp Asp Pro Leu Thr Lys Met Trp Leu Gly
1               5                   10                  15

Thr Ser

<210> SEQ ID NO 595
<211> LENGTH: 8
<212> TYPE: PRT
<213> ORGANISM: Artificial Sequence
<220> FEATURE:
<223> OTHER INFORMATION: Preferred linker

<400> SEQUENCE: 595

Gly Gly Gly Lys Gly Gly Gly Gly
1               5

<210> SEQ ID NO 596
<211> LENGTH: 8
<212> TYPE: PRT
<213> ORGANISM: Artificial Sequence
<220> FEATURE:
<223> OTHER INFORMATION: Preferred linker

<400> SEQUENCE: 596

Gly Gly Gly Asn Gly Ser Gly Gly
1               5

<210> SEQ ID NO 597
<211> LENGTH: 8
<212> TYPE: PRT
<213> ORGANISM: Artificial Sequence
<220> FEATURE:
<223> OTHER INFORMATION: Preferred linker

<400> SEQUENCE: 597

Gly Gly Gly Cys Gly Gly Gly Gly
1               5

<210> SEQ ID NO 598
<211> LENGTH: 5
<212> TYPE: PRT
<213> ORGANISM: Artificial Sequence
<220> FEATURE:
<223> OTHER INFORMATION: Preferred linker

<400> SEQUENCE: 598

Gly Pro Asn Gly Gly
1               5

<210> SEQ ID NO 599
<211> LENGTH: 228
<212> TYPE: PRT
<213> ORGANISM: Homo sapiens

<400> SEQUENCE: 599

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60
```

```
Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 600
<211> LENGTH: 275
<212> TYPE: PRT
<213> ORGANISM: Homo sapiens

<400> SEQUENCE: 600

Ala Gly Lys Ser Val Thr Cys His Val Lys His Tyr Thr Asn Pro Ser
1               5                   10                  15

Gln Asp Val Thr Val Pro Cys Pro Val Pro Ser Thr Pro Thr Pro
            20                  25                  30

Ser Pro Ser Thr Pro Pro Thr Pro Ser Pro Ser Cys Cys His Pro Arg
        35                  40                  45

Leu Ser Leu His Arg Pro Ala Leu Glu Asp Leu Leu Leu Gly Ser Glu
    50                  55                  60

Ala Asn Leu Thr Cys Thr Leu Thr Gly Leu Arg Asp Ala Ser Gly Val
65                  70                  75                  80

Thr Phe Thr Trp Thr Pro Ser Ser Gly Lys Ser Ala Val Gln Gly Pro
                85                  90                  95

Pro Glu Arg Asp Leu Cys Gly Cys Tyr Ser Val Ser Ser Val Leu Pro
            100                 105                 110

Gly Cys Ala Glu Pro Trp Asn His Gly Lys Thr Phe Thr Cys Thr Ala
        115                 120                 125

Ala Tyr Pro Glu Ser Lys Thr Pro Leu Thr Ala Thr Leu Ser Lys Ser
    130                 135                 140

Gly Asn Thr Phe Arg Pro Glu Val His Leu Leu Pro Pro Pro Ser Glu
145                 150                 155                 160

Glu Leu Ala Leu Asn Glu Leu Val Thr Leu Thr Cys Leu Ala Arg Gly
                165                 170                 175

Phe Ser Pro Lys Asp Val Leu Val Arg Trp Leu Gln Gly Ser Gln Glu
            180                 185                 190

Leu Pro Arg Glu Lys Tyr Leu Thr Trp Ala Ser Arg Gln Glu Pro Ser
        195                 200                 205
```

```
Gln Gly Thr Thr Thr Phe Ala Val Thr Ser Ile Leu Arg Val Ala Ala
            210                 215                 220
Glu Asp Trp Lys Lys Gly Asp Thr Phe Ser Cys Met Val Gly His Glu
225                 230                 235                 240
Ala Leu Pro Leu Ala Phe Thr Gln Lys Thr Ile Asp Arg Leu Ala Gly
                245                 250                 255
Lys Pro Thr His Val Asn Val Ser Val Val Met Ala Glu Val Asp Gly
            260                 265                 270
Thr Cys Tyr
        275

<210> SEQ ID NO 601
<211> LENGTH: 262
<212> TYPE: PRT
<213> ORGANISM: Homo sapiens

<400> SEQUENCE: 601

Asp Gly Lys Ser Val Thr Cys His Val Lys His Tyr Thr Asn Pro Ser
1               5                   10                  15
Gln Asp Val Thr Val Pro Cys Pro Val Pro Pro Pro Pro Cys Cys
            20                  25                  30
His Pro Arg Leu Ser Leu His Arg Pro Ala Leu Glu Asp Leu Leu Leu
            35                  40                  45
Gly Ser Glu Ala Asn Leu Thr Cys Thr Leu Thr Gly Leu Arg Asp Ala
50                  55                  60
Ser Gly Ala Thr Phe Thr Trp Thr Pro Ser Ser Gly Lys Ser Ala Val
65                  70                  75                  80
Gln Gly Pro Pro Glu Arg Asp Leu Cys Gly Cys Tyr Ser Val Ser Ser
            85                  90                  95
Val Leu Pro Gly Cys Ala Gln Pro Trp Asn His Gly Glu Thr Phe Thr
                100                 105                 110
Cys Thr Ala Ala His Pro Glu Leu Lys Thr Pro Leu Thr Ala Asn Ile
            115                 120                 125
Thr Lys Ser Gly Asn Thr Phe Arg Pro Glu Val His Leu Leu Pro Pro
            130                 135                 140
Pro Ser Glu Glu Leu Ala Leu Asn Glu Leu Val Thr Leu Thr Cys Leu
145                 150                 155                 160
Ala Arg Gly Phe Ser Pro Lys Asp Val Leu Val Arg Trp Leu Gln Gly
                165                 170                 175
Ser Gln Glu Leu Pro Arg Glu Lys Tyr Leu Thr Trp Ala Ser Arg Gln
            180                 185                 190
Glu Pro Ser Gln Gly Thr Thr Thr Phe Ala Val Thr Ser Ile Leu Arg
            195                 200                 205
Val Ala Ala Glu Asp Trp Lys Lys Gly Asp Thr Phe Ser Cys Met Val
210                 215                 220
Gly His Glu Ala Leu Pro Leu Ala Phe Thr Gln Lys Thr Ile Asp Arg
225                 230                 235                 240
Leu Ala Gly Lys Pro Thr His Val Asn Val Ser Val Val Met Ala Glu
                245                 250                 255
Val Asp Gly Thr Cys Tyr
            260

<210> SEQ ID NO 602
<211> LENGTH: 253
<212> TYPE: PRT
<213> ORGANISM: Homo sapiens
```

```
<400> SEQUENCE: 602

Glu Gly Lys Gln Val Gly Ser Gly Val Thr Thr Asp Gln Val Gln Ala
1               5                   10                  15

Glu Ala Lys Glu Ser Gly Pro Thr Thr Tyr Lys Val Thr Ser Thr Leu
            20                  25                  30

Thr Ile Lys Glu Asp His Arg Gly Leu Thr Phe Gln Gln Asn Ala Ser
        35                  40                  45

Ser Met Cys Val Pro Asp Gln Asp Thr Ala Ile Arg Val Phe Ala Ile
    50                  55                  60

Pro Pro Ser Phe Ala Ser Ile Phe Leu Thr Lys Ser Thr Lys Leu Thr
65                  70                  75                  80

Cys Leu Val Thr Asp Leu Thr Thr Tyr Asp Ser Val Thr Ile Ser Trp
                85                  90                  95

Asn Ser Gly Glu Arg Phe Thr Cys Thr Val Thr His Thr Asp Leu Pro
            100                 105                 110

Ser Pro Leu Lys Gln Thr Ile Ser Arg Pro Lys Gly Val Ala Leu His
        115                 120                 125

Arg Pro Asp Val Tyr Leu Leu Pro Pro Ala Arg Glu Gln Leu Asn Leu
    130                 135                 140

Arg Glu Ser Ala Thr Ile Thr Cys Leu Val Thr Gly Phe Ser Pro Ala
145                 150                 155                 160

Asp Val Phe Val Gln Trp Met Gln Arg Gly Gln Pro Leu Ser Pro Glu
                165                 170                 175

Lys Tyr Val Thr Ser Ala Pro Met Pro Glu Pro Gln Ala Pro Gly Arg
            180                 185                 190

Tyr Phe Ala His Ser Ile Leu Thr Val Ser Glu Glu Glu Trp Asn Thr
        195                 200                 205

Gly Glu Thr Tyr Thr Cys Val Ala His Asp Ala Leu Pro Asn Arg Val
    210                 215                 220

Thr Glu Arg Thr Val Asp Lys Ser Thr Gly Lys Pro Thr Leu Tyr Asn
225                 230                 235                 240

Val Ser Leu Val Met Ser Asp Thr Ala Gly Thr Cys Tyr
                245                 250

<210> SEQ ID NO 603
<211> LENGTH: 232
<212> TYPE: PRT
<213> ORGANISM: Homo sapiens

<400> SEQUENCE: 603

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 604
<211> LENGTH: 232
<212> TYPE: PRT
<213> ORGANISM: Homo sapiens

<400> SEQUENCE: 604

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 605
<211> LENGTH: 279
<212> TYPE: PRT
<213> ORGANISM: Homo sapiens

<400> SEQUENCE: 605

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Phe
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 606
<211> LENGTH: 228
<212> TYPE: PRT
<213> ORGANISM: Homo sapiens

<400> SEQUENCE: 606

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

-continued

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 607
<211> LENGTH: 229
<212> TYPE: PRT
<213> ORGANISM: Homo sapiens

<400> SEQUENCE: 607

Glu Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

-continued

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 608
<211> LENGTH: 253
<212> TYPE: PRT
<213> ORGANISM: Artificial Sequence
<220> FEATURE:
<223> OTHER INFORMATION: Consensus sequence.
<220> FEATURE:
<221> NAME/KEY: MISC_FEATURE
<222> LOCATION: (2)..(2)
<223> OTHER INFORMATION: Xaa is any amino acid or is absent.
<220> FEATURE:
<221> NAME/KEY: MISC_FEATURE
<222> LOCATION: (5)..(5)
<223> OTHER INFORMATION: Xaa is any amino acid or is absent.
<220> FEATURE:
<221> NAME/KEY: MISC_FEATURE
<222> LOCATION: (7)..(7)
<223> OTHER INFORMATION: Xaa is any amino acid or is absent.
<220> FEATURE:
<221> NAME/KEY: MISC_FEATURE
<222> LOCATION: (13)..(13)
<223> OTHER INFORMATION: Xaa is any amino acid or is absent.
<220> FEATURE:
<221> NAME/KEY: MISC_FEATURE
<222> LOCATION: (23)..(34)
<223> OTHER INFORMATION: Xaa is any amino acid or is absent.
<220> FEATURE:
<221> NAME/KEY: MISC_FEATURE
<222> LOCATION: (71)..(71)
<223> OTHER INFORMATION: Xaa is any amino acid or is absent.
<220> FEATURE:
<221> NAME/KEY: MISC_FEATURE
<222> LOCATION: (138)..(138)
<223> OTHER INFORMATION: Xaa is any amino acid or is absent.
<220> FEATURE:
<221> NAME/KEY: MISC_FEATURE
<222> LOCATION: (152)..(152)
<223> OTHER INFORMATION: Xaa is any amino acid or is absent.
<220> FEATURE:
<221> NAME/KEY: MISC_FEATURE
<222> LOCATION: (186)..(187)
<223> OTHER INFORMATION: Xaa is any amino acid or is absent.
<220> FEATURE:
<221> NAME/KEY: MISC_FEATURE
<222> LOCATION: (204)..(206)
<223> OTHER INFORMATION: Xaa is any amino acid or is absent.
<220> FEATURE:
<221> NAME/KEY: MISC_FEATURE
<222> LOCATION: (252)..(253)
<223> OTHER INFORMATION: Xaa is any amino acid or is absent.

<400> SEQUENCE: 608

Glu Xaa Lys Ser Xaa Asp Xaa Thr Val Pro Cys Pro Xaa Cys Pro Ala
1               5                   10                  15

Pro Glu Leu Leu Gly Gly Xaa Xaa Xaa Xaa Xaa Xaa Xaa Xaa Xaa Xaa
            20                  25                  30

Xaa Xaa Pro Ser Val Phe Leu Phe Pro Pro Lys Pro Lys Asp Thr Leu
        35                  40                  45

Met Ile Ser Arg Thr Pro Glu Val Thr Cys Val Val Val Asp Val Ser
    50                  55                  60

His Glu Asp Pro Glu Val Xaa Phe Asn Trp Tyr Val Asp Gly Val Glu
65                  70                  75                  80
```

```
Val His Asn Ala Lys Thr Lys Pro Arg Glu Glu Gln Phe Asn Ser Thr
                85                  90                  95

Tyr Arg Val Val Ser Val Leu Thr Val Leu His Gln Asp Trp Leu Asn
            100                 105                 110

Gly Lys Glu Tyr Lys Cys Lys Val Ser Asn Lys Ala Leu Pro Ala Pro
        115                 120                 125

Ile Glu Lys Thr Ile Ser Lys Ala Lys Xaa Gly Gln Pro Arg Glu Pro
    130                 135                 140

Gln Val Tyr Thr Leu Pro Pro Xaa Ser Arg Glu Glu Met Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Xaa Xaa Pro Glu Asn Asn Tyr
            180                 185                 190

Lys Thr Thr Pro Pro Met Leu Asp Ser Asp Gly Xaa Xaa Xaa Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys Xaa Xaa
                245                 250

<210> SEQ ID NO 609
<211> LENGTH: 183
<212> TYPE: PRT
<213> ORGANISM: Artificial Sequence
<220> FEATURE:
<223> OTHER INFORMATION: Amgen Fc sequence

<400> SEQUENCE: 609

Glu Gly Gly Gly Gly Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Ser Arg Trp Gln Gln Gly Asn Val Phe Ser
145                 150                 155                 160

Cys Ser Val Met His Glu Ala Leu His Asn His Tyr Thr Gln Lys Ser
                165                 170                 175

Leu Ser Leu Ser Pro Gly Lys
            180
```

```
<210> SEQ ID NO 610
<211> LENGTH: 205
<212> TYPE: PRT
<213> ORGANISM: Rattus rattus

<400> SEQUENCE: 610

Ser Val Phe Ile Phe Pro Pro Lys Thr Lys Asp Val Leu Thr Ile Thr
 1               5                  10                  15

Leu Thr Pro Lys Val Thr Cys Val Val Val Asp Ile Ser Gln Asn Asp
            20                  25                  30

Pro Glu Val Arg Phe Ser Trp Phe Ile Asp Asp Val Glu Val His Thr
        35                  40                  45

Ala Gln Thr His Ala Pro Glu Lys Gln Ser Asn Ser Thr Leu Arg Ser
    50                  55                  60

Val Ser Glu Leu Pro Ile Val His Arg Asp Trp Leu Asn Gly Lys Thr
65                  70                  75                  80

Phe Lys Cys Lys Val Asn Ser Gly Ala Phe Pro Ala Pro Ile Glu Lys
                85                  90                  95

Ser Ile Ser Lys Pro Glu Gly Thr Pro Arg Gly Pro Gln Val Tyr Thr
            100                 105                 110

Met Ala Pro Pro Lys Glu Glu Met Thr Gln Ser Gln Val Ser Ile Thr
        115                 120                 125

Cys Met Val Lys Gly Phe Tyr Pro Pro Asp Ile Tyr Thr Glu Trp Lys
130                 135                 140

Met Asn Gly Gln Pro Gln Glu Asn Tyr Lys Asn Thr Pro Pro Thr Met
145                 150                 155                 160

Asp Thr Asp Gly Ser Tyr Phe Leu Tyr Ser Lys Leu Asn Val Lys Lys
                165                 170                 175

Glu Thr Trp Gln Gln Gly Asn Thr Phe Thr Cys Ser Val Leu His Glu
            180                 185                 190

Gly Leu His Asn His His Thr Glu Lys Ser Leu Ser His
        195                 200                 205

<210> SEQ ID NO 611
<211> LENGTH: 205
<212> TYPE: PRT
<213> ORGANISM: Artificial Sequence
<220> FEATURE:
<223> OTHER INFORMATION: Consensus sequence.
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
```

```
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: MISC_FEATURE
<222> LOCATION: (69)..(69)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (86)..(88)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (101)..(102)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
```

```
<220> FEATURE:
<221> NAME/KEY: misc_feature
<222> LOCATION: (116)..(116)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (140)..(141)
<223> OTHER INFORMATION: Xaa can be any naturally occurring amino acid
<220> FEATURE:
<221> NAME/KEY: misc_feature
<222> LOCATION: (144)..(145)
<223> OTHER INFORMATION: Xaa can be any naturally occurring amino acid
<220> FEATURE:
<221> NAME/KEY: misc_feature
<222> LOCATION: (150)..(151)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (177)..(178)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid

<400> SEQUENCE: 611

Ser Val Phe Ile Phe Pro Pro Lys Xaa Lys Asp Xaa Leu Xaa Ile Ser
1               5                   10                  15

Xaa Thr Pro Xaa Val Thr Cys Val Val Val Asp Ile Ser Xaa Xaa Asp
                20                  25                  30

Pro Glu Val Lys Phe Xaa Trp Phe Ile Asp Xaa Val Glu Val His Xaa
            35                  40                  45

Ala Xaa Thr Xaa Xaa Xaa Glu Xaa Gln Xaa Asn Ser Thr Xaa Arg Xaa
    50                  55                  60

Val Ser Xaa Leu Xaa Ile Leu His Xaa Asp Trp Leu Asn Gly Lys Xaa
65                  70                  75                  80

Phe Lys Cys Lys Val Xaa Xaa Xaa Ala Xaa Pro Ala Pro Ile Glu Lys
                85                  90                  95

Ser Ile Ser Lys Xaa Xaa Gly Xaa Pro Arg Xaa Pro Gln Val Tyr Thr
            100                 105                 110
```

```
Leu Xaa Pro Xaa Lys Asp Glu Leu Thr Xaa Xaa Gln Val Ser Ile Thr
        115                 120                 125

Cys Leu Val Lys Gly Phe Tyr Pro Xaa Asp Ile Xaa Xaa Glu Trp Xaa
        130                 135                 140

Xaa Asn Gly Gln Pro Xaa Xaa Asn Tyr Lys Xaa Thr Pro Pro Xaa Leu
145                 150                 155                 160

Asp Ser Asp Gly Ser Phe Phe Leu Tyr Ser Lys Leu Xaa Val Xaa Lys
                165                 170                 175

Xaa Xaa Trp Gln Gln Gly Asn Xaa Phe Ser Cys Ser Val Leu His Glu
        180                 185                 190

Ala Leu His Asn His His Thr Xaa Lys Ser Leu Ser Xaa
        195                 200                 205

<210> SEQ ID NO 612
<211> LENGTH: 252
<212> TYPE: PRT
<213> ORGANISM: Artificial Sequence
<220> FEATURE:
<223> OTHER INFORMATION: Myostatin binding peptide sequence.

<400> SEQUENCE: 612

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Leu Ala Asp
    130                 135                 140

His Gly Gln Cys Ile Arg Trp Pro Trp Met Cys Pro Pro Glu Gly Trp
145                 150                 155                 160

Glu Gly Gly Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250
```

<210> SEQ ID NO 613
<211> LENGTH: 255
<212> TYPE: PRT
<213> ORGANISM: Artificial Sequence
<220> FEATURE:
<223> OTHER INFORMATION: Peptibody fusion sequence

<400> SEQUENCE: 613

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ala Gln Leu Ala Asp His Gly
225                 230                 235                 240

Gln Cys Ile Arg Trp Pro Trp Met Cys Pro Pro Glu Gly Trp Glu
                245                 250                 255
```

<210> SEQ ID NO 614
<211> LENGTH: 9
<212> TYPE: PRT
<213> ORGANISM: Artificial Sequence
<220> FEATURE:
<223> OTHER INFORMATION: Peptibody fusion sequence

<400> SEQUENCE: 614

```
Lys Ser Arg Trp Gln Gln Gly Asn Ile
1               5
```

<210> SEQ ID NO 615
<211> LENGTH: 252
<212> TYPE: PRT
<213> ORGANISM: Artificial Sequence
<220> FEATURE:
<223> OTHER INFORMATION: EPO-mimetic peptide

<400> SEQUENCE: 615

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gly Gly Thr
130                 135                 140

Tyr Ser Cys His Phe Gly Pro Leu Thr Trp Val Cys Lys Pro Gln Gly
145                 150                 155                 160

Gly Gly Gly Thr Lys Asn Gln Val Ser Leu Thr Cys Leu Val Lys Gly
            165                 170                 175

Phe Tyr Pro Ser Asp Ile Ala Val Glu Trp Glu Ser Asn Gly Gln Pro
        180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250
```

<210> SEQ ID NO 616
<211> LENGTH: 246
<212> TYPE: PRT
<213> ORGANISM: Artificial Sequence
<220> FEATURE:
<223> OTHER INFORMATION: TPO-mimetic peptide sequences

<400> SEQUENCE: 616

```
Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95
```

```
Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Gly Gly Ile Glu Gly
        130                 135                 140

Pro Thr Leu Arg Gln Trp Leu Ala Ala Arg Ala Gly Gly Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 617
<211> LENGTH: 269
<212> TYPE: PRT
<213> ORGANISM: Artificial Sequence
<220> FEATURE:
<223> OTHER INFORMATION: TPO-mimetic peptide sequences

<400> SEQUENCE: 617

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205
```

```
Met His Glu Ala Leu His Asn His Tyr Thr Gln Lys Ser Leu Ser Leu
        210                 215                 220
Ser Pro Gly Lys Gly Gly Gly Gly Ile Glu Gly Pro Thr Leu Arg
225                 230                 235                 240
Gln Trp Leu Ala Ala Arg Ala Gly Gly Gly Gly Gly Gly Gly Ile
                245                 250                 255
Glu Gly Pro Thr Leu Arg Gln Trp Leu Ala Ala Arg Ala
                260                 265

<210> SEQ ID NO 618
<211> LENGTH: 246
<212> TYPE: PRT
<213> ORGANISM: Artificial Sequence
<220> FEATURE:
<223> OTHER INFORMATION: Ang-2 binding peptide sequence

<400> SEQUENCE: 618

Met Asp Lys Thr His Thr Cys Pro Pro Cys Pro Ala Pro Glu Leu Leu
1               5                   10                  15
Gly Gly Pro Ser Val Phe Leu Phe Pro Pro Lys Pro Lys Asp Thr Leu
                20                  25                  30
Met Ile Ser Arg Thr Pro Glu Val Thr Cys Val Val Val Asp Val Ser
            35                  40                  45
His Glu Asp Pro Glu Val Lys Phe Asn Trp Tyr Val Asp Gly Val Glu
        50                  55                  60
Val His Asn Ala Lys Thr Lys Pro Arg Glu Glu Gln Tyr Asn Ser Thr
65                  70                  75                  80
Tyr Arg Val Val Ser Val Leu Thr Val Leu His Gln Asp Trp Leu Asn
                85                  90                  95
Gly Lys Glu Tyr Lys Cys Lys Val Ser Asn Lys Ala Leu Pro Ala Pro
                100                 105                 110
Ile Glu Lys Thr Ile Ser Lys Ala Lys Gly Gln Pro Arg Glu Pro Gln
            115                 120                 125
Val Tyr Thr Leu Pro Pro Ser Arg Asp Glu Leu Gly Gly Gln Glu Glu
        130                 135                 140
Cys Glu Trp Asp Pro Trp Thr Cys Glu His Met Gly Gly Thr Lys Asn
145                 150                 155                 160
Gln Val Ser Leu Thr Cys Leu Val Lys Gly Phe Tyr Pro Ser Asp Ile
                165                 170                 175
Ala Val Glu Trp Glu Ser Asn Gly Gln Pro Glu Asn Asn Tyr Lys Thr
                180                 185                 190
Thr Pro Pro Val Leu Asp Ser Asp Gly Ser Phe Phe Leu Tyr Ser Lys
            195                 200                 205
Leu Thr Val Asp Lys Ser Arg Trp Gln Gln Gly Asn Val Phe Ser Cys
        210                 215                 220
Ser Val Met His Glu Ala Leu His Asn His Tyr Thr Gln Lys Ser Leu
225                 230                 235                 240
Ser Leu Ser Pro Gly Lys
                245

<210> SEQ ID NO 619
<211> LENGTH: 251
<212> TYPE: PRT
<213> ORGANISM: Artificial Sequence
<220> FEATURE:
<223> OTHER INFORMATION: Polypeptide capable of binding to Ang-2
```

```
<400> SEQUENCE: 619

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Gly Gly Gly Gly Ala Gln Gln Glu Glu Cys Glu
225                 230                 235                 240

Trp Asp Pro Trp Thr Cys Glu His Met Leu Glu
                245                 250

<210> SEQ ID NO 620
<211> LENGTH: 9
<212> TYPE: PRT
<213> ORGANISM: Homo sapiens

<400> SEQUENCE: 620

Lys Ser Arg Trp Gln Glu Gly Asn Val
1               5

<210> SEQ ID NO 621
<211> LENGTH: 2
<212> TYPE: PRT
<213> ORGANISM: Homo sapiens

<400> SEQUENCE: 621

Pro Pro
1

<210> SEQ ID NO 622
<211> LENGTH: 8
<212> TYPE: PRT
<213> ORGANISM: Homo sapiens
```

```
<400> SEQUENCE: 622

Asp Val Ser His Glu Asp Pro Glu
1               5

<210> SEQ ID NO 623
<211> LENGTH: 3
<212> TYPE: PRT
<213> ORGANISM: Homo sapiens

<400> SEQUENCE: 623

Ser His Glu
1

<210> SEQ ID NO 624
<211> LENGTH: 4
<212> TYPE: PRT
<213> ORGANISM: Homo sapiens

<400> SEQUENCE: 624

Val His Asn Ala
1

<210> SEQ ID NO 625
<211> LENGTH: 7
<212> TYPE: PRT
<213> ORGANISM: Homo sapiens

<400> SEQUENCE: 625

Glu Glu Gln Tyr Asn Ser Thr
1               5

<210> SEQ ID NO 626
<211> LENGTH: 3
<212> TYPE: PRT
<213> ORGANISM: Homo sapiens

<400> SEQUENCE: 626

Tyr Asn Ser
1

<210> SEQ ID NO 627
<211> LENGTH: 11
<212> TYPE: PRT
<213> ORGANISM: Homo sapiens

<400> SEQUENCE: 627

Val Leu His Gln Asp Trp Leu Asn Gly Lys Glu
1               5                   10

<210> SEQ ID NO 628
<211> LENGTH: 22
<212> TYPE: PRT
<213> ORGANISM: Homo sapiens

<400> SEQUENCE: 628

Asn Lys Ala Leu Pro Ala Pro Ile Glu Lys Thr Ile Ser Lys Ala Lys
1               5                   10                  15

Gly Gln Pro Arg Glu Pro
            20

<210> SEQ ID NO 629
<211> LENGTH: 3
<212> TYPE: PRT
<213> ORGANISM: Homo sapiens
```

-continued

<400> SEQUENCE: 629

Asn Lys Ala
1

<210> SEQ ID NO 630
<211> LENGTH: 5
<212> TYPE: PRT
<213> ORGANISM: Homo sapiens

<400> SEQUENCE: 630

Asp Glu Leu Thr Lys
1               5

<210> SEQ ID NO 631
<211> LENGTH: 3
<212> TYPE: PRT
<213> ORGANISM: Homo sapiens

<400> SEQUENCE: 631

Leu Thr Lys
1

<210> SEQ ID NO 632
<211> LENGTH: 7
<212> TYPE: PRT
<213> ORGANISM: Homo sapiens

<400> SEQUENCE: 632

Asn Gly Gln Pro Glu Asn Asn
1               5

<210> SEQ ID NO 633
<211> LENGTH: 3
<212> TYPE: PRT
<213> ORGANISM: Homo sapiens

<400> SEQUENCE: 633

Glu Asn Asn
1

<210> SEQ ID NO 634
<211> LENGTH: 11
<212> TYPE: PRT
<213> ORGANISM: Homo sapiens

<400> SEQUENCE: 634

Thr Thr Pro Pro Val Leu Asp Ser Asp Gly Ser
1               5                   10

<210> SEQ ID NO 635
<211> LENGTH: 5
<212> TYPE: PRT
<213> ORGANISM: Homo sapiens

<400> SEQUENCE: 635

Val Leu Asp Ser Asp
1               5

<210> SEQ ID NO 636
<211> LENGTH: 9
<212> TYPE: PRT
<213> ORGANISM: Homo sapiens -continued

<400> SEQUENCE: 636

Lys Ser Arg Trp Gln Gln Gly Asn Val
1               5

<210> SEQ ID NO 637
<211> LENGTH: 3
<212> TYPE: PRT
<213> ORGANISM: Homo sapiens

<400> SEQUENCE: 637

Gln Gly Asn
1

<210> SEQ ID NO 638
<211> LENGTH: 8
<212> TYPE: PRT
<213> ORGANISM: Homo sapiens

<400> SEQUENCE: 638

Asp Val Ser Gln Glu Asp Pro Glu
1               5

<210> SEQ ID NO 639
<211> LENGTH: 7
<212> TYPE: PRT
<213> ORGANISM: Homo sapiens

<400> SEQUENCE: 639

Glu Glu Gln Phe Asn Ser Thr
1               5

<210> SEQ ID NO 640
<211> LENGTH: 11
<212> TYPE: PRT
<213> ORGANISM: Homo sapiens

<400> SEQUENCE: 640

Val Val His Gln Asp Trp Leu Asn Gly Lys Glu
1               5                   10

<210> SEQ ID NO 641
<211> LENGTH: 22
<212> TYPE: PRT
<213> ORGANISM: Homo sapiens

<400> SEQUENCE: 641

Asn Lys Ala Leu Pro Ala Pro Ile Glu Lys Thr Ile Ser Lys Thr Lys
1               5                   10                  15

Gly Gln Pro Arg Glu Pro
            20

<210> SEQ ID NO 642
<211> LENGTH: 22
<212> TYPE: PRT
<213> ORGANISM: Homo sapiens

<400> SEQUENCE: 642

Asn Lys Gly Leu Pro Ala Pro Ile Glu Lys Thr Ile Ser Lys Thr Lys
1               5                   10                  15

Gly Gln Pro Arg Glu Pro
            20

```
<210> SEQ ID NO 643
<211> LENGTH: 18
<212> TYPE: PRT
<213> ORGANISM: Homo sapiens

<400> SEQUENCE: 643

Asn Lys Gly Leu Pro Ser Ser Ile Glu Lys Ala Lys Gly Gln Pro Arg
1               5                   10                  15

Glu Pro

<210> SEQ ID NO 644
<211> LENGTH: 5
<212> TYPE: PRT
<213> ORGANISM: Homo sapiens

<400> SEQUENCE: 644

Glu Glu Met Thr Lys
1               5

<210> SEQ ID NO 645
<211> LENGTH: 7
<212> TYPE: PRT
<213> ORGANISM: Homo sapiens

<400> SEQUENCE: 645

Ser Gly Gln Pro Glu Asn Asn
1               5

<210> SEQ ID NO 646
<211> LENGTH: 11
<212> TYPE: PRT
<213> ORGANISM: Homo sapiens

<400> SEQUENCE: 646

Thr Thr Pro Pro Met Leu Asp Ser Asp Gly Ser
1               5                   10

<210> SEQ ID NO 647
<211> LENGTH: 14
<212> TYPE: PRT
<213> ORGANISM: Artificial Sequence
<220> FEATURE:
<223> OTHER INFORMATION: Myostatin binding peptide sequence

<400> SEQUENCE: 647

Lys Asp Lys Cys Lys Met Trp His Trp Met Cys Lys Pro Pro
1               5                   10

<210> SEQ ID NO 648
<211> LENGTH: 246
<212> TYPE: PRT
<213> ORGANISM: Artificial Sequence
<220> FEATURE:
<223> OTHER INFORMATION: Preferred embodiments

<400> SEQUENCE: 648

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60
```

```
Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Thr Tyr Ser Cys
    130                 135                 140

His Phe Gly Pro Leu Thr Trp Val Cys Lys Pro Gln Gly Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 649
<211> LENGTH: 248
<212> TYPE: PRT
<213> ORGANISM: Artificial Sequence
<220> FEATURE:
<223> OTHER INFORMATION: Preferred embodiments

<400> SEQUENCE: 649

Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
 65                  70                  75                  80

Tyr Arg Val Val Ser Val Leu Thr Val Leu His Gln Asp Trp Leu Asn
                 85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Thr Tyr Ser
    130                 135                 140

Cys His Phe Gly Pro Leu Thr Trp Val Cys Lys Pro Gln Gly Gly Thr
145                 150                 155                 160

Lys Asn Gln Val Ser Leu Thr Cys Leu Val Lys Gly Phe Tyr Pro Ser
                165                 170                 175
```

-continued

Asp Ile Ala Val Glu Trp Glu Ser Asn Gly Gln Pro Glu Asn Asn Tyr
            180                 185                 190

Lys Thr Thr Pro Pro Val Leu Asp Ser Asp Gly Ser Phe Phe Leu Tyr
        195                 200                 205

Ser Lys Leu Thr Val Asp Lys Ser Arg Trp Gln Gln Gly Asn Val Phe
    210                 215                 220

Ser Cys Ser Val Met His Glu Ala Leu His Asn His Tyr Thr Gln Lys
225                 230                 235                 240

Ser Leu Ser Leu Ser Pro Gly Lys
            245

<210> SEQ ID NO 650
<211> LENGTH: 250
<212> TYPE: PRT
<213> ORGANISM: Artificial Sequence
<220> FEATURE:
<223> OTHER INFORMATION: Preferred embodiments

<400> SEQUENCE: 650

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gly Thr Tyr
    130                 135                 140

Ser Cys His Phe Gly Pro Leu Thr Trp Val Cys Lys Pro Gln Gly Gly
145                 150                 155                 160

Gly Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys
                245                 250

<210> SEQ ID NO 651
<211> LENGTH: 252
<212> TYPE: PRT
<213> ORGANISM: Artificial Sequence

```
<220> FEATURE:
<223> OTHER INFORMATION: Preferred embodiments

<400> SEQUENCE: 651

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Gly Gly Gly Gly Thr
        130                 135                 140

Tyr Ser Cys His Phe Gly Pro Leu Thr Trp Val Cys Lys Pro Gln Gly
145                 150                 155                 160

Gly Gly Gly Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
                180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
        210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 652
<211> LENGTH: 252
<212> TYPE: PRT
<213> ORGANISM: Artificial Sequence
<220> FEATURE:
<223> OTHER INFORMATION: Preferred embodiments

<400> SEQUENCE: 652

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80
```

```
Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gly Gly Thr
130                 135                 140

Tyr Ser Ala His Phe Gly Pro Leu Thr Trp Val Ala Lys Pro Gln Gly
145                 150                 155                 160

Gly Gly Gly Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 653
<211> LENGTH: 254
<212> TYPE: PRT
<213> ORGANISM: Artificial Sequence
<220> FEATURE:
<223> OTHER INFORMATION: Preferred embodiments

<400> SEQUENCE: 653

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gln Gly Tyr
130                 135                 140

Cys Asp Glu Gly Pro Thr Leu Lys Gln Trp Leu Val Cys Leu Gly Leu
145                 150                 155                 160

Gln His Ser Gly Gly Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190
```

Gln Pro Glu Asn Asn Tyr Lys Thr Thr Pro Pro Val Leu Asp Ser Asp
            195                 200                 205

Gly Ser Phe Phe Leu Tyr Ser Lys Leu Thr Val Asp Lys Ser Arg Trp
210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 654
<211> LENGTH: 254
<212> TYPE: PRT
<213> ORGANISM: Artificial Sequence
<220> FEATURE:
<223> OTHER INFORMATION: Preferred embodiments

<400> SEQUENCE: 654

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gln Gly Tyr
    130                 135                 140

Ala Asp Glu Gly Pro Thr Leu Lys Gln Trp Leu Val Ala Leu Gly Leu
145                 150                 155                 160

Gln His Ser Gly Gly Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly Lys
                245                 250

<210> SEQ ID NO 655
<211> LENGTH: 263
<212> TYPE: PRT
<213> ORGANISM: Artificial Sequence
<220> FEATURE:
<223> OTHER INFORMATION: Preferred embodiments -continued

```
<400> SEQUENCE: 655

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly His Ala Glu
    130                 135                 140

Gly Thr Phe Thr Ser Asp Val Ser Ser Tyr Leu Glu Gly Gln Ala Ala
145                 150                 155                 160

Lys Glu Phe Ile Ala Trp Leu Val Lys Gly Arg Gly Gly Thr Lys
                165                 170                 175

Asn Gln Val Ser Leu Thr Cys Leu Val Lys Gly Phe Tyr Pro Ser Asp
            180                 185                 190

Ile Ala Val Glu Trp Glu Ser Asn Gly Gln Pro Glu Asn Asn Tyr Lys
        195                 200                 205

Thr Thr Pro Pro Val Leu Asp Ser Asp Gly Ser Phe Phe Leu Tyr Ser
    210                 215                 220

Lys Leu Thr Val Asp Lys Ser Arg Trp Gln Gln Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Pro Gly Lys
            260

<210> SEQ ID NO 656
<211> LENGTH: 267
<212> TYPE: PRT
<213> ORGANISM: Artificial Sequence
<220> FEATURE:
<223> OTHER INFORMATION: Preferred embodiments

<400> SEQUENCE: 656

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80
```

```
Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gly His
130                 135                 140

Ala Glu Gly Thr Phe Thr Ser Asp Val Ser Ser Tyr Leu Glu Gly Gln
145                 150                 155                 160

Ala Ala Lys Glu Phe Ile Ala Trp Leu Val Lys Gly Arg Gly Gly Gly
                165                 170                 175

Gly Gly Thr Lys Asn Gln Val Ser Leu Thr Cys Leu Val Lys Gly Phe
            180                 185                 190

Tyr Pro Ser Asp Ile Ala Val Glu Trp Glu Ser Asn Gly Gln Pro Glu
        195                 200                 205

Asn Asn Tyr Lys Thr Thr Pro Pro Val Leu Asp Ser Asp Gly Ser Phe
210                 215                 220

Phe Leu Tyr Ser Lys Leu Thr Val Asp Lys Ser Arg Trp Gln Gln Gly
225                 230                 235                 240

Asn Val Phe Ser Cys Ser Val Met His Glu Ala Leu His Asn His Tyr
                245                 250                 255

Thr Gln Lys Ser Leu Ser Leu Ser Pro Gly Lys
            260                 265

<210> SEQ ID NO 657
<211> LENGTH: 246
<212> TYPE: PRT
<213> ORGANISM: Artificial Sequence
<220> FEATURE:
<223> OTHER INFORMATION: Preferred embodiments

<400> SEQUENCE: 657

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gln Glu Glu
        130                 135                 140

Cys Glu Trp Asp Pro Trp Thr Cys Glu His Met Gly Gly Thr Lys Asn
145                 150                 155                 160

Gln Val Ser Leu Thr Cys Leu Val Lys Gly Phe Tyr Pro Ser Asp Ile
                165                 170                 175
```

```
Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 658
<211> LENGTH: 258
<212> TYPE: PRT
<213> ORGANISM: Artificial Sequence
<220> FEATURE:
<223> OTHER INFORMATION: Preferred embodiments

<400> SEQUENCE: 658

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Gly Gly Gly Gly Gly
    130                 135                 140

Asp Trp Thr Gly Asp Met Gln Val Lys Phe Asp Ala Met Met Phe Gly
145                 150                 155                 160

Pro Arg Lys Glu Gly Gly Gly Gly Thr Lys Asn Gln Val Ser Leu
            165                 170                 175

Thr Cys Leu Val Lys Gly Phe Tyr Pro Ser Asp Ile Ala Val Glu Trp
        180                 185                 190

Glu Ser Asn Gly Gln Pro Glu Asn Asn Tyr Lys Thr Thr Pro Pro Val
    195                 200                 205

Leu Asp Ser Asp Gly Ser Phe Phe Leu Tyr Ser Lys Leu Thr Val Asp
    210                 215                 220

Lys Ser Arg Trp Gln Gln Gly Asn Val Phe Ser Cys Ser Val Met His
225                 230                 235                 240

Glu Ala Leu His Asn His Tyr Thr Gln Lys Ser Leu Ser Leu Ser Pro
                245                 250                 255

Gly Lys
```

-continued

```
<210> SEQ ID NO 659
<211> LENGTH: 281
<212> TYPE: PRT
<213> ORGANISM: Artificial Sequence
<220> FEATURE:
<223> OTHER INFORMATION: Preferred embodiments

<400> SEQUENCE: 659

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
                100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Gly Gly Gly Gly Gly
    130                 135                 140

Asp Trp Thr Gly Asp Met Gln Val Lys Phe Asp Ala Met Met Phe Gly
145                 150                 155                 160

Pro Arg Lys Glu Gly Gly Gly Asp Trp Thr Gly Asp Met Gln Val Lys
                165                 170                 175

Phe Asp Ala Met Met Phe Gly Pro Arg Lys Glu Gly Gly Gly Gly Gly
                180                 185                 190

Thr Lys Asn Gln Val Ser Leu Thr Cys Leu Val Lys Gly Phe Tyr Pro
            195                 200                 205

Ser Asp Ile Ala Val Glu Trp Glu Ser Asn Gly Gln Pro Glu Asn Asn
    210                 215                 220

Tyr Lys Thr Thr Pro Pro Val Leu Asp Ser Asp Gly Ser Phe Phe Leu
225                 230                 235                 240

Tyr Ser Lys Leu Thr Val Asp Lys Ser Arg Trp Gln Gln Gly Asn Val
                245                 250                 255

Phe Ser Cys Ser Val Met His Glu Ala Leu His Asn His Tyr Thr Gln
                260                 265                 270

Lys Ser Leu Ser Leu Ser Pro Gly Lys
                275                 280
```

MODIFIED FC MOLECULES

This application is a continuation of U.S. Non-provisional application Ser. No. 11/234,731, filed Sep. 23, 2005, now U.S. Pat. No. 7,422,778, which claims the benefit of U.S. Provisional Application No. 60/612,680, filed Sep. 24, 2004, both of which are hereby incorporated by reference in their entireties.

BACKGROUND OF THE INVENTION

The success of the drug Enbrel® (etanercept) brought to fruition the promise of therapeutic agents modified with the constant domain of an antibody. Antibodies comprise two functionally independent parts, a variable domain known as "Fab", which binds antigen, and a constant domain known as "Fc", which links to such effector functions as complement activation and attack by phagocytic cells. An Fc has a long serum half-life, whereas an Fab is short-lived. Capon et al. (1989), *Nature* 337: 525-31. When constructed together with a therapeutic protein, an Fc domain can provide longer half-life or incorporate such functions as Fc receptor binding, protein A binding, complement fixation and perhaps even placental transfer. Id. Table 1 summarizes use of Fc fusion proteins known in the art.

Phage display peptide libraries have emerged as a powerful method in identifying such peptide agonists and antagonists. See, for example, Scott et al. (1990), *Science* 249: 386; Devlin et al. (1990), *Science* 249: 404; U.S. Pat. No. 5,223,409, issued Jun. 29, 1993; U.S. Pat. No. 5,733,731, issued Mar. 31, 1998; U.S. Pat. No. 5,498,530, issued Mar. 12, 1996; U.S. Pat. No. 5,432,018, issued Jul. 11, 1995; U.S. Pat. No. 5,338,665, issued Aug. 16, 1994; U.S. Pat. No. 5,922,545, issued Jul. 13, 1999; WO 96/40987, published Dec. 19, 1996; and WO 98/15833, published Apr. 16, 1998 (each of which is incorporated by reference). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. See, e.g., Cwirla et al. (1997), *Science* 276: 1696-9, in which two distinct families were identified. The peptide sequences may also suggest which residues may be safely replaced by alanine scanning or by mutagenesis at the DNA level. Mutagenesis libraries may be created and screened to

TABLE 1

Fc fusion with therapeutic proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al. (1995), J. Immunol. 154: 5590-600 |
| IgG1 | TNF receptor | septic shock | Fisher et al. (1996), N. Engl. J. Med. 334: 1697-1702; Van Zee, K. et al. (1996), J. Immunol. 156: 2221-30 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al. (1989), Nature 337: 525-31 |
| IgG1, IgG3 | N-terminus of IL-2 | anti-cancer, antiviral | Harvill et al. (1995), Immunotech. 1: 95-105 |
| IgG1 | C-terminus of OPG | osteoarthritis; bone density | WO 97/23614, published Jul. 3, 1997 |
| IgG1 | N-terminus of leptin | anti-obesity | WO 98/28427, filed Dec. 11, 1997 |
| Human Ig Cγ1 | CTLA-4 | autoimmune disorders | Linsley (1991), J. Exp. Med. 174: 561-9 |

A much different approach to development of therapeutic agents is peptide library screening. The interaction of a protein ligand with its receptor often takes place at a relatively large interface. However, as demonstrated for human growth hormone and its receptor, only a few key residues at the interface contribute to most of the binding energy. Clackson et al. (1995), *Science* 267: 383-6. The bulk of the protein ligand merely displays the binding epitopes in the right topology or serves functions unrelated to binding. Thus, molecules of only "peptide" length (2 to 40 amino acids) can bind to the receptor protein of a given large protein ligand. Such peptides may mimic the bioactivity of the large protein ligand ("peptide agonists") or, through competitive binding, inhibit the bioactivity of the large protein ligand ("peptide antagonists").

further optimize the sequence of the best binders. Lowman (1997), *Ann. Rev. Biophys. Biomol. Struct.* 26: 401-24.

Other methods compete with phage display in peptide research. A peptide library can be fused to the carboxyl terminus of the lac repressor and expressed in *E. coli*. Another *E. coli*-based method allows display on the cell's outer membrane by fusion with a peptidoglycan-associated lipoprotein (PAL). Hereinafter, these and related methods are collectively referred to as "*E. coli* display." Another biological approach to screening soluble peptide mixtures uses yeast for expression and secretion. See Smith et al. (1993), *Mol. Pharmacol.* 43: 741-8. Hereinafter, the method of Smith et al. and related methods are referred to as "yeast-based screening." In another method, translation of random RNA is halted prior to ribosome release, resulting in a library of polypeptides with their associated RNA still attached. Hereinafter, this and related methods are collectively referred to as "ribosome display." Other methods employ chemical linkage of peptides to RNA; see, for example, Roberts & Szostak (1997), *Proc. Natl. Acad. Sci. USA* 94: 12297-303. Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells & Lowman (1992), *Curr. Opin. Biotechnol.* 3: 355-62.

In the case of known bioactive peptides, rational design of peptide ligands with favorable therapeutic properties can be completed. In such an approach, one makes stepwise changes to a peptide sequence and determines the effect of the substitution upon bioactivity or a predictive biophysical property of the peptide (e.g., solution structure). Hereinafter, these techniques are collectively referred to as "rational design." In one such technique, one makes a series of peptides in which one replaces a single residue at a time with alanine. This technique is commonly referred to as an "alanine walk" or an "alanine scan." When two residues (contiguous or spaced apart) are replaced, it is referred to as a "double alanine walk." The resultant amino acid substitutions can be used alone or in combination to result in a new peptide entity with favorable therapeutic properties.

Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed. See, e.g., Takasaki et al. (1997), *Nature Biotech.* 15: 1266-70. Hereinafter, these and related methods are referred to as "protein structural analysis." These analytical methods may also be used to investigate the interaction between a receptor protein and peptides selected by phage display, which may suggest further modification of the peptides to increase binding affinity.

Conceptually, one may discover peptide mimetics of any protein using phage display and the other methods mentioned above. These methods have been used for epitope mapping, for identification of critical amino acids in protein-protein interactions, and as leads for the discovery of new therapeutic agents. E.g., Cortese et al. (1996), *Curr. Opin. Biotech.* 7: 616-21. Peptide libraries are now being used most often in immunological studies, such as epitope mapping. Kreeger (1996), *The Scientist* 10(13): 19-20.

Of particular interest here is use of peptide libraries and other techniques in the discovery of pharmacologically active peptides. A number of such peptides identified in the art are summarized in Table 2. The peptides are described in the listed publications, each of which is hereby incorporated by reference. The pharmacologic activity of the peptides is described, and in many instances is followed by a shorthand term therefore in parentheses. Some of these peptides have been modified (e.g., to form C-terminally cross-linked dimers). Typically, peptide libraries were screened for binding to a receptor for a pharmacologically active protein (e.g., EPO receptor). In at least one instance (CTLA4), the peptide library was screened for binding to a monoclonal antibody.

TABLE 2

Pharmacologically active peptides

| Form of peptide | Binding partner/ protein of interest[a] | Pharmacologic activity | Reference |
| --- | --- | --- | --- |
| intrapeptide disulfide-bonded | EPO receptor | EPO-mimetic | Wrighton et al. (1996), Science 273: 458-63; U.S. Pat. No. 5,773,569, issued Jun. 30, 1998 to Wrighton et al. |
| C-terminally cross-linked dimer | EPO receptor | EPO-mimetic | Livnah et al. (1996), Science 273: 464-71; Wrighton et al. (1997), Nature Biotechnology 15: 1261-5; International patent application WO 96/40772, published Dec. 19, 1996 |
| linear | EPO receptor | EPO-mimetic | Naranda et al. (1999), Proc. Natl. Acad. Sci. USA, 96: 7569-74; WO 99/47151, published Sep. 23, 1999 |
| linear; C-terminally cross-linked dimer | c-Mpl | TPO-mimetic | Cwirla et al.(1997) Science 276: 1696-9; U.S. Pat. No. 5,869,451, issued Feb. 9, 1999; WO 00/24770, published May 4, 2000; U.S. Pat. App. No. 2003/0176352, published Sept. 18, 2003; WO 03/031589, published Apr. 17, 2003 |

TABLE 2-continued

Pharmacologically active peptides

| Form of peptide | Binding partner/ protein of interest[a] | Pharmacologic activity | Reference |
|---|---|---|---|
| disulfide-linked dimer | | stimulation of hematopoiesis ("G-CSF-mimetic") | Paukovits et al. (1984), Hoppe-Seylers Z. Physiol. Chem. 365: 303-11; Laerum et al. (1988), Exp. Hemat. 16: 274-80 |
| alkylene-linked dimer | | G-CSF-mimetic | Bhatnagar et al. (1996), J. Med. Chem. 39: 3814-9; Cuthbertson et al. (1997), J. Med. Chem. 40: 2876-82; King et al. (1991), Exp. Hematol. 19: 481; King et al. (1995), Blood 86 (Suppl. 1): 309a |
| linear | IL-1 receptor | inflammatory and autoimmune diseases ("IL-1 antagonist" or "IL-1ra-mimetic") | U.S. Pat. No. 5,608,035; U.S. Pat. No. 5,786,331; U.S. Pat. No. 5,880,096; Yanofsky et al. (1996), Proc. Natl. Acad. Sci. 93: 7381-6; Akeson et al. (1996), J. Biol. Chem. 271: 30517-23; Wiekzorek et al. (1997), Pol. J. Pharmacol. 49: 107-17; Yanofsky (1996), PNAs, 93: 7381-7386. |
| linear | Facteur thymique serique (FTS) | stimulation of lymphocytes ("FTS-mimetic") | Inagaki-Ohara et al. (1996), Cellular Immunol. 171: 30-40; Yoshida (1984), Int. J. Immunopharmacol, 6: 141-6. |
| intrapeptide disulfide bonded | CTLA4 MAb | CTLA4-mimetic | Fukumoto et al. (1998), Nature Biotech. 16: 267-70 |
| exocyclic | TNF-α receptor | TNF-α antagonist | Takasaki et al. (1997), Nature Biotech. 15: 1266-70; WO 98/53842, published Dec. 3, 1998 |
| linear | TNF-α receptor | TNF-α antagonist | Chirinos-Rojas ( ), J. Imm., 5621-5626. |
| intrapeptide disulfide bonded | C3b | inhibition of complement activation; autoimmune diseases ("C3b-antagonist") | Sahu et al. (1996), J. Immunol. 157: 884-91; Morikis et al. (1998), Protein Sci. 7: 619-27 |
| linear | vinculin | cell adhesion processes-cell growth, differentiation, wound healing, tumor metastasis ("vinculin binding") | Adey et al. (1997), Biochem. J. 324: 523-8 |
| linear | C4 binding protein (C4BP) | anti-thrombotic | Linse et al. (1997), J. Biol. Chem. 272: 14658-65 |
| linear | urokinase receptor | processes associated with urokinase interaction with its receptor (e.g., angiogenesis, tumor cell invasion and metastasis); ("UKR antagonist") | Goodson et al. (1994), Proc. Natl. Acad. Sci. 91: 7129-33; International application WO 97/35969, published Oct. 2, 1997 |
| linear | Mdm2, Hdm2 | Inhibition of inactivation of p53 mediated by Mdm2 or hdm2; anti-tumor ("Mdm/hdm antagonist") | Picksley et al. (1994), Oncogene 9: 2523-9; Bottger et al. (1997) J. Mol. Biol. 269: 744-56; Bottger et al. (1996), Oncogene 13: 2141-7 |
| linear | p21[WAF1] | anti-tumor by mimicking the activity of p21[WAF1] | Ball et al. (1997), Curr. Biol. 7: 71-80 |

TABLE 2-continued

Pharmacologically active peptides

| Form of peptide | Binding partner/ protein of interest[a] | Pharmacologic activity | Reference |
|---|---|---|---|
| linear | farnesyl transferase | anti-cancer by preventing activation of ras oncogene | Gibbs et al. (1994), Cell 77: 175-178 |
| linear | Ras effector domain | anti-cancer by inhibiting biological function of the ras oncogene | Moodie et al. (1994), Trends Genet 10: 44-48 Rodriguez et al. (1994), Nature 370: 527-532 |
| linear | SH2/SH3 domains | anti-cancer by inhibiting tumor growth with activated tyrosine kinases; treatment of SH3-mediated disease states ("SH3 antagonist") | Pawson et al (1993), Curr. Biol. 3: 434-432 Yu et al. (1994), Cell 76: 933-945; Rickles et al. (1994), EMBO J. 13: 5598-5604; Sparks et al. (1994), J. Biol. Chem. 269: 23853-6; Sparks et al. (1996), Proc. Natl. Acad. Sci. 93: 1540-4; U.S. Pat. No. 5,886,150, issued Mar. 23, 1999; U.S. Pat. No. 5,888,763, issued Mar. 30, 1999 |
| linear | $p16^{INK4}$ | anti-cancer by mimicking activity of p16; e.g., inhibiting cyclin D-Cdk complex ("p16-mimetic") | Fåhraeus et al. (1996), Curr. Biol. 6: 84-91 |
| linear | Src, Lyn | inhibition of Mast cell activation, IgE-related conditions, type I hypersensitivity ("Mast cell antagonist") | Stauffer et al. (1997), Biochem. 36: 9388-94 |
| linear | Mast cell protease | treatment of inflammatory disorders mediated by release of tryptase-6 ("Mast cell protease inhibitors") | International application WO 98/33812, published Aug. 6, 1998 |
| linear | HBV core antigen (HBcAg) | treatment of HBV viral infections ("anti-HBV") | Dyson & Muray (1995), Proc. Natl. Acad. Sci. 92: 2194-8 |
| linear | selectins | neutrophil adhesion; inflammatory diseases ("selectin antagonist") | Martens et al. (1995), J. Biol. Chem. 270: 21129-36; European patent application EP 0 714 912, published Jun. 5, 1996 |
| linear, cyclized | calmodulin | calmodulin antagonist | Pierce et al. (1995), Molec. Diversity 1: 259-65; Dedman et al. (1993), J. Biol. Chem. 268: 23025-30; Adey & Kay (1996), Gene 169: 133-4 |
| linear, cyclized- | integrins | tumor-homing; treatment for conditions related to integrin-mediated cellular events, including platelet aggregation, thrombosis, wound healing, osteoporosis, tissue repair, angiogenesis (e.g., for treatment of cancer), and tumor invasion ("integrin-binding") | International applications WO 95/14714, published Jun. 1, 1995; WO 97/08203, published Mar. 6, 1997; WO 98/10795, published Mar. 19, 1998; WO 99/24462, published May 20, 1999; Kraft et al. (1999), J. Biol. Chem. 274: 1979-1985 |
| cyclic, linear | fibronectin and extracellular matrix components of T cells and macrophages | treatment of inflammatory and autoimmune conditions | WO 98/09985, published Mar. 12, 1998 |

TABLE 2-continued

Pharmacologically active peptides

| Form of peptide | Binding partner/ protein of interest[a] | Pharmacologic activity | Reference |
|---|---|---|---|
| linear | somatostatin and cortistatin | treatment or prevention of hormone-producing tumors, acromegaly, giantism, dementia, gastric ulcer, tumor growth, inhibition of hormone secretion, modulation of sleep or neural activity | European patent application 0 911 393, published Apr. 28, 1999 |
| linear | bacterial lipopolysaccharide | antibiotic; septic shock; disorders modulatable by CAP37 | U.S. Pat. No. 5,877,151, issued Mar. 2, 1999 |
| linear or cyclic, including D-amino acids | pardaxin, mellitin | antipathogenic | WO 97/31019, published 28 Aug. 1997 |
| linear, cyclic | VIP | impotence, neurodegenerative disorders | WO 97/40070, published Oct. 30, 1997 |
| linear | CTLs | cancer | EP 0 770 624, published May 2, 1997 |
| linear | THF-gamma2 | | Burnstein (1988), Biochem., 27: 4066-71. |
| linear | Amylin | | Cooper (1987), Proc. Natl. Acad. Sci., 84: 8628-32. |
| linear | Adrenomedullin | | Kitamura (1993), BBRC, 192: 553-60. |
| cyclic, linear | VEGF | anti-angiogenic; cancer, rheumatoid arthritis, diabetic retinopathy, psoriasis ("VEGF antagonist") | Fairbrother (1998), Biochem., 37: 17754-17764. |
| cyclic | MMP | inflammation and autoimmune disorders; tumor growth ("MMP inhibitor") | Koivunen (1999), Nature Biotech., 17: 768-774. |
| | HGH fragment | treatment of obesity | U.S. Pat. No. 5,869,452 |
| | Echistatin | inhibition of platelet aggregation | Gan (1988), J. Biol. Chem., 263: 19827-32. |
| linear | SLE autoantibody | SLE | WO 96/30057, published Oct. 3, 1996 |
| | GD1alpha | suppression of tumor metastasis | Ishikawa et al. (1998), FEBS Lett. 441 (1): 20-4 |
| | antiphospholipid beta-2-glycoprotein-I (•2GPI) antibodies | endothelial cell activation, antiphospholipid syndrome (APS), thromboembolic phenomena, thrombocytopenia, and recurrent fetal loss | Blank et al. (1999), Proc. Natl. Acad. Sci. USA 96: 5164-8 |
| linear | T Cell Receptor beta chain | diabetes | WO 96/11214, published Apr. 18, 1996. |
| | | Antiproliferative, antiviral | WO 00/01402, published Jan. 13, 2000. |
| | | anti-ischemic, growth hormone-liberating | WO 99/62539, published Dec. 9, 1999. |
| | | anti-angiogenic | WO 99/61476, published Dec. 2, 1999. |
| linear | | Apoptosis agonist; treatment of T cell-associated disorders (e.g., autoimmune diseases, viral infection, T cell leukemia, T cell lymphoma) | WO 99/38526, published Aug. 5, 1999. |
| linear | MHC class II | treatment of autoimmune diseases | US Pat. No. 5,880,103, issued Mar. 9, 1999. |
| linear | androgen R, p75, MJD, DCC, huntingtin | proapoptotic, useful in treating cancer | WO 99/45944, published Sep. 16, 1999. |

TABLE 2-continued

Pharmacologically active peptides

| Form of peptide | Binding partner/ protein of interest[a] | Pharmacologic activity | Reference |
|---|---|---|---|
| linear | von Willebrand Factor; Factor VIII | inhibition of Factor VIII interaction; anticoagulants | WO 97/41220, published Apr. 29, 1997. |
| linear | lentivirus LLP1 | antimicrobial | US Pat. No. 5,945,507, issued Aug. 31, 1999. |
| linear | Delta-Sleep Inducing Peptide | sleep disorders | Graf (1986), Peptides 7: 1165. |
| linear | C-Reactive Protein (CRP) | inflammation and cancer | Barna (1994), Cancer Immunol. Immunother. 38: 38 (1994). |
| linear | Sperm-Activating Peptides | infertility | Suzuki (1992), Comp. Biochem. Physiol. 102B: 679. |
| linear | angiotensins | hematopoietic factors for hematocytopenic conditions from cancer, AIDS, etc. | Lundergan (1999), J. Periodontal Res. 34(4): 223-228. |
| linear | HIV-1 gp41 | anti-AIDS | Chan (1998), Cell 93: 681-684. |
| linear | PKC | inhibition of bone resorption | Moonga (1998), Exp. Physiol. 83: 717-725. |
| linear | defensins (HNP-1, -2, -3, -4) | antimicrobial | Harvig (1994), Methods Enz. 236: 160-172. |
| linear | $p185^{HER2/neu}$, C-erbB-2 | AHNP-mimetic: anti-tumor | Park (2000), Nat. Biotechnol. 18: 194-198. |
| linear | gp130 | IL-6 antagonist | WO 99/60013, published Nov. 25, 1999. |
| linear | collagen, other joint, cartilage, arthritis-related proteins | autoimmune diseases | WO 99/50282, published Oct. 7, 1999. |
| linear | HIV-1 envelope protein | treatment of neurological degenerative diseases | WO 99/51254, published Oct. 14, 1999. |
| linear | IL-2 | autoimmune disorders (e.g., graft rejection, rheumatoid arthritis) | WO 00/04048, published Jan. 27, 2000; WO 00/11028, published Mar. 2, 2000. |
| linear, cyclic | various | inflammatory conditions, autoimmune disease, others | U.S. Pat. No. 6,660,843 |
| linear, cyclic | Ang-2 | inhibition of angiogenesis (e.g., for treatment of tumor) | U.S. Pat. App. No. 2003/0229023, published Dec. 11, 2003; WO 03/057134, published Jul. 17, 2003; U.S. 2003/0236193, published Dec. 25, 2003 |
| | NGF | chronic pain, migraine, asthma, hyperactive bladder, psoriasis, cancer, other conditions linked to NGF | WO 04/026329, published Apr. 1, 2004 |
| | myostatin | | U.S. Ser. No. 10/742,379, filed Dec. 19, 2003; PCT/US03/40781, filed Dec. 19, 2003 |
| | BAFF/TALL-1 | B-cell mediated autoimmune diseases and cancers (e.g., lupus, B-cell lymphoma) | U.S. 2003/0195156, published Oct. 16, 2003; WO 02/092620, published Nov. 21, 2002 |
| linear | GLP-1 | Diabetes, metabolic syndrome | |

[a]The protein listed in this column may be bound by the associated peptide (e.g., EPO receptor, IL-1 receptor) or mimicked by the associated peptide. The references listed for each clarify whether the molecule is bound by or mimicked by the peptides.

Peptides identified by peptide library screening were for a long time regarded simply as "leads" in development of therapeutic agents rather than as therapeutic agents themselves. Like other proteins and peptides, they would be rapidly removed in vivo either by renal filtration, cellular clearance mechanisms in the reticuloendothelial system, or proteolytic degradation. Francis (1992), *Focus on Growth Factors* 3: 4-11. As a result, the art used the identified peptides to validate drug targets or as scaffolds for design of organic compounds that might not have been as easily or as quickly identified through chemical library screening. Lowman (1997), *Ann. Rev. Biophys. Biomol. Struct.* 26: 401-24; Kay et al. (1998), *Drug Disc. Today* 3: 370-8.

A more recent development is fusion of randomly generated peptides with the Fc domain. See U.S. Pat. No. 6,660,843, issued Dec. 9, 2003 to Feige et al. (incorporated by reference in its entirety). Such molecules have come to be known as "peptibodies." They include one or more peptides linked to the N-terminus, C-terminus, amino acid sidechains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Ser. No. 09/422,838, filed Oct. 22, 1999 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Ser. No. 10/666,480, filed Sep. 18, 2003 (corresponding to WO 04/026329, published Apr. 1, 2004), each of which is hereby incorporated by reference in its entirety. The art would benefit from further technology enabling such rational design of polypeptide therapeutic agents.

SUMMARY OF THE INVENTION

The present invention concerns a process in which at least one biologically active peptide is incorporated as an internal sequence into an Fc domain. Such an internal sequence may be added by insertion (i.e., between amino acids in the previously existing Fc domain) or by replacement of amino acids in the previously existing Fc domain (i.e., removing amino acids in the previously existing Fc domain and adding peptide amino acids). In the latter case, the number of peptide amino acids added need not correspond to the number of amino acids removed from the previously existing Fc domain; for example, this invention concerns a molecule in which 10 amino acids are removed and 15 amino acids are added. In this invention, pharmacologically active compounds are prepared by a process comprising:

a) selecting at least one peptide that modulates the activity of a protein of interest; and b) preparing a pharmacologic agent comprising an amino acid sequence of the selected peptide as an internal sequence of an Fc domain.

This process may be employed to modify an Fc domain that is already linked through an N— or C-terminus or sidechain to a polypeptide (e.g., etanercept) or to a peptide (e.g., as described in U.S. Pat. App. Nos. 2003/0195156, 2003/0176352, 2003/0229023, and 2003/0236193; WO 00/24770; WO 04/026329). The process described throughout may also be employed to modify an Fc domain that is part of an antibody (e.g., adalimumab, epratuzumab, infliximab, Herceptin®, and the like). In this way, different molecules can be produced that have additional functionalities, such as a binding domain to a different epitope or an additional binding domain to the precursor molecule's existing epitope. The peptide can be selected, for example, by phage display (which is preferred), *E. coli* display, ribosome display, RNA-peptide screening, yeast-based screening, chemical-peptide screening, rational design, or protein structural analysis or may be a naturally occurring peptide (e.g. PTH, GLP-1).

The invention further relates to molecules comprising an Fc domain modified to comprise a peptide as an internal sequence (preferably in a loop region) of the Fc domain. Molecules comprising an internal peptide sequence are referred to throughout as "Fc internal peptibodies" or "Fc internal peptide molecules." These molecules are further described herein below.

The Fc internal peptide molecules may include more than one peptide sequence in tandem in a particular internal region, and they may include further peptides in other internal regions. While the putative loop regions are preferred, insertions in any other non-terminal domains of the Fc are also considered part of this invention. Variants and derivatives of the above compounds (described below) are also encompassed by this invention.

The compounds of this invention may be prepared by standard synthetic methods, recombinant DNA techniques, or any other methods of preparing peptides and fusion proteins.

The primary use contemplated for Fc internal peptide molecules is as therapeutic or prophylactic agents. A selected peptide may have activity comparable to—or even greater than—the natural ligand mimicked by the peptide. In addition, certain natural ligand-based therapeutic agents might induce antibodies against the patient's own endogenous ligand. In contrast, the unique sequence of the vehicle-linked peptide avoids this pitfall by having little or typically no sequence identity with the natural ligand. Furthermore, the Fc internal peptibodies may have advantages in refolding and purification over N— or C-terminally linked Fc molecules. Further still, Fc internal peptibodies may be more stable in both thermodynamically, due to the stabilization of chimeric domains, and chemically, due to increased resistance to proteolytic degradation from amino- and carboxy-peptidases. Fc internal peptibodies may also exhibit improved pharmacokinetic properties.

Although mostly contemplated as therapeutic agents, compounds of this invention may also be useful in screening for such agents. For example, one could use an Fc internal peptibody (e.g., Fc-loop-SH2 domain peptide) in an assay employing anti-Fc coated plates. Fc internal peptibodies may make insoluble peptides soluble and thus useful in a number of assays.

The compounds of this invention may be used for therapeutic or prophylactic purposes by formulating them with appropriate pharmaceutical carrier materials and administering an effective amount to a patient, such as a human (or other mammal) in need thereof. Other related aspects are also included in the instant invention.

Numerous additional aspects and advantages of the present invention will become apparent upon consideration of the figures and detailed description of the invention.

DESCRIPTION OF THE FIGURES

FIG. 1A shows the monomeric rat IgG2a Fc domain (Protein Database file #1I1C, www.rcsb.org/pdb/). This figure shows a three dimensional model of rat IgG2a Fc domain monomer from x-ray diffraction crystal structure (pdb #1I1C). Potential Fc loop insertion sites are shown for both CH2 and CH3 domains with the preferred CH3 domain Fc loop insertion site specifically identified.

FIG. 1B shows the monomeric murine IgG1 Fc domain (Protein Database file #1IGY). This figure shows a three-dimensional model of murine IgG1 Fc domain monomer from x-ray diffraction crystal structure (pdb #1IGY). Potential Fc loop insertion sites are shown for both CH2 and CH3 domains with the preferred CH3 domain Fc loop insertion site specifically identified.

FIG. 1C shows the monomeric human IgG1 Fc domain (Protein Database file #1H3T). This figure shows a three-dimensional model of human IgG1 Fc domain monomer from x-ray diffraction crystal structure (pdb #1H3T). Potential Fc loop insertion sites are shown for both CH2 and CH3 domains with the preferred CH3 domain Fc loop insertion site specifically identified.

These structures illustrate the high degree of homology in the secondary and tertiary structural conformations within the Fc domains of different IgG subtypes and between species. The x-ray crystal structure coordinates for these structures can be found in the RCSB Protein Data Bank (www.rcsb.org/pdb/).

Figure 1A:
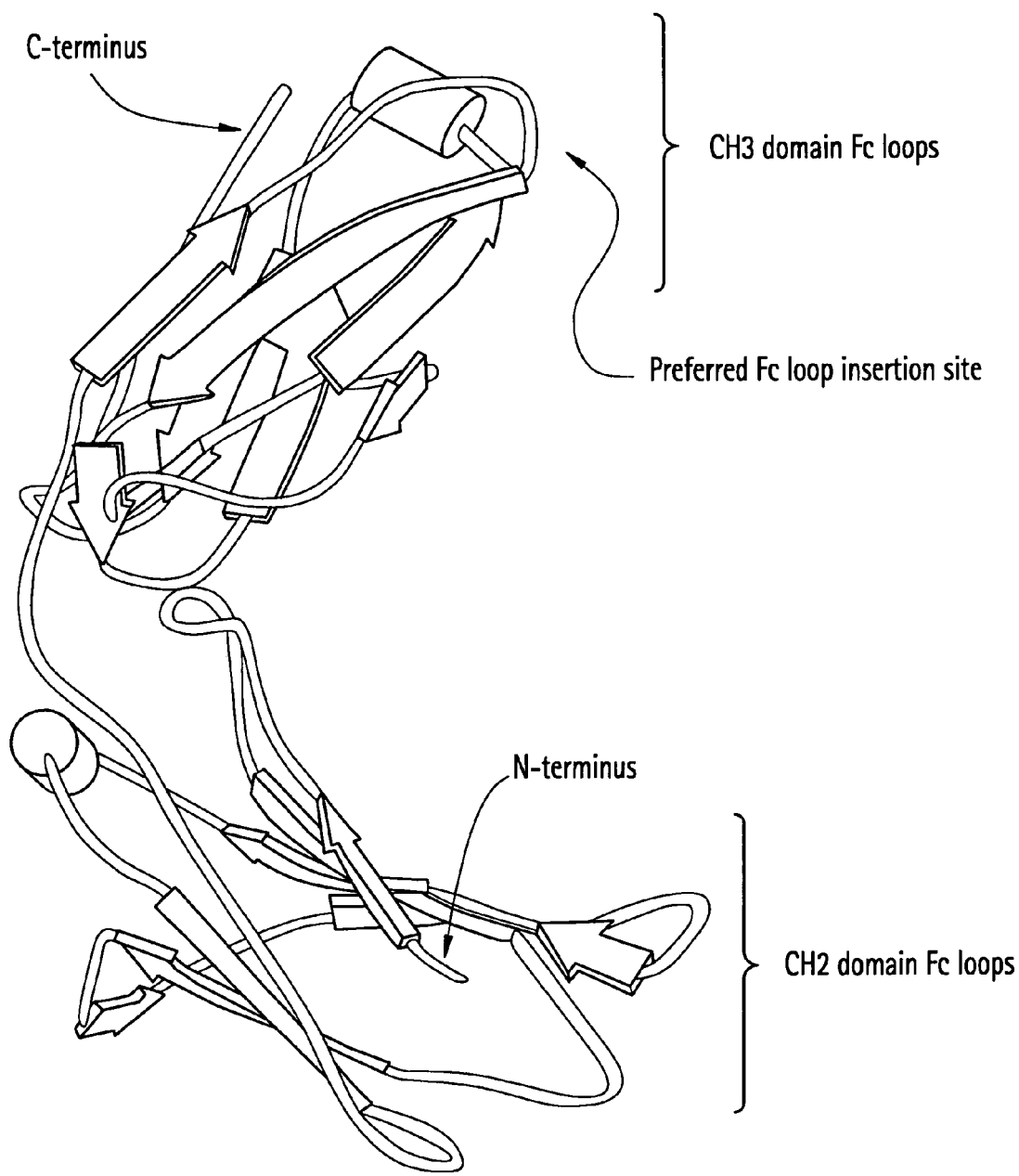
FIGS. 1A, 1B and 1C show loop regions of Fc domains that may be modified in accordance with this invention. In these structural representations of the CH2 and CH3 domains of Fc, the loop regions may be considered any part of the model not shown as β-sheet (flat arrows) or α-helix (cylinder).
Figure 1B:
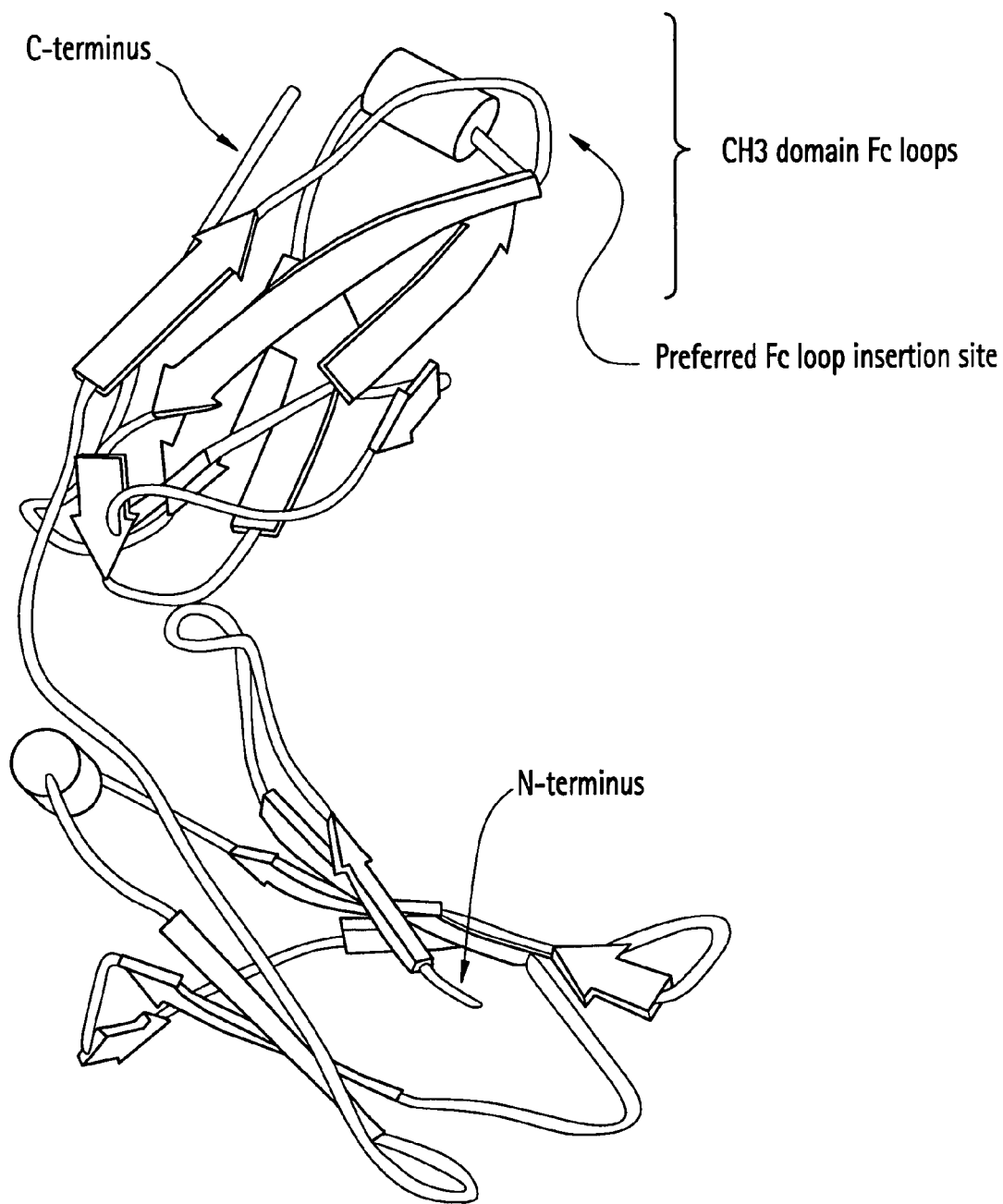
Figure 1C:
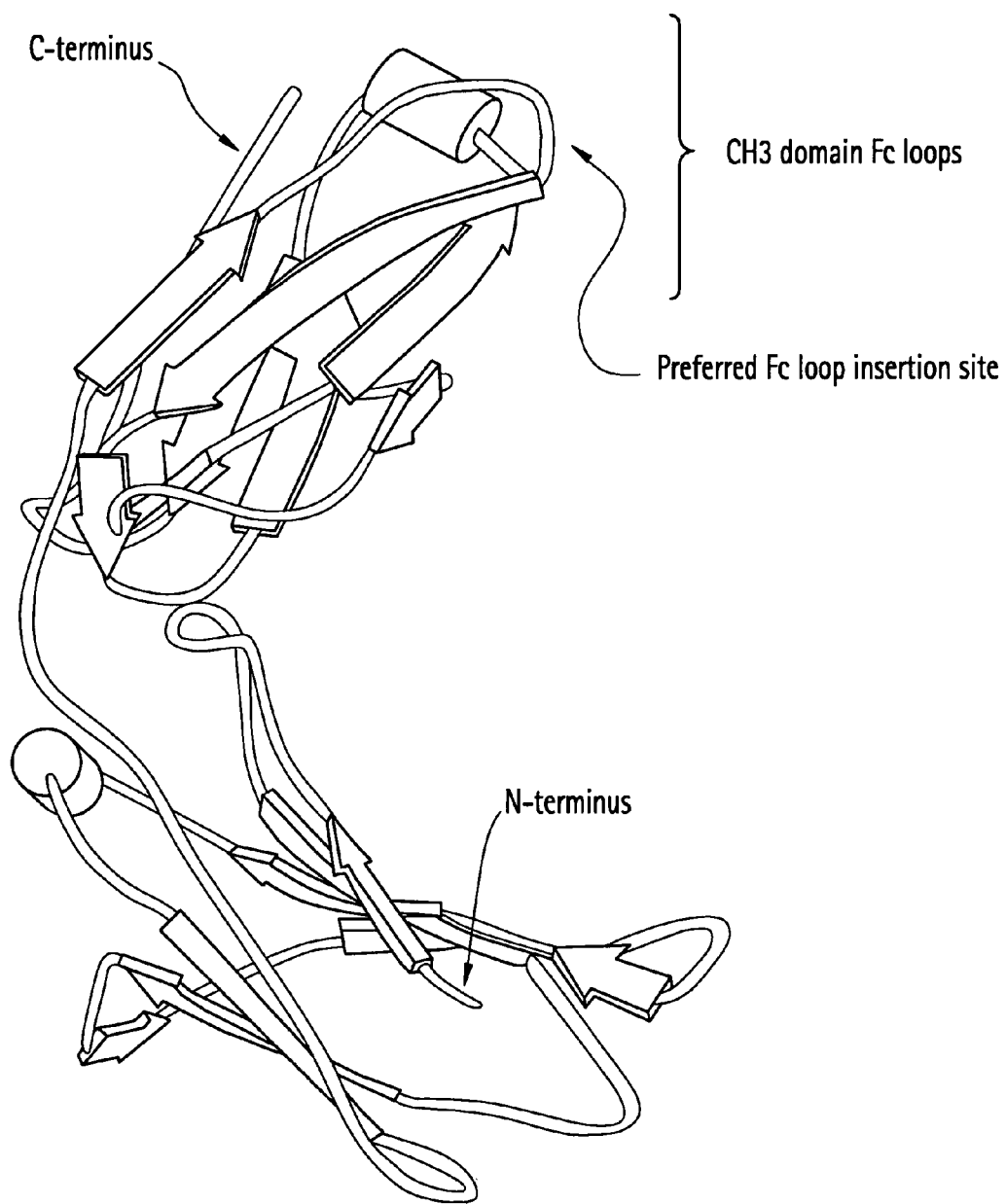

FIG. 2A shows a sequence of human IgG1 Fc sequence (SEQ ID NO: 599) used for peptibody fusions with predicted loop sequences in boldface. FIG. 2A shows, in the context of the human IgG1 sequence used for this invention, the Fc loop regions in boldface (SEQ ID NOS: 621, 622, 624, 625, 627, 628, 630, 632, 634, and 636), which are suggested by the structures shown in FIGS. 1A, 1B and 1C. Any, or all of the sites shown in boldface may be suitable for full or partial replacement by or insertion of peptide sequences and are considered part of this invention. Specifically preferred internal sites are underlined (SEQ ID NOS: 623, 626, 629, 631, 633, 635, and 637). One preferred site is SEQ ID NO: 631, between $Leu_{139}$ and $Thr_{140}$ in the DELTK (SEQ ID NO: 630) loop. Potential loop sites in other Ig subtypes are understood in the art based on the alignments provided in FIGS. 2B and 2C.

FIGS. 2B and 2C show a sequence alignment of human Fc domains from IgA, IgM and IgG subclasses. FIGS. 2B and 2C show exemplary amino acid sequences (SEQ ID NOS: 600 to 607) of human Fc regions from IgA, IgM and IgG subtypes that may be useful in this invention. Also shown in FIGS. 2B and 2C is a consensus sequence (SEQ ID NO: 608).

FIGS. 2B and 2C also show in boldface the preferred internal sites for peptide addition that correspond to those of the Fc sequence shown in FIG. 2A (SEQ ID NO: 599). In particular, FIGS. 2B and 2C show as such preferred sites the following:

SEQ ID NO: 621 as shown in boldface within SEQ ID NOS: 603 to 608;
SEQ ID NO: 622 within SEQ ID NOS: 603 to 606 and 608;
SEQ ID NO: 638 within SEQ ID NO: 607;
SEQ ID NO: 624 within SEQ ID NO: 603 to 608;
SEQ ID NO: 625 within SEQ ID NOS: 603 and 604;
SEQ ID NO: 639 within SEQ ID NOS: 605 to 608;
SEQ ID NO: 627 within SEQ ID NOS: 603 to 605, 607, and 608;
SEQ ID NO: 640 within SEQ ID NO: 606;
SEQ ID NO: 628 within SEQ ID NOS: 603, 604, and 608;
SEQ ID NO: 641 within SEQ ID NO: 605;
SEQ ID NO: 642 within SEQ ID NO: 606;
SEQ ID NO: 643 within SEQ ID NO: 607;
SEQ ID NO: 630 within SEQ ID NO: 603;
SEQ ID NO: 644 within SEQ ID NOS: 604 to 608;
SEQ ID NO: 632 within SEQ ID NOS: 603, 604, 606, 607, and 608;
SEQ ID NO: 645 within SEQ ID NO: 605;
SEQ ID NO: 634 within SEQ ID NOS: 603, 604, and 607;
SEQ ID NO: 646 within SEQ ID NOS: 605, 606 and 608;
SEQ ID NO: 636 within SEQ ID NOS: 603, 604, 606, and 608;
SEQ ID NO: 614 within SEQ ID NO: 605; and
SEQ ID NO: 620 within SEQ ID NO: 607.

The sequence alignments of FIGS. 2B and 2C suggest two more Potential insertion sites at $Q_{167}/P_{168}$ and/or $G_{183}/S_{184}$ (using the numbering of SEQ ID NO: 599 in FIG. 2A). These positions correspond to gaps in the IgG sequences where there are 2 and 3 residue insertions found in the aligned IgA and IgM sequences. Other preferred insertion sites correspond to the sequence in FIG. 2A. The preferred insertion sites are underlined FIGS. 2B and 2C and are as follows:

$H_{53}/E_{54}$ in SEQ ID NOS: 603 and 604;
$H_{100}/E_{101}$ in SEQ ID NO: 605;
$H_{49}/E_{50}$ in SEQ ID NO: 606;
$Q_{50}/E_{51}$ in SEQ ID NO: 607;
$H_{65}/E_{66}$ in SEQ ID NO: 608;
$Y_{81}/N_{82}$ in SEQ ID NOS: 603 and 604;
$F_{128}/N_{129}$ in SEQ ID NO: 605;
$F_{77}/N_{78}$ in SEQ ID NO: 606;
$F_{78}/N_{79}$ in SEQ ID NO: 607;
$F_{93}/N_{94}$ in SEQ ID NO: 608;
$N_{110}/K_{111}$ in SEQ ID NOS: 603 and 604;
$N_{157}/K_{158}$ in SEQ ID NO: 605;
$N_{106}/K_{107}$ in SEQ ID NO: 606;
$N_{107}/K_{108}$ in SEQ ID NO: 607;
$N_{122}/K_{123}$ in SEQ ID NO: 608;
$L_{143}/T_{144}$ and $M_{143}/T_{144}$ in SEQ ID NOS: 603 and 604, respectively;
$M_{190}/T_{191}$ in SEQ ID NO: 605;
$M_{139}/T_{140}$ in SEQ ID NO: 606;
$M_{140}/T_{141}$ in SEQ ID NO: 607;
$M_{157}/T_{158}$ in SEQ ID NO: 608;
$Q_{171}P_{172}$ in SEQ ID NOS: 603 and 604;
$Q_{218}/P_{219}$ in SEQ ID NO: 605;
$Q_{167}/P_{168}$ in SEQ ID NO: 606;
$Q_{168}/P_{169}$ in SEQ ID NO: 607;
$Q_{185}/P_{188}$ in SEQ ID NO: 608;
$E_{173}N_{174}$ in SEQ ID NOS: 603 and 604;
$E_{220}/N_{221}$ in SEQ ID NO: 605;
$E_{169}/N_{170}$ in SEQ ID NO: 606;
$E_{170}/N_{171}$ in SEQ ID NO: 607;
$E_{189}/N_{190}$ in SEQ ID NO: 608;
$S_{185}/D_{186}$ in SEQ ID NOS: 603 and 604;
$S_{232}/D_{233}$ in SEQ ID NO: 605;
$S_{181}/D_{182}$ in SEQ ID NO: 606;
$S_{182}/D_{183}$ in SEQ ID NO: 607;
$S_{201}/D_{202}$ in SEQ ID NO: 608;
$G_{187}/S_{188}$ in SEQ ID NOS: 603 and 604;
$G_{234}/S_{235}$ in SEQ ID NO: 605;
$G_{183}/S_{184}$ in SEQ ID NO: 606;
$G_{184}/S_{185}$ in SEQ ID NO: 607;

$G_{203}/S_{207}$ in SEQ ID NO: 608;
$G_{205}/N_{206}$ in SEQ ID NOS: 603 and 604;
$G_{252}/N_{253}$ in SEQ ID NO: 605;
$G_{201}/N_{202}$ in SEQ ID NO: 606;
$G_{202}/N_{203}$ in SEQ ID NO: 607; and
$G_{224}/N_{225}$ in SEQ ID NO: 608.

FIG. 2D shows an alignment of human IgG1 Fc domain (Amgen Fc, SEQ ID NO: 609) used for the peptibody platform with rat IgG2A from crystal structure of FcRn/Fc complex (1I1A.pdb, SEQ ID NO: 610 The resulting consensus sequence (SEQ ID NO: 611) is also shown.

FIG. 3A shows the amino acid sequence (SEQ ID NO: 612) of a human IgG1 Fc domain having insertion of a myostatin binding peptide (SEQ ID NO: 365). Hereinafter, this molecule is referred to as the "myostatin loop peptibody" or "Fc-loop-myo7." The inserted peptide is shown in boldface and the glycine linkers in italics.

FIG. 3B shows the amino acid sequence (SEQ ID NO: 613) of a C-terminally linked peptibody referred to as TN8-19-07. This peptibody incorporates the same peptide sequence as Fc-loop-myo7 (SEQ ID NO: 365). The TN8-19-07 peptide is shown in boldface and the glycine and alanine linkers in italics.

FIG. 3C shows the amino acid sequence (SEQ ID NO: 615) of an Fc internal peptibody referred to hereinafter as Fc-loop-EMP. This peptibody incorporates an EPO-mimetic peptide (SEQ ID NO: 2). The inserted peptide is shown in boldface and the glycine linkers in italics. The cysteines that form a disulfide bond are underlined.

FIG. 3D shows the amino acid sequence (SEQ ID NO: 616) of an Fc internal peptibody referred to hereinafter as Fc-loop-Amp2. Bioactive peptide (SEQ ID NO: 28) is highlighted in boldface and glycine linkers in italics. There is no disulfide constraint in the AMP-2 peptide insertion.

FIG. 3E shows the amino acid sequence (SEQ ID NO: 617) of a C-terminally linked peptibody referred to hereinafter as Fc-loop-AMP2-dimer. This tandem-linked therapeutic peptide dimer shows the therapeutic peptide sequence (SEQ ID NO: 28) in boldface and the linkers in italics. This molecule incorporates a tandem peptide dimer of the same peptide sequence as found in Fc-loop-AMP-2.

Figure 4A:
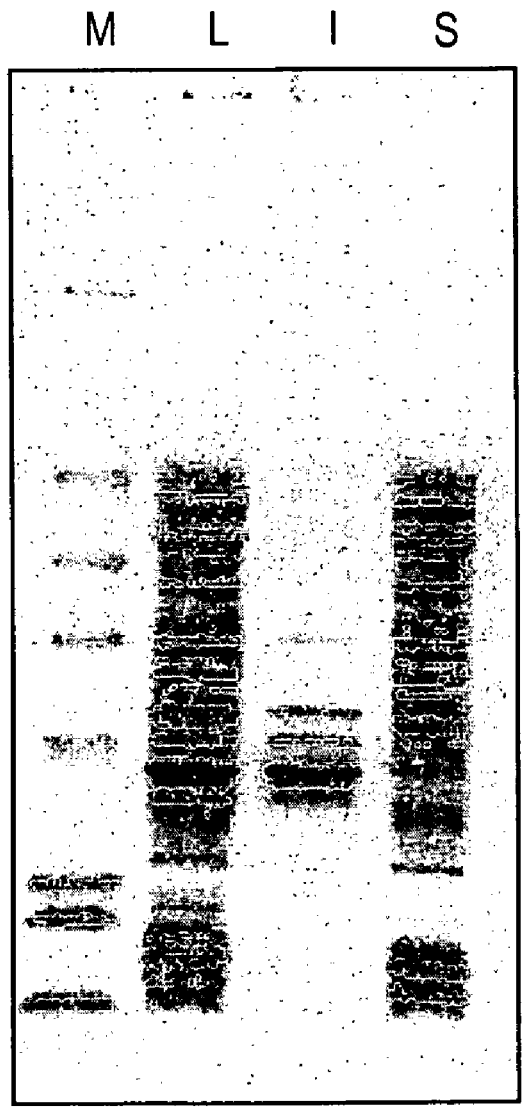
Figure 4B:
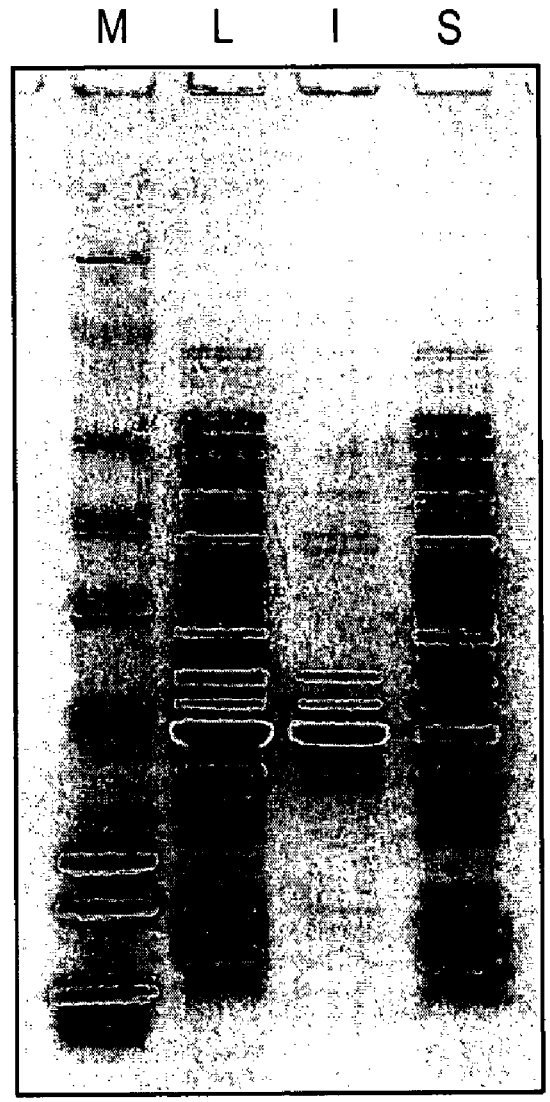

FIGS. 4A and 4B shows the expression in *E. coli* of Fc-loop-myo7 and TN8-19-07 by SDS-PAGE (4-20%). Samples of the crude cell lysate (lys), the insoluble fraction (insol) and the soluble (sol) fraction for both the Fc-loop-Myo7 (#6951) and TN8-19-07 (#6826) are shown in reducing gels. SeeBlue and molecular weight markers (lane 1), whole cell lysate (lane 2), insoluble fraction (lane 3) and insoluble fraction (lane 4).

Figure 5:
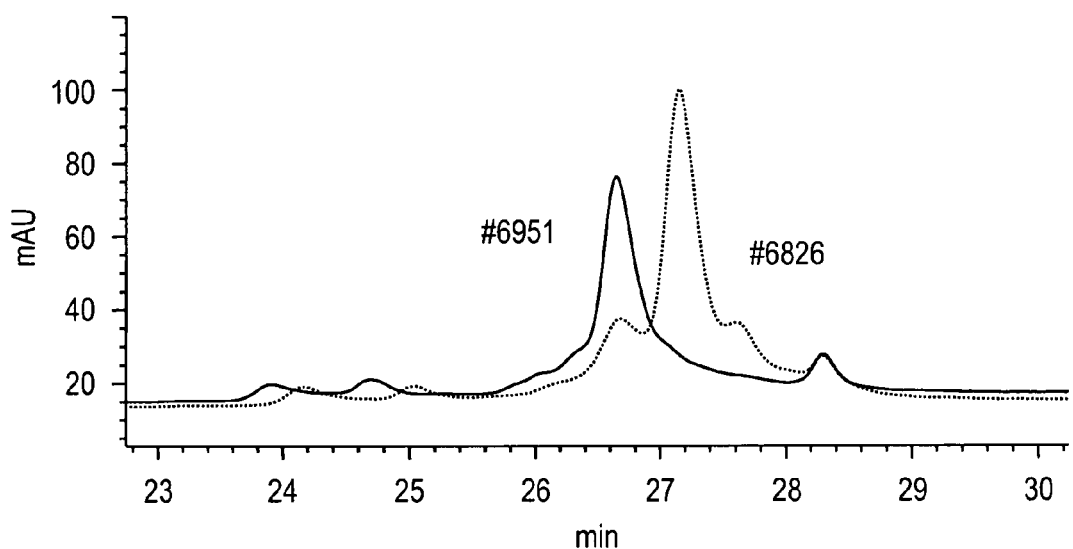

FIG. 5 shows a reverse phase, high performance liquid chromatography (RP-HPLC) comparison of the unpurified refold reactions of the Fc-loop-Myo7 (#6951) and TN8-19-07 (#6826). Approximately 10 μg of peptibody was loaded directly from a refold reaction to a Vydak C4 column (5 μM, 300 angstrom, 4.6×250 mm) and eluted with a linear 40-50% ACN gradient at 0.5%/min.

Figure 6:
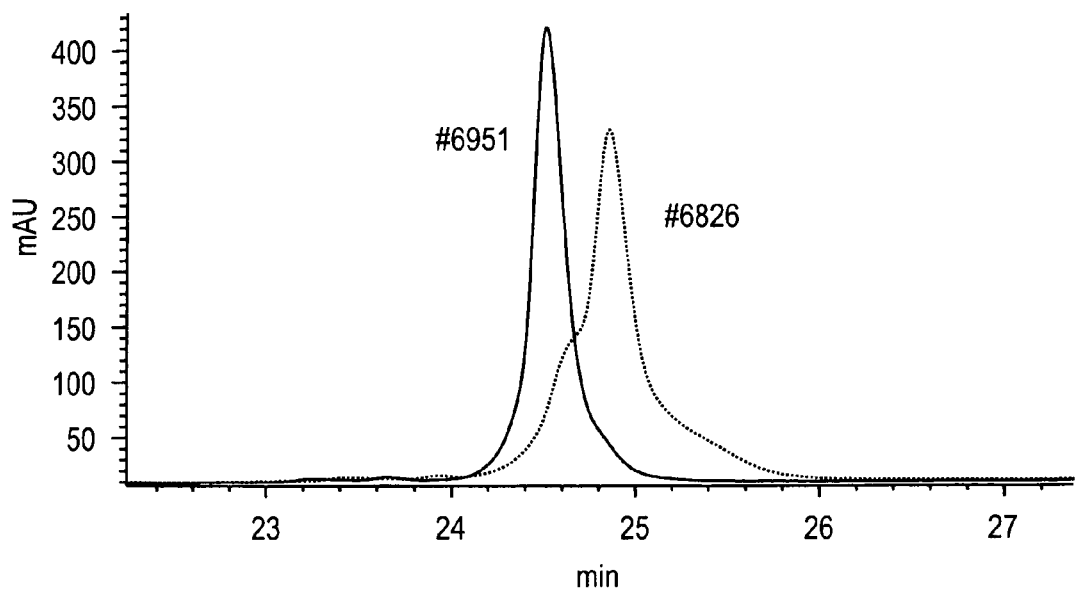

FIG. 6 shows reversed-phase high performance liquid chromatography (RP-HPLC) comparison of the final, purified pools of Fc-loop TN8-19-07 (#6951) and carboxy-terminal Fc TN8-19-07 (#6826). Loaded 10 μg purified peptibody to Vydak C4 column (5 μM, 300 angstrom, 4.6×250 mm) and eluted with a linear 40-50% ACN gradient at 0.5%/min.

Figure 7:

FIG. 7 shows the analyses of final purified pools of Fc-loop TN8-19-07 (#6951) and carboxy-terminal Fc TN8-19-07 (#6826) by SDS-PAGE (4-20% gel). Five μg of each sample was loaded as follows: #6951 (lane 1), #6826 (lane 2), See-Blue+markers (lane M), #6951 reduced (lane 3), #6826 reduced (lane 4).

Figure 8:
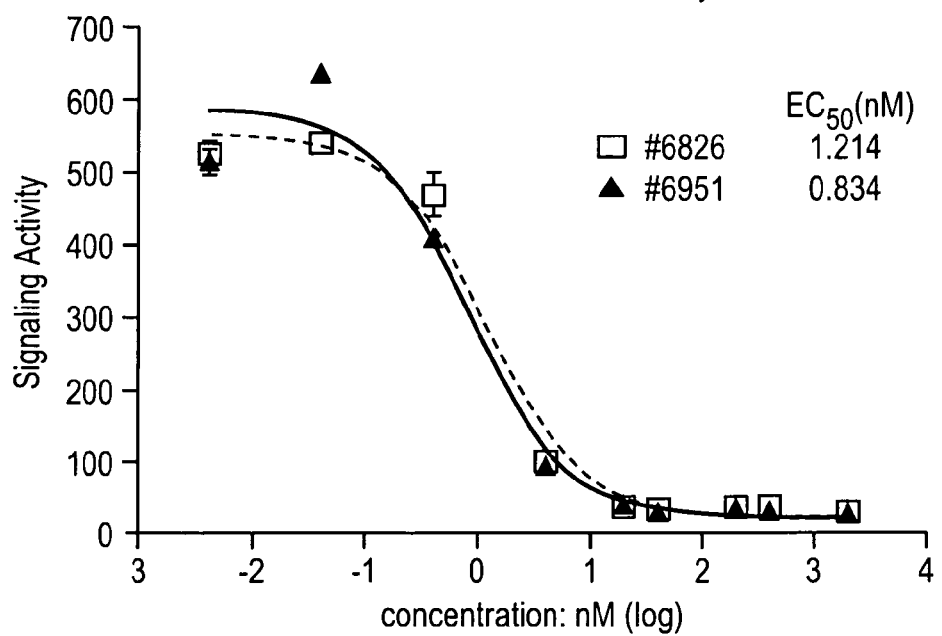

FIG. 8 shows an in vitro cell-based bioassay for measuring myostatin inhibitory compounds. Fc-loop TN8-19-07 (#6951) retains full inhibitory activity relative to the carboxy-terminal TN8-19-07 peptibody (#6826).

FIG. 9 shows a western blot analysis of an in vivo stability study for Fc-loop TN8-19-07 (#6951) and the carboxy-terminal TN8-19-07 peptibody (#6826). Sera pools from five mice were evaluated for each time point (0, 4, 24 and 48 hours). Lanes 1-3 are Fc-loop TN8-19-07 standards at 2 ng, 5 ng and 10 ng respectively. Lanes 4 & 5 are the Fc-loop vs. carboxy terminal peptibodies, respectively, at 4 hours. Lanes 6 & 7 are the Fc-loop vs. carboxy terminal peptibodies respectively at 24 hours. Lanes 8 & 9 are the Fc-loop vs. carboxy terminal peptibodies respectively at 48 hours. Lanes 10-12 are the carboxy-terminal peptibody standard at 2 ng, 5 ng and 10 ng, respectively. The gel was a 1 mm 4-12% SDS-PAGE gel run in MES reducing buffer and the western blot was developed using a goat anti-human IgG Fc-HRP conjugate.

FIG. 10A shows the amino acid sequence (SEQ ID NO: 618) of a human IgG1 Fc domain having insertion of an Ang2 binding peptide (SEQ ID NO: 147). Hereinafter, this molecule is referred to as "Ang2 loop peptibody" or "Fc-loop-Ang2." Bioactive peptide is highlighted in boldface and Glycine linkers in italics.

FIG. 10B shows the amino acid sequence (SEQ ID NO: 619) of a C-terminally linked peptibody referred to herein as TN8-Con4. This molecule incorporates the same peptide sequence as Fc-loop-ang2 (SEQ ID NO: 147). The bioactive peptide is highlighted in boldface and the glycine and alanine linkers in italics.

Figure 11A:
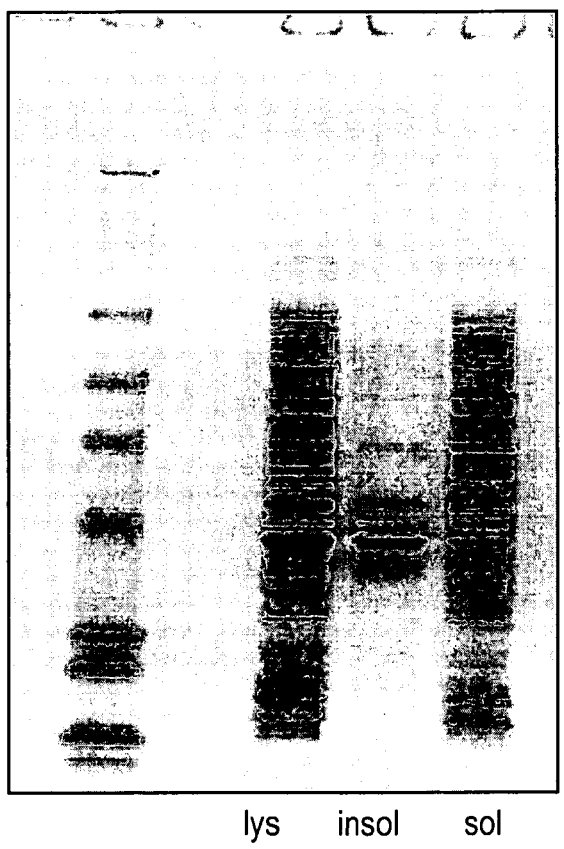
Figure 11B:
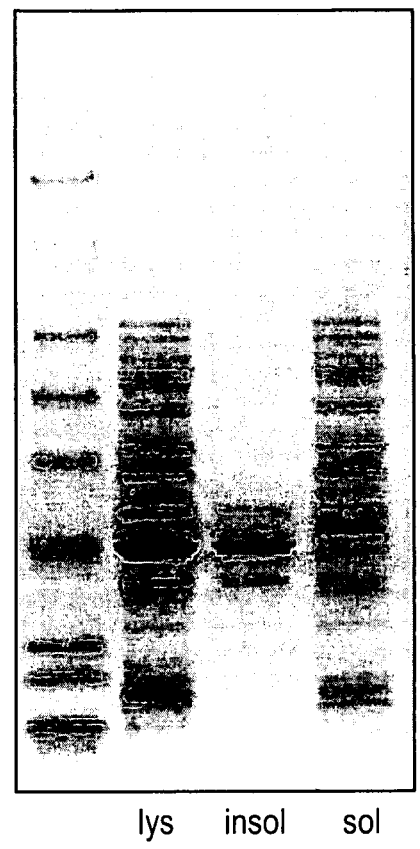

FIG. 11 shows the expression and distribution in *E. coli* of the Fc-loop TN8-Con4 (#6888) and carboxy-terminal TN8-Con4 (#5564) peptibodies by SDS-PAGE. Samples of the crude cell lysate (lys), the insoluble fraction (insol) and the soluble (sol) fraction for both the Fc-loop-Tn8-Con4 (#6888) and TN8-Con4 (#5564) are shown in reducing gels.

Figure 12:
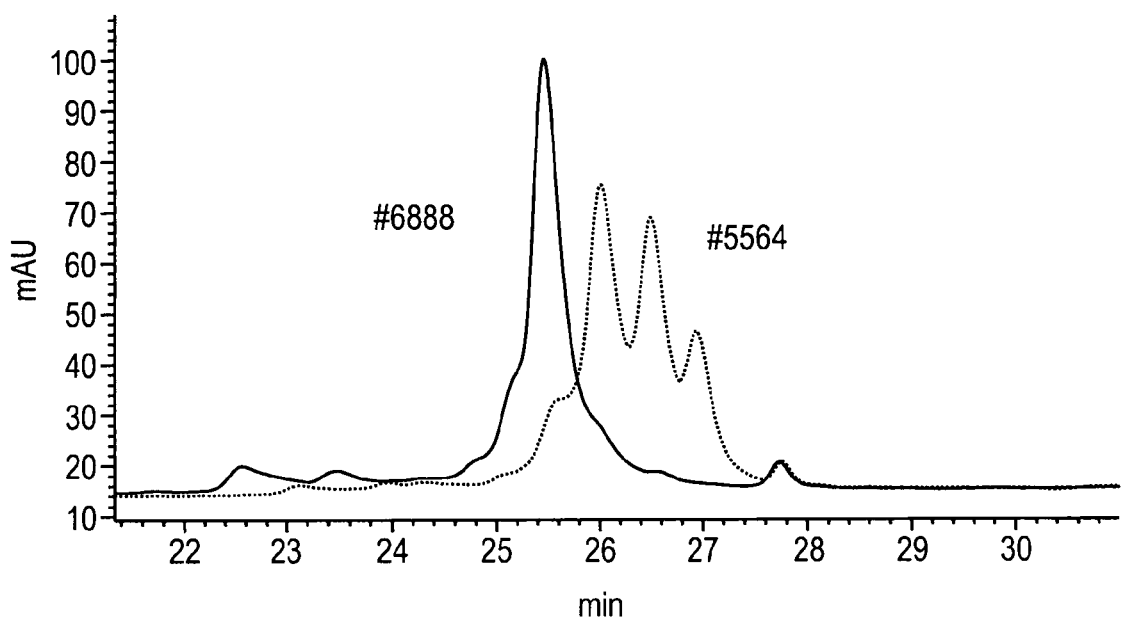

FIG. 12 shows a RP-HPLC comparison of Fc-loop Ang2 (#6888) and carboxy-terminal Fc TN8-19-07 (#5564) refold reactions. Loaded 20 μl refold reaction to Vydak C4 column (5 μM, 300 angstrom, 4.6×250 mm) and eluted with a linear 40-50% ACN gradient at 0.5%/min.

Figure 13:
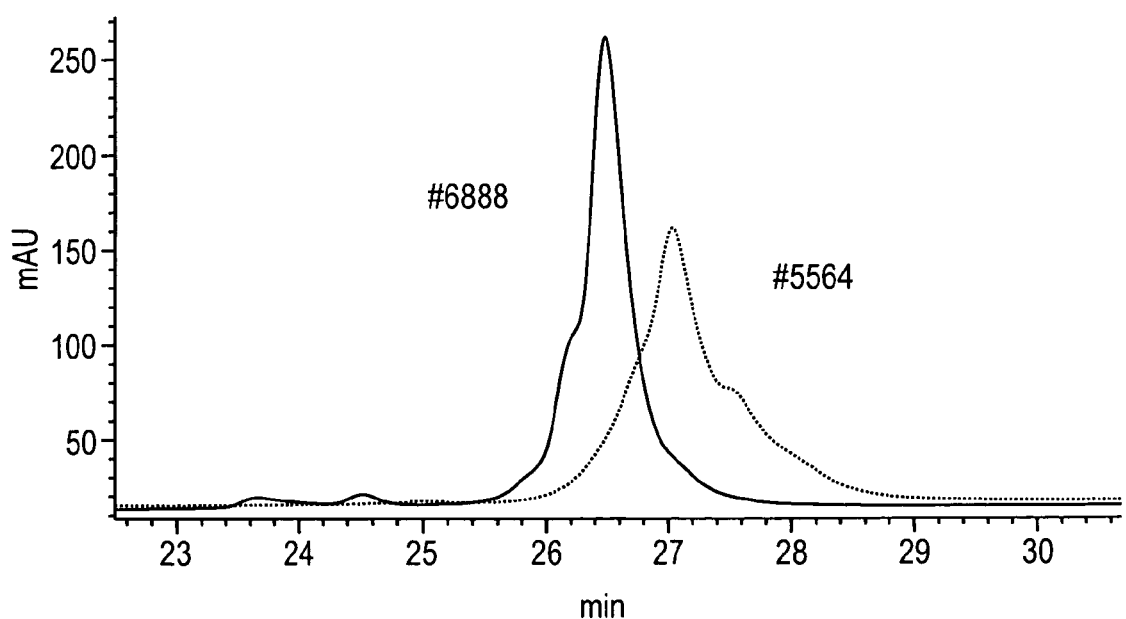

FIG. 13 shows a RP-HPLC comparison of the final purified pools of Fc-loop Ang2 (#6888) and carboxy-terminal Fc TN8-Con4 (#5564). Ten μg purified peptibody was loaded to a Vydak C4 column (5 μM, 300 angstrom, 4.6×250 mm) and eluted with a linear 40-50% ACN gradient at 0.5%/min.

Figure 14:
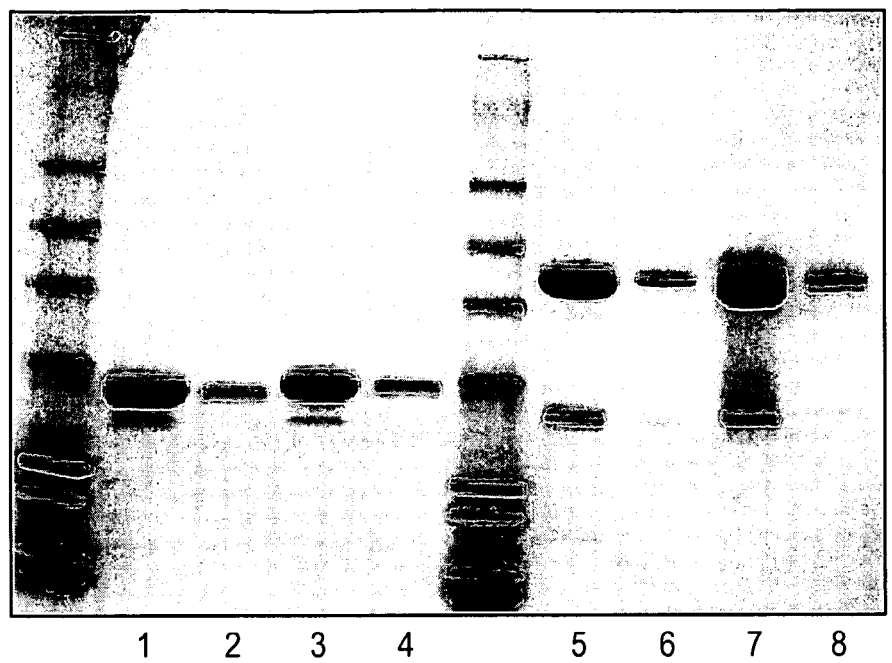

FIG. 14 shows purified Fc-loop-myo7 and TN8-19-7.

Figure 15:
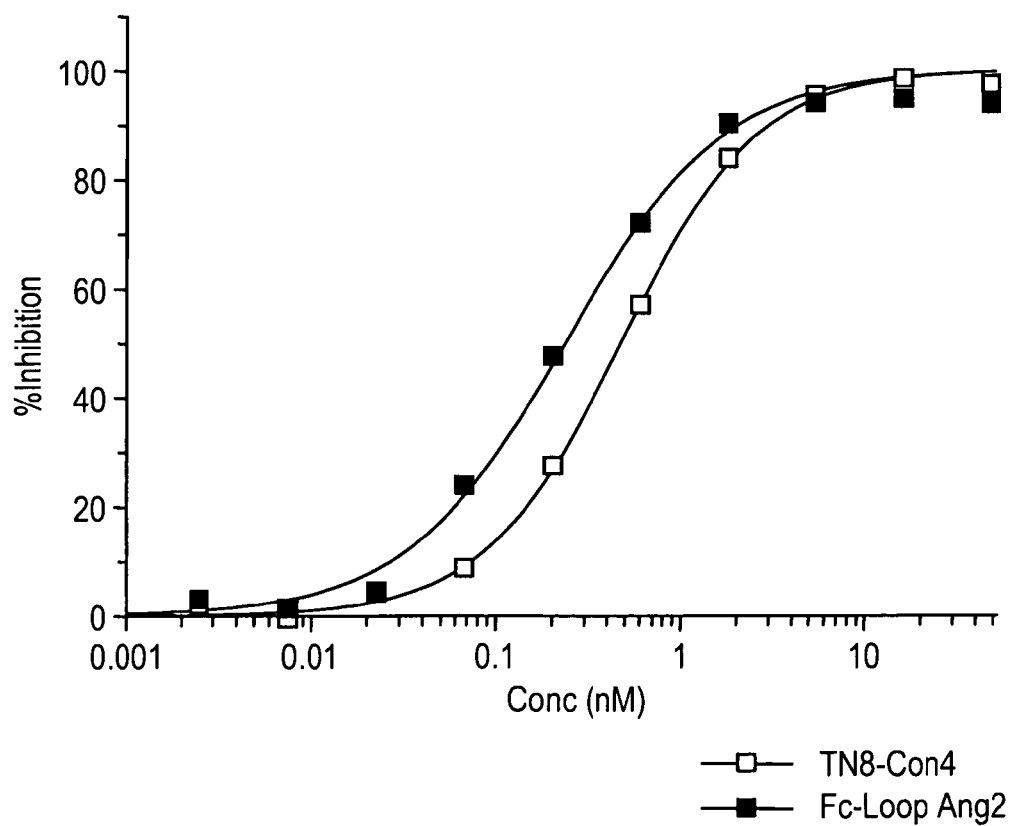

FIG. 15 shows Biacore binding analysis of Fc-loop-ang2 and Fc-ang2-tandem.

Figure 16:
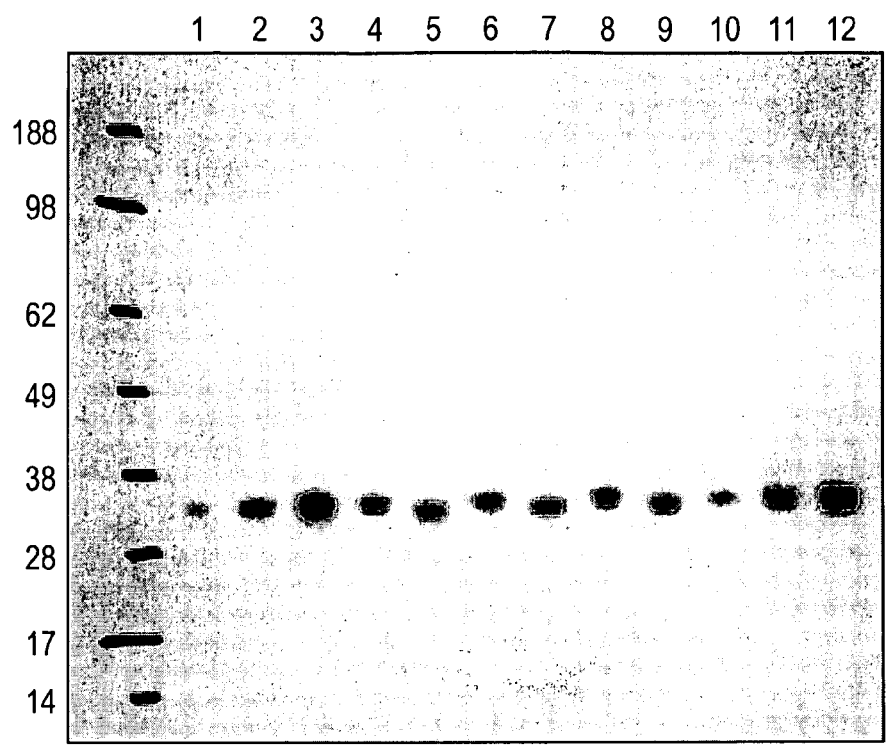

FIG. 16 shows the results of an in vitro enzyme-linked immunosorbent assay (ELISA) for Fc-loop-ang2, TN8-Con4, and Fc-ang2-tandem.

Figure 17:
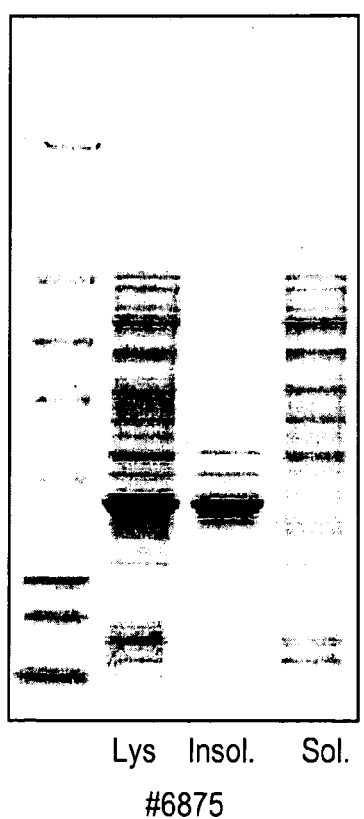

FIG. 17 shows the results of a UT7 erythropoietin proliferation assay for Fc-loop-EMP. In the assay, the activity of two different of Fc-loop-EMP molecules is compared to that of epoetin alfa.

Figure 18:
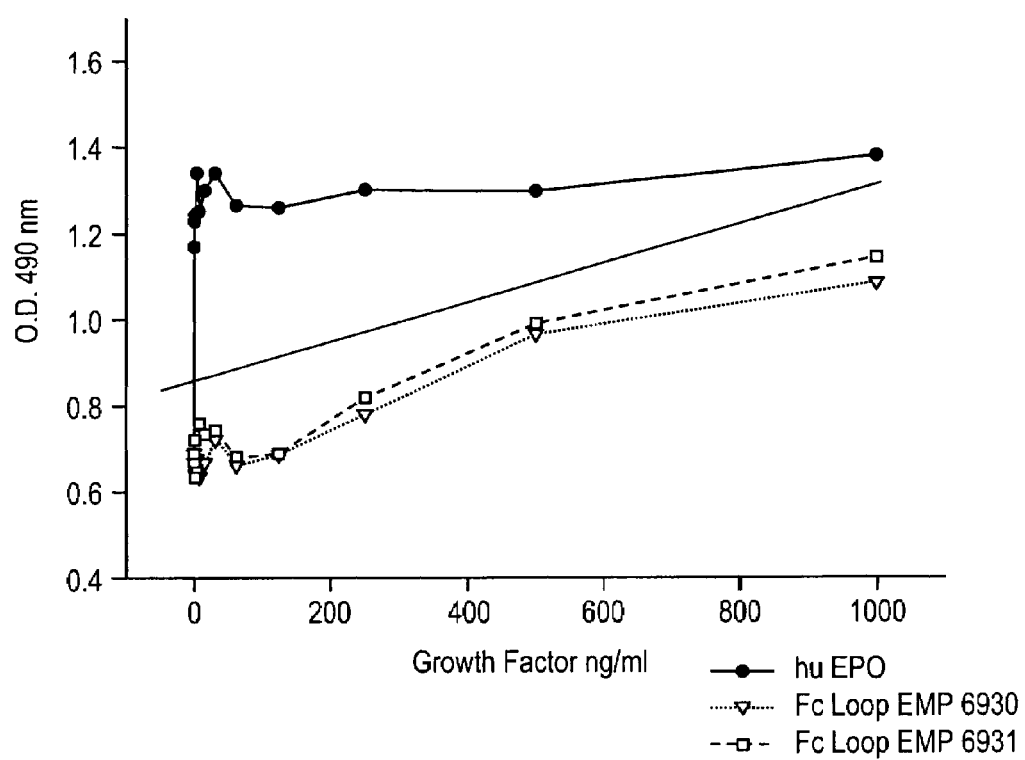

FIG. 18 shows the expression and distribution in *E. coli* of the Fc-loop TN8-Amp2 (#6875) peptibody by SDS-PAGE. Samples of the crude cell lysate (lys), the insoluble fraction (insol) and the soluble (sol) fraction for the Fc-loop-Amp2 (#6888) are shown in reducing gels.

Figure 19:
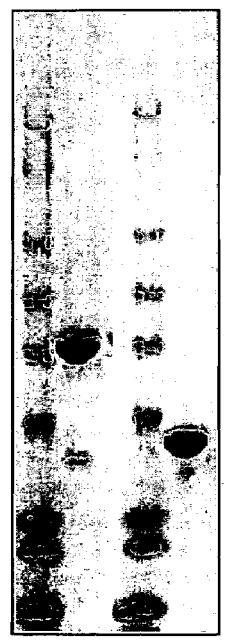

FIG. 19 shows an analysis of the final purified pool of Fc-loop AMP 2 (#6875) by SDS-PAGE (4-20% gel). Lane 2 was loaded with 5 μg Fc-loop AMP 2 peptibody; lane 4 with 5 µg reduced Fc-loop AMP 2 peptibody; lanes 1 and 3 with SeeBlue and two molecular weight markers.

Figure 20:
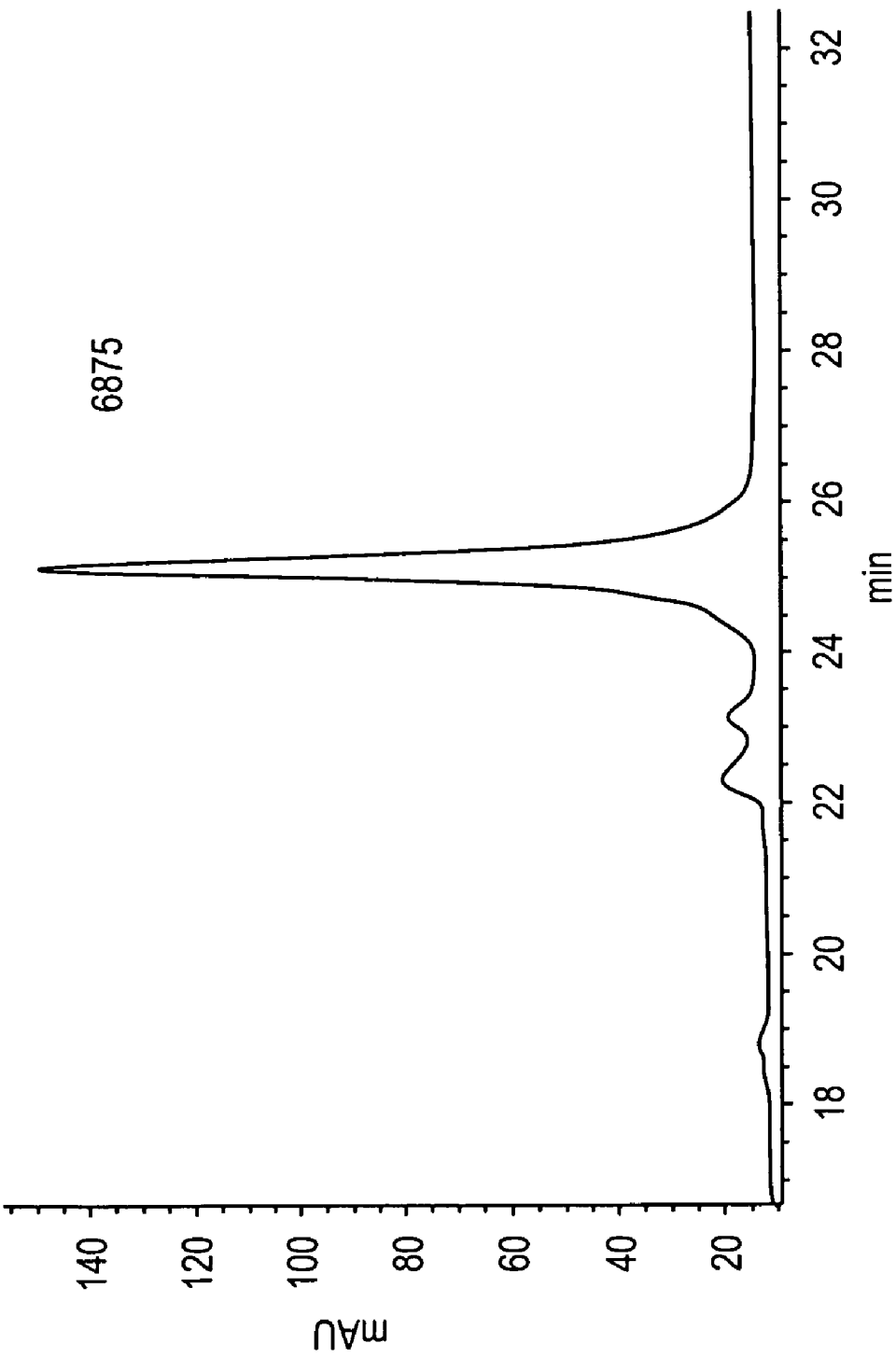

FIG. 20 shows an RP-HPLC analysis of the final purified pool of Fc-loop AMP 2 (#6875). Ten µg purified peptibody was loaded to Vydak C4 column (5 µM, 300 angstrom, 4.6× 250 mm) and eluted with a linear 40-50% ACN gradient at 0.5%/min.

Figure 21:
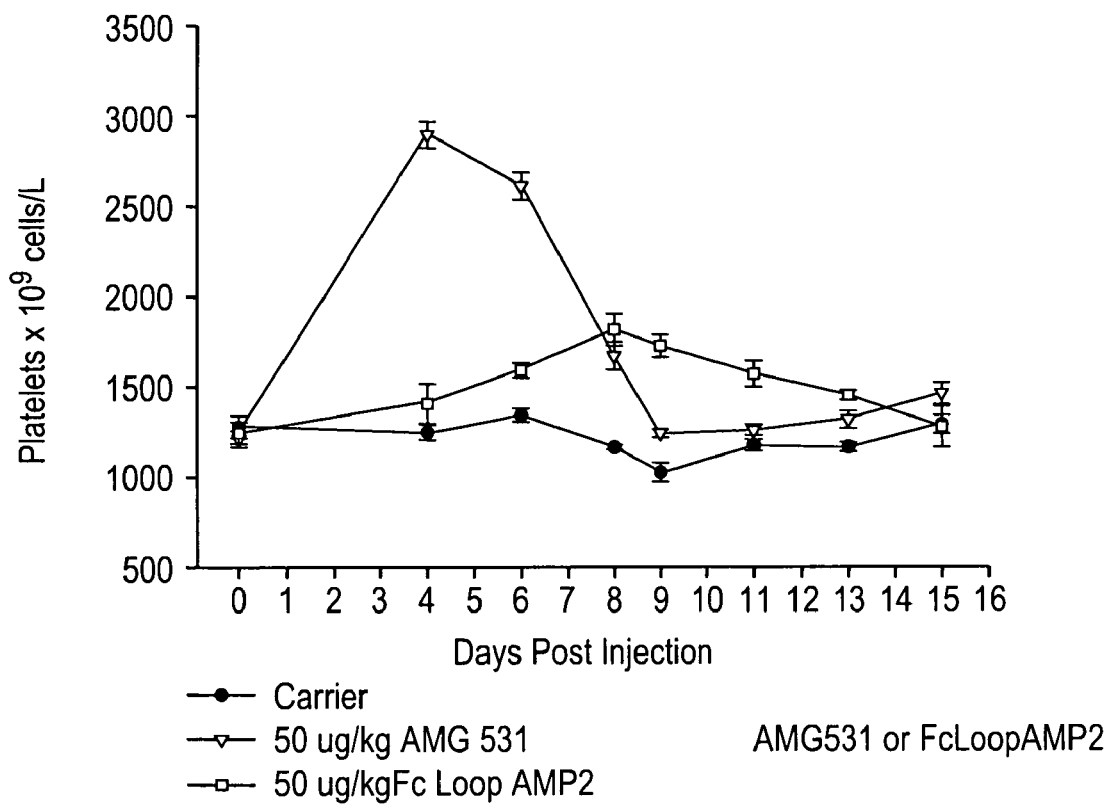

FIG. 21 shows a murine in vivo bioassay of Fc-loop AMP 2 and AMG 531 peptibodies. Mice dosed with a single subcutaneous injection of 50 µg/kg peptibody or carrier alone. See example 9 for assay methodology.

Figure 22:
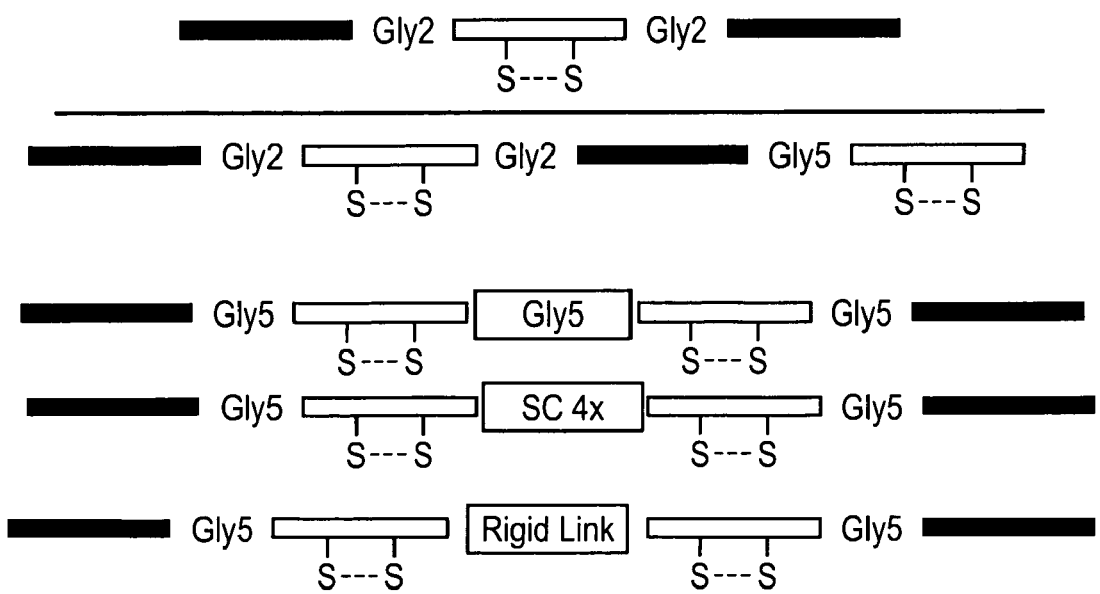

FIG. 22 shows several strategies for incorporating 2 bioactive peptides into an Fc-loop peptibody.

Figure 23:
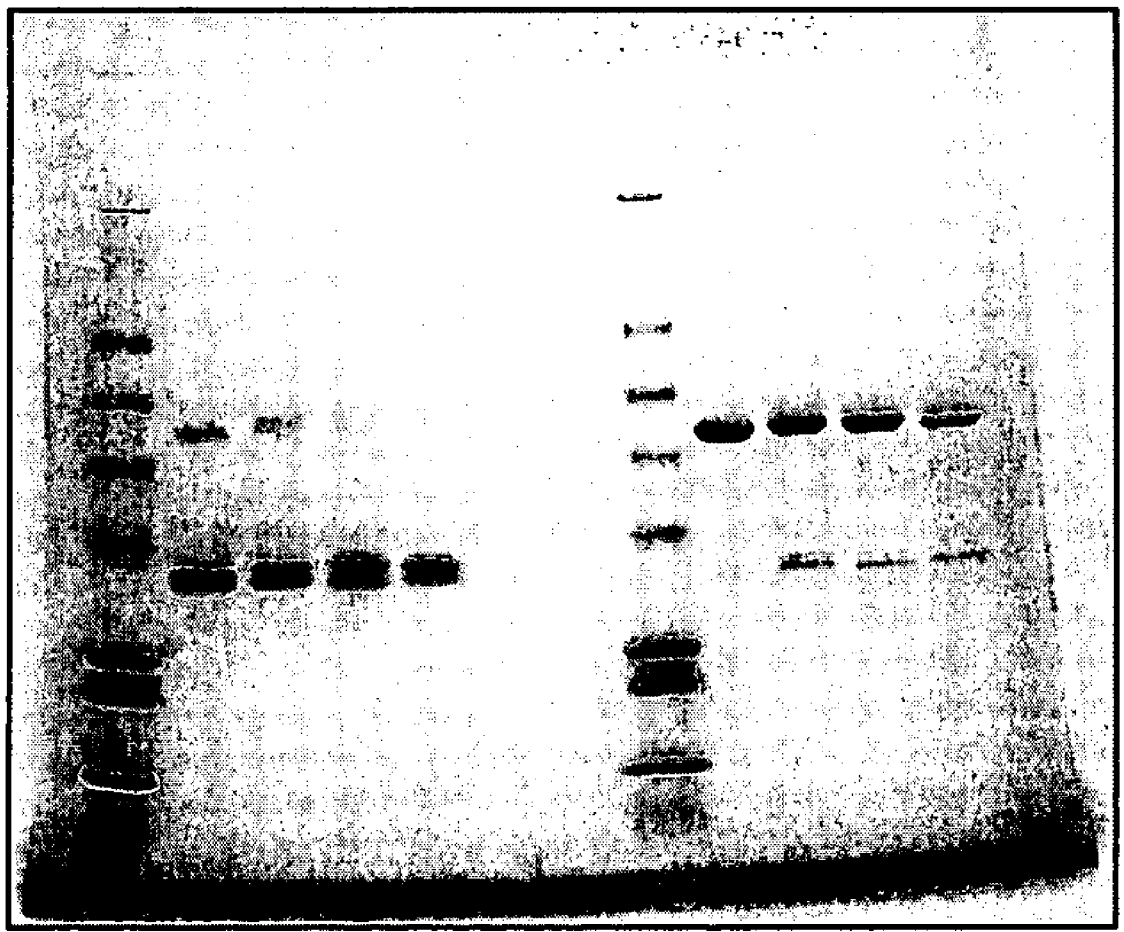

FIG. 23 shows SDS-PAGE Gels of purified Fc-loop constructs. Samples (2 ug/lane) were run +/−reducing buffer on a 4-20% Tris-Glycine SDS-PAGE gel.

FIG. 24 shows RP-HPLC of Fc-loop constructs.

DETAILED DESCRIPTION OF THE INVENTION

Definition of Terms

The terms used throughout this specification are defined as follows, unless otherwise limited in specific instances.

When used in connection with an amino acid sequence, the term "comprising" means that a compound may include additional amino acids on either or both of the N— or C-termini of the given sequence.

"Antibody" or "antibody peptide(s)" refer to an intact antibody, or a binding fragment thereof that competes with the intact antibody for specific binding and includes chimeric, humanized, fully human, and bispecific antibodies. In certain embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies.

The term "native Fc" refers to a molecule or sequence comprising the sequence of a non-antigen-binding fragment resulting from digestion of whole antibody, whether in monomeric or multimeric form, into which a peptide sequence may be added by insertion into or replacement of a loop region. The original immunoglobulin source of the native Fc is preferably of human origin and may be any of the immunoglobulins, although IgG1 and IgG2 are preferred Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10: 4071-9). The term "native Fc" as used herein is generic to the monomeric, dimeric, and multimeric forms.

The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by other means.

The term "multimer" as applied to Fc domains or molecules comprising Fc domains refers to molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The term "dimer" as applied to Fc domains or molecules comprising Fc domains refers to molecules having two polypeptide chains associated covalently or non-covalently. Exemplary dimers within the scope of this invention are as shown in U.S. Pat. No. 6,660,843, FIG. 2, which is hereby incorporated by reference.

The terms "derivatizing" and "derivative" or "derivatized" comprise processes and resulting compounds respectively in which (1) the compound has a cyclic portion; for example, cross-linking between cysteinyl residues within the compound; (2) the compound is cross-linked or has a cross-linking site; for example, the compound has a cysteinyl residue and thus forms cross-linked dimers in culture or in vivo; (3) one or more peptidyl linkage is replaced by a non-peptidyl linkage; (4) the N-terminus is replaced by —NRR$^1$, NRC(O)R$^1$, —NRC(O)OR$^1$, —NRS(O)$_2$R$^1$, —NHC(O)NHR, a succinimide group, or substituted or unsubstituted benzyloxy-carbonyl-NH—, wherein R and R$^1$ and the ring substituents are as defined hereinafter; (5) the C-terminus is replaced by —C(O)R$^2$ or —NR$^3$R$^4$ wherein R$^2$, R$^3$ and R$^4$ are as defined hereinafter; and (6) compounds in which individual amino acid moieties are modified through treatment with agents capable of reacting with selected side chains or terminal residues. Derivatives are further described hereinafter.

The term "polypeptide" refers to molecules of greater than 40 amino acids, whether existing in nature or not, provided that such molecules are not membrane-bound. Exemplary polypeptides include IL-1ra, leptin, soluble TNF receptors type 1 and type 2 (sTNF-R1, sTNF-R2), KGF, EPO, TPO, G-CSF, darbepoietin, Fab fragments and the like.

The term "peptide" refers to molecules of 2 to 40 amino acids, with molecules of 3 to 20 amino acids preferred and those of 6 to 15 amino acids most preferred. Exemplary peptides may be randomly generated by any of the methods cited above, carried in a peptide library (e.g., a phage display library), or derived by digestion of proteins.

The term "randomized" as used to refer to peptide sequences refers to fully random sequences (e.g., selected by phage display methods) and sequences in which one or more residues of a naturally occurring molecule is replaced by an amino acid residue not appearing in that position in the naturally occurring molecule. Exemplary methods for identifying peptide sequences include phage display, *E. coli* display, ribosome display, yeast-based screening, RNA-peptide screening, chemical screening, rational design, protein structural analysis, and the like.

The term "pharmacologically active" means that a substance so described is determined to have activity that affects a medical parameter (e.g., blood pressure, blood cell count, cholesterol level) or disease state (e.g., cancer, autoimmune disorders). Thus, pharmacologically active peptides comprise agonistic or mimetic and antagonistic peptides as defined below.

The terms "-mimetic peptide" and "-agonist peptide" refer to a peptide having biological activity comparable to a protein (e.g., EPO, TPO, G-CSF) that interacts with a protein of interest. These terms further include peptides that indirectly mimic the activity of a protein of interest, such as by potentiating the effects of the natural ligand of the protein of interest; see, for example, the G-CSF-mimetic peptides listed in Table 2 hereof and in Table 7 of U.S. Pat. No. 6,660,843, which is hereby incorporated by reference. Thus, the term "EPO-mimetic peptide" comprises any peptides that can be identified or derived as described in Wrighton et al. (1996), *Science* 273: 458-63, Naranda et al. (1999), *Proc. Natl. Acad. Sci. USA* 96: 7569-74, or any other reference in Table 2 identified as having EPO-mimetic subject matter. Those of ordinary skill in the art appreciate that each of these references enables one to select different peptides than actually disclosed therein by following the disclosed procedures with different peptide libraries.

The term "antagonist peptide" or "inhibitor peptide" refers to a peptide that blocks or in some way interferes with the biological activity of the associated protein of interest, or has biological activity comparable to a known antagonist or inhibitor of the associated protein of interest. Thus, the term "TNF-antagonist peptide" comprises peptides that can be identified or derived as described in Takasaki et al. (1997), *Nature Biotech.* 15: 1266-70 or any of the references in Table 2 identified as having TNF-antagonistic subject matter. Those of ordinary skill in the art appreciate that each of these references enables one to select different peptides than actually disclosed therein by following the disclosed procedures with different peptide libraries.

The term "TPO-mimetic peptide" comprises peptides that can be identified or derived as described in Cwirla et al. (1997), *Science* 276: 1696-9, U.S. Pat. Nos. 5,869,451; U.S. Pat. App. No. 2003/0176352, published Sep. 18, 2003; WO 03/031589, published Apr. 17, 2003 and any other reference in Table 2 identified as having TPO-mimetic subject matter, as well as WO 00/24770, published May 4, 2000, which is hereby incorporated by reference. Those of ordinary skill in the art appreciate that each of these references enables one to select different peptides than actually disclosed therein by following the disclosed procedures with different peptide libraries.

The term "ang-2-binding peptide" comprises peptides that can be identified or derived as described in U.S. Pat. App. No. 2003/0229023, published Dec. 11, 2003; WO 03/057134, published Jul. 17, 2003; U.S. 2003/0236193, published Dec. 25, 2003; and any other reference in Table 2 identified as having subject matter related to ang-2. Those of ordinary skill in the art appreciate that each of these references enables one to select different peptides than actually disclosed therein by following the disclosed procedures with different peptide libraries.

The term "NGF-binding peptide" comprises peptides that can be identified or derived as described in WO 04/026329, published Apr. 1, 2004 and any other reference in Table 2 identified as having subject matter related to NGF. Those of ordinary skill in the art appreciate that each of these references enables one to select different peptides than actually disclosed therein by following the disclosed procedures with different peptide libraries.

The term "myostatin-binding peptide" comprises peptides that can be identified or derived as described in U.S. Ser. No. 10/742,379, filed Dec. 19, 2003 and any other reference in Table 2 identified as having subject matter related to myostatin. Those of ordinary skill in the art appreciate that each of these references enables one to select different peptides than actually disclosed therein by following the disclosed procedures with different peptide libraries.

Additionally, physiologically acceptable salts of the compounds of this invention are also encompassed herein. By "physiologically acceptable salts" is meant any salts that are known or later discovered to be pharmaceutically acceptable. Some specific examples are: acetate; trifluoroacetate; hydrohalides, such as hydrochloride and hydrobromide; sulfate; citrate; tartrate; glycolate; and oxalate.

Structure of Compounds

In General

In the compositions of matter prepared in accordance with this invention, the peptide may be attached to the vehicle through the peptide's N-terminus or C-terminus. Thus, the vehicle-peptide molecules of this invention may be described by the following formula I:

$$(X^1)_a—F^1—(X^2)_b \qquad \qquad I$$

wherein:

$F^1$ is an Fc domain modified so that it comprises at least one $X^3$ in a loop region;

$X^1$ and $X^2$ are each independently selected from $-(L^1)_c-P^1$, $-(L^1)_c-P^1-(L^2)_d-P^2$, $-(L^1)_c-P^1-(L^2)_d-P^2-(L^3)_e-P^3$ and $-(L^1)_c-P^1-(L^2)_d-P^2-(L^3)_e-P^3-(L^4)_f-P^4$;

$X^3$ is independently selected from $-(L^5)_c-P^5$, $-(L^5)_c-P^5-(L^6)_d-P^6$, $-(L^5)_c-P^5-(L^6)_d-P^6-(L^7)_e-P^7$, and $-(L^5)_c-P^5-(L^6)_d-P^6-(L^7)_e-P^7-(L^8)_f-P^8$;

$P^1$, $P^2$, $P^3$, and $P^4$ are each independently sequences of pharmacologically active polypeptides or pharmacologically active peptides;

$P^5$, $P^6$, $P^7$, and $P^8$ are each independently sequences of pharmacologically active peptides;

$L^1$, $L^2$, $L^3$, $L^4$, $L^5$, $L^6$, $L^7$, and $L^8$ are each independently linkers; and a, b, c, d, e, and f are each independently 0 or 1.

In preferred embodiments, a and b are both zero—i.e., neither $X^1$ nor $X^2$ groups appear at the N-terminus or C-terminus of the Fc domain.

Those of ordinary skill in the art will appreciate that more than one $X^3$ substituent may be present in the Fc domain, and that the multiple $X^3$ substituents may be different; for example, comprising different $P^5$ peptides, different linkers attached to the same peptide sequence, and so on. Likewise, $X^1$ and $X^2$ may be the same or different, and the integers c through f may be different for $X^1$, $X^2$, and $X^3$.

Thus, compound I comprises compounds of the formulae $$X^1—F^1 \qquad \qquad II$$

and multimers thereof wherein $F^1$ is attached at the C-terminus of $X^1$;

$$F^1—X^2 \qquad \qquad III$$

and multimers thereof wherein $F^1$ is attached at the N-terminus of $X^2$;

$$F^1-(L^1)_c-P^1 \qquad \qquad IV$$

and multimers thereof wherein $F^1$ is attached at the N-terminus of $-(L^1)_c-P^1$; and $$F^1-(L^1)_c-P^1-(L^2)_d-P^2 \qquad \qquad V$$

and multimers thereof wherein $F^1$ is attached at the N-terminus of $-L^1-P^1-L^2-P^2$.

Peptides

Any number of peptides may be used in conjunction with the present invention. Preferred peptides bind to angiopoietin-2 (ang-2), myostatin, nerve growth factor (NGF), tumor necrosis factor (TNF), B cell activating factor (BAFF, also referred to as TALL-1) or mimic the activity of EPO, TPO, or G-CSF. Targeting peptides are also of interest, including tumor-homing peptides, membrane-transporting peptides, and the like. All of these classes of peptides may be discovered by methods described in the references cited in this specification and other references.

Phage display, in particular, is useful in generating peptides for use in the present invention. It has been stated that affinity selection from libraries of random peptides can be used to identify peptide ligands for any site of any gene product. Dedman et al. (1993), *J. Biol. Chem.* 268: 23025-30. Phage display is particularly well suited for identifying peptides that bind to such proteins of interest as cell surface receptors or any proteins having linear epitopes. Wilson et al. (1998), *Can. J. Microbiol.* 44: 313-29; Kay et al. (1998), *Drug Disc. Today* 3: 370-8. Such proteins are extensively reviewed in Herz et al. (1997), *J. Receptor & Signal Transduction Res.* 17(5): 671-776, which is hereby incorporated by reference. Such proteins of interest are preferred for use in this invention.

A particularly preferred group of peptides are those that bind to cytokine receptors. Cytokines have recently been classified according to their receptor code. See Inglot (1997), *Archivum Immunologiae et Therapiae Experimentalis* 45: 353-7, which is hereby incorporated by reference. Among these receptors, most preferred are the CKRs (family I in Table 3). The receptor classification appears in Table 3.

TABLE 3

| Cytokine Receptors Classified by Receptor Code | | | |
|---|---|---|---|
| Cytokines (ligands) | | Receptor Type | |
| family | subfamily | family | subfamily |
| I. Hematopoietic cytokines | 1. IL-2, IL-4, IL-7, IL-9, IL-13, IL-15 | I. Cytokine R (CKR) | 1. shared $\gamma$Cr, IL-9R, IL-4R |
| | 2. IL-3, IL-5, GM-CSF | | 2. shared GP 140 $\beta$R |
| | 3. IL-6, IL-11, IL-12, LIF, OSM, CNTF, Leptin (OB) | | 3. 3.shared RP 130, IL-6 R, Leptin R |
| | 4. G-CSF, EPO, TPO, PRL, GH | | 4. "single chain" R, GCSF-R, TPO-R, GH-R |
| | 5. IL-17, HVS-IL-17 | | 5. other $R^b$ |
| II. IL-10 ligands | IL-10, BCRF-1, HSV-IL-10 | II. IL-10 R | |
| III. Interferons | 1. IFN-$\alpha$1, $\alpha$2, $\alpha$4, m, t, IFN-$\beta^c$ | III. Interferon R | 1. IFNAR |
| | 2. IFN-$\gamma$ | | 2. IFNGR |
| IV. IL-1 and IL-1 like ligands | 1. IL-1$\alpha$, IL-1$\beta$, IL-1Ra | IV. IL-1R | 1. IL-1R, IL-1RAcP |
| | 2. IL-18, IL-18BP | | 2. IL-18R, IL-18RAcP |
| V. TNF family | 1. TNF-$\alpha$, TNF-$\beta$ (LT), FASL, CD40 L, CD30L, CD27 L, OX40L, OPGL, TRAIL, APRIL, AGP-3, BLys, TL5, Ntn-2, KAY, Neutrokine-$\alpha$ | 3. NGF/TNF $R^d$ | TNF-RI, AGP-3R, DR4, DR5, OX40, OPG, TACI, CD40, FAS, ODR |
| VI. Chemokines | 1. $\alpha$ chemokines: IL-8, GRO $\alpha$, $\beta$, $\gamma$, IF-10, PF-4, SDF-1 | 4. Chemokine R | 1. CXCR |
| | 2. $\beta$ chemokines: MIP1$\alpha$, MIP1$\beta$, MCP-1,2,3,4, RANTES, eotaxin | | 2. CCR |
| | 3. $\gamma$ chemokines: lymphotactin | | 3. CR |
| | | | 4. DARC$^e$ |

TABLE 3-continued

Cytokine Receptors Classified by Receptor Code

| Cytokines (ligands) | | Receptor Type | |
|---|---|---|---|
| family | subfamily | family | subfamily |
| VII. Growth factors | 1.1 SCF, M-CSF, PDGF-AA, AB, BB, KDR, FLT-1, FLT-3L, VEGF, SSV-PDGF, HGF, SF | VII. RKF | 1. TK sub-family 1.1 IgTK III R, VEGF-RI, VEGF-RII |
| | 1.2 FGFα, FGFβ | | 1.2 IgTK IV R |
| | 1.3 EGF, TGF-α, VV-F19 (EGF-like) | | 1.3 Cysteine-rich TK-I |
| | 1.4 IGF-I, IGF-II, Insulin | | 1.4 Cysteine rich TK-II, IGF-RI |
| | 1.5 NGF, BDNF, NT-3, NT-4[f] | | 1.5 Cysteine knot TK V |
| | 2. TGF-β1, β2, β3 | | 2. Serine-threonine kinase subfamily (STKS)[g] |

[1]IL-17R - belongs to CKR family but is unassigned to 4 indicated subfamilies.
[2]Other IFN type I subtypes remain unassigned. Hematopoietic cytokines, IL-10 ligands and interferons do not possess functional intrinsic protein kinases. The signaling molecules for the cytokines are JAK's, STATs and related non-receptor molecules. IL-14, IL-16 and IL-18 have been cloned but according to the receptor code they remain unassigned.
[3]TNF receptors use multiple, distinct intracellular molecules for signal transduction including "death domain" of FAS R and 55 kDa TNF-αR that participates in their cytotoxic effects. NGF/TNF R can bind both NGF and related factors as well as TNF ligands. Chemokine receptors are seven transmembrane (7TM, serpentine) domain receptors. They are G protein-coupled.
[4]The Duffy blood group antigen (DARC) is an erythrocyte receptor that can bind several different chemokines. IL-1R belongs to the immunoglobulin superfamily but their signal transduction events characteristics remain unclear.
[5]The neurotrophic cytokines can associate with NGF/TNF receptors also.
[6]STKS may encompass many other TGF-β-related factors that remain unassigned. The protein kinases are intrinsic part of the intracellular domain of receptor kinase family (RKF). The enzymes participate in the signals transmission via the receptors.

Particular proteins of interest as targets for peptide generation in the present invention include the following:
αvβ3
αVβ1
Ang-2
BAFF/TALL-1
B7
B7RP1
CRP1
Calcitonin
CD28
CETP
cMet
Complement factor B
C4b
CTLA4
Glucagon
Glucagon Receptor
LIPG
MPL
myostatin
splice variants of molecules preferentially expressed on tumor cells; e.g., CD44, CD30
unglycosylated variants of mucin and Lewis Y surface glycoproteins
CD19, CD20, CD33, CD45
prostate specific membrane antigen and prostate specific cell antigen
matrix metalloproteinases (MMPs), both secreted and membrane-bound (e.g., MMP-9)
Cathepsins
angiopoietin-2
TIE-2 receptor
heparanase
urokinase plasminogen activator (UPA), UPA receptor parathyroid hormone (PTH), parathyroid hormone-related protein (PTHrP), PTH-RI, PTH-RII
Her2
Her3
Insulin Exemplary peptides for this invention appear in Tables 4 through 20 of U.S. Pat. No. 6,660,843, which are hereby incorporated by reference. Additional preferred peptides appear in U.S. 2003/0229023, published Dec. 11, 2003; WO 03/057134, published Jul. 17, 2003; U.S. 2003/0236193, published Dec. 25, 2003; WO 00/24770, published May 4, 2000; U.S. 2003/0176352, published Sep. 18, 2003; WO 03/031589, published Apr. 17, 2003; U.S. Ser. No. 10/666,480, filed Sep. 18, 2003; WO 04/026329, published Apr. 1, 2004; U.S. Ser. No. 10/742,379, filed Dec. 19, 2003; PCT/US03/40781, filed Dec. 19, 2003, each of which are hereby incorporated by reference. Such peptides may be prepared by methods disclosed in the art.

Particularly preferred peptides appear in the tables below. Single letter amino acid abbreviations are used. Any of these peptides may be linked in tandem (i.e., sequentially), with or without linkers. Any peptide containing a cysteinyl residue may be cross-linked with another Cys-containing peptide or protein. Any peptide having more than one Cys residue may form an intrapeptide disulfide bond, as well. Any of these peptides may be derivatized as described herein. All peptides are linked through peptide bonds unless otherwise noted.

TABLE 4

EPO-mimetic peptide sequences

| SEQUENCE | SEQ ID NO: |
|---|---|
| YXCXXGPXTWXCXP | 1 |
| GGTYSCHFGPLTWVCKPQGG | 2 |
| GGDYHCRMGPLTWVCKPLGG | 3 |
| GGVYACRMGPITWVCSPLGG | 4 |
| VGNYMCHFGPITWVCRPGGG | 5 |
| GGLYLCRFGPVTWDCGYKGG | 6 |
| GGTYSCHFGPLTWVCKPQGGSSK | 7 |
| GGTYSCHGPLTWVCKPQGG | 8 |
| VGNYMAHMGPITWVCRPGG | 9 |
| GGPHHVYACRMGPLTWIC | 10 |
| GGTYSCHFGPLTWVCKPQ | 11 |
| GGLYACHMGPMTWVCQPLRG | 12 |
| TIAQYICYMGPETWECRPSPKA | 13 |
| YSCHFGPLTWVCK | 14 |
| YCHFGPLTWVC | 15 |
| GGLYLCRFGPVTWDCGYKGG | 16 |
| GGTYSCHFGPLTWVCKPQGG | 17 |
| GGDYHCRMGPLTWVCKPLGG | 18 |
| VGNYMCHFGPITWVCRPGGG | 19 |
| GGVYACRMGPITWVCSPLGG | 20 |
| VGNYMAHMGPITWVCRPGG | 21 |
| GGTYSCHFGPLTWVCKPQ | 22 |
| GGLYACHMGPMTWVCQPLRG | 23 |
| TIAQYICYMGPETWECRPSPKA | 24 |
| YSCHFGPLTWVCK | 25 |
| YCHFGPLTWVC | 26 |
| SCHFGPLTWVCK | 27 |

TABLE 5

TPO-mimetic peptide sequences

| SEQUENCE | SEQ ID NO: |
|---|---|
| IEGPTLRQWLAARA | 28 |
| IEGPTLRQWLAAKA | 29 |
| IEGPTLREWLAARA | 30 |
| TLREWL | 31 |
| GRVRDQVAGW | 32 |
| GRVKDQIAQL | 33 |
| GVRDQVSWAL | 34 |
| ESVREQVMKY | 35 |
| SVRSQISASL | 36 |
| GVRETVYRHM | 37 |
| GVREVIVMHML | 38 |
| GRVRDQIWAAL | 39 |
| AGVRDQILIWL | 40 |
| GRVRDQIMLSL | 41 |
| CTLRQWLQGC | 42 |
| CTLQEFLEGC | 43 |
| CTRTEWLHGC | 44 |
| CTLREWLHGGFC | 45 |
| CTLREWVFAGLC | 46 |
| CTLRQWLILLGMC | 47 |
| CTLAEFLASGVEQC | 48 |
| CSLQEFLSHGGYVC | 49 |
| CTLREFLDPTTAVC | 50 |
| CTLKEWLVSHEVWC | 51 |
| REGPTLRQWM | 52 |
| EGPTLRQWLA | 53 |
| ERGPFWAKAC | 54 |
| REGPRCVMWM | 55 |
| CGTEGPTLSTWLDC | 56 |
| CEQDGPTLLEWLKC | 57 |
| CELVGPSLMSWLTC | 58 |
| CLTGPFVTQWLYEC | 59 |
| CRAGPTLLEWLTLC | 60 |
| CADGPTLREWISFC | 61 |
| GGCTLREWLHGGFCGG | 62 |
| GGCADGPTLREWISFCGG | 63 |
| GNADGPTLRQWLEGRRPKN | 64 |
| LAIEGPTLRQWLHGNGRDT | 65 |
| HGRVGPTLREWKTQVATKK | 66 |
| TIKGPTLRQWLKSREHTS | 67 |
| ISDGPTLKEWLSVTRGAS | 68 |

TABLE 5-continued

TPO-mimetic peptide sequences

| SEQUENCE | SEQ ID NO: |
|---|---|
| SIEGPTLREWLTSRTPHS | 69 |
| GAREGPTLRQWLEWVRVG | 70 |
| RDLDGPTLRQWLPLPSVQ | 71 |
| ALRDGPTLKQWLEYRRQA | 72 |
| ARQEGPTLKEWLFWVRMG | 73 |
| EALLGPTLREWLAWRRAQ | 74 |
| MARDGPTLREWLRTYRMM | 75 |
| WMPEGPTLKQWLFHGRGQ | 76 |
| HIREGPTLRQWLVALRMV | 77 |
| QLGHGPTLRQWLSWYRGM | 78 |
| ELRQGPTLHEWLQHLASK | 79 |
| VGIEGPTLRQWLAQRLNP | 80 |
| WSRDGPTLREWLAWRAVG | 81 |
| AVPQGPTLKQWLLWRRCA | 82 |
| RJREGPTLKEWLAQRRGE | 83 |
| REAEGPTLREWLEQRKLV | 84 |
| DREQGPTLREWLAAIRSV | 85 |
| AGREGPTLREWLNMRVWQ | 86 |
| ALQEGPTLRQWLGWGQWG | 87 |
| YCDEGPTLKQWLVCLGLQ | 88 |
| WCKEGPTLREWLRWGFLC | 89 |
| CSSGGPTLREWLQCRRMQ | 90 |
| CSWGGPTLKQWLQCVRAK | 91 |
| CQLGGPTLREWLACRLGA | 92 |
| CWEGGPTLKEWLQCLVER | 93 |
| CRGGGPTLHQWLSCFRWQ | 94 |
| CRDGGPTLRQWLACLQQK | 95 |
| ELRSGPTLKEWLVWRLAQ | 96 |
| GCRSGPTLREWLACREVQ | 97 |
| TCEQGPTLRQWLLCRQGR | 98 |
| QGYCDEGPTLKQWLVCLGLQHS | 99 |

TABLE 6

Ang-2 binding peptide sequences

| SEQUENCE | SEQ ID NO. |
|---|---|
| WDPWT | 100 |
| WDPWTC | 101 |
| $Cz^2$WDPWT (wherein $z^2$ is an acidic or neutral polar amino acid residue) | 102 |
| $Cz^2$WDPWTC (wherein $z^2$ is an acidic or neutral polar amino acid residue) | 103 |
| PIRQEECDWDPWTCEHMWEV | 104 |
| TNIQEECEWDPWTCDHMPGK | 105 |
| WYEQDACEWDPWTCEHMAEV | 106 |
| NRLQEVCEWDPWTCEHMENV | 107 |
| AATQEECEWDPWTCEHMPRS | 108 |
| LRHQEGCEWDPWTCEHMFDW | 109 |
| VPRQKDCEWDPWTCEHMYVG | 110 |
| SISHEECEWDPWTCEHMQVG | 111 |
| WAAQEECEWDPWTCEHMGRM | 112 |
| TWPQDKCEWDPWTCEHMGST | 113 |
| GHSQEECGWDPWTCEHMGTS | 114 |
| QHWQEECEWDPWTCDHMPSK | 115 |
| NVRQEKCEWDPWTCEHMPVR | 116 |
| KSGQVECNWDPWTCEHMPRN | 117 |
| VKTQEHCDWDPWTCEHMREW | 118 |
| AWGQEGCDWDPWTCEHMLPM | 119 |
| PVNQEDCEWDPWTCEHMPPM | 120 |
| RAPQEDCEWDPWTCAHMDJK | 121 |
| HGQNMECEWDPWTCEHMFRY | 122 |
| PRLQEECVWDPWTCEHMPLR | 123 |
| RTTQEKCEWDPWTCEHMESQ | 124 |
| QTSQEDCVWDPWTCDHMVSS | 125 |
| QVIGRPCEWDPWTCEHLEGL | 126 |
| WAQQEECAWDPWTCDHMVGL | 127 |
| LPGQEDCEWDPWTCEHMVRS | 128 |
| PMNQVECDWDPWTCEHMPRS | 129 |
| FGWSHGCEWDPWTCEHMGST | 130 |
| KSTQDDCDWDPWTCEHMVGP | 131 |
| GPRISTCQWDPWTCEHMDQL | 132 |
| STIGDMCEWDPWTCAHMQVD | 133 |
| VLGGQGCEWDPWTCRLLQGW | 134 |
| VLGGQGCQWDPWTCSHLEDG | 135 |
| TTIGSMCEWDPWTCAHMQGG | 136 |
| TKGKSVCQWDPWTCSHMQSG | 137 |

TABLE 6-continued

Ang-2 binding peptide sequences

| SEQUENCE | SEQ ID NO. |
|---|---|
| TTIGSMCQWDPWTCAHMQGG | 138 |
| WVNEVVCEWDPWTCNBWDTP | 139 |
| VVQVGMCQWDPWTCKHMRLQ | 140 |
| AVGSQTCEWDPWTCAHLVEV | 141 |
| QGMKMFCEWDPWTCAHIVYR | 142 |
| TTIGSMCQWDPWTCEHMQGG | 143 |
| TSQRVGCEWDPWTCQHLTYT | 144 |
| QWSWPPCEWDPWTCQTVWPS | 145 |
| GTSPSFCQWDPWTCSHMVQG | 146 |
| QEECEWDPWTCEHM | 147 |
| QNYKPLDELDATLYEHFLFHYT | 148 |
| LNFTPLDELEQTLYEQWTLQQS | 149 |
| TKFNPLDELEQTLYEQWTLQHQ | 150 |
| VKFKPLDALEQTLYEHWMFQQA | 151 |
| VKYKPLDELDEILYEQQTFQER | 152 |
| TNFMPMDDLEQRLYEQFILQQG | 153 |
| SKFKPLDELEQTLYEQWTLQHA | 154 |
| QKFQPLDELEQTLYEQFMLQQA | 155 |
| QNFKPMDELEDTLYKQFLFQHS | 156 |
| YKETPLDDLEQTLYEQWTHQHV | 157 |
| QEYEPLDELDETLYNQWMFHQR | 158 |
| SNFMPLDELEQTLYEQFMLQHQ | 159 |
| QKYQPLDELDKTLYDQFMLQQG | 160 |
| QKFQPLDELEETLYKQWTLQQR | 161 |
| VKYKPLDELDEWLYHQFTLHHQ | 162 |
| QKFMPLDELDEILYEQFMFQQS | 163 |
| QTFQPLDDLEEYLYEQWIRRYH | 164 |
| EDYMPLDALDAQLYEQFILLHG | 165 |
| HTFQPLDELEETLYYQWLYDQL | 166 |
| YKFNPMDELEQTLYEEFLFQHA | 167 |
| TNYKPLDELDATLYEHWILQHS | 168 |
| QKFKPLDELEQTLYEQWTLQQR | 169 |
| TKEQPLDELDQTLYEQWTLQQR | 170 |
| TNFQPLDELDQTLYEQWTLQQR | 171 |
| KENPLDELEETLYEQFTEQQ | 172 |
| AGGMRPYDGMLGWPNYDVQA | 173 |
| QTWDDPCMHILGPVTWRRCI | 174 |
| APGQRPYDGMLGWPTYQRIV | 175 |

TABLE 6-continued

Ang-2 binding peptide sequences

| SEQUENCE | SEQ ID NO. |
|---|---|
| SGQLRPCEEIFGCGTQNLAL | 176 |
| FGDKRPLECMFGGPIQLCPR | 177 |
| GQDLRPCEDMFGCGTKDWYG | 178 |
| KRPCEEIFGGCTYQ | 179 |
| GFEYCDGMEDPFTFGCDKQT | 180 |
| KLEYCDGMEDPFTQGCDNQS | 181 |
| LQEWCEGVEDPFTFGCEKQR | 182 |
| AQDYCEGMEDPETFGCEMQK | 183 |
| LLDYCEGVQDPFTFGCENLD | 184 |
| HQEYCEGMEDPFTFGCEYQG | 185 |
| MLDYCEGMDDPFTFGCDKQM | 186 |
| LQDYCEGVEDPFTEGCENQR | 187 |
| LQDYCEGVEDPFTFGCEKQR | 188 |
| FDYCEGVEDPFTFGCDNH | 189 |

TABLE 7

NGF-Binding Peptide Sequences

| SEQUENCE | SEQ ID NO. |
|---|---|
| TGYTEYTEEWPMGFGYQWSF | 190 |
| TDWLSDFPFYEQYFGLMPPG | 191 |
| FMRFPNPWKLVEPPQGWYYG | 192 |
| VVKAPHFEFLAPPHFHEFPF | 193 |
| FSYIWIDETPSNIDRYMLWL | 194 |
| VNFPKVPEDVEPWPWSLKLY | 195 |
| TWHPKTYEEFALPFFVPEAP | 196 |
| WHFGTPYIQQQPGVYWLQAP | 197 |
| VWNYGPFFMNFPDSTYFLHE | 198 |
| WRIHSKPLDYSHVWFFPADF | 199 |
| FWDGNQPPDLLVDWPWNPPV | 200 |
| FYSLEWLKDHSEFFQTVTEW | 201 |
| QFMELLKFFNSPGDSSHHFL | 202 |
| TNVDWISNNWEHMKSFFTED | 203 |
| PNEKPYQMQSWFPPDWPVPY | 204 |
| WSHTEWVPQVWWKPPNHFYV | 205 |
| WGEWINDAQVHMHEGFISES | 206 |
| VPWEHDHDLWEIISQDWHIA | 207 |
| VLHLQDPRGWSNFPPGVLEL | 208 |

TABLE 7-continued

NGF-Binding Peptide Sequences

| SEQUENCE | SEQ ID NO. |
|---|---|
| IHGCWFTEEGCVWQ | 209 |
| YMQCQFARDGCPQW | 210 |
| KLQCQYSESGCPTI | 211 |
| FLQCEISGGACPAP | 212 |
| KLQCEFSTSGCPDL | 213 |
| KLQCEFSTQGCPDL | 214 |
| KLQCEFSTSGCPWL | 215 |
| IQGCWFTEEGCPWQ | 216 |
| SFDCDNPWGHVLQSCFGF | 217 |
| SFDCDNPWGHKLQSCFGF | 218 |

TABLE 8

Myostatin binding peptide sequences

| SEQUENCE | SEQ ID NO: |
|---|---|
| KDKCKMWHWMCKPP | 647 |
| KDLCAMWHWMCKPP | 219 |
| KDLCKMWKWMCKPP | 220 |
| KDLCKMWHWMCKPK | 221 |
| WYPCYEFHFWCYDL | 222 |
| WYPCYEGHFWCYDL | 223 |
| IFGCKWWDVQCYQF | 224 |
| IFGCKWWDVDCYQF | 225 |
| ADWCVSPNWFCMVM | 226 |
| HKFCPWWALFCWDF | 227 |
| KDLCKMWHWMCKPP | 228 |
| IDKCAIWGWMCPPL | 229 |
| WYPCGEFGMWCLNV | 230 |
| WFTCLWNCDNE | 231 |
| HTPCPWEAPLCVEW | 232 |
| KEWCWRWKWMCKPE | 233 |
| FETCPSWAYFCLDI | 234 |
| AYKCEANDWGCWWL | 235 |
| NSWCEDQWHRCWWL | 236 |
| WSACYAGHFWCYDL | 237 |
| ANWCVSPNWFCMVM | 238 |
| WTECYQQEFWCWNL | 239 |
| ENTCERWKWMCPPK | 240 |

TABLE 8-continued

Myostatin binding peptide sequences

| SEQUENCE | SEQ ID NO: |
|---|---|
| WLPCHQEGFWCMNF | 241 |
| STMCSQWHWMCNPF | 242 |
| IFGCHWWDVDCYQF | 243 |
| IYGCKWWDIQCYDI | 244 |
| PDWCIDPDWWCKFW | 245 |
| QGHCTRWPWMCPPY | 246 |
| WQECYREGFWCLQT | 247 |
| WFDCYGPGFKCWSP | 248 |
| GVRCPKGHLWCLYP | 249 |
| HWACGYWPWSCKWV | 250 |
| GPACHSPWWWCVFG | 251 |
| TTWCISPMWFCSQQ | 252 |
| HKFCPPWAIFCWDF | 253 |
| PDWCVSPRWYCNMW | 254 |
| VWKCHWFGMDCEPT | 255 |
| KKHCQIWTWMCAPK | 256 |
| WFQCGSTLFWCYNL | 257 |
| WSPCYDHYFYCYTI | 258 |
| SWMCGFFKEVCMWV | 259 |
| EMLCMIHPVFCNPH | 260 |
| LKTCNLWPWMCPPL | 261 |
| VVGCKWYEAWCYNK | 262 |
| PIHCTQWAWMCPPT | 263 |
| DSNCPWYFLSCVIF | 264 |
| HIWCNLAMMKCVEM | 265 |
| NLQCIYFLGKCIYF | 266 |
| AWRCMWFSDVCTPG | 267 |
| WFRCFLDADWCTSV | 268 |
| EKICQMWSWMCAPP | 269 |
| WFYCHLNKSECTEP | 270 |
| FWRCAIGIDKCKRV | 271 |
| NLGCKWYEVWCFTY | 272 |
| IDLCNMWDGMCYPP | 273 |
| EMPCNIWGWMCPPV | 274 |
| WFRCVLTGIVDWSECFGL | 275 |
| GFSCTFGLDEFYVDCSPF | 276 |
| LPWCHDQVNADWGFCMLW | 277 |
| YPTCSEKFWIYGQTCVLW | 278 |

TABLE 8-continued

Myostatin binding peptide sequences

| SEQUENCE | SEQ ID NO: |
|---|---|
| LGPCPIHHGPWPQYCVYW | 279 |
| PFPCETHQISWLGHCLSF | 280 |
| HWGCEDLMWSWHPLCRRP | 281 |
| LPLCDADMMPTIGFCVAY | 282 |
| SHWCEDTFWMNYAKCVHA | 283 |
| LPKCTHVPFDQGGFCLWY | 284 |
| FSSCWSPVSRQDMFCVFY | 285 |
| SHKCEYSGWLQPLCYRP | 286 |
| PWWCQDNYVQHMLHCDSP | 287 |
| WFRCMLMNSFDAFQCVSY | 288 |
| PDACRDQPWYMFMGCMLG | 289 |
| FLACFVEFELCFDS | 290 |
| SAYCIITESDPYVLCVPL | 291 |
| PSICESYSTMWLPMCQHN | 292 |
| WLDCHDDSWAWTKMCRSH | 293 |
| YLNCVMMNTSPFVECVEN | 294 |
| YPWCDGFMIQQGITCMFY | 295 |
| FDYCTWLNGFKDWKCWSR | 296 |
| LPLCNLKEISHVQACVLF | 297 |
| SPECAFARWLGIEQCQRD | 298 |
| YPQCFNLHLLEWTECDWF | 299 |
| RWRCEIYDSEFLPKCWFF | 300 |
| LVGCDNVWHRCKLF | 301 |
| AGWCHVWGEMFGMGCSAL | 302 |
| HHECEWMARWMSLDCVGL | 303 |
| FPMCGIAGMKDFDFCVWY | 304 |
| RDDCTFWPEWLWKLCERP | 305 |
| YNFCSYLFGVSKEACQLP | 306 |
| AHWCEQGPWRYGNICMAY | 307 |
| NLVCGKISAWGDEACARA | 308 |
| HNVCTIMGPSMKWFCWND | 309 |
| NDLCAMWGWRNTIWCQNS | 310 |
| PPFCQNDNDMLQSLCKLL | 311 |
| WYDCNVPNELLSGLCRLF | 312 |
| YGDCDQNHWMWPFTCLSL | 313 |
| GWMCHFDLHDWGATCQPD | 314 |
| YFHCMFGGHEFEVHCESF | 315 |
| AYWCWHGQCVRE | 316 |

TABLE 8-continued

Myostatin binding peptide sequences

| SEQUENCE | SEQ ID NO: |
|---|---|
| SEHWTFTDWDGNEWWVRPF | 317 |
| MEMLDSLFELLKDMVPISKA | 318 |
| SPPEEALMEWLGWQYGKFT | 319 |
| SPENLLNDLYILMTKQEWYG | 320 |
| FHWEEGIPFHVVTPYSYDRM | 321 |
| KRLLEQFMNDLAELVSGHS | 322 |
| DTRDALFQEFYEFVRSRLVI | 323 |
| RMSAAPRPLTYRDIMDQYWH | 324 |
| NDKAHFFEMFMFDVHNFVES | 325 |
| QTQAQKIDGLWELLQSLRNQ | 326 |
| MLSEFEEFLGNLVHRQEA | 327 |
| YTPKMGSEWTSFWHNRIHYL | 328 |
| LNDTLLRELKMVLNSLSDMK | 329 |
| FDVERDLMRWLEGFMQSAAT | 330 |
| HHGWNYLRKGSAPQWFEAWV | 331 |
| VESLHQLQMWLDQKLASGPH | 332 |
| RATLLKDFWQLVEGYGDN | 333 |
| EELLREFYRIFVSAFDY | 334 |
| GLLDEFSHFIAEQFYQMPGG | 335 |
| YREMSMLEGLLDVLERLQHY | 336 |
| HNSSQMLLSELIMLVGSMMQ | 337 |
| WREHFLNSDYIRDKLIAIDG | 338 |
| QFPFYVFDDLPAQLEYWIA | 339 |
| EFFHWLHNHRSEVNHWLDMN | 340 |
| EALFQNEFRDVLTLSEREY | 341 |
| QYWEQQWMTYFRENGLHVQY | 342 |
| NQRMMLEDLWRIMTPMFGRS | 343 |
| FLDELKAELSRHYALDDLDE | 344 |
| GKLIEGLLNELMQLETFMPD | 345 |
| WLLDEYKKDWKSWF | 346 |
| QGHCTRWPWMCPPYGSGSAT GGSGSTASSGSGSATGQGHC TRWPWMCPPY | 347 |
| WYPCYEGHFWCYDLGSGSTA SSGSGSATGWYPCYEGHFWC YDL | 348 |
| HTPCPWFAPLCVEWGSGSAT GGSGSTASSGSGSATGHTPC PWFAPLCVEW | 349 |
| PDWCIDPDWWCKFWGSGSAT GGSGSTASSGSGSATGPDWC IDPDWWCKFW | 350 |

TABLE 8-continued

Myostatin binding peptide sequences

| SEQUENCE | SEQ ID NO: |
|---|---|
| ANWCVSPNWFCMVMGSGSATGGSGSTASSGSGSATGANWCVSPNWFCMVM | 351 |
| PDWCIDPDWWCKFWGSGSATGGSGSTASSGSGSATGPDWCIDPDWWCKFW | 352 |
| HWACGYWPWSCKWVGSGSATGGSGSTASSGSGSATGHWACGYWPWSCKWV | 353 |
| KKHCQIWTWMCAPKGSGSATGGSGSTASSGSGSATGQGHCTRWPWMCPPY | 354 |
| QGHCTRWPWMCPPYGSGSATGGSGSTASSGSGSATGKKHCQIWTWMCAPK | 355 |
| KKHCQJWTWMCAPKGSGSATGGSGSTASSGSGSATGQGHCTRWPWMCPPY | 356 |
| KKHCQJWTWMCAPKGGGGGGGGQGHCTRWPWMCPPY | 357 |
| QGHCTRWPWMCPPYGGGGGGGKKHCQIWTWMCAPK | 358 |
| VALHGQCTRWPWMCPPQREG | 359 |
| YPEQGLCTRWPWMCPPQTLA | 360 |
| GLNQGHCTRWPWMCPPQDSN | 361 |
| MITQGQCTRWPWMCPPQPSG | 362 |
| AGAQEHCTRWPWMCAPNDWI | 363 |
| GVNGQCTRWRWMCPPNGWE | 364 |
| LADHGQCIRWPWMCPPEGWE | 365 |
| ILEQAQCTRWPWMCPPQRGG | 366 |
| TQTHAQCTRWPWMCPPQWEG | 367 |
| VVTQGHCTLWPWMCPPQRWR | 368 |
| IYPHDQCTRWPWMCPPQPYP | 369 |
| SYWQGQCTRWPWMCPPQWRG | 370 |
| MWQQGHCTRWPWMCPPQGWG | 371 |
| EFTQWHCTRWPWMCPPQRSQ | 372 |
| LDDQWQCTRWPWMCPPQGFS | 373 |
| YQTQGLCTRWPWMCPPQSQR | 374 |
| ESNQGQCTRWPWMCPPQGGW | 375 |
| WTDRGPCTRWPWMCPPQANG | 376 |
| VGTQGQCTRWPWMCPPYETG | 377 |
| PYEQGKCTRWPWMCPPYEVE | 378 |
| SEYQGLCTRWPWMCPPQGWK | 379 |
| TFSQGHCTRWPWMCPPQGWG | 380 |
| PGAHDHCTRWPWMCPPQSRY | 381 |
| VAEEWHCRRWPWMCPPQDWR | 382 |
| VGTQGHCTRWPWMCPPQPAG | 383 |
| EEDQAHCRSWPWMCPPQGWV | 384 |
| ADTQGHCTRWPWMCPPQHWF | 385 |
| SGPQGHCTRWPWMCAPQGWF | 386 |
| TLVQGHCTRWPWMCPPQRWV | 387 |
| GMAHGKCTRWAWMCPPQSWK | 388 |
| ELYHGQCTRWPWMCPPQSWA | 389 |
| VADHGCTRWPWMCPPQGWG | 390 |
| PESQGHCTRWPWMCPPQGWG | 391 |
| IPAHGHCTRWPWMCPPQRWR | 392 |
| FTVHGHCTRWPWMCPPYGWV | 393 |
| PDFPGHCTRWRWMCPPQGWE | 394 |
| QLWQGPCTQWPWMCPPKGRY | 395 |
| HANDGHCTRWQWMCPPQWGG | 396 |
| ETDHGLCTRWPWMCPPYGAR | 397 |
| GTWQGLCTRWPWMCPPQGWQ | 398 |
| VATQGQCTRWPWMCPPQGWG | 399 |
| VATQGQCTRWPWMCPPQRWG | 400 |
| QREWYPCYGGHLWCYDLHKA | 401 |
| ISAWYSCYAGHFWCWDLKQK | 402 |
| WTGWYQCYGGHLWCYDLRRK | 403 |
| KTFWYPCYDGHFWCYNLKSS | 404 |
| ESRWYPCYEGHLWCFDLTET | 405 |
| MEMLDSLFELLKDMVPISKA | 406 |
| RMEMLESLLELLKEIVPMSKAG | 407 |
| RMEMLESLLELLKEIVPMSKAR | 408 |
| RMEMLESLLELLKDIVPMSKPS | 409 |
| GMEMLESLFELLQEIVPMSKAP | 410 |
| RMEMLESLLELLKDIVPISNPP | 411 |
| RIEMLESLLELLQEIVPISKAE | 412 |
| RMEMLQSLLELLKDIVPMSNAR | 413 |
| RMEMLESLLELLKEIVPTSNGT | 414 |
| RMEMLESLFELLKEIVPMSKAG | 415 |
| RMEMLGSLLELLKEIVPMSKAR | 416 |
| QMELLDSLFELLKEIVPKSQPA | 417 |
| RMEMLDSLLELLKEIVPMSNAR | 418 |
| RMEMLESLLELLHEIVPMSQAG | 419 |

TABLE 8-continued

Myostatin binding peptide sequences

| SEQUENCE | SEQ ID NO: |
|---|---|
| QMEMLESLLQLLKEIVPMSKAS | 420 |
| RMEMLDSLLELLKDMVPMTTGA | 421 |
| RIEMLESLLELLKDMVPMANAS | 422 |
| RMEMLESLLQLLNEIVPMSRAR | 423 |
| RMEMLESLFDLLKELVPMSKGV | 424 |
| RIEMLESLLELLKDIVPIQKAR | 425 |
| RMELLESLFELLKDMVPMSDSS | 426 |
| RMEMLESLLEVLQEIVPRAKGA | 427 |
| RMEMLDSLLQLLNEIVPMSHAR | 428 |
| RMEMLESLLELLKDIVPMSNAG | 429 |
| RMEMLQSLFELLKGMVPISKAG | 430 |
| RMEMLESLLELLKEIVPNSTAA | 431 |
| RMEMLQSLLELLKEIVPISKAG | 432 |
| RIEMLDSLLELLNELVPMSKAR | 433 |
| HHGWNYLRKGSAPQWFEAWV | 434 |
| QVESLQQLLMWLDQKLASGPQG | 435 |
| RMELLESLFELLKEMVPRSKAV | 436 |
| QAVSLQHLLMWLDQKLASGPQH | 437 |
| DEDSLQQLLMWLDQKLASGPQL | 438 |
| PVASLQQLLIWLDQKLAQGPHA | 439 |
| EVDELQQLLNWLDHKLASGPLQ | 440 |
| DVESLEQLLMWLDHQLASGPHG | 441 |
| QVDSLQQVLLWLEHKLALGPQV | 442 |
| GDESLQHLLMWLEQKLALGPHG | 443 |
| QIEMLESLLDLLRDMVPMSNAF | 444 |
| EVDSLQQLLMWLDQKLASGPQA | 445 |
| EDESLQQLLIYLDKMLSSGPQV | 446 |
| AMDQLHQLLLWLDHKLASGPQA | 447 |
| RIEMLESLLELLDEIALIPKAW | 448 |
| EVVSLQHLLMWLEHKLASGPDG | 449 |
| GGESLQQLLMWLDQQLASGPQR | 450 |
| GVESLQQLLIFLDHMLVSGPHD | 451 |
| NWESLEHLMMWLERLLASGPYA | 452 |
| QVDSLQQLLIWLDHQLASGPKR | 453 |
| EVESLQQLLMWLEHKLAQGPQG | 454 |
| EVDSLQQLLMWLDQKLASGPHA | 455 |
| EVDSLQQLLMWLDQQLASGPQK | 456 |
| GVEQLPQLLMWLEQKLASGPQR | 457 |
| GEDSLQQLLMWLDQQLAAGPQV | 458 |
| ADDSLQQLLMWLDRKLASGPHV | 459 |
| PVDSLQQLLIWLDQKLASGPQG | 460 |
| RATLLKDFWQLVEGYGDN | 461 |
| DWRATLLKEFWQLVEGLGDNLV | 462 |
| QSRATLLKEFWQLVEGLGDKQA | 463 |
| DGRATLLTEFWQLVQGLGQKEA | 464 |
| LARATLLKEFWQLVEGLGEKVV | 465 |
| GSRDTLLKEFWQLVVGLGDMQT | 466 |
| DARATLLKEFWQLVDAYGDRMV | 467 |
| NDRAQLLRDFWQLVDGLGVKSW | 468 |
| GVRETLLYELWYLLKGLGANQG | 469 |
| QARATLLKEFCQLVGCQGDKLS | 470 |
| QERATLLKEFWQLVAGLGQNMR | 471 |
| SGRATLLKEFWQLVQGLGEYRW | 472 |
| TMRATLLKEFWLFVDGQREMQW | 473 |
| GERATLLNDFWQLVDGQGDNTG | 474 |
| DERETLLKEFWQLVHGWGDNVA | 475 |
| GGRATLLKELWQLLEGQGANLV | 476 |
| TARATLLNELVQLVKGYGDKLV | 477 |
| GMRATLLQEFWQLVGGQGDNWM | 478 |
| STRATLLNDLWQLMKGWAEDRG | 479 |
| SERATLLKELWQLVGGWGDNFG | 480 |
| VGRATLLKEFWQLVEGLVGQSR | 481 |
| EIRATLLKEFWQLVDEWREQPN | 482 |
| QLRATLLKEFLQLVHGLGETDS | 483 |
| TQRATLLKEFWQLIEGLGGKHV | 484 |
| HYRATLLKEFWQLVDGLREQGV | 485 |
| QSRVTLLREFWQLVESYRPIVN | 486 |
| LSRATLLNEFWQFVDGQRDKRM | 487 |
| WDRATLLNDFWHLMEELSQKPG | 488 |
| QERATLLKEFWRMVEGLGKNRG | 489 |
| NERATLLREFWQLVGGYGVNQR | 490 |
| YREMSMLEGLLDVLERLQHY | 491 |
| HQRDMSMLWELLDVLDGLRQYS | 492 |
| TQRDMSMLDGLLEVLDQLRQQR | 493 |
| TSRDMSLLWELLEELDRLGHQR | 494 |
| MQHDMSMLYGLVELLESLGHQI | 495 |

TABLE 8-continued

Myostatin binding peptide sequences

| SEQUENCE | SEQ ID NO: |
|---|---|
| WNRDMRMLESLFEVLDGLRQQV | 496 |
| GYRDMSMLEGLLAVLDRLGPQL | 497 |
| TQRDMSMLEGLLEVLDRLGQQR | 498 |
| WYRDMSMLEGLLEVLDRLGQQR | 499 |
| HNSSQMLLSELIMLVGSMMQ | 500 |
| TQNSRQMLLSDFMMLVGSMIQG | 501 |
| MQTSRHILLSEFMMLVGSIMHG | 502 |
| HDNSRQMLLSDLLHLVGTMIQG | 503 |
| MENSRQNLLRELIMLVGNMSHQ | 504 |
| QDTSRHMLLREFMMLVGEMIQG | 505 |
| DQNSRQMLLSDLMILVGSMIQG | 506 |
| EFFHWLHNHRSEVNHWLDMN | 507 |
| NVFFQWVQKHGRVVYQWLDINV | 508 |
| FDFLQWLQNHRSEVEHWLVMDV | 509 |

TABLE 9

BAFF binding peptide sequences

| SEQUENCE | SEQ ID NO: |
|---|---|
| PGTCFPFPWECTHA | 510 |
| WGACWPFPWECFKE | 511 |
| VPFCDLLTKHCFEA | 512 |
| GSRCYKWDVLTKQCFHH | 513 |
| LPGCKWDLLIKQWVCDPL | 514 |
| SADCYFDILTKSDVCTSS | 515 |
| SDDCMYDQLTRMFICSNL | 516 |
| DLNCKYDELTYKEWCQFN | 517 |
| FHDCKYDLLTRQMVCHGL | 518 |
| RNHCFWDHLLKQDICPSP | 519 |
| ANQCWWDSLTKKNVCEFF | 520 |
| YKGRQQMWDILTRSWVVSL | 521 |
| QQDVGLWWDILTRAWMPNI | 522 |
| QQNAQRVWDLLIRTWVYPQ | 523 |
| GWNEAWWDELTKIWVLEQQ | 524 |
| RITCDTWDSLIKKCVPQQS | 525 |
| GAIMQQFWDSLTKTWLRQS | 526 |
| WLHSGWWDPLTKHWLQQKV | 527 |
| SEWFFWFDPLTRAQQLKFR | 528 |

TABLE 9-continued

BAFF binding peptide sequences

| SEQUENCE | SEQ ID NO: |
|---|---|
| GVWFWWFDPLTKQWTQQAG | 529 |
| MQQCKGYYDILTKWCVTNG | 530 |
| LWSKEVWDILTKSWVSQQA | 531 |
| KAAGWWFDWLTKVWVPAP | 532 |
| AYQQTWFWDSLTRLWLSTT | 533 |
| SGQQHFWWDLLTRSWTPST | 534 |
| LGVGQQKWDPLTKQWVSRG | 535 |
| VGKMCQQWDPLIKRTVCVG | 536 |
| CRQGAKFDLLTKQCLLGR | 537 |
| GQAIRHWDVLTKQWVDSQQ | 538 |
| RGPCGSWDLLTKHCLDSQQ | 539 |
| WQWKQQQWDLLTKQMVWVG | 540 |
| PITICRKDLLTKQVVCLD | 541 |
| KTCNGKWDLLTKQCLQQQA | 542 |
| KCLKGKWDLLTKQCVTEV | 543 |
| RCWNGKWDLLTKQCIHPW | 544 |
| NRDMRKWDPLIKQWTVRP | 545 |
| QQAAAATWDLLTKQWLVPP | 546 |
| PEGGPKWDPLTKQQFLPPV | 547 |
| QQTPQQKKWDLLTKQWFTRN | 548 |
| IGSPCKWDLLTKQMICQQT | 549 |
| CTAAGKWDLLTKQCIQQEK | 550 |
| VSQCMKWDLLTKQCLQQGW | 551 |
| VWGTWKWDLLTKQYLPPQQ | 552 |
| GWWEMKWDLLTKQWYRPQQ | 553 |
| TAQQVSKWDLLTKQWLPLA | 554 |
| QLWGTKWDLLTKQYIQQIM | 555 |
| WATSQKWDLLTKQWVQQNM | 556 |
| QQRQCAKWDLLTKQCVLFY | 557 |
| KTTDCKWDLLTKQRICQQV | 558 |
| LLCQQGKWDLLTKQCLKLR | 559 |
| LMWFWKWDLLTKQLVPTF | 560 |
| QQTWAWKWDLLTKQWIGPM | 561 |
| NKELLKWDLLTKQCRGRS | 562 |
| GQQKDLKWDLLTKQYVRQS | 563 |
| PKPCQQKWDLLTKQCLGSV | 564 |
| GQIGWKWDLLTKQWIQQTR | 565 |
| VWLDWKWDLLTKQWIHPQQ | 566 |

TABLE 9-continued

BAFF binding peptide sequences

| SEQUENCE | SEQ ID NO: |
|---|---|
| QQEWEYKWDLLTKQWGWLR | 567 |
| HWDSWKWDLLTKQWVVQQA | 568 |
| TRPLQQKWDLLTKQWLRVG | 569 |
| SDQWQQKWDLLTKQWFWDV | 570 |
| QQQTEMKWDLLTKQWIRRH | 571 |
| QQGECRKWDLLTKQCFPGQ | 572 |
| GQQMGWRWDPLIKMCLGPS | 573 |
| QQLDGCKWDLLTKQKVCIP | 574 |
| HGYWQQKWDLLTKQWVSSE | 575 |
| HQQGQCGWDLLTRIYLPCH | 576 |
| LHKACKWDLLTKQCWPMQQ | 577 |
| GPPGSVWDLLTKIWIQQTG | 578 |
| ITQQDWRFDTLTRLWLPLR | 579 |
| QQGGFAAWDVLTKMWITVP | 580 |
| GHGTPWWDALTRIWILGV | 581 |
| VWPWQQKWDLLTKQFVEQD | 582 |
| WQQWSWKWDLLTRQYISSS | 583 |
| NQQTLWKWDLLTKQFITYM | 584 |
| PVYQQGWWDTLTKLYIWDG | 585 |
| WLDGGWRDPLIKRSVQQLG | 586 |
| GHQQQFKWDLLTKQWVQSN | 587 |
| QQRVGQFWDVLTKMFITGS | 588 |
| QQAQGWSYDALIKTWIRWP | 589 |
| GWMHWKWDPLTKQQALPWM | 590 |
| GHPTYKWDLLTKQWILQQM | 591 |
| WNNWSLWDPLTKLWLQQQN | 592 |
| WQWGWKWDLLTKQWVQQQ | 593 |
| GQMGWRWDPLTKMWLGTS | 594 |

Fc Domains

This invention requires the presence of at least one Fc domain modified to comprise a peptide sequence.

As noted above, both native Fc's and Fc variants are suitable Fc domains for use within the scope of this invention. A native Fc may be extensively modified to form an Fc variant in accordance with this invention, provided binding to the salvage receptor is maintained; see, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). In particular, one may truncate the N-terminal 20-amino acid segment of SEQ ID NO: 599 or delete or substitute the cysteine residues at positions 7 and 10 of SEQ ID NO: 599 Even when cysteine residues are removed, the single chain Fc domains can still form a dimeric Fc domain that is held together non-covalently.

2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionine residue, especially when the molecule is expressed recombinantly in a bacterial cell such as *E. coli*. The Fc domain of SEQ ID NO: 599 (FIG. 2A) is one such Fc variant.

3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.

4. One or more glycosylation sites are removed. Residues that are typically glycosylated (e.g., asparagine) may confer cytolytic response. Such residues may be deleted or substituted with unglycosylated residues (e.g., alanine).

5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.

6. Sites are removed that affect binding to Fc receptors other than a salvage receptor. A native Fc may have sites for interaction with certain white blood cells that are not required for the fusion molecules of the present invention and so may be removed.

7. The ADCC site is removed. ADCC sites are known in the art; see, for example, *Molec. Immunol.* 29 (5): 633-9 (1992) with regard to ADCC sites in IgG1. These sites, as well, are not required for the fusion molecules of the present invention and so may be removed.

8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

Preferred Fc variants include the following. In SEQ ID NO: 599 (FIG. 2A) the leucine at position 15 may be substituted with glutamate; the glutamate at position 99, with alanine; and the lysines at positions 101 and 103, with alanines. In addition, one or more tyrosine residues can be replaced by phenylalanine residues.

Additional Vehicles

The invention further embraces molecules covalently modified to include one or more water soluble polymer attachments, such as polyethylene glycol, polyoxyethylene glycol, or polypropylene glycol, as described U.S. Pat. Nos. 4,640,835; 4,496,689; 4,301,144; 4,670,417; 4,791,192; and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are peptibodies covalently modified with polyethylene glycol (PEG) subunits. Water-soluble polymers may be bonded at specific positions, for example at the amino terminus of the peptibodies, or randomly attached to one or more side chains of the polypeptide. The use of PEG for improving the therapeutic capacity for specific binding agents, e.g. peptibodies, and for humanized antibodies in particular, is described in U.S. Pat. No. 6,133,426 to Gonzales et al. issued Oct. 17, 2000.

Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kD") to about 100 kD, more preferably from about 5 kDa to about 50 kDa, most preferably from about 5 kD to about 20 kD. The PEG groups will generally be attached to the compounds of the invention via acylation or reductive alkylation through a reactive group on the PEG moiety (e.g., an aldehyde, maleimide, amino, thiol, or ester group) to a reactive group on the inventive compound (e.g., an aldehyde, amino, thiol or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis (see, for example, FIGS. 5 and 6 and the accompanying text herein). The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by α1-6 linkages. The dextran itself is available in many molecular weight ranges, and is readily available in molecular weights from about 1 kD to about 70 kD. Dextran is a suitable water soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kD to about 20 kD is preferred when dextran is used as a vehicle in accordance with the present invention.

An additional vehicle may also be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" in this invention. Such vehicles should be selected for increased half-life (e.g., by avoiding sequences recognized by proteases) and decreased immunogenicity (e.g., by favoring non-immunogenic sequences, as discovered in antibody humanization).

Linkers

Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly (Gly)$_4$, (Gly)$_5$), poly(Gly-Ala), and polyalanines. Other specific examples of linkers are:

| | |
|---|---|
| (Gly)$_3$Lys(Gly)$_4$; | (SEQ ID NO: 595) |
| (Gly)$_3$AsnGlySer(Gly)$_2$; | (SEQ ID NO: 596) |
| (Gly)$_3$Cys(Gly)$_4$; and | (SEQ ID NO: 597) |
| GlyProAsnGlyGly. | (SEQ ID NO: 598) |

To explain the above nomenclature, for example, (Gly)$_3$Lys (Gly)$_4$ means Gly-Gly-Gly-Lys-Gly-Gly-Gly-Gly. Combinations of Gly and Ala are also preferred. The linkers shown here are exemplary; linkers within the scope of this invention may be much longer and may include other residues.

Non-peptide linkers are also possible. For example, alkyl linkers such as —NH—(CH$_2$)$_s$—C(O)—, wherein s=2-20 could be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. An exemplary non-peptide linker is a PEG linker,

VI

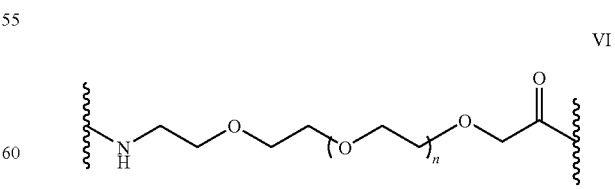

wherein n is such that the linker has a molecular weight of 100 to 5000 kD, preferably 100 to 500 kD. The peptide linkers may be altered to form derivatives in the same manner as described above.

Derivatives

The invention also provides "derivatives" that include molecules bearing modifications other than, or in addition to, insertions, deletions, or substitutions of amino acid residues. Preferably, the modifications are covalent in nature, and include for example, chemical bonding with polymers, lipids, other organic, and inorganic moieties. Derivatives of the invention may be prepared to increase circulating half-life of a molecule; to improve targeting capacity for the molecule to desired cells, tissues, or organs; to improve the solubility or absorption of a molecule; or to eliminate or attenuate any undesirable side-effect of a molecule. Exemplary derivatives include compounds in which:

1. The compound or some portion thereof is cyclic. For example, the peptide portion may be modified to contain two or more Cys residues (e.g., in the linker), which could cyclize by disulfide bond formation. For citations to references on preparation of cyclized derivatives, see Table 2.
2. The compound is cross-linked or is rendered capable of cross-linking between molecules. For example, the peptide portion may be modified to contain one Cys residue and thereby be able to form an intermolecular disulfide bond with a like molecule. The compound may also be cross-linked through its C-terminus, as in the molecule shown below.

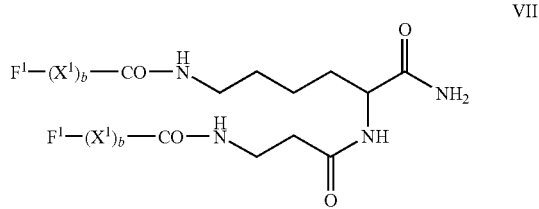

VII

3. One or more peptidyl [—C(O)NR—] linkages (bonds) is replaced by a non-peptidyl linkage. Exemplary non-peptidyl linkages are —$CH_2$-carbamate [—$CH_2$—OC(O)NR—], phosphonate, —$CH_2$-sulfonamide [—$CH_2$—S(O)$_2$NR—], urea [—NHC(O)NH—], —$CH_2$-secondary amine, and alkylated peptide [—C(O)NR$^6$— wherein R$^6$ is lower alkyl].
4. The N-terminus is derivatized. Typically, the N-terminus may be acylated or modified to a substituted amine. Exemplary N-terminal derivative groups include —NRR$^1$ (other than —NH$_2$), —NRC(O)R$^1$, —NRC(O)OR$^1$, —NRS(O)$_2$R$^1$, —NHC(O)NHR$^1$, succinimide, or benzyloxycarbonyl-NH— (CBZ-NH—), wherein R and R$^1$ are each independently hydrogen or lower alkyl and wherein the phenyl ring may be substituted with 1 to 3 substituents selected from the group consisting of $C_1$-$C_4$ alkyl, $C_1$-$C_4$ alkoxy, chloro, and bromo.
5. The free C-terminus is derivatized. Typically, the C-terminus is esterified or amidated. For example, one may use methods described in the art to add (NH—$CH_2$—$CH_2$—NH$_2$)$_2$ to compounds of this invention. Likewise, one may use methods described in the art to add —NH$_2$ to compounds of this invention. Exemplary C-terminal derivative groups include, for example, —C(O)R$^2$ wherein R$^2$ is lower alkoxy or —NR$^3$R$^4$ wherein R$^3$ and R$^4$ are independently hydrogen or $C_1$-$C_8$ alkyl (preferably $C_1$-$C_4$ alkyl).
6. A disulfide bond is replaced with another, preferably more stable, cross-linking moiety (e.g., an alkylene). See, e.g., Bhatnagar et al. (1996), *J. Med. Chem.* 39: 3814-9; Alberts et al. (1993) *Thirteenth Am. Pep. Symp.*, 357-9.
7. One or more individual amino acid residues is modified. Various derivatizing agents are known to react specifically with selected sidechains or terminal residues, as described in detail below.

Lysinyl residues and amino terminal residues may be reacted with succinic or other carboxylic acid anhydrides, which reverse the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with any one or combination of several conventional reagents, including phenylglyoxal, 2,3-butanedione, 1,2-cyclohexanedione, and ninhydrin. Derivatization of arginyl residues requires that the reaction be performed in alkaline conditions because of the high pKa of the guanidine functional group. Furthermore, these reagents may react with the groups of lysine as well as the arginine epsilon-amino group.

Specific modification of tyrosyl residues has been studied extensively, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl sidechain groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be deamidated to the corresponding glutamyl and aspartyl residues. Alternatively, these residues are deamidated under mildly acidic conditions. Either form of these residues falls within the scope of this invention.

Cysteinyl residues can be replaced by amino acid residues or other moieties either to eliminate disulfide bonding or, conversely, to stabilize cross-linking. See, e.g., Bhatnagar et al. (1996), *J. Med. Chem.* 39: 3814-9.

Derivatization with bifunctional agents is useful for cross-linking the peptides or their functional derivatives to a water-insoluble support matrix or to other macromolecular vehicles. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Carbohydrate (oligosaccharide) groups may conveniently be attached to sites that are known to be glycosylation sites in proteins. Generally, O-linked oligosaccharides are attached to serine (Ser) or threonine (Thr) residues while N-linked oligosaccharides are attached to asparagine (Asn) residues when they are part of the sequence Asn-X-Ser/Thr, where X can be any amino acid except proline. X is preferably one of the 19 naturally occurring amino acids other than proline. The structures of N-linked and O-linked oligosaccharides and the sugar residues found in each type are different. One type of sugar that is commonly found on both is N-acetylneuraminic acid (referred to as sialic acid). Sialic acid is usually the terminal residue of both N-linked and O-linked oligosaccharides and, by virtue of its negative charge, may confer acidic properties to the glycosylated compound. Such site(s) may be incorporated in the linker of the compounds of this invention and are preferably glycosylated by a cell during recombinant production of the polypeptide compounds (e.g., in mammalian cells such as CHO, BHK, COS). However, such sites may further be glycosylated by synthetic or semi-synthetic procedures known in the art.

Other possible modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains. Creighton, *Proteins: Structure and Molecule Properties* (W. H. Freeman & Co., San Francisco), pp. 79-86 (1983).

Such derivatized moieties preferably improve one or more characteristics including anti-angiogenic activity, solubility, absorption, biological half life, and the like of the compounds. Alternatively, derivatized moieties may result in compounds that have the same, or essentially the same, characteristics and/or properties of the compound that is not derivatized. The moieties may alternatively eliminate or attenuate any undesirable side effect of the compounds and the like.

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes.

Isotope- and toxin-conjugated derivatives. Another set of useful derivatives are the above-described molecules conjugated to toxins, tracers, or radioisotopes. Such conjugation is especially useful for molecules comprising peptide sequences that bind to tumor cells or pathogens. Such molecules may be used as therapeutic agents or as an aid to surgery (e.g., radioimmunoguided surgery or RIGS) or as diagnostic agents (e.g., radioimmunodiagnostics or RID).

As therapeutic agents, these conjugated derivatives possess a number of advantages. They facilitate use of toxins and radioisotopes that would be toxic if administered without the specific binding provided by the peptide sequence. They also can reduce the side-effects that attend the use of radiation and chemotherapy by facilitating lower effective doses of the conjugation partner.

Useful conjugation partners include:
radioisotopes, such as $^{90}$Yttrium, $^{131}$Iodine, $^{225}$Actinium, and $^{213}$Bismuth;
ricin A toxin, microbially derived toxins such as *Pseudomonas* endotoxin (e.g., PE38, PE40), and the like;
partner molecules in capture systems (see below);
biotin, streptavidin (useful as either partner molecules in capture systems or as tracers, especially for diagnostic use); and
cytotoxic agents (e.g., doxorubicin).

One useful adaptation of these conjugated derivatives is use in a capture system. In such a system, the molecule of the present invention would comprise a benign capture molecule. This capture molecule would be able to specifically bind to a separate effector molecule comprising, for example, a toxin or radioisotope. Both the vehicle-conjugated molecule and the effector molecule would be administered to the patient. In such a system, the effector molecule would have a short half-life except when bound to the vehicle-conjugated capture molecule, thus minimizing any toxic side-effects. The vehicle-conjugated molecule would have a relatively long half-life but would be benign and non-toxic. The specific binding portions of both molecules can be part of a known specific binding pair (e.g., biotin, streptavidin) or can result from peptide generation methods such as those described herein.

Such conjugated derivatives may be prepared by methods known in the art. In the case of protein effector molecules (e.g., *Pseudomonas* endotoxin), such molecules can be expressed as fusion proteins from correlative DNA constructs. Radioisotope conjugated derivatives may be prepared, for example, as described for the BEXA antibody (Coulter). Derivatives comprising cytotoxic agents or microbial toxins may be prepared, for example, as described for the BR96 antibody (Bristol-Myers Squibb). Molecules employed in capture systems may be prepared, for example, as described by the patents, patent applications, and publications from NeoRx. Molecules employed for RIGS and RID may be prepared, for example, by the patents, patent applications, and publications from NeoProbe.

A process for preparing conjugation derivatives is also contemplated. Tumor cells, for example, exhibit epitopes not found on their normal counterparts. Such epitopes include, for example, different post-translational modifications resulting from their rapid proliferation. Thus, one aspect of this invention is a process comprising:

a) selecting at least one randomized peptide that specifically binds to a target epitope; and
b) preparing a pharmacologic agent comprising (i) at least one vehicle (Fc domain preferred), (ii) at least one amino acid sequence of the selected peptide or peptides, and (iii) an effector molecule.

The target epitope is preferably a tumor-specific epitope or an epitope specific to a pathogenic organism. The effector molecule may be any of the above-noted conjugation partners and is preferably a radioisotope.

Variants

Variants are also included within the scope of the present invention. Included within variants are insertional, deletional, and substitutional variants. It is understood that a particular molecule of the present invention may contain one, two or all three types of variants. Insertional and substitutional variants may contain natural amino acids, unconventional amino acids (as set forth below), or both.

In one example, insertional variants are provided wherein one or more amino acid residues, either naturally occurring or unconventional amino acids, supplement a peptide or a peptibody amino acid sequence. Insertions may be located at either or both termini of the protein, or may be positioned within internal regions of the peptibody amino acid sequence. Insertional variants with additional residues at either or both termini can include, for example, fusion proteins and proteins including amino acid tags or labels. Insertional variants include peptides and peptibodies wherein one or more amino acid residues are added to the peptide or peptibody amino acid sequence, or fragment thereof.

Variants of the invention also include mature peptides and peptibodies wherein leader or signal sequences are removed, and the resulting proteins having additional amino terminal residues, which amino acids may be natural or non-natural. Molecules of this invention (such as peptibodies) with an additional methionyl residue at amino acid position −1 ($Met^{-1}$-peptibody) are contemplated, as are specific binding agents with additional methionine and lysine residues at positions −2 and −1 ($Met^{-2}$-$Lys^{-1}$-). Variants having additional Met, Met-Lys, Lys residues (or one or more basic residues, in general) are particularly useful for enhanced recombinant protein production in bacterial host cells.

The invention also embraces variants having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position −1 after cleavage of the GST component from the desired polypeptide. Variants which result from expression in other vector systems are also contemplated, including those wherein poly-histidine tags are incorporated into the amino acid sequence, generally at the carboxy and/or amino terminus of the sequence.

Insertional variants also include fusion proteins wherein the amino and/or carboxy termini of the peptide or peptibody is fused to another polypeptide, a fragment thereof or amino acids which are not generally recognized to be part of any specific protein sequence. Examples of such fusion proteins are immunogenic polypeptides, proteins with long circulating half lives, such as immunoglobulin constant regions, marker proteins, proteins or polypeptides that facilitate purification of the desired peptide or peptibody, and polypeptide sequences that promote formation of multimeric proteins (such as leucine zipper motifs that are useful in dimer formation/stability).

This type of insertional variant generally has all or a substantial portion of the native molecule, linked at the N— or C-terminus, to all or a portion of a second polypeptide. For example, fusion proteins typically employ leader sequences from other species to permit the recombinant expression of a protein in a heterologous host. Another useful fusion protein includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present invention. Particularly useful systems include but are not limited to the glutathione-S-transferase (GST) system (Pharmacia), the maltose binding protein system (NEB, Beverley, Mass.), the FLAG system (IBI, New Haven, Conn.), and the 6×His system (Qiagen, Chatsworth, Calif.). These systems are capable of producing recombinant peptides and/or peptibodies bearing only a small number of additional amino acids, which are unlikely to significantly affect the activity of the peptide or peptibody. For example, both the FLAG system and the 6×His system add only short sequences, both of which are known to be poorly antigenic and which do not adversely affect folding of a polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

Other fusion systems produce polypeptide hybrids where it is desirable to excise the fusion partner from the desired peptide or peptibody. In one embodiment, the fusion partner is linked to the recombinant peptibody by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The invention also provides fusion polypeptides which comprises all or part of a peptibody or peptide of the present invention, in combination with truncated tissue factor (tTF). tTF is a vascular targeting agent consisting of a truncated form of a human coagulation-inducing protein that acts as a tumor blood vessel clotting agent, as described U.S. Pat. Nos. 5,877,289; 6,004,555; 6,132,729; 6,132,730; 6,156,321; and European Patent No. EP 0988056. The fusion of tTF to the anti-Ang-2 peptibody or peptide, or fragments thereof facilitates the delivery of anti-Ang-2 to target cells.

In another aspect, the invention provides deletion variants wherein one or more amino acid residues in a peptide or peptibody are removed.

Deletions can be effected at one or both termini of the peptibody, or from removal of one or more residues within the peptibody amino acid sequence. Deletion variants necessarily include all fragments of a peptide or peptibody.

In still another aspect, the invention provides substitution variants of peptides and peptibodies of the invention. Substitution variants include those peptides and peptibodies wherein one or more amino acid residues are removed and replaced with one or more alternative amino acids, which amino acids may be naturally occurring or non-naturally occurring. Substitutional variants generate peptides or peptibodies that are "similar" to the original peptide or peptibody, in that the two molecules have a certain percentage of amino acids that are identical. Substitution variants include substitutions of 1, 2, 3, 4, 5, 6, 7, 8, 9, 10, 15, 20, 25, 30, amino acids within a peptide or peptibody, wherein the number of substitutions may be up to ten percent or more, of the amino acids of the peptide or peptibody. In one aspect, the substitutions are conservative in nature, however, the invention embraces substitutions that are also non-conservative and also includes unconventional amino acids.

Identity and similarity of related peptides and peptibodies can be readily calculated by known methods. Such methods include, but are not limited to, those described in *Computational Molecular Biology*, Lesk, A. M., ed., Oxford University Press, New York (1988); *Biocomputing: Informatics and Genome Projects*, Smith, D. W., ed., Academic Press, New York (1993); *Computer Analysis of Sequence Data Part 1*, Griffin, A. M., and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., M. Stockton Press, New York (1991); and Carillo et al. *SIAM J. Applied Math.*, 48:1073 (1988).

Preferred methods to determine the relatedness or percent identity of two peptides or polypeptides, or a polypeptide and a peptide, are designed to give the largest match between the sequences tested. Methods to determine identity are described in publicly available computer programs. Preferred computer program methods to determine identity between two sequences include, but are not limited to, the GCG program package, including GAP (Devereux et al. *Nucl. Acid.*

Res., 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least ten percent of the full length of the target polypeptide being compared, i.e. at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see Dayhoff et al. *Atlas of Protein Sequence and Structure*, 5(3)(1978) for the PAM 250 comparison matrix; Henikoff et al., *Proc. Natl. Acad. Sci. USA*, 89:10915-10919 (1992) for the BLOSUM 62 comparison matrix) is also used by the algorithm.

In certain embodiments, the parameters for a polypeptide sequence comparison include the following:

Algorithm: Needleman et al., *J. Mol. Biol.*, 48:443-453 (1970);

Comparison matrix: BLOSUM 62 from Henikoff et al., supra (1992);

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, the parameters for polynucleotide molecule sequence (as opposed to an amino acid sequence) comparisons include the following:

Algorithm: Needleman et al., supra (1970);

Comparison matrix: matches=+10, mismatch=0

Gap Penalty: 50

Gap Length Penalty: 3

The GAP program may also be useful with the above parameters. The aforementioned parameters are the default parameters for polynucleotide molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference for any purpose.

The amino acids may have either L or D stereochemistry (except for Gly, which is neither L nor D) and the polypeptides and compositions of the present invention may comprise a combination of stereochemistries. However, the L stereochemistry is preferred. The invention also provides reverse molecules wherein the amino terminal to carboxy terminal sequence of the amino acids is reversed. For example, the reverse of a molecule having the normal sequence $X_1$-$X_2$-$X_3$ would be $X_3$-$X_2$-$X_1$. The invention also provides retro-reverse molecules wherein, as above, the amino terminal to carboxy terminal sequence of amino acids is reversed and residues that are normally "L" enantiomers are altered to the "D" stereoisomer form.

Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include, without limitation: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

It will be appreciated that amino acid residues can be divided into classes based on their common side chain properties:

1. Neutral Hydrophobic: Alanine (Ala; A), Valine (Val; V), Leucine (Leu; L), Isoleucine (Ile; I), Proline (Pro; P), Tryptophan (Trp; W), Phenylalanine (Phe; F), and Methionine (Met, M).
2. Neutral Polar: Glycine (Gly; G); Serine (Ser; S), Threonine (Thr; T), Tyrosine (Tyr; Y), Cysteine (Cys; C), Glutamine (Glu; Q), Asparagine (Asn; N), and Norleucine.
3. Acidic: Aspartic Acid (Asp; D), Glutamic Acid (Glu; E);
4) Basic: Lysine (Lys; K), Arginine (Arg; R), Histidine (His; H).

See Lewin, B., *Genes V*, Oxford University Press (1994), p. 11.

Conservative amino acid substitutions may encompass unconventional amino acid residues, which are typically incorporated by chemical peptide synthesis rather than by synthesis in biological systems. These include, without limitation, peptidomimetics and other reversed or inverted forms of amino acid moieties. Non-conservative substitutions may involve the exchange of a member of one of these classes for a member from another class.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional peptibody or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e. with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 10 below.

TABLE 10

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln, Glu, Asp | Gln |
| Asp | Glu, Gln, Asp | Glu |
| Cys | Ser, Ala | Ser |
| Gln | Asn, Glu, Asp | Asn |
| Glu | Asp, Gln, Asn | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar peptides or polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al, *Biochemistry* 113(2):211-222 (1974); Chou et al. *Adv. Enzymol. Relat. Areas Mol. Biol.* 47:45-148 (1978); Chou et al. *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested (Brenner et al., *Curr. Op. Struct. Biol.*, 7(3): 369-376 (1997)) that there are a limited number of folds in a given polypeptide or protein and that once a critical number of structures have been resolved, structural prediction will become dramatically more accurate.

Additional methods of predicting secondary structure include "threading" (Jones, D., *Curr. Opin. Struct. Biol.*, 7(3): 377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.* 84(13):4355-4358 (1987)), and "evolutionary linkage" (See Holm, supra (1999), and Brenner supra (1997)).

In certain embodiments, peptibody variants include glycosylation variants wherein one or more glycosylation sites, such as a N-linked glycosylation site, has been added to the peptibody. An N-linked glycosylation site is characterized by the sequence: Asn-X-Ser or Asn-X-Thr, wherein the amino acid residue designated as X may be any amino acid residue except proline. The substitution or addition of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

Compounds of the present invention may be changed at the DNA level, as well. The DNA sequence of any portion of the compound may be changed to codons more compatible with the chosen host cell. For *E. coli*, which is the preferred host cell, optimized codons are known in the art. Codons may be substituted to eliminate restriction sites or to include silent restriction sites, which may aid in processing of the DNA in the selected host cell. The vehicle, linker and peptide DNA sequences may be modified to include any of the foregoing sequence changes. Thus, all modifications, substitution, derivitizations, etc. discussed herein apply equally to all aspects of the present invention, including but not limited to peptides, peptide dimers and multimers, linkers, and vehicles.

Affinity Maturation

One embodiment of the present invention includes "affinity matured" peptides and peptibodies. This procedure contemplates increasing the affinity or the bio-activity of the peptides and peptibodies of the present invention using phage display or other selection technologies. Based on a consensus sequence (which is generated for a collection of related peptides), directed secondary phage display libraries can be generated in which the "core" amino acids (determined from the consensus sequence) are held constant or are biased in frequency of occurrence. Alternatively, an individual peptide sequence can be used to generate a biased, directed phage display library. Panning of such libraries can yield peptides (which can be converted to peptibodies) with enhanced binding to the target or with enhanced bio-activity.

Non-Peptide Analogs/Protein Mimetics

Furthermore, non-peptide analogs of peptides that provide a stabilized structure or lessened biodegradation, are also contemplated. Peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g. bioactive, confirmation which retains the ability to recognize and bind Ang-2. In one aspect, the resulting analog/mimetic exhibits increased binding affinity for Ang-2. One example of methods for preparation of nonpeptide mimetic analogs from peptides is described in Nachman et al., *Regul. Pept.* 57:359-370 (1995). If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptibodies also can be modified to create peptide derivatives by forming covalent or noncovalent complexes with other moieties. Covalently-bound complexes can be prepared by linking the chemical moieties to functional groups on the side chains of amino acids comprising the peptibodies, or at the N— or C-terminus.

In particular, it is anticipated that the peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The invention accordingly provides a molecule comprising a peptibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g. biotin labels are particularly contemplated. The use of such labels is well known to those of skill in the art and is described in, e.g. U.S. Pat. Nos. 3,817,837; 3,850,752; 3,996,345; and 4,277,437. Other labels that will be useful include but are not limited to radioactive labels, fluorescent labels and chemiluminescent labels. U.S. patents concerning use of such labels include, for example, U.S. Pat. Nos. 3,817, 837; 3,850,752; 3,939,350; and 3,996,345. Any of the peptibodies of the present invention may comprise one, two, or more of any of these labels.

Methods of Making

The compounds of this invention largely may be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), *Chem. Polypeptides, pp.* 335-61 (Katsoyannis and Panayotis eds.); Merrifield (1963), *J. Am. Chem. Soc.* 85: 2149; Davis et al. (1985), *Biochem. Intl.* 10: 394-414; Stewart and Young (1969), *Solid Phase Peptide Synthesis*; U.S. Pat. No. 3,941,763; Finn et al. (1976), *The Proteins* (3rd ed.) 2: 105-253; and Erickson et al. (1976), *The Proteins* (3rd ed.) 2: 257-527. Solid phase synthesis is the preferred technique of making individual peptides since it is the most cost-effective method of making small peptides.

Compounds that contain derivatized peptides or which contain non-peptide groups may be synthesized by well-known organic chemistry techniques.

Uses of the Compounds

In general. The compounds of this invention have pharmacologic activity resulting from their ability to bind to proteins of interest as agonists, mimetics or antagonists of the native ligands of such proteins of interest. The utility of specific compounds is shown in Table 2. The activity of these compounds can be measured by assays known in the art. For the TPO-mimetic and EPO-mimetic compounds, in vivo assays are further described in the Examples section herein.

In addition to therapeutic uses, the compounds of the present invention are useful in diagnosing diseases characterized by dysfunction of their associated protein of interest. In one embodiment, a method of detecting in a biological sample a protein of interest (e.g., a receptor) that is capable of being activated comprising the steps of: (a) contacting the sample with a compound of this invention; and (b) detecting activation of the protein of interest by the compound. The biological samples include tissue specimens, intact cells, or extracts thereof. The compounds of this invention may be used as part of a diagnostic kit to detect the presence of their associated proteins of interest in a biological sample. Such kits employ the compounds of the invention having an attached label to allow for detection. The compounds are useful for identifying normal or abnormal proteins of interest. For the EPO-mimetic compounds, for example, presence of abnormal protein of interest in a biological sample may be indicative of such disorders as Diamond Blackfan anemia, where it is believed that the EPO receptor is dysfunctional.

Therapeutic Uses of EPO-Mimetic Molecules

The EPO-mimetic compounds of the invention are useful for treating disorders characterized by low red blood cell levels. Included in the invention are methods of modulating the endogenous activity of an EPO receptor in a mammal, preferably methods of increasing the activity of an EPO receptor. In general, any condition treatable by erythropoietin, such as anemia, may also be treated by the EPO-mimetic compounds of the invention. These compounds are administered by an amount and route of delivery that is appropriate for the nature and severity of the condition being treated and may be ascertained by one skilled in the art. Preferably, administration is by injection, either subcutaneous, intramuscular, or intravenous.

Therapeutic Uses of TPO-Mimetic Compounds

For the TPO-mimetic compounds, one can utilize such standard assays as those described in WO95/26746 entitled "Compositions and Methods for Stimulating Megakaryocyte Growth and Differentiation". In vivo assays also appear in the Examples hereinafter.

The conditions to be treated are generally those that involve an existing megakaryocyte/platelet deficiency or an expected megakaryocyte/platelet deficiency (e.g., because of planned surgery or platelet donation). Such conditions will usually be the result of a deficiency (temporary or permanent) of active Mpl ligand in vivo. The generic term for platelet deficiency is thrombocytopenia, and hence the methods and compositions of the present invention are generally available for treating thrombocytopenia in patients in need thereof.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The TPO-mimetic compounds of this invention may also be useful in stimulating certain cell types other than megakaryocytes if such cells are found to express Mpl receptor. Conditions associated with such cells that express the Mpl receptor, which are responsive to stimulation by the Mpl ligand, are also within the scope of this invention.

The TPO-mimetic compounds of this invention may be used in any situation in which production of platelets or platelet precursor cells is desired, or in which stimulation of the c-Mpl receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The TPO-mimetic compounds of this invention may also be useful in maintaining the viability or storage life of platelets and/or megakaryocytes and related cells. Accordingly, it could be useful to include an effective amount of one or more such compounds in a composition containing such cells.

Therapeutic Uses of Ang-2 Binding Molecules

Agents that modulate Ang-2 binding activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of Ang-2 activity in a cell. These diseases include cancers, and other hyperproliferative conditions, such as hyperplasia, psoriasis, contact dermatitis, immunological disorders, and infertility.

The present invention also provides methods of treating cancer in an animal, including humans, comprising administering to the animal an effective amount of a specific binding agent, such as a peptibody, that inhibits or decreases Ang-2 activity. The invention is further directed to methods of inhibiting cancer cell growth, including processes of cellular proliferation, invasiveness, and metastasis in biological systems. Methods include use of a compound of the invention as an inhibitor of cancer cell growth. Preferably, the methods are employed to inhibit or reduce cancer cell growth, invasiveness, metastasis, or tumor incidence in living animals, such as mammals. Methods of the invention are also readily adaptable for use in assay systems, e.g. assaying cancer cell growth and properties thereof, as well as identifying compounds that affect cancer cell growth.

The cancers treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep, and cattle.

Tumors or neoplasms include growths of tissue cells in which the multiplication of the cells is uncontrolled and progressive. Some such growths are benign, but others are termed malignant and may lead to death of the organism. Malignant neoplasms or cancers are distinguished from benign growths in that, in addition to exhibiting aggressive cellular proliferation, they may invade surrounding tissues and metastasize. Moreover, malignant neoplasms are characterized in that they show a greater loss of differentiation (greater dedifferentiation), and of their organization relative to one another and their surrounding tissues. This property is also called "anaplasia."

Neoplasms treatable by the present invention also include solid tumors, i.e. carcinomas and sarcomas. Carcinomas include those malignant neoplasms derived from epithelial cells that infiltrate (invade) the surrounding tissues and give rise to metastases. Adenocarcinomas are carcinomas derived from glandular tissue, or which form recognizable glandular structures. Another broad category or cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The ang-2 binding molecules of this invention are thus useful for the treatment of a wide variety of cancers, including solid tumors and leukemias. Types of cancer or tumor cells amenable to treatment according to the invention include, for example, ACTH-producing tumor; acute lymphocytic leukemia; acute nonlymphocytic leukemia; adenoma; cancer of the adrenal cortex; adenocarcinoma of the breast, prostate, and colon; ameloblastoma; apudoma; bladder cancer; brain cancer; branchioma; breast cancer; all forms of bronchogenic carcinoma of the lung; carcinoid heart disease; carcinoma (e.g. Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); malignant carcinoid syndrome; immunoproliferative small lung cell carcinoma; cementoma; cervical cancer; chondroblastoma; chondroma; chondrosarcoma; choristoma; chronic lymphocytic leukemia; chronic myelocytic leukemia; colorectal cancer; chordoma; craniopharyngioma; cutaneous T-cell lymphoma; dysgerminoma; endometrial cancer; esophageal cancer; Ewing's sarcoma; fibroma; fibrosarcoma; gallbladder cancer; giant cell tumors; glioma; hairy cell leukemia; hamartoma; head and neck cancer; hepatoma; histiocytic disorders; histiocytosis; Hodgkin's lymphoma; Kaposi's sarcoma; kidney cancer; lipoma; liposarcoma; liver cancer; lung cancer (small and non-small cell); malignant peritoneal effusion; malignant pleural effusion; melanoma; mesenchymoma; mesonephroma; mesothelioma; multiple myeloma; myosarcoma; myxoma; myxosarcoma; neuroblastoma; non-Hodgkin's lymphoma; odontoma; osteoma; osteosarcoma; ovarian cancer; ovarian (germ cell) cancer; pancreatic cancer; papilloma; penile cancer; plasmacytoma; prostate cancer; reticuloendotheliosis; retinoblastoma; skin cancer; soft tissue sarcoma; squamous cell carcinomas; stomach cancer; teratoma; testicular cancer; thymoma; thyroid cancer; trophoblastic neoplasms; uterine cancer; vaginal cancer; cancer of the vulva; Wilms' tumor.

Further, the following types of cancers may also be treated: cholangioma; cholesteatoma; cyclindroma; cystadenocarcinoma; cystadenoma; granulosa cell tumor; gynandroblastoma; hidradenoma; islet cell tumor; Leydig cell tumor; papilloma; Sertoli cell tumor; theca cell tumor; leiomyoma; leiomyosarcoma; myoblastoma; myoma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Therapeutic Uses of NGF Binding Molecules

The NGF binding molecules may be used in the prevention or treatment of NGF-related diseases and disorders. Such indications include but are not limited to pain (including, but not limited to, inflammatory pain and associated hyperalgesia and allodynia, neuropathic pain and associated hyperalgesia and allodynia, diabetic neuropathy pain, causalgia, sympathetically maintained pain, deafferentation syndromes, acute pain, tension headache, migraine, dental pain, pain from trauma, surgical pain, pain resulting from amputation or abscess, causalgia, demyelinating diseases, and trigeminal neuralgia). The peptides and modified peptides of the invention have therapeutic value for the prevention or treatment of other diseases linked to NGF as a causative agent, including, but not limited to, asthma, urge incontinence (i.e., hyperactive bladder), psoriasis, cancer (especially, pancreatic cancer and melanoma), chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, colitis, gastric ulceration, duodenal ulcers, vasomotor or allergic rhinitis, or bronchial disorders.

Therapeutic Uses of Myostatin Binding Molecules

The myostatin binding agents of the present invention bind to myostatin and block or inhibit myostatin signaling within targeted cells. The present invention provides methods and reagents for reducing the amount or activity of myostatin in an animal by administering an effective dosage of one or more myostatin binding agents to the animal. In one aspect, the present invention provides methods and reagents for treating myostatin-related disorders in an animal comprising administering an effective dosage of one or more binding agents to the animal. These myostatin-related disorders include but are not limited to various forms of muscle wasting, as well as metabolic disorders such as diabetes and related disorders, and bone degenerative diseases such as osteoporosis.

As shown in the Example 8 of U.S. Ser. No. 10/742,379, exemplary peptibodies of the present invention dramatically increases lean muscle mass in the CD1 nu/nu mouse model. This in vivo activity correlates to the in vitro binding and inhibitory activity described below for the same peptibodies.

Muscle wasting disorders include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. For example, blocking myostatin through use of antibodies in vivo improved the dystrophic phenotype of the mdx mouse model of Duchenne muscular dystrophy (Bogdanovich et al. (2002), *Nature* 420: 28). Use of an exemplary peptibody increases lean muscle mass and increases the ratio of lean muscle to fat in mdx mouse models as described in Example 9 below.

Additional muscle wasting disorders arise from chronic disease such as amyotrophic lateral sclerosis, congestive obstructive pulmonary disease, cancer, AIDS, renal failure, and rheumatoid arthritis. For example, cachexia or muscle wasting and loss of body weight was induced in athymic nude mice by a systemically administered myostatin (Zimmers et al., supra). In another example, serum and intramuscular concentrations of myostatin-immunoreactive protein was found to be increased in men exhibiting AIDS-related muscle wasting and was inversely related to fat-free mass (Gonzalez-Cadavid et al. (1998), *PNAS USA* 95: 14938-14943). Additional conditions resulting in muscle wasting may arise from inactivity due to disability such as confinement in a wheelchair, prolonged bedrest due to stroke, illness, bone fracture or trauma, and muscular atrophy in a microgravity environment (space flight). For example, plasma myostatin immunoreactive protein was found to increase after prolonged bedrest (Zachwieja et al. *J Gravit Physiol.* 6(2):11(1999). It was also found that the muscles of rats exposed to a microgravity environment during a space shuttle flight expressed an increased amount of myostatin compared with the muscles of rats which were not exposed (Lalani et al. (2000), *J. Endocrin.* 167 (3):417-28).

In addition, age-related increases in fat to muscle ratios, and age-related muscular atrophy appear to be related to myostatin. For example, the average serum myostatin-immunoreactive protein increased with age in groups of young (19-35 yr old), middle-aged (36-75 yr old), and elderly (76-92 yr old) men and women, while the average muscle mass and fat-free mass declined with age in these groups (Yarasheski et al. *J Nutr Aging* 6(5):343-8 (2002)). It has also been shown that myostatin gene knockout in mice increased myogenesis and decreased adipogenesis (Lin et al. (2002), *Biochem Biophys Res Commun* 291(3):701-6, resulting in adults with increased muscle mass and decreased fat accumulation and leptin secretion. Exemplary molecules improve the lean muscle mass to fat ratio in aged mdx mice as shown below.

In addition, myostatin has now been found to be expressed at low levels in heart muscle and expression is upregulated after cardiomyocytes after infarct (Sharma et al. (1999), *J Cell Physiol.* 180 (1):1-9). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. supra). In addition, increasing muscle mass by reducing myostatin levels may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick et al. (2002), *Calcif Tissue Int* 71(1): 63-8). In the present invention, an exemplary peptibody increases the lean muscle mass to fat ratio in mdx mouse models as shown below.

The present invention also provides methods and reagents for increasing muscle mass in food animals by administering an effective dosage of the myostatin binding agent to the animal. Since the mature C-terminal myostatin polypeptide is identical in all species tested, myostatin binding agents would be expected to be effective for increasing muscle mass and reducing fat in any agriculturally important species including cattle, chicken, turkeys, and pigs.

The myostatin-binding molecules of the present invention may be used alone or in combination with other therapeutic agents to enhance their therapeutic effects or decrease potential side effects. The molecules of the present invention possess one or more desirable but unexpected combination of properties to improve the therapeutic value of the agents. These properties include increased activity, increased solubility, reduced degradation, increased half-life, reduced toxicity, and reduced immunogenicity. Thus the molecules of the present invention are useful for extended treatment regimes. In addition, the properties of hydrophilicity and hydrophobicity of the compounds of the invention are well balanced, thereby enhancing their utility for both in vitro and especially in vivo uses. Specifically, compounds of the invention have an appropriate degree of solubility in aqueous media that permits absorption and bioavailability in the body, while also having a degree of solubility in lipids that permits the compounds to traverse the cell membrane to a putative site of action, such as a particular muscle mass.

The myostatin-binding molecules of the present invention are useful for treating a "subject" or any animal, including humans, when administered in an effective dosages in a suitable composition.

In addition, the mystatin-binding molecules of the present invention are useful for detecting and quantitating myostatin in a number of assays. These assays are described in detail in U.S. Ser. No. 10/742,379.

In general, the myostatin-binding molecules of the present invention are useful as capture agents to bind and immobilize myostatin in a variety of assays, similar to those described, for example, in Asai, ed., *Methods in Cell Biology* 37, *Antibodies in Cell Biology*, Academic Press, Inc., New York (1993). The myostatin-binding molecule may be labeled in some manner or may react with a third molecule such as an anti-binding molecule antibody which is labeled to enable myostatin to be detected and quantitated. For example, a myostatin-binding molecule or a third molecule can be modified with a detectable moiety, such as biotin, which can then be bound by a fourth molecule, such as enzyme-labeled streptavidin, or other proteins. (Akerstrom (1985), *J Immunol* 135:2589; Chaubert (1997), *Mod Pathol* 10:585).

Throughout any particular assay, incubation and/or washing steps may be required after each combination of reagents. Incubation steps can vary from about 5 seconds to several hours, preferably from about 5 minutes to about 24 hours. However, the incubation time will depend upon the assay format, volume of solution, concentrations, and the like. Usually, the assays will be carried out at ambient temperature, although they can be conducted over a range of temperatures.

Therapeutic uses of BAFF-binding molecules. BAFF-binding molecules of this invention may be particularly useful in treatment of B-cell mediated autoimmune diseases. In particular, they may be useful in treating, preventing, ameliorating, diagnosing or prognosing lupus, including systemic lupus erythematosus (SLE), and lupus-associated diseases and conditions. Other preferred indications include B-cell mediated cancers, including B-cell lymphoma.

The compounds of this invention can also be used to treat inflammatory conditions of the joints. Inflammatory conditions of a joint are chronic joint diseases that afflict and disable, to varying degrees, millions of people worldwide. Rheumatoid arthritis is a disease of articular joints in which the cartilage and bone are slowly eroded away by a proliferative, invasive connective tissue called pannus, which is derived from the synovial membrane. The disease may involve peri-articular structures such as bursae, tendon sheaths and tendons as well as extra-articular tissues such as the subcutis, cardiovascular system, lungs, spleen, lymph nodes, skeletal muscles, nervous system (central and peripheral) and eyes (Silberberg (1985), Anderson's Pathology, Kissane (ed.), II:1828). Osteoarthritis is a common joint disease characterized by degenerative changes in articular cartilage and reactive proliferation of bone and cartilage around the joint. Osteoarthritis is a cell-mediated active process that may result from the inappropriate response of chondrocytes to catabolic and anabolic stimuli. Changes in some matrix molecules of articular cartilage reportedly occur in early osteoarthritis (Thonar et al. (1993), Rheumatic disease clinics of North America, Moskowitz (ed.), 19:635-657 and Shinmei et al. (1992), *Arthritis Rheum.*, 35:1304-1308). TALL-1, TALL-1R and modulators thereof are believed to be useful in the treatment of these and related conditions.

BAFF-binding molecules may also be useful in treatment of a number of additional diseases and disorders, including acute pancreatitis; ALS; Alzheimer's disease; asthma; atherosclerosis; autoimmune hemolytic anemia; cancer, particularly cancers related to B cells; cachexia/anorexia; chronic fatigue syndrome; cirrhosis (e.g., primary biliary cirrhosis); diabetes (e.g., insulin diabetes); fever; glomerulonephritis, including IgA glomerulonephritis and primary glomerulonephritis; Goodpasture's syndrome; Guillain-Barre syndrome; graft versus host disease; Hashimoto's thyroiditis; hemorrhagic shock; hyperalgesia; inflammatory bowel disease; inflammatory conditions of a joint, including osteoarthritis, psoriatic arthritis and rheumatoid arthritis; inflammatory conditions resulting from strain, sprain, cartilage damage, trauma, orthopedic surgery, infection or other disease processes; insulin-dependent diabetes mellitus; ischemic injury, including cerebral ischemia (e.g., brain injury as a result of trauma, epilepsy, hemorrhage or stroke, each of which may lead to neurodegeneration); learning impairment; lung diseases (e.g., ARDS); lupus, particularly systemic lupus erythematosus (SLE); multiple myeloma; multiple sclerosis; Myasthenia gravis; myelogenous (e.g., AML and CML) and other leukemias; myopathies (e.g., muscle protein metabolism, esp. in sepsis); neurotoxicity (e.g., as induced by HIV); osteoporosis; pain; Parkinson's disease; Pemphigus; polymyositis/dermatomyositis; pulmonary inflammation, including autoimmune pulmonary inflammation; pre-term labor; psoriasis; Reiter's disease; reperfusion injury; septic shock; side effects from radiation therapy; Sjogren's syndrome; sleep disturbance; temporal mandibular joint disease; thrombocytopenia, including idiopathic thrombocytopenia and autoimmune neonatal thrombocytopenia; tumor metastasis; uveitis; and vasculitis.

Combination Therapy. The therapeutic methods, compositions and compounds of the present invention may also be employed, alone or in combination with other cytokines, soluble Mpl receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), SCF, GM-CSF, granulocyte colony stimulating factor (G-CSF), EPO, interferon-alpha (IFN-alpha), consensus interferon, IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of an inventive compound (to enhance the number of mature megakaryocytes) followed by administration of the soluble Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

In cases where the inventive compounds are added to compositions of platelets and/or megakaryocytes and related cells, the amount to be included will generally be ascertained experimentally by techniques and assays known in the art. An exemplary range of amounts is 0.1 µg-1 mg inventive compound per $10^6$ cells.

Pharmaceutical Compositions

In General

The present invention also provides methods of using pharmaceutical compositions of the inventive compounds. Such pharmaceutical compositions may be for administration for injection, or for oral, pulmonary, nasal, transdermal or other forms of administration. In general, the invention encompasses pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Oral Dosage Forms

Contemplated for use herein are oral solid dosage forms, which are described generally in Chapter 89 of *Remington's Pharmaceutical Sciences* (1990), 18th Ed., Mack Publishing Co. Easton Pa. 18042, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given in Chapter 10 of Marshall, K., *Modern Pharmaceutics* (1979), edited by G. S. Banker and C. T. Rhodes, herein incorporated by reference. In general, the formulation will include the inventive compound, and inert ingredients which allow for protection against the stomach environment, and release of the biologically active material in the intestine.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached vehicles in this invention may also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis, *Soluble Polymer-Enzyme Adducts, Enzymes as Drugs* (1981), Hocenberg and Roberts, eds., Wiley-Interscience, New York, N.Y., pp 367-83; Newmark, et al. (1982), *J. Appl. Biochem.* 4:185-9. Other polymers that could be used are poly-1,3-dioxolane and poly-1,3, 6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl]amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The compounds of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the compound of the invention with an inert material. These diluents could include carbohydrates, especially mannitol, α-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the compound of this invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives may also be included in the formulation to enhance uptake of the compound. Additives potentially having this property are for instance the fatty acids oleic acid, linoleic acid and linolenic acid.

Controlled release formulation may be desirable. The compound of this invention could be incorporated into an inert matrix which permits release by either diffusion or leaching mechanisms e.g., gums. Slowly degenerating matrices may also be incorporated into the formulation, e.g., alginates, polysaccharides. Another form of a controlled release of the compounds of this invention is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Pulmonary Delivery Forms

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., *Pharma. Res.* (1990) 7: 565-9; Adjei et al. (1990), *Internatl. J. Pharmaceutics* 63: 135-44 (leuprolide acetate); Braquet et al. (1989), *J. Cardiovasc. Pharmacol.* 13 (suppl..5): s. 143-146 (endothelin-1); Hubbard et al. (1989), *Annals Int. Med.* 3: 206-12 ($\alpha$1-antitrypsin); Smith et al. (1989), *J. Clin. Invest.* 84: 1145-6 ($\alpha$1-proteinase); Oswein et al. (March 1990), "Aerosolization of Proteins", *Proc. Symp. Resp. Drug Delivery II*, Keystone, Colo. (recombinant human growth hormone); Debs et al. (1988), *J. Immunol.* 140: 3482-8 (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 $\mu$m (or microns), most preferably 0.5 to 5 $\mu$m, for most effective delivery to the distal lung.

Pharmaceutically acceptable carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. PEG may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant may be any conventional material employed for this purpose, such as a chloro fluorocarbon, a hydrochlorofluoro carbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the inventive compound and may also include a bulking agent, such as lactose, sorbitol, sucrose, mannitol, trehalose, or xylitol in amounts which facilitate dispersal of the powder from the device, e.g., 50 to 90% by weight of the formulation.

Other Delivery Forms

Nasal delivery of the inventive compound is also contemplated. Nasal delivery allows the passage of the protein to the blood stream directly after administering the therapeutic product to the nose, without the necessity for deposition of the product in the lung. Formulations for nasal delivery include those with dextran or cyclodextran. Delivery via transport across other mucous membranes is also contemplated.

Buccal delivery of the inventive compound is also contemplated. Buccal delivery formulations are known in the art for use with peptides.

Dosages

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

SPECIFIC PREFERRED EMBODIMENTS

The inventors have determined preferred peptide sequences for molecules having many different kinds of activity. The inventors have further determined preferred structures of these preferred peptides combined with preferred linkers and vehicles. Preferred structures for these preferred peptides listed in Table 11 below. Linker sequences are shown in bold. Active peptide sequences are shown in bold and are underlined.

TABLE 11

Preferred embodiments

| Sequence/structure | SEQ ID NO: | Activity |
|---|---|---|
| 1 MDKTHTCPPC PAPELLGGPS VPLFPPKPKD TLMISRTPEV TCVVVDVSHE<br>51 DPEVKFNWYV DGVEVHNAKT KPREEQYNST YRVVSVLTVL HQDWLNGKEY<br>101 KCKVSNKALP APIEKTISKA KGQPREPQVY TLPPSRDELG GIEGPTLRQW<br>151 LAARAGGTKN QVSLTCLVKG FYPSDIAVEW ESNGQPENNY KTTPPVLDSD<br>201 GSFFLYSKLT VDKSRWQQGN VFSCSVMHEA LHNHYTQKSL SLSPGK* | 616 | Fc-loop-Amp2 |
| 1 MDKTHTCFPC PAPELLGGPS VPLFPPKPKD TLMISRTPEV TCVVVDVSHE<br>51 DPEVKFNWYV DGVEVHNAKT KPREEQYNST YRVVSVLTVL HQDWLNGKEY<br>101 KCKVSNKALP APIEKTISKA KGQPREPQVY TLPPSRDEL GGGTYSCHFGPL<br>151 TWVCKPQGGG TKNQVSLTCLV KGFYPSDIAV EWESNGQPEN NYKTTPPVLD<br>201 SDGSFFLYSK LTVDKSRWQQ GNVFSCSVMH EALHNHYTQK SLSLSPGK* | 648 | Fc-Loop-EMP1 (1 Gly linkers) |
| 1 MDKTHTCPPC PAPELLGGPS VPLFPPKFKD TLMISRTPEV TCVVVDVSHE<br>51 DPEVKFNWYV DGVEVHNAKT KPREEQYNST YRVVSVLTVL HQDWLNGKEY<br>101 KCKVSNKALP APIEKTISKA KGQPREPQVY TLPPSRDELG GTYSCHFGPL<br>151 TWVCKPQGGT KNQVSLTCLV KGFYPSDIAV EWESNGQPEN NYKTTPPVLD<br>201 SDGSFFLYSK LTVDKSRWQQ GNVFSCSVMH EALHNHYTQK SLSLSPGK* | 649 | Fc-loop-EMP1 (2Gly linkers) |
| 1 MDKTHTCPPC PAPELLGGPS VPLFPPKPKD TLMISRTPEV TCVVVDVSHE<br>51 DPEVKFNWYV DGVEVHNAKT KPREEQYNST YRVVSVLTVL HQDWLNGKEY<br>101 KCKVSNKALP APIEKTISKA KGQPREPQVY TLPPSRDELG GGTYSCHFGP<br>151 LTWVCKPQGG GTKNQVSLTC LVKGFYPSDI AVEWESNGQP ENNYKTTPPV<br>201 LDSDGSFFLY SKLTVDKSRW QQGNVFSCSV MHEALHNHYT QKSLSLSPGK | 650 | Fc-loop-EMP1 (3Gly linkers) |
| 1 MDKTHTCPPC PAPELLGGPS VPLFPPKPKD TLMISRTPEV TCVVVDVSHE<br>51 DPEVKFNWYV DGVEVHNAKT KPREEQYNST YRVVSVLTVL HQDWLNGKEY<br>101 KCKVSNKALF APIEKTISKA KGQPREPQVY TLPPSRDELG GGGTYSCHFG<br>151 PLTWVCKPQG GGGTKNQVSL TCLVKGFYPS DIAVEWESNG QPENNYKTTP<br>201 PVLDSDGSFF LYSKLTVDKS RWQQGNVFSC SVMHEALHNH YTQKSLSLSP<br>251 GK* | 651 | Fc-loop-EMP1 (4Gly linkers) |
| 1 MDKTHTCPPC PAPELLGGPS VPLFPPKPKD TLMISRTPEV TCVVVDVSHE<br>51 DPEVKFNWYV DGVEVHNAKT KPREEQYNST YRVVSVLTVL HQDWLNGKEY<br>101 KCKVSNKALP APIERTISKA KGQPREPQVY TLPPSRDELG GGGTYSAHFG<br>151 PLTWVAKPQG GGGTKNQVSL TCLVKGFYPS DIAVEWESNG QPENNYKTTP<br>201 PVLDSDGSFF LYSKLTVDKS RWQQGNVFSC SVMHEALHNH YTQKSLSLSP<br>251 GK* | 652 | Fc-loop-EMP1 (Cys>Ala variant w/4Gly linkers) |
| 1 MDKTHTCPPC PAPELLGGPS VPLFPPKPKD TLMISRTPEV TCVVVDVSHE<br>51 DPEVKFNWYV DGVEVHNAKT KPREEQYNST YRVVSVLTVL HQDWLNGKEY<br>101 KCKVSNKALP APIEKTISKA KGQPREPQVY TLPPSRDELG GQGYCDEGPT<br>151 LKQWLVCLGL QHSGGTKNQV SLTCLVKGFY PSDIAVEWES NGQPENNYKT<br>201 TPPVLDSDGS FFLYSKLTVD KSRWQQGNVF SCSVMHEALH NHYTQKSLSL<br>251 SPGK* | 653 | Fc-loop-TMP2Q (2Gly linkers) |

TABLE 11-continued

Preferred embodiments

|  | Sequence/structure |  |  |  |  | SEQ ID NO: | Activity |
|---|---|---|---|---|---|---|---|
| 1 | MDKTHTCPPC | PAPELLGGPS | VFLFPPKPKD | TLMISRTPEV | TCVVVDVSHE | 654 | Fc- |
| 51 | DPEVKFNWYV | DGVEVHNAKT | KPREEQYNST | YRVVSVLTVL | HQDWLNGKEY |  | loop- |
| 101 | KCKVSNKALP | APTEKTISKA | KGQPREPQVY | TLPPSRDELG | GQGYADEGPT |  | TMP20 |
| 151 | LKQWLVALGL | QHSGGTKNQV | SLTCLVKGFY | PSDIAVEWES | NGQPENNYKT |  | (Cys>A |
| 201 | TPPVLDSDGS | FFLYSKLTVD | KSRWQQGNVF | SCSVMHEALH | NHYTQKSLSL |  | Ia |
| 251 | SPGK* |  |  |  |  |  | variant, w/2Gly linkers) |
| 1 | MDKTHTCPPC | PAPELLGGPS | VFLFPPKPKD | TLMISRTPEV | TCVVVDVSHE | 655 | Fc- |
| 51 | DPEVKFNWYV | DGVEVHNAKT | KPREEQYNST | YRVVSVLTVL | HQDWLNGKEY |  | loop- |
| 101 | KCKVSNKALP | APIEKTISKA | KGQPREPQVY | TLPPSROELG | GHAEGTFTSD |  | GLP1 |
| 151 | VSSYLEGQAA | KEFIAWLVKG | RGGGTKNQVS | LTCLVKGFYP | SDIAVEWESN |  | (2Gly |
| 201 | GQPENNYKTT | PPVLOSDGSF | FLYSKLTVDK | SRWQQGNVFS | CSVMHEALHN |  | linkers) |
| 251 | HYTQKSLSLS | PGK* |  |  |  |  |  |
| 1 | MDKTHTCPPC | PAPELLGGPS | VFLFPPKPKD | TLMISRTPEV | TCVVVDVSHE | 656 | Fc- |
| 51 | DPEVKFNWYV | DGVEVHNAKT | KPREEQYNST | YRVVSVLTVL | HQDWLNCKEY |  | loop |
| 101 | KCKVSNKALP | APIEKTISKA | KGQPREPQVY | TLPPSRDELG | GGGHAEGTFT |  | GLPI |
| 151 | SDVSSYLEGQ | AAKEFIAWLV | KGRGGGGGTK | NQVSLTCLVK | GFYPSDIAVE |  | (4Gly |
| 201 | WESNGQPENN | YKTTPPVLDS | DGSFFLYSKL | TVDKSRWQQG | NVFSCSVMHE |  | linkers) |
| 251 | ALHNHYTQKS | LSLSPGK* |  |  |  |  |  |
| 1 | MDKTHTCPPC | PAPELLGGPS | VFLFPPKPKD | TLMISRTPEV | TCVVVDVSHE | 657 | Fc- |
| 51 | DPEVKFNWYV | DGVEVHNAKT | KPREEQYNST | YRVVSVLTVL | HQDWLNGKEY |  | loop- |
| 101 | KCKVSNKALP | APIEKTISKA | KGQPREPQVY | TLPPSRDELG | GQEECEWDPW |  | ANG2 |
| 151 | TCEHMGGTKN | QVSLTCLVKG | FYPSDIAVEW | ESNGQPENNY | KTTPPVLDSD |  | (2Gly |
| 201 | GSFFLYSKLT | VDKSRWQQGN | VFSCSVMHEA | LHNHYTQKSL | SLSPGK* |  | linkers) |
| 1 | NDKTHTCPPC | PAPELLGGPS | VFLFPPKPKD | TLMISRTPEV | TCVVVDVSHE | 612 | Fc- |
| 51 | DPEVKFNWYV | DGVEVHNAKT | KPREEQYNST | YRVVSVLTVL | HQDWLNGKEY |  | loop |
| 101 | KCKVSNKALP | APIEKTISKA | KGQPREPQVY | TLPPSRDELG | GLADHGQCIR |  | Myo7 |
| 151 | WPWMCPPEGW | EGGTKNQVSL | TCLVKGFYPS | DIAVEWESNG | QPENNYKTTP |  | (2Gly |
| 201 | PVLDSDGSFF | LYSKLTVDKS | RWQQGNVFSC | SVMHEALHNH | YTQKSLSLSP |  | linkers) |
| 251 | GK* |  |  |  |  |  |  |
| 1 | MDKTHTCPPC | PAPELLGGPS | VFLFPPKPKD | TLMISRTPEV | TCVVVDVSHE | 658 | Fc- |
| 51 | DPEVKFNWYV | DGVEVHNAKT | KPREEQYNST | YRVVSVLTVL | HQDWLNGKEY |  | loop |
| 101 | KCKVSNKALP | APIEKTISKA | KGQPREPQVY | TLPPSRDELG | GGGGDWTGDM |  | ANG1 |
| 151 | QVKFDAMMFG | PRKEGGGGT | KNQVSLTCLV | KGFYPSDIAV | EWESNGQPEN |  | (4Gly |
| 201 | NYKTTPPVLD | SDGSFFLYSK | LTVDKSRWQQ | GNVFSCSVMH | EALHNHYTQK |  | linkers) |
| 251 | SLSLSPGK |  |  |  |  |  |  |
| 1 | MDKTHTCPPC | PAPELLGGPS | VFLFPPKPKD | TLMISRTPEV | TCVVVDVSHE | 659 | Fc- |
| 51 | DPEVKFNWYV | DGVEVHNAKT | KPREEQYNST | YRVVSVLTVL | HQDWLNGKEY |  | loop- |
| 101 | KCKVSNKALP | APIEKTISKA | KGQPREPQVY | TLPPSRDELG | GGGGDWTGDM |  | ANG1 |
| 151 | QVKFDAMMFG | PRKEGGGDWT | GDMQVKFDAM | MFGPRKEGGG | GGTKNQVSLT |  | (2x |
| 201 | CLVKGFYPSD | IAVEWESNGQ | PENNYKTTPP | VLDSDGSFFL | YSKLTVDKSR |  | peptide |
| 251 | WQQGNVFSCS | VMHEALHNHY | TQKSLSLSPG | K |  |  | w/4Gly linkers) |

WORKING EXAMPLES

The compounds described above may be prepared as described below. These examples comprise preferred embodiments of the invention and are illustrative rather than limiting.

Example 1

Preparation of Fc-loop-ang2

In this example of the invention, the disulphide-constrained peptide TN8-Con4 was inserted into the human IgG1 Fc-loop domain, defined as the sequence $D_{137}E_{138}L_{139}T_{140}K_{141}$ (FIG. 2A.).

TN8-Con4 QEEC̲EWDPWTC̲EHM (SEQ ID NO: 147)

The peptide insertion is between Fc residues $Leu_{139}$ and $Thr_{140}$ and includes 2 Gly residues as linkers flanking either side of the inserted peptide (FIG. 10A). The Fc-loop TN8-Con4 construct is labeled with Amgen clone #6888. The carboxy-terminal TN8-Con4 fusion peptibody (FIG. 10B) includes a 5 Gly linker and is labeled with Amgen clone #5564.

Both clones #6888 and #5564 were transformed into E. coli by conventional methods known to those familiar in the art. Both clones were found to express at high levels and almost exclusively in the insoluble inclusion body fraction (FIG. 11). The isolated inclusion body fraction (1 g) was solubilized in 6 M guanidine-HCl, 50 mM Tris, 8 mM DTT, pH 9 (10 ml) at room temperature with mixing, for 1 hour. The denatured and reduced peptibodies were refolded from the solubilized inclusion bodies by a 1:25 (v/v) dilution into a refold buffer consisting of 2 M urea, 50 mM Tris, 4 mM cysteine, 1 mM cystamine, pH 8.5. The solubilized peptibodies were added drop wise to the refold buffer at 4° C. with stirring. The refold reactions were allowed to stir for 48 hours, and then aliquots were evaluated by SDS-PAGE and reverse-phase HPLC. The Fc-loop TN8-Con4 (#6888) is considerably more homogeneous in the refold reaction than the carboxy-terminal Fc TN8-Con4 peptibody (#5564) as shown by RP-HPLC (FIG. 12).

Purification of the refolded Fc-loop TN8-Con4 and carboxy-terminal Fc TN8-Con4 was achieved using a 2-column process. First a recombinant Protein-A column was equilibrated in 2 M urea, 50 mM Tris, pH 8.5 and loaded with the filtered peptibody refold reaction. The column was then washed with 2 column volumes of equilibration buffer, followed by 2 column volumes of PBS. The peptibody fraction was eluted with 50 mM NaOAc, pH3 and quickly neutralized by a 1:4 dilution into 10 mM NaOAc, 50 mM NaCl, pH 5. The diluted Protein-A eluate was again filtered and loaded to an SP Sepharose HP cation exchange column (Pharmacia) equilibrated in 10 mM NaOAc, 50 mM NaCl, pH 5. The peptibody fractions were then eluted with a linear 50-500 mM NaCl gradient, pooled and concentrated to about 2 mg/ml. The final pools of Fc-loop TN8-Con4 (#6888) and the carboxy-terminal Fc TN8-Con4 (#5564) were evaluated by RP-HPLC (FIG. 13) and SDS-PAGE (FIG. 14). Both RP-HPLC and SDS-PAGE demonstrate that improved product homogeneity is achieved with the Fc-loop TN8-Con4 (#6888) relative to the comparable carboxy-terminal fused peptibody (#5564).

Both the Fc-loop TN8-Con4 and carboxy-terminal fused TN8-Con4 peptibodies were further evaluated in an in vitro ELISA for competitive inhibition of the angiopoietin 2 receptor. In this format the peptibody competes with an angiopoietin 2 receptor-Fc fusion for binding to immobilized angiopoietin 2. Binding of the angiopoietin 2 receptor-Fc fusion is monitored by fluorescence using an enzyme-linked immunodetection method and reported as an inhibition constant at 50% inhibition ($IC_{50}$). This experiment shows that the Fc-loop TN8-Con4 is fully active relative to the carboxy-terminal Fc TN8-Con4 (FIG. 15).

Stability in vivo of the Fc-loop TN8-Con4 peptibody was compared to the carboxy-terminal TN8-Con4 peptibody in mice. In this study groups of 15 mice were dosed subcutaneously with either peptibody construct at 5 mg/kg. At 4 hours after injection, 5 mice were sacrificed and serum collected. At 24 hours, another 5 mice were harvested and likewise at 48 hours. Each individual serum sample was evaluated by western blot for detectable human IgG-Fc peptibody. Since all the serum within each 5-mouse group was very similar, the groups were pooled to allow representative samples to be run together on a single gel/blot. The result of that analysis (FIG. 16) clearly shows that both the Fc-loop TN8-Con4 peptibody and the carboxy-terminal TN8-Con4 peptibody persists in the pooled mouse sera throughout the 48-hour time course with no apparent loss. This result demonstrates that the Fc-loop designed peptibodies are not destabilized in vivo by the peptide insertion.

Example 2

Preparation of Fc-loop-myo7

In another embodiment of this invention, a novel, disulphide-constrained peptide TN8-19-7 (U.S. Pat App 2004-0181033-A1, which is incorporated by reference) of the sequence:
TN8-19-07LADHGQCIRWPWMCPPEGWE (SEQ ID NO:365)
was engineered between Leu139 and Thr140 as an internal fusion in the putative Fc-loop sequence DELTK of an IgG1 Fc sequence (FIG. 2A). An additional two Gly residues were also added at each end of the TN8-19-07 peptide as flanking linkers. The final Fc-loop TN8-19-07 sequence is given in FIG. 3A and is labeled clone # 6951. Alternatively, a carboxy terminal fusion of TN8-19-07 with the same IgG1 Fc sequence was prepared to serve as a control (FIG. 3B) and labeled clone #6826. The carboxy-terminal fusion included five Gly residues between the Fc and TN8-19-07 to serve as a linker.

Both clones #6951 and #6826 were transformed into E. coli by conventional methods used by those familiar in the art, and were found to express at high levels and almost exclusively in the insoluble inclusion body fraction (FIGS. 4A and 4B). The isolated inclusion body fraction (1 g) was solubilized in 6 M guanidine-HCl, 50 mM Tris, 8 mM DTT, pH 9 (10 ml) at room temperature with mixing for 1 hour. The denatured and reduced peptibodies were refolded from the solubilized inclusion body fraction by a 1:25 (v/v) dilution into 2 M urea, 50 mM Tris, 4 mM cysteine, 1 mM cystamine, pH 8.5. The solubilized peptibodies were added drop-wise to the refold buffer at 4° C. with stirring. The refold reactions were allowed to stir for 48 hours, and then aliquots were evaluated by SDS-PAGE and reverse-phase HPLC. The Fc-loop TN8-19-07 (#6951) was found to be considerably more homogeneous by RP-HPLC (FIG. 5) in the refold reaction than the carboxy-terminal Fc-TN8-19-07 peptibody (#6826).

Purification was achieved by a 2-column process. First a recombinant Protein-A column was equilibrated in 2 M urea, 50 mM Tris, pH 8.5 and loaded with the filtered peptibody refold reaction. The column was then washed with 2 column volumes of equilibration buffer, followed by 2 column volumes of PBS. The peptibody fraction was eluted with 50 mM NaOAc, pH 3 and quickly neutralized by a 1:4 dilution into 10 mM NaOAc, 50 mM NaCl, pH 5. The diluted Protein-A eluate was again filtered and loaded to an SP Sepharose HP cation exchange column (Pharmacia) equilibrated in 10 mM NaOAc, 50 mM NaCl, pH 5. The peptibody fractions were then eluted with a linear 50-500 mM NaCl gradient, pooled and concentrated to about 2 mg/ml. The final pools of Fc-loop TN8-19-07 (#6951) and the carboxy-terminal Fc TN8-19-07 (#6826) were evaluated by RP-HPLC (FIG. 6) and SDS-PAGE (FIG. 7). Both RP-HPLC and SDS-PAGE demonstrate that improved homogeneity in the final product is achieved with the Fc-loop TN8-19-07 (#6951) relative to the comparable carboxy-terminal fused peptibody (#6826).

An in vitro cell-based assay, which measures the inhibition of myostatin signaling activity, was used to determine the bioactivity of the Fc-loop TN8-19-07 (#6951) compared to the carboxy-terminal fusion (#6826). In this assay, both constructs were titrated against 4 nM myostatin and evaluated for their ability to inhibit the myostatin signaling activity as measured by a luciferase reporter system. The relative peptibody activities are reported as the effective concentration for 50% inhibition ($EC_{50}$). This experiment shows that the Fc-loop TN8-19-07 peptibody (#6951) retains full in vitro bioactivity (FIG. 8).

Stability in vivo of the Fc-loop TN8-19-07 peptibody was compared to the carboxy-terminal TN8-19-07 peptibody in mice. In this study, groups of 15 mice were dosed subcutaneously with either peptibody construct at 5 mg/kg. At 4 hours post injection 5 mice were sacrificed and serum collected. At 24 hours another 5 mice were harvested and likewise at 48 hours. Each individual serum sample was evaluated by western blot for detectable human IgG-Fc peptibody. Since all the serum within each 5-mouse group was very similar, the groups were pooled to allow representative samples to be run together on a single gel/blot. The result of that analysis (FIG. 9) clearly shows that the Fc-loop TN8-19-07 peptibody persists in the pooled mouse sera throughout the 48-hour time course with no apparent loss. In contrast, the concentration of the carboxy-terminal TN8-19-07 peptibody diminishes steadily through the course of the study until it is nearly undetectable at the 48-hour time point. This result suggests that the Fc-loop design approach may confer additional in vivo stability to the TN8-19-07 peptibody.

Example 3

Preparation of TN8-Con4

This molecule was prepared as described above in Example 1 and in U.S. Pat. App. No. 2003/0236192 (also PCT/US04/10989), which is hereby incorporated by reference.

Example 4

Preparation of Fc-ang2-tandem

This molecule was prepared as described in U.S. 2003/0236193, published Dec. 25, 2003 (also PCT/US04/10989, filed Apr. 8, 2004), which is hereby incorporated by reference.

Example 5

Preparation of TN8-19-7

This molecule was prepared as described above in example 2 and in U.S. Ser. No. 10/742,379, filed Dec. 19, 2003 (also PCT/US03/40781, filed Dec. 19, 2003), which is hereby incorporated by reference.

Example 6

Preparation of Fc-Loop-EMP

This molecule was prepared as previously described in example 1.

Example 7

Preparation of Fc-loop-Amp2

In another embodiment of this invention a linear, non-constrained peptide, AMP 2 was inserted into the human IgG1 Fc-loop domain, defined as the sequence $D_{137}E_{138}L_{139}T_{140}K_{141}$ (FIG. 2A).

AMP-2: IEGPTLRQWLAARA (SEQ ID NO: 28)

The Fc insertion is between $Leu_{139}$ and $Thr_{140}$ and includes 2 Gly residues as linkers flanking either side of the inserted peptide (FIG. 3D). The Fc-loop AMP 2 construct is labeled as Amgen clone #6875.

The Fc-loop AMP 2 clone (#6875) was transformed into *E. coli* by conventional methods known to those in the art and was found to express at high levels and almost exclusively in the insoluble inclusion body fraction (FIG. 17). The isolated inclusion body fraction (1 g) was solubilized in 6 M guanidine-HCl, 50 mM Tris, 8 mM DTT, pH 9 (10 ml) at room temperature with mixing, for 1 hour. The denatured and reduced peptibody was refolded from the solubilized inclusion body fraction by a 1:25 (v/v) dilution into 2 M urea, 50 mM Tris, 4 mM cysteine, 1 mM cystamine, pH 8.5. The solubilized peptibody was added drop wise to the refold buffer at 4° C. with stirring. The refold reactions were allowed to stir for 48 hours, and then aliquots were evaluated by SDS-PAGE and reversed-phase HPLC.

Purification was achieved using a 2-column process. First a recombinant Protein-A column was equilibrated in 2 M urea, 50 mM Tris, pH 8.5 and loaded with the filtered peptibody refold reaction. The column was then washed with 2 column volumes of equilibration buffer, followed by 2 column volumes of PBS. The peptibody fraction was eluted with 50 mM NaOAc, pH3 and quickly neutralized by a 1:4 dilution into 10 mM NaOAc, 50 mM NaCl, pH 5. The diluted Protein-A eluate was again filtered and loaded to an SP Sepharose HP cation exchange column (Pharmacia) equilibrated in 10 mM NaOAc, 50 mM NaCl, pH 5. The peptibody fractions were then eluted with a linear 50-500 mM NaCl gradient, pooled and concentrated to about 2 mg/ml. The final pools of Fc-loop AMP 2 (#6875) were evaluated by SDS-PAGE (FIG. 19) and RP-HPLC (FIG. 20).

The final preparation of Fc-loop AMP 2 was tested in an in vivo mouse bioassay against a carboxy-terminal peptibody fusion of two AMP 2 sequences linked in tandem (Fc tandem AMP2). In this comparison, the Fc-tandem-AMP2 has a total valence of four AMP 2 peptides compared to the Fc-loop AMP 2 with only two peptides. The mice received a single subcutaneous injection of 50 μg/kg of either peptibody while their platelet levels were monitored over 15 days (FIG. 21). While the Fc-tandem-AMP2 induced a significant initial platelet increase, the total response was complete by day 9. In contrast, the Fc-loop AMP 2 elicited a much smaller response that peaked at day 8 and persisted for 15 days. These results suggest that the efficacious half-life of the Fc-loop AMP 2 peptibody may be much greater than the conventional carboxy-terminal fused peptibody. The difference in overall amplitude of the response may be a consequence of the greater valence of Fc-tandem-Amp2.

Example 8

Preparation of Amp2

This molecule was prepared as described above in example 7, and in U.S. Pat. No. 6,660,843.

Example 9

In Vitro Cell-Based Assay and the Measurement of Myostatin-Signaling Activity (FIG. 8)

To quantitate myostatin activity and its blockade, a luciferase reporter system was developed, referred to as pMARE-Luc, which senses Myostatin/Activin signaling strength. The pMARE-luc vector was constructed by sub-cloning a Smad-responsive CAGA tandem repeat sequence into a basic reporter plasmid pLuc-MCS containing a minimal promoter element (TATA box). The pMARE-luc vector was stably transfected into a skeletal muscle-derived C2C12 cell line (murine).

Characterization of myostatin responses of the stable clones led to the identification of C2C12-based clonal reporter cell lines that were capable of detecting both myostatin and Activin signaling activities in 96-well format in a highly sensitive and reproducible manner.

Example 10

In Vitro HTRF (Homogeneous Time-Resolved Fluorescence) Ang-2 Binding Assay (FIG. 15)

Starting from a concentration of 100 nM, Fc-loop peptibody and proper controls were serially diluted in HTRF buffer 3-fold, 9-times across a 96-well plate. Dilutions were then mixed with the following reagents on a 96-well black, round-bottomed assay plate: Streptavidin-Europium (1.6 nM), Biotinylated human angiopoietin-2 (8.0 nM), human Tie2-Fc-APC (10 nM). Assay plate was then incubated at room temperature with shaking for 2 hours. Plate next read on a Rubystar microplate reader (BMG Labtechnologies Inc.). Results were converted to % inhibition, and IC50s were then calculated by analyzing the % inhibition values in the program GRAFIT 5.0 (IC50, 0-100% parameter).

Example 11

In Vivo AMP-2 Efficacy Assay( FIG. 21)

Female BDF1 mice are injected subcutaneously with either carrier fluid (1×PBS with 0.1% BSA), 50 mcg/kg of Fc-tandem-AMP2, or 50 mcg/kg of Fc-loop-AMP2. The injection volume is 0.2 mL. Blood is collected from each mouse via a puncture of the retro orbital sinus into a heparinized capillary tube, and then transferred to microtainers containing EDTA. Complete blood counts (CBC) including differential white blood cell counts are obtained using an ADVIA120 blood analyzer calibrated for mouse blood (Bayer Corp., Tarrytown, N.Y.). Standard bleed days are 0, 3, 5, 7 and 10. Platelet counts are plotted as a function of time post-injection.

Example 12

UT-7 EPO Proliferation Assay for EMP Activity
(FIG. 18)

The UT-7Epo proliferation assay uses human megakaryoblastic leukemia cell line that responds to murine EPO (mEPO) and human EPO (huEPO) or other EPO like molecules for growth and survival.

Growth factors are serially diluted from 1000 ng/ml to 0.488 ng/ml in triplicate, in 100 µl of 10% FBS—Iscoves Modified Dulbelcco's medium (IMDM) across the 96 well plate. 15000 cells/well are added to the 96 well plate in 100 µl of 10% FBS IMDM. The total volume per well is 200 µl of media with 15000 cells per well. Cells and media alone are the zero control. Cells are incubated in a humidified chamber at 37° C.

After incubation for 72 hours with the growth factor to be examined, viable cells are determined by MTS (3-(4,5-dimethylthiazol-2-yl)-5-(3-carboxymethoxyphenyl)-2-(4-sulfophenyl)2H-tetrazolium, inner salt) incorporation (5+/−1 hr at 37° C.) and growth is measured by O.D. (490 nm absorbance), limits not >4.0 O.D. Reference: Yasusada Miura, Keita Kirito, and Norio Komatsu (1998), "Regulation of Both Erythroid and Megakaryocytic Differentiation of a Human Leukemia Cell Line, UT-7," *Acta Haematologica*, 99:180-184.

Example 13

Alternate Fc-Loop Insertion Sites

Having proven the feasibility of Fc-Loop insertion-style peptibodies with the L139/T140 insertion site using several different peptides, additional loops were surveyed in the Fc crystal structure. Using Fc-domain homology modeling, twelve different potential insertion sites were selected based on solvent accessible surface exposure, steric constraints within the loop, proximity to the Fc dimer interface and juxtaposition to sites of known effector function, such as the FcRn binding interface. The Fc-Loop sites that were identified as potential insertion sites are detailed and ranked. See FIG. 2A and Table 12 below.

TABLE 12

Specific insertion sites for the human IgG1 Fc sequence

| Domain | Loop | Insertion | Comments |
|---|---|---|---|
| CH2 | $P_{25}$-$P_{26}$ | Not preferred | Tight turn |
| CH2 | $D_{46}$-$E_{53}$ | $H_{49}/E_{50}$ - $1^{st}$<br>$E_{50}/D_{51}$ - $2^{nd}$ | No homology H/E site |
| CH2 | $V_{65}$-$A_{68}$ | Not preferred | FcRn interactive |
| CH2 | $E_{74}$-$T_{80}$ | $Y_{77}/N_{78}$ - $1^{st}$<br>$N_{78}/S_{79}$ - $2^{nd}$ | Low homology Y/N site |
| CH2 | $V_{89}$-$E_{99}$ | Not preferred | FcRn interactive |
| CH2—CH3 linker | $N_{106}$-$P_{127}$ | $K_{107}/A_{108}$ - $1^{st}$<br>$N_{106}/K_{107}$ - $2^{nd}$ | Exposed turn |
| CH3 | $D_{137}$-$K_{141}$ | $L_{139}/T_{140}$ - $1^{st}$<br>$E_{138}/L_{139}$ - $2^{nd}$ | Successfully tested $L_{139}/T_{140}$ |
| CH3 | $N_{165}$-$N_{177}$ | $E_{169}/N_{170}$ - $1^{st}$<br>$N_{170}/N_{171}$ - $2^{nd}$ | Avoid tight turn $N_{165}$-$P_{168}$. No homology E/N site |
| CH3 | $T_{175}$-$S_{184}$ | $S_{181}/D_{182}$ - $1^{st}$<br>$V_{178}/L_{179}$ - $2^{nd}$ | No homology V/L site. S/D site poss. better exposed |
| CH3 | $K_{195}$-$V_{203}$ | $G_{201}/N_{202}$ - $1^{st}$<br>$N_{202}/V_{203}$ - $2^{nd}$ | α/β content. G/N site exposed. N/V site low homology |
| CH3 | NA | $Q_{167}/P_{168}$ | IgA, IgM insertion site |
| CH3 | NA | $G_{183}/S_{184}$ | IgA, IgM insertion site |

Of these potential insertion sites, six were expressed using the TN8-19-7 peptide insert (Example 2) and evaluated for refolding efficiency and in vitro activity. An additional construct was added which contained an asymmetric linker system Gly4/Gly6 engineered into the original loop insertion site (L139/T140) previously described. In all, seven new Fc Loop Myostatin constructs were refolded, purified, and tested for activity.

The seven new Fc-Loop TN8-19-7 constructs that were tested included insertions in both CH2 and CH3 domains of human IgG1 Fc. Specifically, these insertions were: G201/N202 (CH3), E169/N170 (CH3), S181/D182 (CH3), H49/E50 (CH2), L139/T140 (G4-6) (CH3), Y77/N78 (CH2), and K107/A108 (CH2-CH3 linker domain). These constructs were transformed into *E. coli* by conventional methods known in the art, and were found to express almost exclusively in the insoluble inclusion body fraction. Interestingly, the H49/E50, L139/T140 (G4-6) and Y77/N78 constructs appeared to have the highest levels of expression. The E169/N170, S181/D182, K107/108 showed moderate expression, and the G201/202 construct showed some expression, but very little.

Those Fc-Loop TN8-19-7 constructs which expressed well in *E. coli* were purified by first solubilizing the isolated inclusion body fractions in 6 M Guanidine-HCl, 50 mM Tris, 8 mM DTT pH 9.0 (10 mL per 1 g inclusion body) at room temperature with mixing for 1 hour. Then, a variety of refolding conditions were evaluated for each of the denatured and reduced Fc-Loop TN8-19-7 constructs to identify optimal refolding conditions. The three G201/N202, E169/N170, and S181/D182 constructs did not refold well under any of the conditions tested. Of the remaining four Fc-Loop TN8-19-7 constructs, L139/T140 (G4-6) refolded the best, while the remaining three H49/E50, Y77/N78 and K107/A108 refolded with sufficient yield to pursue further purification.

Using optimized refold conditions, the denatured and reduced Fc-Loop TN8-19-7 constructs were refolded from the solubilized inclusion body fractions by a 1:25 (v/v) dilution into 4 M Urea, 50 mM Tris-HCl, 0.16 M Arg-HCl, 20% glycerol, 3 M Cystine, 5 mM Cystamine pH 8.5. The solubilized peptibodies were added drop-wise to the refold buffer at 4° C. with stirring. The refold reactions were allowed to stir for 72 hours, and subsequently purified chromatographically. Final purification was achieved by a 2-column chromatographic process, as described in Example 2.

The final pools of L139/T140 (G4-6), H49/E50, Y77/N78, and K107/108 were evaluated by RP-HPLC and SDS-PAGE, as illustrated in FIGS. 23 and 24. The yields from these four constructs are tabulated in Table 13.

TABLE 13

Expression and purification yields of recoverable Fc-loop constructs

| Insertion Site | Grams IB per Grams Paste | mg product per gram of IB |
|---|---|---|
| H49/E50 (CH2 domain) | 0.182 | 2.08 |
| L139/T140 (G4-6) (CH3 domain) | 0.156 | 14.58 |
| Y77/N78 (CH2 domain) | 0.162 | 10.26 |
| K107/A108 | 0.140 | 0.22 |

Among the four analogs purified the L139/T140 (G4-6) insertion site analog was produced with the best purity and in the highest yield.

The purified Fc-loop insertion analogs were further analyzed for functional myostatin receptor binding activity using an in vitro cell based inhibition assay, as described in Example 9. The results are shown in Table 14.

TABLE 14

In vitro cell based myostatin inhibition assay results

| Fc-Loop insertion analogs | $IC_{50}$ (nM) |
|---|---|
| H49/E50 | 13.94 |
| L139/T140 (G4-6) | 0.8727 |
| Y77/N78 | 17.06 |
| Fc-Loop #6951 (139/140) | 0.8335 |

The purified Fc-loop insertion analogs were further analyzed for FcRn binding using a Biacore assay system. Sample K107/A108 was not tested due to insufficient sample remaining after analysis. The $IC_{50}$ values determined using the in vitro cell based Myostatin inhibition assay, were similar for the L139/T140 (G4-6) insertion and the original Fc-Loop #6951, whereas the Fc-loop insertions at H49/E50 and Y77/N78 showed a reduced ability to inhibit myostatin (FIG. 30). The Biacore FcRn binding experiments showed that H49/E50 and Y77/N78 bound the Fc receptor comparably to the control (Fc-Loop-1×TN8-19-7, #6951) with an $EC_{50}$ of about 680 nM, but L139/T140 (G4-6) had a lower and more favorable $EC_{50}$ at around 220 nM.

In summary, of the six new insertion sites evaluated, three failed to refold efficiently. Among the three new insertion site analogs recovered, K107/A108 folded poorly, H49/E50 (CH2 domain) refolded marginally well, and the two remaining insertions at Y77/N78 (CH2 domain) and the original insertion site of L139/T140 (CH3 domain) with an extended, asymmetric linker folded with a higher efficiency. Interestingly, all of these novel insertion site analogs refolded with significantly lower yield than the original Fc-loop construct (#6951) with TN8-19-7 in position L139/T140 using symmetric Gly2 linkers.

When tested for retention of FcRn binding capacity, all the Fc-loop molecules appeared similar in affinity with the possible exception of the extended, asymmetric linker construct, which seemed slightly better. This was consistent with the design paradigm to minimize steric interactions between the inserted peptide and the FcRn binding interface.

While all the purified Fc-loop constructs were active by the in vitro, cell-based functional assay (Table 14), the original insertion site (L139/T140) and the extended, asymmetric linker insertion at the same site appeared to be the most potent.

This work demonstrates that multiple loop domains within the human IgG1 Fc, as identified in FIG. 23, will tolerate insertion of bioactive peptides while preserving the activity of both the peptide and Fc effector functions such as FcRn binding. Peptide insertion analogs utilizing these Fc-loop domains can vary significantly in refolding efficiency and peptide activity. Each peptide/insertion combination can be individually optimized to maximize recovery and potency.

More preferable would be peptide insertions targeting the underlined sub-domains in FIG. 23. Most preferable are the insertion site (L139/T140) and two additional loops in the CH2 domain (H49/E50 and Y77/N78).

ABBREVIATIONS

Abbreviations used throughout this specification are as defined below, unless otherwise defined in specific circumstances.

Ac acetyl (used to refer to acetylated residues)
AcBpa acetylated p-benzoyl-L-phenylalanine
ACN acetonitrile
ADCC antibody-dependent cellular cytotoxicity
Aib aminoisobutyric acid
bA beta-alanine
Bpa p-benzoyl-L-phenylalanine
BrAc bromoacetyl ($BrCH_2C(O)$)
BSA Bovine serum albumin
Bzl Benzyl
Cap Caproic acid
CTL Cytotoxic T lymphocytes
CTLA4 Cytotoxic T lymphocyte antigen 4
DARC Duffy blood group antigen receptor
DCC Dicylcohexylcarbodiimide
Dde 1-(4,4-dimethyl-2,6-dioxo-cyclohexylidene)ethyl
EDTA ethylene diamine tetraacetic acid
EMP Erythropoietin-mimetic peptide
ESI-MS Electron spray ionization mass spectrometry
EPO Erythropoietin
Fmoc fluorenylmethoxycarbonyl
G-CSF Granulocyte colony stimulating factor
GH Growth hormone
HCT hematocrit
HGB hemoglobin
hGH Human growth hormone
HOBt 1-Hydroxybenzotriazole
HPLC high performance liquid chromatography
IL interleukin
IL-R interleukin receptor
IL-1R interleukin-1 receptor
IL-1ra interleukin-1 receptor antagonist
Lau Lauric acid
LPS lipopolysaccharide
LYMPH lymphocytes
MALDI-MS Matrix-assisted laser desorption ionization mass spectrometry
Me methyl
MeO methoxy
MES (2-[N-Morpholino]ethanesulfonic acid)
MHC major histocompatibility complex
MMP matrix metalloproteinase MMPI matrix metalloproteinase inhibitor
NaOAc sodium acetate
1-Nap 1-napthylalanine
NEUT neutrophils
NGF nerve growth factor
Nle norleucine
NMP N-methyl-2-pyrrolidinone
PAGE polyacrylamide gel electrophoresis
PBS Phosphate-buffered saline
Pbf 2,2,4,6,7-pendamethyldihydrobenzofuran-5-sulfonyl
PCR polymerase chain reaction
Pec pipecolic acid
PEG Poly(ethylene glycol)
pGlu pyroglutamic acid
Pic picolinic acid
PLT platelets
pY phosphotyrosine
PTFE polytetrafluoroethylene
RBC red blood cells
RBS ribosome binding site
RP-HPLC reversed phase HPLC
RT room temperature (25° C.)
Sar sarcosine
SDS sodium dodecyl sulfate
STK serine-threonine kinases
t-Boc tert-Butoxycarbonyl
tBu tert-Butyl
TGF tissue growth factor
THF thymic humoral factor
TK tyrosine kinase
TMP Thrombopoietin-mimetic peptide
TNF Tissue necrosis factor
TPO Thrombopoietin
TRAIL TNF-related apoptosis-inducing ligand
Trt trityl
UK urokinase
UKR urokinase receptor
VEGF vascular endothelial cell growth factor
VIP vasoactive intestinal peptide
WBC white blood cells

What is claimed is:

1. A composition of matter of the formula $$(X^1)_a-F^1-(X^2)_b$$

and multimers thereof, wherein:

$F^1$ is an IgG1 Fc domain comprising SEQ ID NO: 604 modified so that it comprises at least one $X^3$ inserted into or replacing all or part of a sequence selected from SEQ ID NOS: 621, 622, 624, 625, 627, 628, 632, 634, 636 and 644 within a loop region of the IgG1 Fc domain, said loop region being in a non-terminal domain of the Fc domain;

$X^1$ and $X^2$ are each independently selected from $-(L^1)_c-P^1$, $-(L^1)_c-P^1-(L^2)_d-P^2$, $-(L^1)_c-P^1-(L^2)_d-P^2-(L^3)_e-P^3$, and $-(L^1)_c-P^1-(L^2)_d-P^2-(L^3)_e-P^3-(L^4)_f-P^4$;

$X^3$ is independently selected from $-(L^5)_c-P^5$, $-(L^5)_c-P^5-(L^6)_d-P^6$, $-(L^5)_c-P^5-(L^6)_d-P^6-(L^7)_e-P^7$, and $-(L^5)_c-P^5-(L^6)_d-P^6-(L^7)_e-P^7-(L^8)_f-P^8$;

$P^1$, $P^2$, $P^3$, and $P^4$ are each independently sequences of pharmacologically active polypeptides or pharmacologically active peptides;

$P^5$, $P^6$, $P^7$, and $P^8$ are each independently sequences of pharmacologically active peptides;

$L^1$, $L^2$, $L^3$, $L^4$, $L^5$, $L^6$, $L^7$, and $L^8$ are each independently linkers; and a, b, c, d, e, and f are each independently 0 or 1.

2. The composition of matter of claim 1, wherein $X^3$ is inserted at $H_{53}/E_{54}$, $Y_{81}/N_{82}$, $N_{110}/K_{111}$, $M_{143}/T_{144}$, $Q_{171}/P_{172}$, $E_{173}/N_{174}$, $S_{185}/D_{186}$, $G_{187}/S_{188}$, or $G_{205}/N_{206}$.

3. The composition of matter of claim 1, wherein $X^3$ comprises a myostatin binding peptide sequence, an erythropoietin-mimetic (EPO-mimetic) peptide sequence, an angiotensin-2 (ang-2) binding peptide sequence, a thrombopoietin-mimetic (TPO-mimetic) peptide sequence, an angiotensin-2 (ang-2) binding peptide sequence, a nerve growth factor (NGF) binding peptide sequence, or a B cell activating factor (BAFF) binding peptide sequence.

4. The composition of matter of claim 3, wherein the myostatin binding peptide sequence is selected from SEQ ID NOS: 218 to 509.

5. The composition of matter of claim 3, wherein the EPO-mimetic peptide sequence is selected from SEQ ID NOS: 1 to 27.

6. The composition of matter of claim 3, wherein the TPO-mimetic peptide sequence is selected from SEQ ID NOS: 28 to 99.

7. The composition of matter of claim 3, wherein the ang-2 binding peptide sequence is selected from SEQ ID NOS: 100 to 189.

8. The composition of matter of claim 3, wherein the NGF binding peptide sequence is selected from SEQ ID NOS: 190 to 218.

9. The composition of matter of claim 3, wherein the BAFF binding peptide sequence is selected from SEQ ID NOS: 510 to 594.

10. A modified antibody, comprising an Fc domain, $F^1$, wherein:

$F^1$ is an IgG1 Fc domain comprising SEQ ID NO: 604 modified so that it comprises at least one $X^3$ inserted into or replacing all or part of a sequence selected from SEQ ID NOS: 621, 622, 624, 625, 627, 628, 632, 634, 636, and 644 within a loop region of the IgG1 Fc domain, said loop region being in a non-terminal domain of the Fc domain, wherein:

$X^3$ is independently selected from $-(L^5)_c-P^5$, $-(L^5)_c-P^5-(L^6)_d-P^6$, $-(L^5)_c-P^5-(L^6)_d-P^6-(L^7)_e-P^7$, and $-(L^5)_c-P^5-(L^6)_d-P^6-(L^7)_e-P^7-(L^8)_f-P^8$;

$P^5$, $P^6$, $P^7$, and $P^8$ are each independently sequences of pharmacologically active peptides;

$L^5$, $L^6$, $L^7$, and $L^8$ are each independently linkers; and c, d, e, and f are each independently 0 or 1.

11. The modified antibody of claim 10, wherein $X^3$ is inserted at $H_{53}/E_{54}$, $Y_{81}/N_{82}$, $N_{110}/K_{111}$, $M_{143}/T_{144}$, $Q_{171}/P_{172}$, $E_{173}/N_{174}$, $S_{185}/D_{188}$, $G_{187}/S_{188}$, or $G_{205}/N_{206}$.

12. The modified antibody of claim 10, wherein $X^3$ comprises a myostatin binding peptide sequence, an erythropoietin-mimetic (EPO-mimetic) peptide sequence, a thrombopoietin-mimetic (TPO-mimetic) peptide sequence, an angiotensin-2 (ang-2) binding peptide sequence, a nerve growth factor (NGF) binding peptide sequence, or a B cell activating factor (BAFF) binding peptide sequence.

13. The modified antibody of claim 12, wherein the myostatin binding peptide sequence is selected from SEQ ID NOS: 218 to 509.

14. The modified antibody of claim 12, wherein the EPO-mimetic peptide sequence is selected from SEQ ID NOS: 1 to 27.

15. The modified antibody of claim 12, wherein the TPO-mimetic peptide sequence is selected from SEQ ID NOS: 28 to 99.

16. The modified antibody of claim 12, wherein the ang-2 binding peptide sequence is selected from SEQ ID NOS: 100 to 189.

17. The modified antibody of claim 12, wherein the NGF binding peptide sequence is selected from SEQ ID NOS: 190 to 218.

18. The modified antibody of claim 12, wherein the BAFF binding peptide sequence is selected from SEQ ID NOS: 510 to 594.

* * * * *